US011484030B2

(12) United States Patent
Fleming et al.

(10) Patent No.: US 11,484,030 B2
(45) Date of Patent: Nov. 1, 2022

(54) ENGINEERED PESTICIDAL PROTEINS AND METHODS OF CONTROLLING PLANT PESTS

(71) Applicant: Syngenta Participations AG, Basel (CH)

(72) Inventors: Christopher Fleming, Research Triangle Park, NC (US); Richard Sessler, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 16/648,323

(22) PCT Filed: Oct. 1, 2018

(86) PCT No.: PCT/US2018/053687
§ 371 (c)(1),
(2) Date: Mar. 18, 2020

(87) PCT Pub. No.: WO2019/070554
PCT Pub. Date: Apr. 11, 2019

(65) Prior Publication Data

US 2020/0299719 A1 Sep. 24, 2020

Related U.S. Application Data

(60) Provisional application No. 62/566,692, filed on Oct. 2, 2017.

(51) Int. Cl.

| | |
|---|---|
| *C07K 14/195* | (2006.01) |
| *C12N 15/82* | (2006.01) |
| *A01N 37/44* | (2006.01) |
| *A01H 1/02* | (2006.01) |
| *A01H 5/10* | (2018.01) |
| *A01N 63/50* | (2020.01) |

(52) U.S. Cl.
CPC .............. *A01N 37/44* (2013.01); *A01H 1/02* (2013.01); *A01H 5/10* (2013.01); *A01N 63/50* (2020.01); *C07K 14/195* (2013.01); *C12N 15/8286* (2013.01)

(58) Field of Classification Search
None
See application file for complete search history.

(56) References Cited

U.S. PATENT DOCUMENTS

| | | | | |
|---|---|---|---|---|
| 8,575,425 B2 * | 11/2013 | Desai | ................. | C12N 15/8286 800/279 |
| 9,862,965 B2 * | 1/2018 | Heinrichs | .............. | A01N 37/46 |
| 2011/0023184 A1 | 1/2011 | Desai et al. | | |
| 2014/0298538 A1 | 10/2014 | Heinrichs et al. | | |
| 2016/0040184 A1 | 2/2016 | Cong et al. | | |

FOREIGN PATENT DOCUMENTS

| | | |
|---|---|---|
| WO | 2011/002992 A1 | 1/2011 |
| WO | 2013016617 A1 | 1/2013 |
| WO | 2016/114973 A1 | 7/2016 |
| WO | 2017/019787 A1 | 2/2017 |

OTHER PUBLICATIONS

Schellenberger et al. Science (2016), vol. 354 (6312), pp. 634-637.*
"Pepsin," Sigma-Aldrich, Aug. 8, 2013 (Aug. 8, 2013), p. 1 of 1. Retrieved from the Internet: <https://www.sigmaaldrich.com/life-science/biochemicals/biochemical-products.html? TablePage=16410613.
Sampson et al.,"Discovery of a Novel Insecticidal Protein from Chromobacterium Piscinae, with activity against Western Corn Rootworm, Diabrotica Virgifera Virgifera", Journal of Invertebrate Pathology, vol. 142, Oct. 28, 2016 (Oct. 28, 2016) pp. 34-43.
Rajamohan et al., "Mutations at Domain II, Loop 3, of Bacillus Thuringiensis CryIAa and CryIAb Delta-Endotoxins Suggest Loop 3 is Involved in Initial Binding to Lepidopteran Midguts", The Journal of Biological Chemistry, Oct. 11, 1996 (Oct. 11, 1996), vol. 274, No. 41, pp. 25220-25226.
International Search Report for International Application No. PCT/US2018/053687 dated Nov. 26, 2018.
Supplementary European Search Report for EP18865234.1, dated Jun. 9, 2021.
Herman, Rod A. et al.: "Rapid Digestion of Cry34Ab1 and Cry35Ab1 in Simulated Gastric Fluid", Journal of Agricultural and Food Chemistry, vol. 51, No. 23, Nov. 1, 2003, pp. 6823-6827, XP055805329.
Database Geneseq [Online] Nov. 20, 2014 (Nov. 20, 2014), "PHI-4 protein mutant K402N (Mut ID No. 390).", retrieved from EBI accession No. GSP:BBO40095, Database accession No. BB040095.

* cited by examiner

*Primary Examiner* — Medina A Ibrahim

(74) *Attorney, Agent, or Firm* — Katherine Seguin

(57) ABSTRACT

The invention provides nucleic acids, polypeptides, transgenic plants, compositions and methods for conferring pesticidal activity (e.g., insecticidal activity) to bacteria, plants, plant cells, tissues and seeds. Nucleic acids encoding the insecticidal proteins can be used to transform prokaryotic and eukaryotic organisms, including plants, to express the insecticidal proteins. The recombinant organisms and compositions containing the recombinant organisms or insecticidal proteins can be used to control a pest (e.g., an insect).

20 Claims, 15 Drawing Sheets

Specification includes a Sequence Listing.

Figure 1.

```
  1  MASAANAGQL GNLPGVTSMG MGYDVNGLYA SPESLLGQPL FDFGGELDSI
 51  EIEGRSYTFP RSMHVHTYFH SDFKQDVSKE IEEYREKMSQ HVGVSGRYKL
101  FSASLSVDFT TTDQQLTEIT YSSTREAHVL WYISLPGAAT LRSMLRRDFR
151  DDLNNPNMPA MELFKRYGPY YISEAAVGGR LDYSAASKTL KMDSSQSLST
201  TAEMSYKALV GEIKIEHGSE MEKQVNSFRS NSTIRLTATG GKPGMTDRIL
251  HGPDSQQAFS QWAESLLDYA TLMDFSTESL QPIWALADKP ERRVELEDAF
301  PE MKQSQQS IPKVDK L M DARPPMVKAG EDSGSGASE   A FNPSTSN
351  GYKMVG  GQ RNHASVADGH API K L   C  KAPVGWQ RVWDDAGSGK
401  SKDYACWRAI PPQGYR LGD VM ATSGYN PPN PDYVCV HQS CADVQ
451   QNRVWDKG TGARKDV  W QPGAAGAVAS SC AGVPNYN NPPNSGDIER
501   RGSIACVKT SAIASMQEMK SM SQHQGME AMMS L
```

SEQ ID NO: 1

```
                              SEQUENCE LISTING

<160> NUMBER OF SEQ ID NOS: 127

<210> SEQ ID NO 1
<211> LENGTH: 536
<212> TYPE: PRT
<213> ORGANISM: Chromobacterium piscinae

<400> SEQUENCE: 1

Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
    130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
        195                 200                 205

Leu Val Gly Glu Ile Lys Ile Glu His Gly Ser Glu Met Glu Lys Gln
```

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
            245                 250                 255

Gln Ala Phe Ser Gln Trp Ala Glu Ser Leu Leu Asp Tyr Ala Thr Leu
        260                 265                 270

Met Asp Phe Ser Thr Glu Ser Leu Gln Pro Ile Trp Ala Leu Ala Asp
    275                 280                 285

Lys Pro Glu Arg Arg Val Glu Leu Gly Asp Ala Phe Pro Glu Phe Met
290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
                325                 330                 335

Ala Ser Glu Asp Leu Ala Val Phe Asn Pro Ser Thr Ser Asn Gly Tyr
            340                 345                 350

Lys Met Val Gly Gln Phe Gly Gln Arg Asn His Ala Ser Val Ala Asp
        355                 360                 365

Gly His Ala Pro Ile Phe Lys Asp Leu Phe Asp Leu Gly Val Leu Lys
    370                 375                 380

Ala Pro Val Gly Trp Gln Arg Val Trp Asp Asp Ala Gly Ser Gly Lys
385                 390                 395                 400

Ser Lys Asp Tyr Ala Cys Trp Arg Ala Ile Pro Pro Gln Gly Tyr Arg
                405                 410                 415

Ala Leu Gly Asp Val Met Met Leu Ala Thr Ser Gly Tyr Asn Pro Pro
            420                 425                 430

Asn Leu Pro Asp Tyr Val Cys Val His Gln Ser Leu Cys Ala Asp Val
        435                 440                 445

Gln Thr Leu Gln Asn Arg Val Trp Trp Asp Lys Gly Thr Gly Ala Arg
    450                 455                 460

Lys Asp Val Ser Leu Trp Gln Pro Gly Ala Ala Gly Ala Val Ala Ser
465                 470                 475                 480

Ser Cys Phe Ala Gly Val Pro Asn Tyr Asn Asn Pro Asn Ser Gly
                485                 490                 495

Asp Ile Glu Arg Leu Arg Gly Ser Ile Ala Cys Val Lys Thr Ser Ala
            500                 505                 510

Ile Ala Ser Met Gln Glu Met Lys Ser Met Leu Ser Gln His Gln Gly
        515                 520                 525

Met Glu Ala Met Met Ser Lys Leu
530                 535

<210> SEQ ID NO 2
<211> LENGTH: 1608
<212> TYPE: DNA
<213> ORGANISM: Chromobacterium piscinae

<400> SEQUENCE: 2
atggcatccg cagcaaatgc aggtcagctt ggcaacctcc ccggcgttac ttccatgggc        60
atgggctatg acgtgaatgg tttgtacgcc agcccggaaa gcctgcttgg ccaacccttg       120
ttcgatttcg gcggcgagct ggacagcatc gaaatcgagg ccgcagcta cacctttccc       180 cgcagcatgc atgtacacac ctatttccat tccgacttca acaggatgt cagcaaggaa       240 atcgaagagt atcggagaa atgagccag cacgtgggcg tgtccggccg ctacaagttg       300

```
ttcagcgctt cgctgagcgt ggatttcacc accacggacc agcaactgac cgagattacc    360
tacagctcca cccgcgaagc ccatgtgctg tggtacatca gcctgcctgg cgcggccacg    420
ctgcgttcga tgctgcgccg cgatttccgc gacgacctga acaacccccaa tatgccggcc    480 atggagctgt tcaagcgcta tggtccctac tacatatcgg aagcggcggt gggcggccgg    540
ctggactaca gcgcggccag caagaccttg aagatggaca gcagccagtc gctgtccacc    600
accgccgaaa tgtcctacaa ggcgctggtg ggcgagatca agatcgagca tggctcggag    660
atggaaaagc aggtcaacag cttccgcagc aactccacca tccgtctcac cgccaccggc    720
ggcaagccgg gcatgaccga tcgcatactg cacggtccgg attcgcagca ggcgttctcg    780
caatgggcgg aatcgctgct cgactatgcg acgctgatgg actttccac cgaaagcctg    840 caaccgatct gggcgctggc cgacaagccc gagcgccgcg tcgagcttga ggacgccttc    900
cccgaattca tgaagcagtc gcagcagtcc atccccaagg tggacaaggt gctgctgatg    960
gacgcgcggc cgcctatggt gaaggctggg gaggatagcg gctccggcgc gtcggaggat   1020
ctggctgtgt tcaatcccag cacctccaat ggctacaaga tggttggcca gttcggtcag   1080
cgcaaccatg ccagcgtggc ggatggccat gcgccgattt tcaaggatct gttcgatctg   1140
ggcgtgctga aggcgccggt gggttggcag cgggtgtggg acgacgccgg ctccggcaag   1200
tccaaggact acgcgtgctg gcgcgcgatt ccgccgcagg gctaccgcgc gctgggcgat   1260
gtgatgatgc tggccaccag cggctataac cgccgaatc tgccggacta tgtttgcgtg   1320
catcaaagcc tgtgcgcgga tgtgcagacg ctgcaaaacc gggtgtggtg ggacaagggc   1380
accggcgcgc gcaaggatgt cagcctgtgg caaccgggcg cggccggcgc ggtggcgtcc   1440
tcttgcttcg ccggcgtgcc taattacaac aacccgccca attccggcga catcgagcgc   1500
ttgcgcggca gcatcgcatg cgtgaagacc agcgcgatcg cgtccatgca ggaaatgaag   1560
tccatgctca gccagcacca aggcatggaa gcgatgatgt ccaagctg              1608
```

<210> SEQ ID NO 3
<211> LENGTH: 536
<212> TYPE: PRT
<213> ORGANISM: Artificial Sequence
<220> FEATURE:
<223> OTHER INFORMATION: eAxmi205 #1 mutant

<400> SEQUENCE: 3

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125
```

```
Val Leu Trp Tyr Ile Ser Leu Pro Gly Ala Ala Thr Leu Arg Ser Met
    130                 135                 140

Leu Arg Arg Asp Phe Arg Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
            195                 200                 205

Leu Val Gly Glu Ile Lys Ile Glu His Gly Ser Glu Met Glu Lys Gln
    210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
            275                 280                 285

Lys Pro Glu Arg Arg Val Glu Leu Glu Asp Ala Phe Pro Glu Phe Met
    290                 295                 300

Lys Gln Ser Gln Gln Ser Ile Pro Lys Val Asp Lys Val Leu Leu Met
305                 310                 315                 320

Asp Ala Arg Pro Pro Met Val Tyr Ala Gly Glu Asp Ser Gly Ser Gly
                325                 330                 335

Ala Ser Glu Asp Leu Ala Val Phe Asn Pro Ser Thr Ser Asn Gly Tyr
            340                 345                 350

Lys Met Val Gly Gln Phe Gly Gln Arg Asn His Ala Ser Val Ala Asp
            355                 360                 365

Gly His Ala Pro Ile Phe Lys Asp Leu Phe Asp Leu Gly Val Leu Lys
    370                 375                 380

Ala Pro Val Gly Trp Gln Arg Val Trp Asp Asp Ala Gly Ser Gly Lys
385                 390                 395                 400

Ser Lys Asp Tyr Ala Cys Trp Arg Ala Ile Pro Pro Gln Gly Tyr Arg
                405                 410                 415

Ala Leu Gly Asp Val Met Met Leu Ala Thr Ser Gly Tyr Asn Pro Pro
            420                 425                 430

Asn Leu Pro Asp Tyr Val Cys Val His Gln Ser Leu Cys Ala Asp Val
            435                 440                 445

Gln Thr Leu Gln Asn Arg Val Trp Trp Asp Lys Gly Thr Gly Ala Arg
    450                 455                 460

Lys Asp Val Ser Leu Trp Gln Pro Gly Ala Ala Gly Ala Val Ala Ser
465                 470                 475                 480

Ser Cys Phe Ala Gly Val Pro Asn Tyr Asn Pro Pro Asn Ser Gly
                485                 490                 495

Asp Ile Glu Arg Leu Arg Gly Ser Ile Ala Cys Val Lys Thr Ser Ala
            500                 505                 510

Ile Ala Ser Met Gln Glu Met Lys Ser Met Leu Ser Gln His Gln Gly
            515                 520                 525

Met Glu Ala Met Met Ser Lys Leu
    530                 535
```

<210> SEQ ID NO 4
<211> LENGTH: 1611
<212> TYPE: DNA
<213> ORGANISM: Artificial Sequence
<220> FEATURE:
<223> OTHER INFORMATION: eAxmi205 #1 mutant

<400> SEQUENCE: 4

```
atggcatccg cagcaaatgc aggtcagctt ggcaacctcc ccggcgttac ttctatgggc    60
atgggctatg acgtgaatgg tttgtacgcc agcccggaaa gcctgcttgg ccaacccttg   120
ttcgatttcg gcggcgagct ggacagcatc gaaatcgagg gccgcagcta cacctttccc   180
cgcagcatgc atgtacacac ctatttccat tccgacttca acaggatgt cagcaaggaa    240
atcgaagagt atcgggagaa atgagccag cacgtgggcg tgtccggccg ctacaagttg    300
ttcagcgctt cgctgagcgt ggatttcacc accacggacc agcaactgac cgagattacc    360
tacagctcca cccgcgaagc ccatgtgctg tggtacatca gcctgcctgg cgcggccacg    420
ctgcgttcga tgctgcgccg cgatttccgc gacgacctga caacccccaa tatgccggcc    480
atggagctgt tcaagcgcta tggtccctac tacatatcgg aagcggcggt gggcggccgg    540
ctggactaca gcgcggccag caagaccttg aagatggaca gcagccagtc gctgtccacc    600
accgccgaaa tgtcctacaa ggcgctggtg ggcgagatca agatcgagca tggctcggag    660
atggaaaagc aggtcaacag cttccgcagc aactccacca tccgtctcac cgccaccggc    720
ggcaagccgg gcatgaccga tcgcatactg cacggtccgg attcgcagca ggcgttctcg    780
caatgggcgg aatcgctgct cgactatgcg acgctgatgg acttttccac cgaaaagcctg   840
caaccgatct gggcgctggc cgacaagccc gagcgccgcg tcgagcttga ggacgccttc    900
cccgaattca tgaagcagtc gcagcagtcc atccccaagg tggacaaggt gctgctgatg    960
gacgcgcggc cgcctatggt gtatgctggg gaggatagcg gctccggcgc gtcggaggat   1020
ctggctgtgt tcaatcccag cacctccaat ggctacaaga tggttggcca gttcggtcag   1080
cgcaaccatg ccagcgtggc ggatggccat gcgccgattt tcaaggatct gttcgatctg   1140
ggcgtgctga aggcgccggt ggggttggcag cgggtgtggg acgacgccgg ctccggcaag   1200
tccaaggact acgcgtgctg gcgcgcgatt ccgccgcagg gctaccgcgc gctgggcgat   1260
gtgatgatgc tggccaccag cggctataac ccgccgaatc tgccggacta tgtttgcgtg   1320
catcaaagcc tgtgcgcgga tgtgcagacg ctgcaaaacc gggtgtggtg ggacaagggc   1380
accggcgcgc gcaaggatgt cagcctgtgg caaccgggcg cggccggcgc ggtggcgtcc   1440
tcttgcttcg ccggcgtgcc taattacaac aacccgccca attccggcga catcgagcgc   1500
ttgcgcggca gcatcgcatg cgtgaagacc agcgcgatcg cgtccatgca ggaaatgaag   1560
tccatgctca gccagcacca aggcatggaa gcgatgatgt ccaagctgtg a             1611
```

<210> SEQ ID NO 5
<211> LENGTH: 536
<212> TYPE: PRT
<213> ORGANISM: Artificial Sequence
<220> FEATURE:
<223> OTHER INFORMATION: eAxmi205 #2 mutant

<400> SEQUENCE: 5

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30
```

```
Glu Ser Leu Leu Gly Gln Pro Leu Phe Asp Phe Gly Glu Leu Asp
         35                  40                  45

Ser Ile Glu Ile Glu Gly Arg Ser Tyr Thr Phe Pro Arg Ser Met His
 50                  55                  60

Val His Thr Tyr Phe His Ser Asp Phe Lys Gln Asp Val Ser Lys Glu
 65                  70                  75                  80

Ile Glu Glu Tyr Arg Glu Lys Met Ser Gln His Val Gly Val Ser Gly
                 85                  90                  95

Arg Tyr Lys Leu Phe Ser Ala Ser Leu Ser Val Asp Phe Thr Thr Thr
             100                 105                 110

Asp Gln Gln Leu Thr Glu Ile Thr Tyr Ser Ser Thr Arg Glu Ala His
             115                 120                 125

Val Leu Trp Tyr Ile Ser Leu Pro Gly Ala Ala Thr Leu Arg Ser Met
130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
             180                 185                 190

Asp Ser Ser Gln Ser Leu Ser Thr Thr Ala Glu Met Ser Tyr Lys Ala
             195                 200                 205

Leu Val Gly Glu Ile Lys Ile Glu His Gly Ser Glu Met Glu Lys Gln
         210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
             260                 265                 270

Met Asp Phe Ser Thr Glu Ser Leu Gln Pro Ile Trp Ala Leu Ala Asp
             275                 280                 285

Lys Pro Glu Arg Arg Val Glu Leu Glu Asp Ala Phe Pro Glu Phe Met
         290                 295                 300

Lys Gln Ser Gln Gln Ser Ile Pro Lys Val Asp Lys Val Leu Leu Met
305                 310                 315                 320

Asp Ala Arg Pro Pro Met Val Leu Ala Gly Glu Asp Ser Gly Ser Gly
                325                 330                 335

Ala Ser Glu Asp Leu Ala Val Phe Asn Pro Ser Thr Ser Asn Gly Tyr
             340                 345                 350

Lys Met Val Gly Gln Phe Gly Gln Arg Asn His Ala Ser Val Ala Asp
             355                 360                 365

Gly His Ala Pro Ile Phe Lys Asp Leu Phe Asp Leu Gly Val Leu Lys
370                 375                 380

Ala Pro Val Gly Trp Gln Arg Val Trp Asp Asp Ala Gly Ser Gly Lys
385                 390                 395                 400

Ser Lys Asp Tyr Ala Cys Trp Arg Ala Ile Pro Pro Gln Gly Tyr Arg
                405                 410                 415

Ala Leu Gly Asp Val Met Met Leu Ala Thr Ser Gly Tyr Asn Pro Pro
             420                 425                 430

Asn Leu Pro Asp Tyr Val Cys Val His Gln Ser Leu Cys Ala Asp Val
             435                 440                 445

Gln Thr Leu Gln Asn Arg Val Trp Trp Asp Lys Gly Thr Gly Ala Arg
```

```
                450                 455                 460
Lys Asp Val Ser Leu Trp Gln Pro Gly Ala Ala Gly Ala Val Ala Ser
465                 470                 475                 480

Ser Cys Phe Ala Gly Val Pro Asn Tyr Asn Asn Pro Pro Asn Ser Gly
                485                 490                 495

Asp Ile Glu Arg Leu Arg Gly Ser Ile Ala Cys Val Lys Thr Ser Ala
                500                 505                 510

Ile Ala Ser Met Gln Glu Met Lys Ser Met Leu Ser Gln His Gln Gly
            515                 520                 525

Met Glu Ala Met Met Ser Lys Leu
            530                 535

<210> SEQ ID NO 6
<211> LENGTH: 1611
<212> TYPE: DNA
<213> ORGANISM: Artificial Sequence
<220> FEATURE:
<223> OTHER INFORMATION: eAxmi205 #2

<400> SEQUENCE: 6
```

| | | | | | |
|---|---|---|---|---|---|
| atggcatccg | cagcaaatgc | aggtcagctt | ggcaacctcc | ccggcgttac | ttctatgggc | 60 |
| atgggctatg | acgtgaatgg | tttgtacgcc | agcccggaaa | gcctgcttgg | ccaacccttg | 120 |
| ttcgatttcg | gcggcgagct | ggacagcatc | gaaatcgagg | gccgcagcta | cacctttccc | 180 |
| cgcagcatgc | atgtacacac | ctatttccat | tccgacttca | acaggatgt | cagcaaggaa | 240 |
| atcgaagagt | atcgggagaa | aatgagccag | cacgtgggcg | tgtccggccg | ctacaagttg | 300 |
| ttcagcgctt | cgctgagcgt | ggatttcacc | accacggacc | agcaactgac | cgagattacc | 360 |
| tacagctcca | cccgcgaagc | ccatgtgctg | tggtacatca | gcctgcctgg | cgcggccacg | 420 |
| ctgcgttcga | tgctgcgccg | cgatttccgc | gacgacctga | caaccccaa | tatgccggcc | 480 |
| atggagctgt | tcaagcgcta | tggtccctac | tacatatcgg | aagcggcggt | gggcggccgg | 540 |
| ctggactaca | gcgcggccag | caagaccttg | aagatggaca | gcagccagtc | gctgtccacc | 600 |
| accgccgaaa | tgtcctacaa | ggcgctggtg | ggcgagatca | agatcgagca | tggctcggag | 660 |
| atggaaaagc | aggtcaacag | cttccgcagc | aactccacca | tccgtctcac | cgccaccggc | 720 |
| ggcaagccgg | gcatgaccga | tcgcatactg | cacggtccgg | attcgcagca | ggcgttctcg | 780 |
| caatgggcgg | aatcgctgct | cgactatgcg | acgctgatgg | acttttccac | cgaaagcctg | 840 |
| caaccgatct | gggcgctggc | cgacaagccc | gagcgccgcg | tcgagcttga | ggacgccttc | 900 |
| cccgaattca | tgaagcagtc | gcagcagtcc | atccccaagg | tggacaaggt | gctgctgatg | 960 |
| gacgcgcggc | cgcctatggt | gctggctggg | gaggatagcg | gctccggcgc | gtcggaggat | 1020 |
| ctggctgtgt | tcaatcccag | cacctccaat | ggctacaaga | tggttggcca | gttcggtcag | 1080 |
| cgcaaccatg | ccagcgtggc | ggatggccat | gcgccgattt | tcaaggatct | gttcgatctg | 1140 |
| ggcgtgctga | aggcgccggt | gggttggcag | cgggtgtggg | acgacgccgg | ctccggcaag | 1200 |
| tccaaggact | acgcgtgctg | gcgcgcgatt | ccgccgcagg | gctaccgcgc | gctgggcgat | 1260 |
| gtgatgatgc | tggccaccag | cggctataac | ccgccgaatc | tgccggacta | tgtttgcgtg | 1320 |
| catcaaagcc | tgtgcgcgga | tgtgcagacg | ctgcaaaacc | gggtgtggtg | ggacaagggc | 1380 |
| accggcgcgc | gcaaggatgt | cagcctgtgg | caaccgggcg | cggccggcgc | ggtggcgtcc | 1440 |
| tcttgcttcg | ccggcgtgcc | taattacaac | aacccgccca | attccggcga | catcgagcgc | 1500 |
| ttgcgcggca | gcatcgcatg | cgtgaagacc | agcgcgatcg | cgtccatgca | ggaaatgaag | 1560 | tccatgctca gccagcacca aggcatggaa gcgatgatgt ccaagctgtg a         1611

<210> SEQ ID NO 7
<211> LENGTH: 536
<212> TYPE: PRT
<213> ORGANISM: Artificial Sequence
<220> FEATURE:
<223> OTHER INFORMATION: eAxmi205 #3

<400> SEQUENCE: 7

Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
    130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
        195                 200                 205

Leu Val Gly Glu Ile Lys Ile Glu His Gly Ser Glu Met Glu Lys Gln
    210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
        275                 280                 285

Lys Pro Glu Arg Arg Val Glu Leu Glu Asp Ala Phe Pro Glu Phe Met
    290                 295                 300

Lys Gln Ser Gln Gln Ser Ile Pro Lys Val Asp Lys Val Leu Leu Met
305                 310                 315                 320

Asp Ala Arg Pro Pro Met Val Phe Ala Gly Asp Ser Gly Ser Gly
                325                 330                 335

Ala Ser Glu Asp Leu Ala Val Phe Asn Pro Ser Thr Ser Asn Gly Tyr
            340                 345                 350

Lys Met Val Gly Gln Phe Gly Gln Arg Asn His Ala Ser Val Ala Asp

```
                355                 360                 365
Gly His Ala Pro Ile Phe Lys Asp Leu Phe Asp Leu Gly Val Leu Lys
                    370                 375                 380

Ala Pro Val Gly Trp Gln Arg Val Trp Asp Asp Ala Gly Ser Gly Lys
385                 390                 395                 400

Ser Lys Asp Tyr Ala Cys Trp Arg Ala Ile Pro Pro Gln Gly Tyr Arg
                405                 410                 415

Ala Leu Gly Asp Val Met Met Leu Ala Thr Ser Gly Tyr Asn Pro Pro
                420                 425                 430

Asn Leu Pro Asp Tyr Val Cys Val His Gln Ser Leu Cys Ala Asp Val
                435                 440                 445

Gln Thr Leu Gln Asn Arg Val Trp Trp Asp Lys Gly Thr Gly Ala Arg
                450                 455                 460

Lys Asp Val Ser Leu Trp Gln Pro Gly Ala Ala Gly Ala Val Ala Ser
465                 470                 475                 480

Ser Cys Phe Ala Gly Val Pro Asn Tyr Asn Asn Pro Pro Asn Ser Gly
                485                 490                 495

Asp Ile Glu Arg Leu Arg Gly Ser Ile Ala Cys Val Lys Thr Ser Ala
                500                 505                 510

Ile Ala Ser Met Gln Glu Met Lys Ser Met Leu Ser Gln His Gln Gly
                515                 520                 525

Met Glu Ala Met Met Ser Lys Leu
                530                 535

<210> SEQ ID NO 8
<211> LENGTH: 1611
<212> TYPE: DNA
<213> ORGANISM: Artificial Sequence
<220> FEATURE:
<223> OTHER INFORMATION: eAxmi205 #3

<400> SEQUENCE: 8
atggcatccg cagcaaatgc aggtcagctt ggcaacctcc ccggcgttac ttctatgggc      60
atgggctatg acgtgaatgg tttgtacgcc agcccggaaa gcctgcttgg ccaacccttg     120
ttcgatttcg gcggcgagct ggacagcatc gaaatcgagg ccgcagcta  cacctttccc     180 cgcagcatgc atgtacacac ctatttccat tccgacttca acaggatgt  cagcaaggaa     240 atcgaagagt atcgggagaa aatgagccag acgtgggcg  tgtccggccg ctacaagttg     300
ttcagcgctt cgctgagcgt ggatttcacc accacggacc agcaactgac cgagattacc     360
tacagctcca cccgcgaagc ccatgtgctg tggtacatca gctgcctgg  cgcggccacg     420 ctgcgttcga tgctgcgccg cgatttccgc gacgacctga caacccccaa tatgccggcc     480
atggagctgt tcaagcgcta tggtccctac tacatatcgg aagcggcggt gggcggccgg     540
ctggactaca gcgcggccag caagaccttg aagatggaca gcagccagtc gctgtccacc     600
accgccgaaa tgtcctacaa ggcgctggtg gcgagatca  agatcgagca tggctcggag     660
atggaaaagc aggtcaacag cttccgcagc aactccacca tccgtctcac cgccaccggc     720
ggcaagccgg gcatgaccga tcgcatactg cacggtccgg attcgcagca ggcgttctcg     780
caatgggcgg aatcgctgct cgactatgcg acgctgatga cttttccac  cgaaagcctg     840 caaccgatct gggcgctggc cgacaagccc gagcgccgcg tcgagcttga ggacgccttc     900
cccgaattca tgaagcagtc gcagcagtcc atccccaagg tggacaaggt gctgctgatg     960
gacgcgcggc cgcctatggt gtttgctggg gaggatagcg gctccggcgc gtcggaggat    1020
```

-continued

```
ctggctgtgt tcaatcccag cacctccaat ggctacaaga tggttggcca gttcggtcag    1080
cgcaaccatg ccagcgtggc ggatggccat gcgccgattt tcaaggatct gttcgatctg    1140
ggcgtgctga aggcgccggt gggttggcag cgggtgtggg acgacgccgg ctccggcaag    1200
tccaaggact acgcgtgctg gcgcgcgatt ccgccgcagg gctaccgcgc gctgggcgat    1260
gtgatgatgc tggccaccag cggctataac ccgccgaatc tgccggacta tgtttgcgtg    1320
catcaaagcc tgtgcgcgga tgtgcagacg ctgcaaaacc gggtgtggtg ggacaagggc    1380
accggcgcgc gcaaggatgt cagcctgtgg caaccgggcg cggccggcgc ggtggcgtcc    1440
tcttgcttcg ccggcgtgcc taattacaac aacccgccca attccggcga catcgagcgc    1500
ttgcgcggca gcatcgcatg cgtgaagacc agcgcgatcg cgtccatgca ggaaatgaag    1560
tccatgctca gccagcacca aggcatggaa gcgatgatgt ccaagctgtg a             1611
```

<210> SEQ ID NO 9
<211> LENGTH: 536
<212> TYPE: PRT
<213> ORGANISM: Artificial Sequence
<220> FEATURE:
<223> OTHER INFORMATION: eAxmi205 #4 mutant

<400> SEQUENCE: 9

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
    130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
        195                 200                 205

Leu Val Gly Glu Ile Lys Ile Glu His Gly Ser Glu Met Glu Lys Gln
    210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
```

```
                    260             265              270
Met Asp Phe Ser Thr Glu Ser Leu Gln Pro Ile Trp Ala Leu Ala Asp
            275                 280             285

Lys Pro Glu Arg Arg Val Glu Leu Glu Asp Ala Phe Pro Glu Phe Met
        290                 295             300

Lys Gln Ser Gln Gln Ser Ile Pro Lys Val Asp Lys Val Leu Leu Met
305                 310             315                 320

Asp Ala Arg Pro Pro Met Val Lys Ala Gly Glu Asp Ser Gly Ser Gly
                325             330                 335

Ala Ser Glu Asp Leu Ala Val Phe Asn Pro Ser Thr Ser Asn Gly Tyr
            340                 345             350

Lys Met Val Gly Gln Phe Gly Gln Arg Asn His Ala Ser Val Ala Asp
        355                 360             365

Gly His Ala Pro Ile Phe Lys Asp Leu Phe Asp Leu Gly Val Leu Lys
    370                 375             380

Ala Pro Val Gly Trp Gln Arg Val Trp Asp Asp Ala Gly Ser Gly Lys
385                 390             395             400

Ser Lys Asp Phe Ala Cys Trp Arg Ala Ile Pro Pro Gln Gly Tyr Arg
                405             410             415

Ala Leu Gly Asp Val Met Met Leu Ala Thr Ser Gly Tyr Asn Pro Pro
            420             425             430

Asn Leu Pro Asp Tyr Val Cys Val His Gln Ser Leu Cys Ala Asp Val
        435             440             445

Gln Thr Leu Gln Asn Arg Val Trp Trp Asp Lys Gly Thr Gly Ala Arg
    450             455             460

Lys Asp Val Ser Leu Trp Gln Pro Gly Ala Ala Gly Ala Val Ala Ser
465             470             475             480

Ser Cys Phe Ala Gly Val Pro Asn Tyr Asn Pro Pro Asn Ser Gly
                485             490             495

Asp Ile Glu Arg Leu Arg Gly Ser Ile Ala Cys Val Lys Thr Ser Ala
            500             505             510

Ile Ala Ser Met Gln Glu Met Lys Ser Met Leu Ser Gln His Gln Gly
        515             520             525

Met Glu Ala Met Met Ser Lys Leu
    530             535
```

<210> SEQ ID NO 10
<211> LENGTH: 1611
<212> TYPE: DNA
<213> ORGANISM: Artificial Sequence
<220> FEATURE:
<223> OTHER INFORMATION: eAxmi205 #4 mutant

<400> SEQUENCE: 10

```
atggcatccg cagcaaatgc aggtcagctt ggcaacctcc ccggcgttac ttctatgggc      60
atgggctatg acgtgaatgg tttgtacgcc agcccggaaa gcctgcttgg ccaacccttg     120
ttcgatttcg gcggcgagct ggacagcatc gaaatcgagg ccgcagcta  caccttccc     180 cgcagcatgc atgtacacac ctatttccat tccgacttca acaggatgt  cagcaaggaa     240 atcgaagagt atcggagaa  aatgagccag cacgtgggcg tgtccggccg ctacaagttg     300
ttcagcgctt cgctgagcgt ggatttcacc accacggacc agcaactgac cgagattacc     360
tacagctcca cccgcgaagc ccatgtgctg tggtacatca gcctgcctgg cgcggccacg     420
ctgcgttcga tgctgcgccg cgatttccgc gacgacctga caaccccaa  tatgccggcc     480
```

```
atggagctgt tcaagcgcta tggtccctac tacatatcgg aagcggcggt gggcggccgg      540
ctggactaca gcgcggccag caagaccttg aagatggaca gcagccagtc gctgtccacc      600
accgccgaaa tgtcctacaa ggcgctggtg ggcgagatca agatcgagca tggctcggag      660
atggaaaagc aggtcaacag cttccgcagc aactccacca tccgtctcac cgccaccggc      720
ggcaagccgg gcatgaccga tcgcatactg cacggtccgg attcgcagca ggcgttctcg      780
caatgggcgg aatcgctgct cgactatgcg acgctgatgg acttttccac cgaaagcctg      840
caaccgatct gggcgctggc cgacaagccc gagcgccgcg tcgagcttga ggacgccttc      900
cccgaattca tgaagcagtc gcagcagtcc atccccaagg tggacaaggt gctgctgatg      960
gacgcgcggc cgcctatggt gaaggctggg gaggatagcg gctccggcgc gtcggaggat     1020
ctggctgtgt tcaatcccag cacctccaat ggctacaaga tggttggcca gttcggtcag     1080
cgcaaccatg ccagcgtggc ggatggccat gcgccgattt tcaaggatct gttcgatctg     1140
ggcgtgctga aggcgccggt ggggttggca gcgggtgtggg acgacgccgg ctccggcaag     1200
tccaaggact ttgcgtgctg gcgcgcgatt ccgccgcagg gctaccgcgc gctgggcgat     1260
gtgatgatgc tggccaccag cggctataac ccgccgaatc tgccggacta tgtttgcgtg     1320
catcaaagcc tgtgcgcgga tgtgcagacg ctgcaaaacc gggtgtggtg ggacaagggc     1380
accggcgcgc gcaaggatgt cagcctgtgg caaccgggcg cggccggcgc ggtggcgtcc     1440
tcttgcttcg ccggcgtgcc taattacaac aacccgccca attccggcga catcgagcgc     1500
ttgcgcggca gcatcgcatg cgtgaagacc agcgcgatcg cgtccatgca ggaaatgaag     1560
tccatgctca gccagcacca aggcatggaa gcgatgatgt ccaagctgtg a               1611
```

<210> SEQ ID NO 11
<211> LENGTH: 536
<212> TYPE: PRT
<213> ORGANISM: Artificial Sequence
<220> FEATURE:
<223> OTHER INFORMATION: eAxmi205 #5 mutant

<400> SEQUENCE: 11

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
    130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
```

```
                165                 170                 175
Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
            195                 200                 205

Leu Val Gly Glu Ile Lys Ile Glu His Gly Ser Glu Met Glu Lys Gln
            210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
            275                 280                 285

Lys Pro Glu Arg Arg Val Glu Leu Glu Asp Ala Phe Pro Glu Phe Met
            290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
                325                 330                 335

Ala Ser Glu Asp Leu Ala Val Phe Asn Pro Ser Thr Ser Asn Gly Tyr
            340                 345                 350

Lys Met Val Gly Gln Phe Gly Gln Arg Asn His Ala Ser Val Ala Asp
            355                 360                 365

Gly His Ala Pro Ile Phe Lys Asp Leu Phe Asp Leu Gly Val Leu Lys
            370                 375                 380

Ala Pro Val Gly Trp Gln Arg Val Trp Asp Asp Ala Gly Ser Gly Lys
385                 390                 395                 400

Ser Phe Asp Tyr Ala Cys Trp Arg Ala Ile Pro Pro Gln Gly Tyr Arg
                405                 410                 415

Ala Leu Gly Asp Val Met Met Leu Ala Thr Ser Gly Tyr Asn Pro Pro
            420                 425                 430

Asn Leu Pro Asp Tyr Val Cys Val His Gln Ser Leu Cys Ala Asp Val
            435                 440                 445

Gln Thr Leu Gln Asn Arg Val Trp Trp Asp Lys Gly Thr Gly Ala Arg
            450                 455                 460

Lys Asp Val Ser Leu Trp Gln Pro Gly Ala Ala Gly Ala Val Ala Ser
465                 470                 475                 480

Ser Cys Phe Ala Gly Val Pro Asn Tyr Asn Asn Pro Asn Ser Gly
                485                 490                 495

Asp Ile Glu Arg Leu Arg Gly Ser Ile Ala Cys Val Lys Thr Ser Ala
            500                 505                 510

Ile Ala Ser Met Gln Glu Met Lys Ser Met Leu Ser Gln His Gln Gly
            515                 520                 525

Met Glu Ala Met Met Ser Lys Leu
530                 535

<210> SEQ ID NO 12
<211> LENGTH: 1611
<212> TYPE: DNA
<213> ORGANISM: Artificial Sequence
<220> FEATURE:
<223> OTHER INFORMATION: eAxmi205 #5
```

<400> SEQUENCE: 12

```
atggcatccg cagcaaatgc aggtcagctt ggcaacctcc ccggcgttac ttctatgggc      60
atgggctatg acgtgaatgg tttgtacgcc agcccggaaa gcctgcttgg ccaacccttg     120
ttcgatttcg gcggcgagct ggacagcatc gaaatcgagg ccgcagcta caccttttccc    180
cgcagcatgc atgtacacac ctatttccat tccgacttca acaggatgt cagcaaggaa     240
atcgaagagt atcgggagaa aatgagccag cacgtgggcg tgtccggccg ctacaagttg    300
ttcagcgctt cgctgagcgt ggatttcacc accacggacc agcaactgac cgagattacc    360
tacagctcca cccgcgaagc ccatgtgctg tggtacatca gcctgcctgg cgcggccacg    420
ctgcgttcga tgctgcgccg cgatttccgc gacgacctga caaccccaa tatgccggcc     480
atggagctgt tcaagcgcta tggtccctac tacatatcgg aagcggcggt gggcggccgg    540
ctggactaca gcgcggccag caagaccttg aagatggaca gcagccagtc gctgtccacc    600
accgccgaaa tgtcctacaa ggcgctggtg ggcgagatca agatcgagca tggctcggag    660
atggaaaagc aggtcaacag cttccgcagc aactccacca tccgtctcac cgccaccggc    720
ggcaagccgg gcatgaccga tcgcatactg cacggtccgg attcgcagca ggcgttctcg    780
caatgggcgg aatcgctgct cgactatgcg acgctgatgg acttttccac cgaaagcctg    840
caaccgatct gggcgctggc cgacaagccc gagcgccgcg tcgagcttga ggacgccttc    900
cccgaattca tgaagcagtc gcagcagtcc atccccaagg tggacaaggt gctgctgatg    960
gacgcgcggc cgcctatggt gaaggctggg gaggatagcg gctccggcgc gtcggaggat   1020
ctggctgtgt tcaatcccag cacctccaat ggctacaaga tggttggcca gttcggtcag   1080
cgcaaccatg ccagcgtggc ggatggccat cgccgattt tcaaggatct gttcgatctg   1140
ggcgtgctga aggcgccggt gggttggcag cgggtgtggg acgacgccgg ctccggcaag   1200
tcctttgact acgcgtgctg gcgcgcgatt ccgccgcagg gctaccgcgc gctgggcgat   1260
gtgatgatgc tggccaccag cggctataac cgccgaatc tgccggacta tgtttgcgtg   1320
catcaaagcc tgtgcgcgga tgtgcagacg ctgcaaaacc gggtgtggtg gacaagggc    1380
accggcgcgc gcaaggatgt cagcctgtgg caaccgggcg cggccggcgc ggtggcgtcc   1440
tcttgcttcg ccggcgtgcc taattacaac aacccgccca attccggcga catcgagcgc   1500
ttgcgcggca gcatcgcatg cgtgaagacc agcgcgatcg cgtccatgca ggaaatgaag   1560
tccatgctca gccagcacca aggcatggaa gcgatgatgt ccaagctgtg a             1611
```

<210> SEQ ID NO 13
<211> LENGTH: 536
<212> TYPE: PRT
<213> ORGANISM: Artificial Sequence
<220> FEATURE:
<223> OTHER INFORMATION: eAxmi205 #6

<400> SEQUENCE: 13

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
```

-continued

```
                65                  70                  75                  80
Ile Glu Glu Tyr Arg Glu Lys Met Ser Gln His Val Gly Val Ser Gly
                    85                  90                  95
Arg Tyr Lys Leu Phe Ser Ala Ser Leu Ser Val Asp Phe Thr Thr Thr
                100                 105                 110
Asp Gln Gln Leu Thr Glu Ile Thr Tyr Ser Ser Thr Arg Glu Ala His
                115                 120                 125
Val Leu Trp Tyr Ile Ser Leu Pro Gly Ala Ala Thr Leu Arg Ser Met
            130                 135                 140
Leu Arg Arg Asp Phe Arg Asp Leu Asn Asn Pro Asn Met Pro Ala
145                 150                 155                 160
Met Glu Leu Phe Lys Arg Tyr Gly Pro Tyr Tyr Ile Ser Glu Ala Ala
                165                 170                 175
Val Gly Gly Arg Leu Asp Tyr Ser Ala Ala Ser Lys Thr Leu Lys Met
                180                 185                 190
Asp Ser Ser Gln Ser Leu Ser Thr Thr Ala Glu Met Ser Tyr Lys Ala
                195                 200                 205
Leu Val Gly Glu Ile Lys Ile Glu His Gly Ser Glu Met Glu Lys Gln
            210                 215                 220
Val Asn Ser Phe Arg Ser Asn Ser Thr Ile Arg Leu Thr Ala Thr Gly
225                 230                 235                 240
Gly Lys Pro Gly Met Thr Asp Arg Ile Leu His Gly Pro Asp Ser Gln
                245                 250                 255
Gln Ala Phe Ser Gln Trp Ala Glu Ser Leu Leu Asp Tyr Ala Thr Leu
                260                 265                 270
Met Asp Phe Ser Thr Glu Ser Leu Gln Pro Ile Trp Ala Leu Ala Asp
            275                 280                 285
Lys Pro Glu Arg Arg Val Glu Leu Glu Asp Ala Phe Pro Glu Phe Met
            290                 295                 300
Lys Gln Ser Gln Gln Ser Ile Pro Lys Val Asp Lys Val Leu Leu Met
305                 310                 315                 320
Asp Ala Arg Pro Pro Met Val Lys Ala Gly Glu Asp Ser Gly Ser Gly
                325                 330                 335
Ala Ser Glu Asp Leu Ala Val Phe Asn Pro Ser Thr Ser Asn Gly Tyr
                340                 345                 350
Lys Met Val Gly Gln Phe Gly Gln Arg Asn His Ala Ser Val Ala Asp
            355                 360                 365
Gly His Ala Pro Ile Phe Lys Asp Leu Phe Asp Leu Gly Val Leu Lys
            370                 375                 380
Ala Pro Val Gly Trp Gln Arg Val Trp Asp Asp Ala Gly Ser Gly Lys
385                 390                 395                 400
Ser Asn Asp Tyr Ala Cys Trp Arg Ala Ile Pro Pro Gln Gly Tyr Arg
                405                 410                 415
Ala Leu Gly Asp Val Met Met Leu Ala Thr Ser Gly Tyr Asn Pro Pro
            420                 425                 430
Asn Leu Pro Asp Tyr Val Cys Val His Gln Ser Leu Cys Ala Asp Val
            435                 440                 445
Gln Thr Leu Gln Asn Arg Val Trp Trp Asp Lys Gly Thr Gly Ala Arg
            450                 455                 460
Lys Asp Val Ser Leu Trp Gln Pro Gly Ala Ala Gly Ala Val Ala Ser
465                 470                 475                 480
Ser Cys Phe Ala Gly Val Pro Asn Tyr Asn Asn Pro Pro Asn Ser Gly
                485                 490                 495
```

Asp Ile Glu Arg Leu Arg Gly Ser Ile Ala Cys Val Lys Thr Ser Ala
        500                 505                 510

Ile Ala Ser Met Gln Glu Met Lys Ser Met Leu Ser Gln His Gln Gly
        515                 520                 525

Met Glu Ala Met Met Ser Lys Leu
        530             535

<210> SEQ ID NO 14
<211> LENGTH: 1611
<212> TYPE: DNA
<213> ORGANISM: Artificial Sequence
<220> FEATURE:
<223> OTHER INFORMATION: eAxmi205 #6

<400> SEQUENCE: 14

```
atggcatccg cagcaaatgc aggtcagctt ggcaacctcc ccggcgttac ttctatgggc      60
atgggctatg acgtgaatgg tttgtacgcc agcccggaaa gcctgcttgg ccaacccttg     120
ttcgatttcg gcggcgagct ggacagcatc gaaatcgagg ccgcagcta cacctttccc      180 cgcagcatgc atgtacacac ctatttccat tccgacttca acaggatgt cagcaaggaa      240 atcgaagagt atcgggagaa aatgagccag cacgtgggcg tgtccggccg ctacaagttg     300
ttcagcgctt cgctgagcgt ggatttcacc accacggacc agcaactgac cgagattacc     360
tacagctcca cccgcgaagc ccatgtgctg tggtacatca gcctgcctgg cgcggccacg     420
ctgcgttcga tgctgcgccg cgatttccgc gacgacctga caaccccaa tatgccggcc      480 atggagctgt tcaagcgcta tggtccctac tacatatcgg aagcggcggt gggcggccgg     540
ctggactaca gcgcggccag caagaccttg aagatggaca gcagccagtc gctgtccacc     600
accgccgaaa tgtcctacaa ggcgctggtg gcgagatca agatcgagca tggctcggag      660
atggaaaagc aggtcaacag cttccgcagc aactccacca tccgtctcac cgccaccggc     720
ggcaagccgg gcatgaccga tcgcatactg cacggtccgg attcgcagca ggcgttctcg     780
caatgggcgg aatcgctgct cgactatgcg acgctgatgg acttttccac cgaaagcctg     840
caaccgatct gggcgctggc cgacaagccc gagcgccgcg tcgagcttga ggacgccttc     900
cccgaattca tgaagcagtc gcagcagtcc atccccaagg tggacaaggt gctgctgatg     960
gacgcgcggc cgcctatggt gaaggctggg gaggatagcg gctccggcgc gtcggaggat    1020
ctggctgtgt tcaatcccag cacctccaat ggctacaaga tggttggcca gttcggtcag    1080
cgcaaccatg ccagcgtggc ggatggccat gcgccgattt tcaaggatct gttcgatctg    1140
ggcgtgctga aggcgccggt gggttggcag cgggtgtggg acgacgccgg ctccggcaag    1200
tccaacgact acgcgtgctg gcgcgcgatt ccgccgcagg gctaccgcgc gctgggcgat    1260
gtgatgatgc tggccaccag cggctataac ccgccgaatc tgccggacta tgtttgcgtg    1320
catcaaagcc tgtgcgcgga tgtgcagacg ctgcaaaacc gggtgtggtg gacaagggc      1380 accggcgcgc gcaaggatgt cagcctgtgg caaccgggcg cggccggcgc ggtggcgtcc    1440
tcttgcttcg ccggcgtgcc taattacaac aacccgccca ttccggcga catcgagcgc     1500 ttgcgcggca gcatcgcatg cgtgaagacc agcgcgatcg cgtccatgca ggaaatgaag    1560
tccatgctca gccagcacca aggcatggaa gcgatgatgt ccaagctgtg a             1611
```

<210> SEQ ID NO 15
<211> LENGTH: 536
<212> TYPE: PRT
<213> ORGANISM: Artificial Sequence
<220> FEATURE:
<223> OTHER INFORMATION: eAxmi205 #7 mutant

<400> SEQUENCE: 15

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
        195                 200                 205

Leu Val Gly Glu Ile Lys Ile Glu His Gly Ser Glu Met Glu Lys Gln
210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
        275                 280                 285

Lys Pro Glu Arg Arg Val Glu Leu Glu Asp Ala Phe Pro Glu Phe Met
290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
                325                 330                 335

Ala Ser Glu Asp Leu Ala Val Phe Asn Pro Ser Thr Ser Asn Gly Tyr
            340                 345                 350

Lys Met Val Gly Gln Phe Gly Gln Arg Asn His Ala Ser Val Ala Asp
        355                 360                 365

Gly His Ala Pro Ile Phe Lys Asp Leu Phe Asp Leu Gly Val Leu Lys
370                 375                 380

Ala Pro Val Gly Trp Gln Arg Val Trp Asp Asp Ala Gly Ser Gly Lys
385                 390                 395                 400
```

```
Ser Leu Asp Tyr Ala Cys Trp Arg Ala Ile Pro Pro Gln Gly Tyr Arg
                405                 410                 415

Ala Leu Gly Asp Val Met Met Leu Ala Thr Ser Gly Tyr Asn Pro Pro
            420                 425                 430

Asn Leu Pro Asp Tyr Val Cys Val His Gln Ser Leu Cys Ala Asp Val
        435                 440                 445

Gln Thr Leu Gln Asn Arg Val Trp Trp Asp Lys Gly Thr Gly Ala Arg
    450                 455                 460

Lys Asp Val Ser Leu Trp Gln Pro Gly Ala Gly Ala Val Ala Ser
465                 470                 475                 480

Ser Cys Phe Ala Gly Val Pro Asn Tyr Asn Pro Pro Asn Ser Gly
                485                 490                 495

Asp Ile Glu Arg Leu Arg Gly Ser Ile Ala Cys Val Lys Thr Ser Ala
            500                 505                 510

Ile Ala Ser Met Gln Glu Met Lys Ser Met Leu Ser Gln His Gln Gly
        515                 520                 525

Met Glu Ala Met Met Ser Lys Leu
    530                 535

<210> SEQ ID NO 16
<211> LENGTH: 1611
<212> TYPE: DNA
<213> ORGANISM: Artificial Sequence
<220> FEATURE:
<223> OTHER INFORMATION: eAxmi205 #7 mutant

<400> SEQUENCE: 16
atggcatccg cagcaaatgc aggtcagctt ggcaaccccc ccggcgttac ttctatgggc      60
atgggctatg acgtgaatgg tttgtacgcc agcccggaaa gcctgcttgg ccaacccttg     120
ttcgatttcg gcggcgagct ggacagcatc gaaatcgagg gccgcagcta cacctttccc     180
cgcagcatgc atgtacacac ctatttccat tccgacttca acaggatgt cagcaaggaa     240
atcgaagagt atcgggagaa atgagccag cacgtgggcg tgtccggccg ctacaagttg     300
ttcagcgctt cgctgagcgt ggatttcacc accacggacc agcaactgac cgagattacc     360
tacagctcca cccgcgaagc ccatgtgctg tggtacatca gcctgcctgg cgcggccacg     420
ctgcgttcga tgctgcgccg cgatttccgc gacgacctga caacccccaa tatgccggcc     480
atggagctgt tcaagcgcta tggtccctac tacatatcgg aagcggcggt gggcggccgg     540
ctggactaca gcgcggccag caagaccttg aagatggaca gcagccagtc gctgtccacc     600
accgccgaaa tgtcctacaa ggcgctggtg gcgagatca agatcgagca tggctcggag     660
atggaaaagc aggtcaacag cttccgcagc aactccacca tccgtctcac cgccaccggc     720
ggcaagccgg gcatgaccga tcgcatactg cacggtccgg attcgcagca ggcgttctcg     780
caatgggcgg aatcgctgct cgactatgcg acgctgatgg actttccac cgaaagcctg     840
caaccgatct gggcgctggc cgacaagccc gagcgccgcg tcgagcttga ggacgccttc     900
cccgaattca tgaagcagtc gcagcagtcc atccccaagg tggacaaggt gctgctgatg     960
gacgcgcggc cgcctatggt gaaggctggg gaggatagcg gctccggcgc gtcggaggat    1020
ctggctgtgt tcaatcccag cacctccaat ggctacaaga tggttggcca gttcggtcag    1080
cgcaaccatg ccagcgtggc ggatggccat gcgccgattt tcaaggatct gttcgatctg    1140
ggcgtgctga aggcgccggt gggttggcag cgggtgtggg acgacgccgg ctccggcaag    1200
tccctggact acgcgtgctg gcgcgcgatt ccgccgcagg gctaccgcgc gctgggcgat    1260
```

-continued

```
gtgatgatgc tggccaccag cggctataac ccgccgaatc tgccggacta tgtttgcgtg    1320
catcaaagcc tgtgcgcgga tgtgcagacg ctgcaaaacc gggtgtggtg ggacaagggc    1380
accggcgcgc gcaaggatgt cagcctgtgg caaccgggcg cggccggcgc ggtggcgtcc    1440
tcttgcttcg ccggcgtgcc taattacaac aacccgccca attccggcga catcgagcgc    1500
ttgcgcggca gcatcgcatg cgtgaagacc agcgcgatcg cgtccatgca ggaaatgaag    1560
tccatgctca gccagcacca aggcatggaa gcgatgatgt ccaagctgtg a             1611
```

<210> SEQ ID NO 17
<211> LENGTH: 536
<212> TYPE: PRT
<213> ORGANISM: Artificial Sequence
<220> FEATURE:
<223> OTHER INFORMATION: eAxmi205 #8

<400> SEQUENCE: 17

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
    130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
        195                 200                 205

Leu Val Gly Glu Ile Lys Ile Glu His Gly Ser Glu Met Glu Lys Gln
    210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
        275                 280                 285

Lys Pro Glu Arg Arg Val Glu Leu Glu Asp Ala Phe Pro Glu Phe Met
    290                 295                 300
```

```
Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
            325                 330                 335

Ala Ser Glu Asp Leu Ala Val Phe Asn Pro Ser Thr Ser Asn Gly Tyr
        340                 345                 350

Lys Met Val Gly Gln Phe Gly Gln Arg Asn His Ala Ser Val Ala Asp
    355                 360                 365

Gly His Ala Pro Ile Phe Lys Asp Leu Phe Asp Leu Gly Val Leu Lys
370                 375                 380

Ala Pro Val Gly Trp Gln Arg Val Trp Asp Asp Ala Gly Ser Gly Lys
385                 390                 395                 400

Ser Leu Asp Phe Ala Cys Trp Arg Ala Ile Pro Pro Gln Gly Tyr Arg
                405                 410                 415

Ala Leu Gly Asp Val Met Met Leu Ala Thr Ser Gly Tyr Asn Pro Pro
            420                 425                 430

Asn Leu Pro Asp Tyr Val Cys Val His Gln Ser Leu Cys Ala Asp Val
        435                 440                 445

Gln Thr Leu Gln Asn Arg Val Trp Trp Asp Lys Gly Thr Gly Ala Arg
    450                 455                 460

Lys Asp Val Ser Leu Trp Gln Pro Gly Ala Ala Gly Ala Val Ala Ser
465                 470                 475                 480

Ser Cys Phe Ala Gly Val Pro Asn Tyr Asn Asn Pro Pro Asn Ser Gly
                485                 490                 495

Asp Ile Glu Arg Leu Arg Gly Ser Ile Ala Cys Val Lys Thr Ser Ala
            500                 505                 510

Ile Ala Ser Met Gln Glu Met Lys Ser Met Leu Ser Gln His Gln Gly
        515                 520                 525

Met Glu Ala Met Met Ser Lys Leu
    530                 535
```

<210> SEQ ID NO 18
<211> LENGTH: 1611
<212> TYPE: DNA
<213> ORGANISM: Artificial Sequence
<220> FEATURE:
<223> OTHER INFORMATION: eAxmi205 #8

<400> SEQUENCE: 18

```
atggcatccg cagcaaatgc aggtcagctt ggcaacctcc ccggcgttac ttctatgggc      60
atgggctatg acgtgaatgg tttgtacgcc agcccggaaa gcctgcttgg ccaacccttg     120
ttcgatttcg gcggcgagct ggacagcatc gaaatcgagg gccgcagcta cacctttccc     180
cgcagcatgc atgtacacac ctatttccat tccgacttca acaggatgt cagcaaggaa      240 atcgaagagt atcgggagaa aatgagccag cacgtgggcg tgtccggccg ctacaagttg     300
ttcagcgctt cgctgagcgt ggatttcacc accacgacc agcaactgac cgagattacc      360
tacagctcca cccgcgaagc ccatgtgctg tggtacatca gcctgcctgg cgcggccacg     420
ctgcgttcga tgctgcgccg cgatttccgc gacgacctga caacccccaa tatgccggcc    480
atggagctgt tcaagcgcta tggtccctac tacatatcgg aagcggcggt gggcggccgg     540
ctggactaca gcgcggccag caagaccttg aagatggaca gcagccagtc gctgtccacc     600
accgccgaaa tgtcctacaa ggcgctggtg ggcgagatca gatcgagca tggctcggag      660 atggaaaagc aggtcaacag cttccgcagc aactccacca tccgtctcac cgccaccggc     720
```

-continued

```
ggcaagccgg gcatgaccga tcgcatactg cacggtccgg attcgcagca ggcgttctcg    780
caatgggcgg aatcgctgct cgactatgcg acgctgatgg acttttccac cgaaagcctg    840
caaccgatct gggcgctggc cgacaagccc gagcgccgcg tcgagcttga ggacgccttc    900
cccgaattca tgaagcagtc gcagcagtcc atccccaagg tggacaaggt gctgctgatg    960
gacgcgcggc cgcctatggt gaaggctggg gaggatagcg gctccggcgc gtcggaggat   1020
ctggctgtgt tcaatcccag cacctccaat ggctacaaga tggttggcca gttcggtcag   1080
cgcaaccatg ccagcgtggc ggatggccat gcgccgattt tcaaggatct gttcgatctg   1140
ggcgtgctga aggcgccggt gggttggcag cgggtgtggg acgacgccgg ctccggcaag   1200
tccctggact ttgcgtgctg gcgcgcgatt ccgccgcagg gctaccgcgc gctgggcgat   1260
gtgatgatgc tggccaccag cggctataac ccgccgaatc tgccggacta tgtttgcgtg   1320
catcaaagcc tgtgcgcgga tgtgcagacg ctgcaaaacc gggtgtggtg ggacaagggc   1380
accggcgcgc gcaaggatgt cagcctgtgg caacccgggcg cggccggcgc ggtggcgtcc   1440
tcttgcttcg ccggcgtgcc taattacaac aacccgccca attccggcga catcgagcgc   1500
ttgcgcggca gcatcgcatg cgtgaagacc agcgcgatcg cgtccatgca ggaaatgaag   1560
tccatgctca gccagcacca aggcatggaa gcgatgatgt ccaagctgtg a            1611
```

<210> SEQ ID NO 19
<211> LENGTH: 536
<212> TYPE: PRT
<213> ORGANISM: Artificial Sequence
<220> FEATURE:
<223> OTHER INFORMATION: eAxmi205 #9

<400> SEQUENCE: 19

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
    130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
        195                 200                 205
```

Leu Val Gly Glu Ile Lys Ile Glu His Gly Ser Glu Met Glu Lys Gln
    210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
        275                 280                 285

Lys Pro Glu Arg Arg Val Glu Leu Glu Asp Ala Phe Pro Glu Phe Met
290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
                325                 330                 335

Ala Ser Glu Asp Leu Ala Val Phe Asn Pro Ser Thr Ser Asn Gly Tyr
            340                 345                 350

Lys Met Val Gly Gln Phe Gly Gln Arg Asn His Ala Ser Val Ala Asp
        355                 360                 365

Gly His Ala Pro Ile Phe Lys Asp Leu Phe Asp Leu Gly Val Leu Lys
370                 375                 380

Ala Pro Val Gly Trp Gln Arg Val Trp Asp Asp Ala Gly Ser Gly Lys
385                 390                 395                 400

Ser Lys Asp Tyr Ala Cys Trp Arg Ala Ile Pro Pro Gln Gly Tyr Leu
                405                 410                 415

Ala Leu Gly Asp Val Met Met Leu Ala Thr Ser Gly Tyr Asn Pro Pro
            420                 425                 430

Asn Leu Pro Asp Tyr Val Cys Val His Gln Ser Leu Cys Ala Asp Val
        435                 440                 445

Gln Thr Leu Gln Asn Arg Val Trp Trp Asp Lys Gly Thr Gly Ala Arg
450                 455                 460

Lys Asp Val Ser Leu Trp Gln Pro Gly Ala Ala Gly Ala Val Ala Ser
465                 470                 475                 480

Ser Cys Phe Ala Gly Val Pro Asn Tyr Asn Asn Pro Pro Asn Ser Gly
                485                 490                 495

Asp Ile Glu Arg Leu Arg Gly Ser Ile Ala Cys Val Lys Thr Ser Ala
            500                 505                 510

Ile Ala Ser Met Gln Glu Met Lys Ser Met Leu Ser Gln His Gln Gly
        515                 520                 525

Met Glu Ala Met Met Ser Lys Leu
    530                 535

<210> SEQ ID NO 20
<211> LENGTH: 1611
<212> TYPE: DNA
<213> ORGANISM: Artificial Sequence
<220> FEATURE:
<223> OTHER INFORMATION: eAxmi205 #9

<400> SEQUENCE: 20
atggcatccg cagcaaatgc aggtcagctt ggcaacctcc ccggcgttac ttctatgggc     60
atgggctatg acgtgaatgg tttgtacgcc agcccggaaa gcctgcttgg ccaacccttg    120
ttcgatttcg gcggcgagct ggacagcatc gaaatcgagg ccgcagcta caccttccc    180

```
cgcagcatgc atgtacacac ctatttccat tccgacttca aacaggatgt cagcaaggaa    240
atcgaagagt atcgggagaa aatgagccag cacgtgggcg tgtccggccg ctacaagttg    300
ttcagcgctt cgctgagcgt ggatttcacc accacggacc agcaactgac cgagattacc    360
tacagctcca cccgcgaagc ccatgtgctg tggtacatca gcctgcctgg cgcggccacg    420
ctgcgttcga tgctgcgccg cgatttccgc gacgacctga caaccccaa tatgccggcc     480 atggagctgt tcaagcgcta tggtccctac tacatatcgg aagcggcggt gggcggccgg    540
ctggactaca gcgcggccag caagaccttg aagatggaca gcagccagtc gctgtccacc    600
accgccgaaa tgtcctacaa ggcgctggtg gcgagatca agatcgagca tggctcggag     660
atggaaaagc aggtcaacag cttccgcagc aactccacca tccgtctcac cgccaccggc    720
ggcaagccgg gcatgaccga tcgcatactg acggtccgg attcgcagca ggcgttctcg     780
caatgggcgg aatcgctgct cgactatgcg acgctgatgg actttccac cgaaagcctg     840 caaccgatct gggcgctggc cgacaagccc gagcgccgcg tcgagcttga ggacgccttc    900
cccgaattca tgaagcagtc gcagcagtcc atccccaagg tggacaaggt gctgctgatg    960
gacgcgcggc cgcctatggt gaaggctggg gaggatagcg gctccggcgc gtcggaggat   1020
ctggctgtgt tcaatcccag cacctccaat ggctacaaga tggttggcca gttcggtcag   1080
cgcaaccatg ccagcgtggc ggatggccat gcgccgattt tcaaggatct gttcgatctg   1140
ggcgtgctga aggcgccggt gggttggcag cgggtgtggg acgacgccgg ctccggcaag   1200
tccaaggact acgcgtgctg gcgcgcgatt ccgccgcagg gctacctggc gctgggcgat   1260
gtgatgatgc tggccaccag cggctataac ccgccgaatc tgccggacta tgtttgcgtg   1320
catcaaagcc tgtgcgcgga tgtgcagacg ctgcaaaacc gggtgtggtg ggacaagggc   1380
accggcgcgc gcaaggatgt cagcctgtgg caaccgggcg cggccggcgc ggtggcgtcc   1440
tcttgcttcg ccggcgtgcc taattacaac aacccgccca attccggcga catcgagcgc   1500
ttgcgcggca gcatcgcatg cgtgaagacc agcgcgatcg cgtccatgca ggaaatgaag   1560
tccatgctca gccagcacca aggcatggaa gcgatgatgt ccaagctgtg a             1611
```

```
<210> SEQ ID NO 21
<211> LENGTH: 536
<212> TYPE: PRT
<213> ORGANISM: Artificial Sequence
<220> FEATURE:
<223> OTHER INFORMATION: eAxmi205 #10 mutant

<400> SEQUENCE: 21
```

Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

-continued

```
Asp Gln Gln Leu Thr Glu Ile Thr Tyr Ser Ser Thr Arg Glu Ala His
        115                 120                 125
Val Leu Trp Tyr Ile Ser Leu Pro Gly Ala Ala Thr Leu Arg Ser Met
    130                 135                 140
Leu Arg Arg Asp Phe Arg Asp Leu Asn Asn Pro Asn Met Pro Ala
145                 150                 155                 160
Met Glu Leu Phe Lys Arg Tyr Gly Pro Tyr Tyr Ile Ser Glu Ala Ala
                165                 170                 175
Val Gly Gly Arg Leu Asp Tyr Ser Ala Ala Ser Lys Thr Leu Lys Met
            180                 185                 190
Asp Ser Ser Gln Ser Leu Ser Thr Thr Ala Glu Met Ser Tyr Lys Ala
        195                 200                 205
Leu Val Gly Glu Ile Lys Ile Glu His Gly Ser Glu Met Glu Lys Gln
    210                 215                 220
Val Asn Ser Phe Arg Ser Asn Ser Thr Ile Arg Leu Thr Ala Thr Gly
225                 230                 235                 240
Gly Lys Pro Gly Met Thr Asp Arg Ile Leu His Gly Pro Asp Ser Gln
                245                 250                 255
Gln Ala Phe Ser Gln Trp Ala Glu Ser Leu Leu Asp Tyr Ala Thr Leu
            260                 265                 270
Met Asp Phe Ser Thr Glu Ser Leu Gln Pro Ile Trp Ala Leu Ala Asp
        275                 280                 285
Lys Pro Glu Arg Arg Val Glu Leu Glu Asp Ala Phe Pro Glu Phe Met
    290                 295                 300
Lys Gln Ser Gln Gln Ser Ile Pro Lys Val Asp Lys Val Leu Leu Met
305                 310                 315                 320
Asp Ala Arg Pro Pro Met Val Lys Ala Gly Glu Asp Ser Gly Ser Gly
                325                 330                 335
Ala Ser Glu Asp Leu Ala Val Phe Asn Pro Ser Thr Ser Asn Gly Tyr
            340                 345                 350
Lys Met Val Gly Gln Phe Gly Gln Arg Asn His Ala Ser Val Ala Asp
        355                 360                 365
Gly His Ala Pro Ile Phe Lys Asp Leu Phe Asp Leu Gly Val Leu Lys
    370                 375                 380
Ala Leu Val Gly Trp Gln Arg Val Trp Asp Asp Ala Gly Ser Gly Lys
385                 390                 395                 400
Ser Lys Asp Tyr Ala Cys Trp Arg Ala Ile Pro Pro Gln Gly Tyr Arg
                405                 410                 415
Ala Leu Gly Asp Val Met Met Leu Ala Thr Ser Gly Tyr Asn Pro Pro
            420                 425                 430
Asn Leu Pro Asp Tyr Val Cys Val His Gln Ser Leu Cys Ala Asp Val
        435                 440                 445
Gln Thr Leu Gln Asn Arg Val Trp Trp Asp Lys Gly Thr Gly Ala Arg
    450                 455                 460
Lys Asp Val Ser Leu Trp Gln Pro Gly Ala Ala Gly Ala Val Ala Ser
465                 470                 475                 480
Ser Cys Phe Ala Gly Val Pro Asn Tyr Asn Asn Pro Asn Ser Gly
                485                 490                 495
Asp Ile Glu Arg Leu Arg Gly Ser Ile Ala Cys Val Lys Thr Ser Ala
            500                 505                 510
Ile Ala Ser Met Gln Glu Met Lys Ser Met Leu Ser Gln His Gln Gly
        515                 520                 525
```

Met Glu Ala Met Met Ser Lys Leu
        530                 535

<210> SEQ ID NO 22
<211> LENGTH: 1611
<212> TYPE: DNA
<213> ORGANISM: Artificial Sequence
<220> FEATURE:
<223> OTHER INFORMATION: eAxmi205 #10 mutant

<400> SEQUENCE: 22

| | | | | | |
|---|---|---|---|---|---|
| atggcatccg | cagcaaatgc | aggtcagctt | ggcaaccctcc | ccggcgttac | ttctatgggc | 60 |
| atgggctatg | acgtgaatgg | tttgtacgcc | agcccggaaa | gcctgcttgg | ccaacccttg | 120 |
| ttcgatttcg | gcggcgagct | ggacagcatc | gaaatcgagg | gccgcagcta | cacctttccc | 180 |
| cgcagcatgc | atgtacacac | ctatttccat | tccgacttca | acaggatgt | cagcaaggaa | 240 |
| atcgaagagt | atcgggagaa | aatgagccag | cacgtgggcg | tgtccggccg | ctacaagttg | 300 |
| ttcagcgctt | cgctgagcgt | ggatttcacc | accacggacc | agcaactgac | cgagattacc | 360 |
| tacagctcca | cccgcgaagc | ccatgtgctg | tggtacatca | gcctgcctgg | cgcggccacg | 420 |
| ctgcgttcga | tgctgcgccg | cgattccgc | gacgacctga | caacccccaa | tatgccggcc | 480 |
| atggagctgt | tcaagcgcta | tggtccctac | tacatatcgg | aagcggcggt | gggcggccgg | 540 |
| ctggactaca | cgcggccag | caagaccttg | aagatggaca | gcagccagtc | gctgtccacc | 600 |
| accgccgaaa | tgtcctacaa | ggcgctggtg | ggcgagatca | gatcgagca | tggctcggag | 660 |
| atggaaaagc | aggtcaacag | cttccgcagc | aactccacca | tccgtctcac | cgccaccggc | 720 |
| ggcaagccgg | gcatgaccga | tcgcatactg | cacggtccgg | attcgcagca | ggcgttctcg | 780 |
| caatgggcgg | aatcgctgct | cgactatgcg | acgctgatgg | acttttccac | cgaaaagcctg | 840 |
| caaccgatct | gggcgctggc | cgacaagccc | gagcgccgcg | tcgagcttga | ggacgccttc | 900 |
| cccgaattca | tgaagcagtc | gcagcagtcc | atccccaagg | tggacaaggt | gctgctgatg | 960 |
| gacgcgcggc | cgcctatggt | gaaggctggg | gaggatagcg | gctccggcgc | gtcggaggat | 1020 |
| ctggctgtgt | tcaatcccag | cacctccaat | ggctacaaga | tggttggcca | gttcggtcag | 1080 |
| cgcaaccatg | ccagcgtggc | ggatggccat | gcgccgatt | tcaaggatct | gttcgatctg | 1140 |
| ggcgtgctga | aggcgctggt | ggggttggcag | cgggtgtggg | acgacgccgg | ctccggcaag | 1200 |
| tccaaggact | acgcgtgctg | gcgcgcgatt | ccgccgcagg | gctaccgcgc | gctgggcgat | 1260 |
| gtgatgatgc | tggccaccag | cggctataac | ccgccgaatc | tgccggacta | tgtttgcgtg | 1320 |
| catcaaagcc | tgtgcgcgga | tgtgcagacg | ctgcaaaacc | gggtgtggtg | ggacaagggc | 1380 |
| accggcgcgc | gcaaggatgt | cagcctgtgg | caaccgggcg | cggccggcgc | ggtggcgtcc | 1440 |
| tcttgcttcg | ccggcgtgcc | taattacaac | aacccgccca | attccggcga | catcgagcgc | 1500 |
| ttgcgcggca | gcatcgcatg | cgtgaagacc | agcgcgatcg | cgtccatgca | ggaaatgaag | 1560 |
| tccatgctca | gccagcacca | aggcatggaa | gcgatgatgt | ccaagctgtg | a | 1611 |

<210> SEQ ID NO 23
<211> LENGTH: 536
<212> TYPE: PRT
<213> ORGANISM: Artificial Sequence
<220> FEATURE:
<223> OTHER INFORMATION: eAxmi205 #11 mutant

<400> SEQUENCE: 23

Met Ala Ser Ala Ala Asn Ala Gly Gln Leu Gly Asn Leu Pro Gly Val
1               5                   10                  15

```
Thr Ser Met Gly Met Gly Tyr Asp Val Asn Gly Leu Tyr Ala Ser Pro
             20                  25                  30

Glu Ser Leu Leu Gly Gln Pro Leu Phe Asp Phe Gly Gly Glu Leu Asp
             35                  40                  45

Ser Ile Glu Ile Glu Gly Arg Ser Tyr Thr Phe Pro Arg Ser Met His
 50                  55                  60

Val His Thr Tyr Phe His Ser Asp Phe Lys Gln Asp Val Ser Lys Glu
 65                  70                  75                  80

Ile Glu Glu Tyr Arg Glu Lys Met Ser Gln His Val Gly Val Ser Gly
             85                  90                  95

Arg Tyr Lys Leu Phe Ser Ala Ser Leu Ser Val Asp Phe Thr Thr Thr
             100                 105                 110

Asp Gln Gln Leu Thr Glu Ile Thr Tyr Ser Ser Thr Arg Glu Ala His
             115                 120                 125

Val Leu Trp Tyr Ile Ser Leu Pro Gly Ala Ala Thr Leu Arg Ser Met
130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
             165                 170                 175

Val Gly Gly Arg Leu Asp Tyr Ser Ala Ala Ser Lys Thr Leu Lys Met
             180                 185                 190

Asp Ser Ser Gln Ser Leu Ser Thr Thr Ala Glu Met Ser Tyr Lys Ala
             195                 200                 205

Leu Val Gly Glu Ile Lys Ile Glu His Gly Ser Glu Met Glu Lys Gln
             210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
             245                 250                 255

Gln Ala Phe Ser Gln Trp Ala Glu Ser Leu Leu Asp Tyr Ala Thr Leu
             260                 265                 270

Met Asp Phe Ser Thr Glu Ser Leu Gln Pro Ile Trp Ala Leu Ala Asp
             275                 280                 285

Lys Pro Glu Arg Arg Val Glu Leu Glu Asp Ala Phe Pro Glu Phe Met
             290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
             325                 330                 335

Ala Ser Glu Asp Leu Ala Val Phe Asn Pro Ser Thr Ser Asn Gly Tyr
             340                 345                 350

Lys Met Val Gly Gln Phe Gly Gln Arg Asn His Ala Ser Val Ala Asp
             355                 360                 365

Gly His Ala Pro Ile Phe Lys Asp Leu Phe Asp Leu Gly Val Leu Lys
             370                 375                 380

Ala Pro Val Gly Trp Gln Leu Val Trp Asp Asp Ala Gly Ser Gly Lys
385                 390                 395                 400

Ser Lys Asp Tyr Ala Cys Trp Arg Ala Ile Pro Pro Gln Gly Tyr Arg
             405                 410                 415

Ala Leu Gly Asp Val Met Met Leu Ala Thr Ser Gly Tyr Asn Pro Pro
             420                 425                 430
```

```
        Asn Leu Pro Asp Tyr Val Cys Val His Gln Ser Leu Cys Ala Asp Val
                    435                 440                 445

Gln Thr Leu Gln Asn Arg Val Trp Trp Asp Lys Gly Thr Gly Ala Arg
            450                 455                 460

Lys Asp Val Ser Leu Trp Gln Pro Gly Ala Ala Gly Ala Val Ala Ser
        465                 470                 475                 480

Ser Cys Phe Ala Gly Val Pro Asn Tyr Asn Asn Pro Pro Asn Ser Gly
                        485                 490                 495

Asp Ile Glu Arg Leu Arg Gly Ser Ile Ala Cys Val Lys Thr Ser Ala
                    500                 505                 510

Ile Ala Ser Met Gln Glu Met Lys Ser Met Leu Ser Gln His Gln Gly
                515                 520                 525

Met Glu Ala Met Met Ser Lys Leu
            530                 535

<210> SEQ ID NO 24
        <211> LENGTH: 1611
        <212> TYPE: DNA
        <213> ORGANISM: Artificial Sequence
        <220> FEATURE:
        <223> OTHER INFORMATION: eAxmi205 #11 mutant

<400> SEQUENCE: 24
atggcatccg cagcaaatgc aggtcagctt ggcaacctcc ccggcgttac ttctatgggc      60
atgggctatg acgtgaatgg tttgtacgcc agcccggaaa gcctgcttgg ccaacccttg     120
ttcgatttcg gcggcgagct ggacagcatc gaaatcgagg ccgcagcta cacctttccc     180 cgcagcatgc atgtacacac ctatttccat tccgacttca acaggatgt cagcaaggaa     240 atcgaagagt atcgggagaa aatgagccag cacgtgggcg tgtccggccg ctacaagttg     300
ttcagcgctt cgctgagcgt ggatttcacc accacgacc agcaactgac cgagattacc     360
tacagctcca cccgcgaagc ccatgtgctg tggtacatca gcctgcctgg cgcggccacg     420
ctgcgttcga tgctgcgccg cgatttccgc gacgacctga caaccccaa tatgccggcc     480 atggagctgt tcaagcgcta tggtccctac tacatatcgg aagcggcggt gggcggccgg     540
ctggactaca gcgcggccag caagaccttg aagatggaca gcagccagtc gctgtccacc     600
accgccgaaa tgtcctacaa ggcgctggtg ggcgagatca agatcgagca tggctcggag     660
atggaaaagc aggtcaacag cttccgcagc aactccacca tccgtctcac cgccaccggc     720
ggcaagccgg gcatgaccga tcgcatactg cacggtccgg attcgcagca ggcgttctcg     780
caatgggcgg aatcgctgct cgactatgcg acgctgatgg actttccac cgaaaagcctg     840 caaccgatct gggcgctggc cgacaagccc gagcgccgcg tcgagcttga ggacgccttc     900
cccgaattca tgaagcagtc gcagcagtcc atccccaagg tggacaaggt gctgctgatg     960
gacgcgcggc cgcctatggt gaaggctggg gaggatagcg gctccggcgc gtcggaggat    1020
ctggctgtgt tcaatcccag cacctccaat ggctacaaga tggttggcca gttcggtcag    1080
cgcaaccatg ccagcgtggc ggatggccat gcgccgattt tcaaggatct gttcgatctg    1140
ggcgtgctga aggcgccggt gggttggcag ctggtgtggg acgacgccgg ctccggcaag    1200
tccaaggact acgcgtgctg gcgcgcgatt ccgccgcagg gctaccgcgc gctgggcgat    1260
gtgatgatgc tggccaccag cggctataac ccgccgaatc tgccggacta tgtttgcgtg    1320
catcaaagcc tgtgcgcgga tgtgcagacg ctgcaaaacc gggtgtggtg gacaagggc     1380 accggcgcgc gcaaggatgt cagcctgtgg caaccgggcg cggccggcgc ggtggcgtcc    1440
```

-continued

```
tcttgcttcg ccggcgtgcc taattacaac aacccgccca attccggcga catcgagcgc    1500
ttgcgcggca gcatcgcatg cgtgaagacc agcgcgatcg cgtccatgca ggaaatgaag    1560
tccatgctca gccagcacca aggcatggaa gcgatgatgt ccaagctgtg a             1611
```

<210> SEQ ID NO 25
<211> LENGTH: 536
<212> TYPE: PRT
<213> ORGANISM: Artificial Sequence
<220> FEATURE:
<223> OTHER INFORMATION: eAxmi205 #12 mutant

<400> SEQUENCE: 25

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
    130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
        195                 200                 205

Leu Val Gly Glu Ile Lys Ile Glu His Gly Ser Glu Met Glu Lys Gln
    210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
        275                 280                 285

Lys Pro Glu Arg Arg Val Glu Leu Glu Asp Ala Phe Pro Glu Phe Met
    290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
                325                 330                 335
```

```
Ala Ser Glu Asp Leu Ala Val Phe Asn Pro Ser Thr Ser Asn Gly Tyr
            340                 345                 350

Lys Met Val Gly Gln Phe Gly Gln Arg Asn His Ala Ser Val Ala Asp
        355                 360                 365

Gly His Ala Pro Ile Phe Lys Asp Leu Phe Asp Leu Gly Val Leu Lys
    370                 375                 380

Ala Pro Val Gly Trp Gln Ile Val Trp Asp Asp Ala Gly Ser Gly Lys
385                 390                 395                 400

Ser Lys Asp Tyr Ala Cys Trp Arg Ala Ile Pro Pro Gln Gly Tyr Arg
                405                 410                 415

Ala Leu Gly Asp Val Met Met Leu Ala Thr Ser Gly Tyr Asn Pro Pro
            420                 425                 430

Asn Leu Pro Asp Tyr Val Cys Val His Gln Ser Leu Cys Ala Asp Val
        435                 440                 445

Gln Thr Leu Gln Asn Arg Val Trp Trp Asp Lys Gly Thr Gly Ala Arg
    450                 455                 460

Lys Asp Val Ser Leu Trp Gln Pro Gly Ala Ala Gly Ala Val Ala Ser
465                 470                 475                 480

Ser Cys Phe Ala Gly Val Pro Asn Tyr Asn Asn Pro Asn Ser Gly
                485                 490                 495

Asp Ile Glu Arg Leu Arg Gly Ser Ile Ala Cys Val Lys Thr Ser Ala
            500                 505                 510

Ile Ala Ser Met Gln Glu Met Lys Ser Met Leu Ser Gln His Gln Gly
        515                 520                 525

Met Glu Ala Met Met Ser Lys Leu
    530                 535

<210> SEQ ID NO 26
<211> LENGTH: 1611
<212> TYPE: DNA
<213> ORGANISM: Artificial Sequence
<220> FEATURE:
<223> OTHER INFORMATION: eAxmi205 #12 mutant

<400> SEQUENCE: 26
atggcatccg cagcaaatgc aggtcagctt ggcaacctcc ccggcgttac ttctatgggc      60
atgggctatg acgtgaatgg tttgtacgcc agcccggaaa gcctgcttgg ccaacccttg     120
ttcgatttcg gcggcgagct ggacagcatc gaaatcgagg ccgcagcta cacctttccc      180 cgcagcatgc atgtacacac ctatttccat tccgacttca acaggatgt cagcaaggaa      240 atcgaagagt atcgggagaa aatgagccag cacgtgggcg tgtccggccg ctacaagttg     300
ttcagcgctt cgctgagcgt ggatttcacc accacggacc agcaactgac cgagattacc     360
tacagctcca cccgcgaagc ccatgtgctg tggtacatca gctgcctgg cgcggccacg      420 ctgcgttcga tgctgcgccg cgatttccgc gacgacctga caacccaaa tatgccggcc     480 atggagctgt tcaagcgcta tggtccctac tacatatcgg aagcggcggt gggcggccgg     540
ctggactaca gcgcggccag caagaccttg aagatggaca gcagccagtc gctgtccacc     600
accgccgaaa tgtcctacaa ggcgctggtg ggcgagatca agatcgagca tggctcggag     660
atggaaaagc aggtcaacag cttccgcagc aactccacca tccgtctcac cgccaccggc     720
ggcaagccgg gcatgaccga tcgcatactg cacggtccgg attcgcagca ggcgttctcg     780
caatgggcgg aatcgctgct cgactatgcg acgctgatgg acttttccac cgaaaagcctg    840 caaccgatct gggcgctggc cgacaagccc gagcgccgcg tcgagcttga ggacgccttc     900
```

```
cccgaattca tgaagcagtc gcagcagtcc atccccaagg tggacaaggt gctgctgatg      960
gacgcgcggc cgcctatggt gaaggctggg gaggatagcg gctccggcgc gtcggaggat     1020
ctggctgtgt tcaatcccag cacctccaat ggctacaaga tggttggcca gttcggtcag     1080
cgcaaccatg ccagcgtggc ggatggccat gcgccgattt tcaaggatct gttcgatctg     1140
ggcgtgctga aggcgccggt gggttggcag attgtgtggg acgacgccgg ctccggcaag     1200
tccaaggact acgcgtgctg gcgcgcgatt ccgccgcagg gctaccgcgc gctgggcgat     1260
gtgatgatgc tggccaccag cggctataac ccgccgaatc tgccggacta tgtttgcgtg     1320
catcaaagcc tgtgcgcgga tgtgcagacg ctgcaaaacc gggtgtggtg ggacaagggc     1380
accggcgcgc gcaaggatgt cagcctgtgg caaccgggcg cggccggcgc ggtggcgtcc     1440
tcttgcttcg ccggcgtgcc taattacaac aacccgccca attccggcga catcgagcgc     1500
ttgcgcggca gcatcgcatg cgtgaagacc agcgcgatcg cgtccatgca ggaaatgaag     1560
tccatgctca gccagcacca aggcatggaa gcgatgatgt ccaagctgtg a               1611
```

<210> SEQ ID NO 27
<211> LENGTH: 536
<212> TYPE: PRT
<213> ORGANISM: Artificial Sequence
<220> FEATURE:
<223> OTHER INFORMATION: eAxmi205 #13 mutant

<400> SEQUENCE: 27

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
    130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
        195                 200                 205

Leu Val Gly Glu Ile Lys Ile Glu His Gly Ser Glu Met Glu Lys Gln
    210                 215                 220

Val Asn Ser Phe Arg Ser Asn Ser Thr Ile Arg Leu Thr Ala Thr Gly
225                 230                 235                 240
```

```
Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
        275                 280                 285

Lys Pro Glu Arg Arg Val Glu Leu Glu Asp Ala Phe Pro Glu Phe Met
    290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
                325                 330                 335

Ala Ser Glu Asp Leu Ala Val Phe Asn Pro Ser Thr Ser Asn Gly Tyr
            340                 345                 350

Lys Met Val Gly Gln Phe Gly Gln Arg Asn His Ala Ser Val Ala Asp
        355                 360                 365

Gly His Ala Pro Ile Phe Lys Asp Leu Phe Asp Leu Gly Val Leu Lys
    370                 375                 380

Ala Pro Val Gly Trp Gln Arg Val Trp Asp Asp Ala Gly Ser Gly Lys
385                 390                 395                 400

Ser Lys Asp Tyr Ala Ser Trp Arg Ala Ile Pro Pro Gln Gly Tyr Arg
                405                 410                 415

Ala Leu Gly Asp Val Met Met Leu Ala Thr Ser Gly Tyr Asn Pro Pro
            420                 425                 430

Asn Leu Pro Asp Tyr Val Cys Val His Gln Ser Leu Cys Ala Asp Val
        435                 440                 445

Gln Thr Leu Gln Asn Arg Val Trp Trp Asp Lys Gly Thr Gly Ala Arg
    450                 455                 460

Lys Asp Val Ser Leu Trp Gln Pro Gly Ala Ala Gly Ala Val Ala Ser
465                 470                 475                 480

Ser Cys Phe Ala Gly Val Pro Asn Tyr Asn Pro Pro Asn Ser Gly
                485                 490                 495

Asp Ile Glu Arg Leu Arg Gly Ser Ile Ala Cys Val Lys Thr Ser Ala
            500                 505                 510

Ile Ala Ser Met Gln Glu Met Lys Ser Met Leu Ser Gln His Gln Gly
        515                 520                 525

Met Glu Ala Met Met Ser Lys Leu
    530                 535

<210> SEQ ID NO 28
<211> LENGTH: 1611
<212> TYPE: DNA
<213> ORGANISM: Artificial Sequence
<220> FEATURE:
<223> OTHER INFORMATION: eAxmi205 #13 mutant

<400> SEQUENCE: 28
atggcatccg cagcaaatgc aggtcagctt ggcaaccctc ccggcgttac ttctatgggc      60
atgggctatg acgtgaatgg tttgtacgcc agcccggaaa gcctgcttgg ccaacccttg     120
ttcgatttcg gcggcgagct ggacagcatc gaaatcgagg ccgcagcta cacctttccc      180 cgcagcatgc atgtacacac ctatttccat tccgacttca acaggatgt cagcaaggaa      240 atcgaagagt atcgggagaa aatgagccag cacgtgggcg tgtccggccg ctacaagttg     300
ttcagcgctt cgctgagcgt ggatttcacc accacggacc agcaactgac cgagattacc     360
```

-continued

```
tacagctcca cccgcgaagc ccatgtgctg tggtacatca gcctgcctgg cgcggccacg    420
ctgcgttcga tgctgcgccg cgatttccgc gacgacctga acaacccccaa tatgccggcc   480
atggagctgt tcaagcgcta tggtccctac tacatatcgg aagcggcggt gggcggccgg    540
ctggactaca gcgcggccag caagaccttg aagatggaca gcagccagtc gctgtccacc    600
accgccgaaa tgtcctacaa ggcgctggtg ggcgagatca agatcgagca tggctcggag    660
atggaaaagc aggtcaacag cttccgcagc aactccacca tccgtctcac cgccaccggc    720
ggcaagccgg gcatgaccga tcgcatactg cacggtccgg attcgcagca ggcgttctcg    780
caatgggcgg aatcgctgct cgactatgcg acgctgatgg acttttccac cgaaagcctg    840
caaccgatct gggcgctggc cgacaagccc gagcgccgcg tcgagcttga ggacgccttc    900
cccgaattca tgaagcagtc gcagcagtcc atccccaagg tggacaaggt gctgctgatg    960
gacgcgcggc cgcctatggt gaaggctggg gaggatagcg gctccggcgc gtcggaggat   1020
ctggctgtgt tcaatcccag cacctccaat ggctacaaga tggttggcca gttcggtcag   1080
cgcaaccatg ccagcgtggc ggatggccat gcgccgattt tcaaggatct gttcgatctg   1140
ggcgtgctga aggcgccggt gggttggcag cgggtgtggg acgacgccgg ctccggcaag   1200
tccaaggact acgcgagctg gcgcgcgatt ccgccgcagg gctaccgcgc gctgggcgat   1260
gtgatgatgc tggccaccag cggctataac ccgccgaatc tgccggacta tgtttgcgtg   1320
catcaaagcc tgtgcgcgga tgtgcagacg ctgcaaaacc gggtgtggtg ggacaagggc   1380
accggcgcgc gcaaggatgt cagcctgtgg caaccgggcg cggccggcgc ggtggcgtcc   1440
tcttgcttcg ccggcgtgcc taattacaac aacccgccca attccggcga catcgagcgc   1500
ttgcgcggca gcatcgcatg cgtgaagacc agcgcgatcg cgtccatgca ggaaatgaag   1560
tccatgctca gccagcacca aggcatggaa gcgatgatgt ccaagctgtg a            1611
```

<210> SEQ ID NO 29
<211> LENGTH: 536
<212> TYPE: PRT
<213> ORGANISM: Artificial Sequence
<220> FEATURE:
<223> OTHER INFORMATION: eAxmi205 #14 mutant

<400> SEQUENCE: 29

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
    130                 135                 140
```

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
            165                 170                 175

Val Gly Gly Arg Leu Asp Tyr Ser Ala Ala Ser Lys Thr Leu Lys Met
        180                 185                 190

Asp Ser Ser Gln Ser Leu Ser Thr Thr Ala Glu Met Ser Tyr Lys Ala
    195                 200                 205

Leu Val Gly Glu Ile Lys Ile Glu His Gly Ser Glu Met Glu Lys Gln
210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
        275                 280                 285

Lys Pro Glu Arg Arg Val Glu Leu Glu Asp Ala Phe Pro Glu Phe Met
290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
                325                 330                 335

Ala Ser Glu Asp Leu Ala Val Phe Asn Pro Ser Thr Ser Asn Gly Tyr
            340                 345                 350

Lys Met Val Gly Gln Phe Gly Gln Arg Asn His Ala Ser Val Ala Asp
        355                 360                 365

Gly His Ala Pro Ile Phe Lys Asp Leu Phe Asp Leu Gly Val Leu Lys
    370                 375                 380

Ala Pro Val Gly Trp Gln Arg Val Trp Asp Asp Ala Gly Ser Gly Lys
385                 390                 395                 400

Ser Lys Asp Tyr Ala Leu Trp Arg Ala Ile Pro Pro Gln Gly Tyr Arg
                405                 410                 415

Ala Leu Gly Asp Val Met Met Leu Ala Thr Ser Gly Tyr Asn Pro Pro
            420                 425                 430

Asn Leu Pro Asp Tyr Val Cys Val His Gln Ser Leu Cys Ala Asp Val
        435                 440                 445

Gln Thr Leu Gln Asn Arg Val Trp Trp Asp Lys Gly Thr Gly Ala Arg
    450                 455                 460

Lys Asp Val Ser Leu Trp Gln Pro Gly Ala Ala Gly Ala Val Ala Ser
465                 470                 475                 480

Ser Cys Phe Ala Gly Val Pro Asn Tyr Asn Asn Pro Pro Asn Ser Gly
                485                 490                 495

Asp Ile Glu Arg Leu Arg Gly Ser Ile Ala Cys Val Lys Thr Ser Ala
            500                 505                 510

Ile Ala Ser Met Gln Glu Met Lys Ser Met Leu Ser Gln His Gln Gly
        515                 520                 525

Met Glu Ala Met Met Ser Lys Leu
        530                 535

<210> SEQ ID NO 30
<211> LENGTH: 1611
<212> TYPE: DNA

<213> ORGANISM: Artificial Sequence
<220> FEATURE:
<223> OTHER INFORMATION: eAxmi205 #14 mutant

<400> SEQUENCE: 30

```
atggcatccg cagcaaatgc aggtcagctt ggcaacctcc ccggcgttac ttctatgggc      60
atgggctatg acgtgaatgg tttgtacgcc agcccggaaa gcctgcttgg ccaacccttg     120
ttcgatttcg gcggcgagct ggacagcatc gaaatcgagg ccgcagcta cacctttccc     180
cgcagcatgc atgtacacac ctatttccat tccgacttca acaggatgt cagcaaggaa     240
atcgaagagt atcgggagaa aatgagccag acgtgggcg tgtccggccg ctacaagttg     300
ttcagcgctt cgctgagcgt ggatttcacc accacggacc agcaactgac cgagattacc     360
tacagctcca cccgcgaagc ccatgtgctg tggtacatca gcctgcctgg cgcggccacg     420
ctgcgttcga tgctgcgccg cgatttccgc gacgacctga caaccccaa tatgccggcc     480
atggagctgt tcaagcgcta tggtccctac tacatatcgg aagcggcggt gggcggccgg     540
ctggactaca gcgcggccag caagaccttg aagatggaca gcagccagtc gctgtccacc     600
accgccgaaa tgtcctacaa ggcgctggtg ggcgagatca agatcgagca tggctcggag     660
atggaaaagc aggtcaacag cttccgcagc aactccacca tccgtctcac cgccaccggc     720
ggcaagccgg gcatgaccga tcgcatactg cacggtccgg attcgcagca ggcgttctcg     780
caatgggcgg aatcgctgct cgactatgcg acgctgatgg acttttccac cgaaagcctg     840
caaccgatct gggcgctggc cgacaagccc gagcgccgcg tcgagcttga ggacgccttc     900
cccgaattca tgaagcagtc gcagcagtcc atccccaagg tggacaaggt gctgctgatg     960
gacgcgcggc cgcctatggt gaaggctggg gaggatagcg gctccggcgc gtcggaggat    1020
ctggctgtgt tcaatcccag cacctccaat ggctacaaga tggttggcca gttcggtcag    1080
cgcaaccatg ccagcgtggc ggatggccat gcgccgattt tcaaggatct gttcgatctg    1140
ggcgtgctga ggcgccggt gggttggcag cgggtgtggg acgacgccgg ctccggcaag    1200
tccaaggact acgcgctgtg gcgcgcgatt ccgccgcagg gctaccgcgc gctgggcgat    1260
gtgatgatgc tggccaccag cggctataac ccgccgaatc tgccggacta tgtttgcgtg    1320
catcaaagcc tgtgcgcgga tgtgcagacg ctgcaaaacc gggtgtggtg ggacaagggc    1380
accggcgcgc gcaaggatgt cagcctgtgg caacccgggcg cggccggcgc ggtggcgtcc    1440
tcttgcttcg ccggcgtgcc taattacaac aacccgccca ttccggcga catcgagcgc    1500
ttgcgcggca gcatcgcatg cgtgaagacc agcgcgatcg cgtccatgca ggaaatgaag    1560
tccatgctca gccagcacca aggcatggaa gcgatgatgt ccaagctgtg a              1611
```

<210> SEQ ID NO 31
<211> LENGTH: 536
<212> TYPE: PRT
<213> ORGANISM: Artificial Sequence
<220> FEATURE:
<223> OTHER INFORMATION: eAxmi205 #15 mutant

<400> SEQUENCE: 31

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45
```

```
Ser Ile Glu Ile Glu Gly Arg Ser Tyr Thr Phe Pro Arg Ser Met His
 50                  55                  60
Val His Thr Tyr Phe His Ser Asp Phe Lys Gln Asp Val Ser Lys Glu
 65                      70                  75                  80
Ile Glu Glu Tyr Arg Glu Lys Met Ser Gln His Val Gly Val Ser Gly
                     85                  90                  95
Arg Tyr Lys Leu Phe Ser Ala Ser Leu Ser Val Asp Phe Thr Thr Thr
                100                 105                 110
Asp Gln Gln Leu Thr Glu Ile Thr Tyr Ser Ser Thr Arg Glu Ala His
                115                 120                 125
Val Leu Trp Tyr Ile Ser Leu Pro Gly Ala Ala Thr Leu Arg Ser Met
130                 135                 140
Leu Arg Arg Asp Phe Arg Asp Leu Asn Asn Pro Asn Met Pro Ala
145                 150                 155                 160
Met Glu Leu Phe Lys Arg Tyr Gly Pro Tyr Tyr Ile Ser Glu Ala Ala
                165                 170                 175
Val Gly Gly Arg Leu Asp Tyr Ser Ala Ala Ser Lys Thr Leu Lys Met
                180                 185                 190
Asp Ser Ser Gln Ser Leu Ser Thr Thr Ala Glu Met Ser Tyr Lys Ala
                195                 200                 205
Leu Val Gly Glu Ile Lys Ile Glu His Gly Ser Glu Met Glu Lys Gln
210                 215                 220
Val Asn Ser Phe Arg Ser Asn Ser Thr Ile Arg Leu Thr Ala Thr Gly
225                 230                 235                 240
Gly Lys Pro Gly Met Thr Asp Arg Ile Leu His Gly Pro Asp Ser Gln
                245                 250                 255
Gln Ala Phe Ser Gln Trp Ala Glu Ser Leu Leu Asp Tyr Ala Thr Leu
                260                 265                 270
Met Asp Phe Ser Thr Glu Ser Leu Gln Pro Ile Trp Ala Leu Ala Asp
                275                 280                 285
Lys Pro Glu Arg Arg Val Glu Leu Glu Asp Ala Phe Pro Glu Phe Met
            290                 295                 300
Lys Gln Ser Gln Gln Ser Ile Pro Lys Val Asp Lys Val Leu Leu Met
305                 310                 315                 320
Asp Ala Arg Pro Pro Met Val Lys Ala Gly Glu Asp Ser Gly Ser Gly
                325                 330                 335
Ala Ser Glu Asp Leu Ala Val Phe Asn Pro Ser Thr Ser Asn Gly Tyr
                340                 345                 350
Lys Met Val Gly Gln Phe Gly Gln Arg Asn His Ala Ser Val Ala Asp
                355                 360                 365
Gly His Ala Pro Ile Phe Lys Asp Leu Phe Asp Leu Gly Val Leu Lys
            370                 375                 380
Ala Pro Val Gly Trp Gln Arg Val Trp Asp Asp Ala Gly Ser Gly Lys
385                 390                 395                 400
Ser Lys Asp Tyr Ala Cys Trp Arg Ala Ile Leu Pro Gln Gly Tyr Arg
                405                 410                 415
Ala Leu Gly Asp Val Met Met Leu Ala Thr Ser Gly Tyr Asn Pro Pro
                420                 425                 430
Asn Leu Pro Asp Tyr Val Cys Val His Gln Ser Leu Cys Ala Asp Val
                435                 440                 445
Gln Thr Leu Gln Asn Arg Val Trp Trp Asp Lys Gly Thr Gly Ala Arg
450                 455                 460
Lys Asp Val Ser Leu Trp Gln Pro Gly Ala Ala Gly Ala Val Ala Ser
```

```
                465                 470                 475                 480
            Ser Cys Phe Ala Gly Val Pro Asn Tyr Asn Asn Pro Pro Asn Ser Gly
                            485                 490                 495

Asp Ile Glu Arg Leu Arg Gly Ser Ile Ala Cys Val Lys Thr Ser Ala
                        500                 505                 510

Ile Ala Ser Met Gln Glu Met Lys Ser Met Leu Ser Gln His Gln Gly
                    515                 520                 525

Met Glu Ala Met Met Ser Lys Leu
                530                 535

<210> SEQ ID NO 32
<211> LENGTH: 1611
<212> TYPE: DNA
<213> ORGANISM: Artificial Sequence
<220> FEATURE:
<223> OTHER INFORMATION: eAxmi205 #15 mutant

<400> SEQUENCE: 32
atggcatccg cagcaaatgc aggtcagctt ggcaacctcc ccggcgttac ttctatgggc      60
atgggctatg acgtgaatgg tttgtacgcc agcccggaaa gcctgcttgg ccaacccttg     120
ttcgatttcg gcggcgagct ggacagcatc gaaatcgagg ccgcagcta cacctttccc      180 cgcagcatgc atgtacacac ctatttccat tccgacttca acaggatgt cagcaaggaa      240 atcgaagagt atcgggagaa aatgagccag acgtgggcg tgtccggccg ctacaagttg      300
ttcagcgctt cgctgagcgt ggatttcacc accacggacc agcaactgac cgagattacc      360
tacagctcca cccgcgaagc ccatgtgctg tggtacatca gctgcctgg cgcggccacg      420 ctgcgttcga tgctgcgccg cgatttccgc gacgacctga caacccca atgccggcc       480 atggagctgt tcaagcgcta tggtccctac tacatatcgg aagcggcggt gggcggccgg     540
ctggactaca gcgcggccag caagaccttg aagatggaca gcagccagtc gctgtccacc     600
accgccgaaa tgtcctacaa ggcgctggtg gcgagatca agatcgagca tggctcggag      660
atggaaaagc aggtcaacag cttccgcagc aactccacca tccgtctcac cgccaccggc     720
ggcaagccgg gcatgaccga tcgcatactg cacggtccgg attcgcagca ggcgttctcg     780
caatgggcgg aatcgctgct cgactatgcg acgctgatgg acttttccac cgaaagcctg     840
caaccgatct gggcgctggc cgacaagccc gagcgccgcg tcgagcttga ggacgccttc     900
cccgaattca tgaagcagtc gcagcagtcc atccccaagg tggacaaggt gctgctgatg     960
gacgcgcggc cgcctatggt gaaggctggg gaggatagcg gctccggcgc gtcggaggat    1020
ctggctgtgt tcaatcccag cacctccaat ggctacaaga tggttggcca gttcggtcag    1080
cgcaaccatg ccagcgtggc ggatggccat gcgccgattt tcaaggatct gttcgatctg    1140
ggcgtgctga aggcgccggt gggttggcag cgggtgtggg acgacgccgg ctccggcaag    1200
tccaaggact acgcgtgctg gcgcgcgatt ctgccgcagg gctaccgcgc gctgggcgat    1260
gtgatgatgc tggccaccag cggctataac cgccgaatc tgccggacta tgtttgcgtg    1320
catcaaagcc tgtgcgcgga tgtgcagacg ctgcaaaacc gggtgtggtg gacaagggc    1380 accggcgcgc gcaaggatgt cagcctgtgg caaccgggcg cggccggcgc ggtggcgtcc    1440
tcttgcttcg ccggcgtgcc taattacaac aacccgccca ttccggcga catcgagcgc    1500 ttgcgcggca gcatcgcatg cgtgaagacc agcgcgatcg cgtccatgca ggaaatgaag    1560
tccatgctca gccagcacca aggcatggaa gcgatgatgt ccaagctgtg a             1611
```

```
<210> SEQ ID NO 33
<211> LENGTH: 536
<212> TYPE: PRT
<213> ORGANISM: Artificial Sequence
<220> FEATURE:
<223> OTHER INFORMATION: eAxmi205 #16 mutant

<400> SEQUENCE: 33

Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
    130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
        195                 200                 205

Leu Val Gly Glu Ile Lys Ile Glu His Gly Ser Glu Met Glu Lys Gln
    210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
        275                 280                 285

Lys Pro Glu Arg Arg Val Glu Leu Glu Asp Ala Phe Pro Glu Phe Met
    290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
                325                 330                 335

Ala Ser Glu Asp Leu Ala Val Phe Asn Pro Ser Thr Ser Asn Gly Tyr
            340                 345                 350

Lys Met Val Gly Gln Phe Gly Gln Arg Asn His Ala Ser Val Ala Asp
        355                 360                 365

Gly His Ala Pro Ile Phe Lys Asp Leu Phe Asp Leu Gly Val Leu Lys
```

Ala Pro Val Gly Trp Gln Arg Val Trp Asp Asp Ala Gly Ser Gly Lys
385                 390                 395                 400

Ser Lys Asp Tyr Ala Cys Trp Arg Ala Ile Pro Pro Gln Gly Tyr Arg
            405                 410                 415

Ala Leu Gly Asp Val Met Met Leu Ala Thr Ser Gly Tyr Asn Pro Pro
        420                 425                 430

Asn Leu Pro Asp Tyr Val Ser Val His Gln Ser Leu Cys Ala Asp Val
    435                 440                 445

Gln Thr Leu Gln Asn Arg Val Trp Trp Asp Lys Gly Thr Gly Ala Arg
450                 455                 460

Lys Asp Val Ser Leu Trp Gln Pro Gly Ala Ala Gly Ala Val Ala Ser
465                 470                 475                 480

Ser Cys Phe Ala Gly Val Pro Asn Tyr Asn Pro Pro Asn Ser Gly
            485                 490                 495

Asp Ile Glu Arg Leu Arg Gly Ser Ile Ala Cys Val Lys Thr Ser Ala
        500                 505                 510

Ile Ala Ser Met Gln Glu Met Lys Ser Met Leu Ser Gln His Gln Gly
    515                 520                 525

Met Glu Ala Met Met Ser Lys Leu
530                 535

<210> SEQ ID NO 34
<211> LENGTH: 1611
<212> TYPE: DNA
<213> ORGANISM: Artificial Sequence
<220> FEATURE:
<223> OTHER INFORMATION: eAxmi205 #16 mutant

<400> SEQUENCE: 34

| | |
|---|---|
| atggcatccg cagcaaatgc aggtcagctt ggcaaccctc ccggcgttac ttctatgggc | 60 |
| atgggctatg acgtgaatgg tttgtacgcc agcccggaaa gcctgcttgg ccaacccttg | 120 |
| ttcgatttcg gcggcgagct ggacagcatc gaaatcgagg gccgcagcta cacctttccc | 180 |
| cgcagcatgc atgtacacac ctatttccat tccgacttca acaggatgt cagcaaggaa | 240 |
| atcgaagagt atcgggagaa atgagccag cacgtgggcg tgtccggccg ctacaagttg | 300 |
| ttcagcgctt cgctgagcgt ggatttcacc accacggacc agcaactgac cgagattacc | 360 |
| tacagctcca cccgcgaagc ccatgtgctg tggtacatca gcctgcctgg cgcggccacg | 420 |
| ctgcgttcga tgctgcgccg cgatttccgc gacgacctga caacccaa tatgccggcc | 480 |
| atggagctgt tcaagcgcta tggtccctac tacatatcgg aagcggcggt gggcggccgg | 540 |
| ctggactaca gcgcggccag caagaccttg aagatggaca gcagccagtc gctgtccacc | 600 |
| accgccgaaa tgtcctacaa ggcgctggtg ggcgagatca agatcgagca tggctcggag | 660 |
| atggaaaagc aggtcaacag cttccgcagc aactccacca tccgtctcac cgccaccggc | 720 |
| ggcaagccgg gcatgaccga tcgcatactg acggtccgg attcgcagca ggcgttctcg | 780 |
| caatgggcgg aatcgctgct cgactatgcg acgctgatgg acttttccac cgaaagcctg | 840 |
| caaccgatct gggcgctggc cgacaagccc gagcgccgcg tcgagcttga ggacgccttc | 900 |
| cccgaattca tgaagcagtc gcagcagtcc atccccaagg tggacaaggt gctgctgatg | 960 |
| gacgcgcggc cgcctatggt gaaggctggg gaggatagcg gctccggcgc gtcggaggat | 1020 |
| ctggctgtgt tcaatcccag cacctccaat ggctacaaga tggttggcca gttcggtcag | 1080 |
| cgcaaccatg ccagcgtggc ggatggccat gcgccgattt tcaaggatct gttcgatctg | 1140 |

-continued

```
ggcgtgctga aggcgccggt gggttggcag cggtgtggg acgacgccgg ctccggcaag      1200
tccaaggact acgcgtgctg gcgcgcgatt ccgccgcagg ctaccgcgc gctgggcgat      1260 gtgatgatgc tggccaccag cggctataac ccgccgaatc tgccggacta tgttagcgtg      1320
catcaaagcc tgtgcgcgga tgtgcagacg ctgcaaaacc gggtgtggtg ggacaagggc      1380
accggcgcgc gcaaggatgt cagcctgtgg caaccgggcg cggccggcgc ggtggcgtcc      1440
tcttgcttcg ccggcgtgcc taattacaac aacccgccca attccggcga catcgagcgc      1500
ttgcgcggca gcatcgcatg cgtgaagacc agcgcgatcg cgtccatgca ggaaatgaag      1560
tccatgctca gccagcacca aggcatggaa gcgatgatgt ccaagctgtg a              1611
```

<210> SEQ ID NO 35
<211> LENGTH: 536
<212> TYPE: PRT
<213> ORGANISM: Artificial Sequence
<220> FEATURE:
<223> OTHER INFORMATION: eAxmi205 #17 mutant

<400> SEQUENCE: 35

```
Met Ala Ser Ala Ala Asn Ala Gly Gln Leu Gly Asn Leu Pro Gly Val
1               5                  10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
    130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
        195                 200                 205

Leu Val Gly Glu Ile Lys Ile Glu His Gly Ser Glu Met Glu Lys Gln
    210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
```

```
           275                 280                 285
Lys Pro Glu Arg Arg Val Glu Leu Glu Asp Ala Phe Pro Glu Phe Met
    290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
                325                 330                 335

Ala Ser Glu Asp Leu Ala Val Phe Asn Pro Ser Thr Ser Asn Gly Tyr
                340                 345                 350

Lys Met Val Gly Gln Phe Gly Gln Arg Asn His Ala Ser Val Ala Asp
                355                 360                 365

Gly His Ala Pro Ile Phe Lys Asp Leu Phe Asp Leu Gly Val Leu Lys
                370                 375                 380

Ala Pro Val Gly Trp Gln Arg Val Trp Asp Asp Ala Gly Ser Gly Lys
385                 390                 395                 400

Ser Lys Asp Tyr Ala Cys Trp Arg Ala Ile Pro Pro Gln Gly Tyr Arg
                405                 410                 415

Ala Leu Gly Asp Val Met Met Leu Ala Thr Ser Gly Tyr Asn Pro Pro
                420                 425                 430

Asn Leu Pro Asp Tyr Val Leu Val His Gln Ser Leu Cys Ala Asp Val
                435                 440                 445

Gln Thr Leu Gln Asn Arg Val Trp Trp Asp Lys Gly Thr Gly Ala Arg
    450                 455                 460

Lys Asp Val Ser Leu Trp Gln Pro Gly Ala Ala Gly Ala Val Ala Ser
465                 470                 475                 480

Ser Cys Phe Ala Gly Val Pro Asn Tyr Asn Asn Pro Pro Asn Ser Gly
                485                 490                 495

Asp Ile Glu Arg Leu Arg Gly Ser Ile Ala Cys Val Lys Thr Ser Ala
                500                 505                 510

Ile Ala Ser Met Gln Glu Met Lys Ser Met Leu Ser Gln His Gln Gly
                515                 520                 525

Met Glu Ala Met Met Ser Lys Leu
    530                 535

<210> SEQ ID NO 36
<211> LENGTH: 1611
<212> TYPE: DNA
<213> ORGANISM: Artificial Sequence
<220> FEATURE:
<223> OTHER INFORMATION: eAxmi205 #17 mutant

<400> SEQUENCE: 36
atggcatccg cagcaaatgc aggtcagctt ggcaacctcc ccggcgttac ttctatgggc      60
atgggctatg acgtgaatgg tttgtacgcc agcccggaaa gcctgcttgg ccaacccttg     120
ttcgatttcg gcggcgagct ggacagcatc gaaatcgagg ccgcagctac cactttcccc     180
cgcagcatgc atgtacacac ctatttccat tccgacttca acaggatgt cagcaaggaa      240 atcgaagagt atcgggagaa atgagccag acgtgggcg tgtccggccg ctacaagttg       300
ttcagcgctt cgctgagcgt ggatttcacc accacggacc agcaactgac cgagattacc     360
tacagctcca cccgcgaagc ccatgtgctg tggtacatca gcctgcctgg cgcggccacg     420
ctgcgttcga tgctgcgccc cgatttccgc gacgacctga acaacccaa tatgccggcc     480 atggagctgt tcaagcgcta tggtccctac tacatatcgg aagcggcggt gggcggccgg     540
ctggactaca gcgcggccag caagaccttg aagatggaca gcagccagtc gctgtccacc     600
```

```
accgccgaaa tgtcctacaa ggcgctggtg ggcgagatca agatcgagca tggctcggag      660
atggaaaagc aggtcaacag cttccgcagc aactccacca tccgtctcac cgccaccggc      720
ggcaagccgg gcatgaccga tcgcatactg cacggtccgg attcgcagca ggcgttctcg      780
caatgggcgg aatcgctgct cgactatgcg acgctgatgg acttttccac cgaaagcctg      840
caaccgatct gggcgctggc cgacaagccc gagcgccgcg tcgagcttga ggacgccttc      900
cccgaattca tgaagcagtc gcagcagtcc atccccaagg tggacaaggt gctgctgatg      960
gacgcgcggc cgcctatggt gaaggctggg gaggatagcg gctccggcgc gtcggaggat     1020
ctggctgtgt tcaatcccag cacctccaat ggctacaaga tggttggcca gttcggtcag     1080
cgcaaccatg ccagcgtggc ggatggccat gcgccgattt tcaaggatct gttcgatctg     1140
ggcgtgctga aggcgccggt gggttggcag cgggtgtggg acgacgccgg ctccggcaag     1200
tccaaggact acgcgtgctg gcgcgcgatt ccgccgcagg gctaccgcgc gctgggcgat     1260
gtgatgatgc tggccaccag cggctataac ccgccgaatc tgccggacta tgttctggtg     1320
catcaaagcc tgtgcgcgga tgtgcagacg ctgcaaaacc gggtgtggtg ggacaagggc     1380
accggcgcgc gcaaggatgt cagcctgtgg caaccgggcg cggccggcgc ggtggcgtcc     1440
tcttgcttcg ccggcgtgcc taattacaac aacccgccca attccggcga catcgagcgc     1500
ttgcgcggca gcatcgcatg cgtgaagacc agcgcgatcg cgtccatgca ggaaatgaag     1560
tccatgctca gccagcacca aggcatggaa gcgatgatgt ccaagctgtg a              1611
```

<210> SEQ ID NO 37
<211> LENGTH: 536
<212> TYPE: PRT
<213> ORGANISM: Artificial Sequence
<220> FEATURE:
<223> OTHER INFORMATION: eAxmi205 #18 mutant

<400> SEQUENCE: 37

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
    130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
```

```
            180                 185                 190
Asp Ser Ser Gln Ser Leu Ser Thr Thr Ala Glu Met Ser Tyr Lys Ala
            195                 200                 205

Leu Val Gly Glu Ile Lys Ile Glu His Gly Ser Glu Met Glu Lys Gln
        210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
        275                 280                 285

Lys Pro Glu Arg Arg Val Glu Leu Glu Asp Ala Phe Pro Glu Phe Met
290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
                325                 330                 335

Ala Ser Glu Asp Leu Ala Val Phe Asn Pro Ser Thr Ser Asn Gly Tyr
            340                 345                 350

Lys Met Val Gly Gln Phe Gly Gln Arg Asn His Ala Ser Val Ala Asp
        355                 360                 365

Gly His Ala Pro Ile Phe Lys Asp Leu Phe Asp Leu Gly Val Leu Lys
370                 375                 380

Ala Pro Val Gly Trp Gln Arg Val Trp Asp Asp Ala Gly Ser Gly Lys
385                 390                 395                 400

Ser Lys Asp Tyr Ala Cys Trp Arg Ala Ile Pro Pro Gln Gly Tyr Arg
                405                 410                 415

Ala Leu Gly Asp Val Met Met Leu Ala Thr Ser Gly Tyr Asn Pro Pro
            420                 425                 430

Asn Leu Pro Asp Tyr Val Cys Val His Gln Ser Leu Ser Ala Asp Val
        435                 440                 445

Gln Thr Leu Gln Asn Arg Val Trp Trp Asp Lys Gly Thr Gly Ala Arg
450                 455                 460

Lys Asp Val Ser Leu Trp Gln Pro Gly Ala Ala Gly Ala Val Ala Ser
465                 470                 475                 480

Ser Cys Phe Ala Gly Val Pro Asn Tyr Asn Asn Pro Pro Asn Ser Gly
                485                 490                 495

Asp Ile Glu Arg Leu Arg Gly Ser Ile Ala Cys Val Lys Thr Ser Ala
            500                 505                 510

Ile Ala Ser Met Gln Glu Met Lys Ser Met Leu Ser Gln His Gln Gly
        515                 520                 525

Met Glu Ala Met Met Ser Lys Leu
530                 535

<210> SEQ ID NO 38
<211> LENGTH: 1611
<212> TYPE: DNA
<213> ORGANISM: Artificial Sequence
<220> FEATURE:
<223> OTHER INFORMATION: eAxmi205 #18 mutant

<400> SEQUENCE: 38
atggcatccg cagcaaatgc aggtcagctt ggcaacctcc ccggcgttac ttctatgggc    60
```

```
atgggctatg acgtgaatgg tttgtacgcc agcccggaaa gcctgcttgg ccaacccttg    120
ttcgatttcg gcggcgagct ggacagcatc gaaatcgagg ccgcagcta caccttttccc   180 cgcagcatgc atgtacacac ctatttccat tccgacttca acaggatgt cagcaaggaa    240 atcgaagagt atcgggagaa aatgagccag cacgtgggcg tgtccggccg ctacaagttg   300
ttcagcgctt cgctgagcgt ggatttcacc accacggacc agcaactgac cgagattacc   360
tacagctcca cccgcgaagc ccatgtgctg tggtacatca gcctgcctgg cgcggccacg   420
ctgcgttcga tgctgcgccg cgatttccgc gacgacctga caaccccaa tatgccggcc    480 atggagctgt tcaagcgcta tggtccctac tacatatcgg aagcggcggt gggcggccgg   540
ctggactaca gcgcggccag caagaccttg aagatggaca gcagccagtc gctgtccacc   600
accgccgaaa tgtcctacaa ggcgctggtg ggcgagatca agatcgagca tggctcggag   660
atggaaaagc aggtcaacag cttccgcagc aactccacca tccgtctcac cgccaccggc   720
ggcaagccgg gcatgaccga tcgcatactg cacggtccgg attcgcagca ggcgttctcg   780
caatgggcgg aatcgctgct cgactatgcg acgctgatgg acttttccac cgaaagcctg   840
caaccgatct gggcgctggc cgacaagccc gagcgccgcg tcgagcttga ggacgccttc   900
cccgaattca tgaagcagtc gcagcagtcc atccccaagg tggacaaggt gctgctgatg   960
gacgcgcggc cgcctatggt gaaggctggg gaggatagcg gctccggcgc gtcggaggat  1020
ctggctgtgt tcaatcccag cacctccaat ggctacaaga tggttggcca gttcggtcag  1080
cgcaaccatg ccagcgtggc ggatggccat gcgccgattt tcaaggatct gttcgatctg  1140
ggcgtgctga aggcgccggt gggttggcag cgggtgtggg acgacgccgg ctccggcaag  1200
tccaaggact acgcgtgctg gcgcgcgatt ccgccgcagg gctaccgcgc gctgggcgat  1260
gtgatgatgc tggccaccag cggctataac ccgccgaatc tgccggacta tgtttgcgtg  1320
catcaaagcc tgagcgcgga tgtgcagacg ctgcaaaaacc gggtgtggtg ggacaagggc  1380
accggcgcgc gcaaggatgt cagcctgtgg caaccgggcg cggccggcgc ggtggcgtcc  1440
tcttgcttcg ccggcgtgcc taattacaac aacccgccca attccggcga catcgagcgc  1500
ttgcgcggca gcatcgcatg cgtgaagacc agcgcgatcc cgtccatgca ggaaatgaag  1560
tccatgctca gccagcacca aggcatggaa gcgatgatgt ccaagctgtg a            1611
```

<210> SEQ ID NO 39
<211> LENGTH: 536
<212> TYPE: PRT
<213> ORGANISM: Artificial Sequence
<220> FEATURE:
<223> OTHER INFORMATION: eAxmi205 #19 mutant

<400> SEQUENCE: 39

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
```

```
            85                  90                  95
Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
            115                 120                 125

Val Leu Trp Tyr Ile Ser Leu Pro Gly Ala Ala Thr Leu Arg Ser Met
130             135                 140

Leu Arg Arg Asp Phe Arg Asp Asp Leu Asn Asn Pro Asn Met Pro Ala
145             150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
                180                 185                 190

Asp Ser Ser Gln Ser Leu Ser Thr Thr Ala Glu Met Ser Tyr Lys Ala
                195                 200                 205

Leu Val Gly Glu Ile Lys Ile Glu His Gly Ser Glu Met Glu Lys Gln
            210                 215                 220

Val Asn Ser Phe Arg Ser Asn Ser Thr Ile Arg Leu Thr Ala Thr Gly
225             230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
                260                 265                 270

Met Asp Phe Ser Thr Glu Ser Leu Gln Pro Ile Trp Ala Leu Ala Asp
            275                 280                 285

Lys Pro Glu Arg Arg Val Glu Leu Glu Asp Ala Phe Pro Glu Phe Met
            290                 295                 300

Lys Gln Ser Gln Gln Ser Ile Pro Lys Val Asp Lys Val Leu Leu Met
305             310                 315                 320

Asp Ala Arg Pro Pro Met Val Lys Ala Gly Glu Asp Ser Gly Ser Gly
                325                 330                 335

Ala Ser Glu Asp Leu Ala Val Phe Asn Pro Ser Thr Ser Asn Gly Tyr
                340                 345                 350

Lys Met Val Gly Gln Phe Gly Gln Arg Asn His Ala Ser Val Ala Asp
            355                 360                 365

Gly His Ala Pro Ile Phe Lys Asp Leu Phe Asp Leu Gly Val Leu Lys
            370                 375                 380

Ala Pro Val Gly Trp Gln Arg Val Trp Asp Asp Ala Gly Ser Gly Lys
385             390                 395                 400

Ser Lys Asp Tyr Ala Cys Trp Arg Ala Ile Pro Pro Gln Gly Tyr Arg
                405                 410                 415

Ala Leu Gly Asp Val Met Met Leu Ala Thr Ser Gly Tyr Asn Pro Pro
                420                 425                 430

Asn Leu Pro Asp Tyr Val Cys Val His Gln Ser Leu Cys Ala Asp Val
                435                 440                 445

Gln Thr Leu Gln Asn Phe Val Trp Trp Asp Lys Gly Thr Gly Ala Arg
            450                 455                 460

Lys Asp Val Ser Leu Trp Gln Pro Gly Ala Ala Gly Ala Val Ala Ser
465             470                 475                 480

Ser Cys Phe Ala Gly Val Pro Asn Tyr Asn Asn Pro Asn Ser Gly
                485                 490                 495

Asp Ile Glu Arg Leu Arg Gly Ser Ile Ala Cys Val Lys Thr Ser Ala
            500                 505                 510
```

Ile Ala Ser Met Gln Glu Met Lys Ser Met Leu Ser Gln His Gln Gly
    515                 520                 525

Met Glu Ala Met Met Ser Lys Leu
    530                 535

<210> SEQ ID NO 40
<211> LENGTH: 1611
<212> TYPE: DNA
<213> ORGANISM: Artificial Sequence
<220> FEATURE:
<223> OTHER INFORMATION: eAxmi205 #19 mutant

<400> SEQUENCE: 40

| | | | | | |
|---|---|---|---|---|---|
| atggcatccg | cagcaaatgc | aggtcagctt | ggcaaccctcc | ccggcgttac | ttctatgggc | 60 |
| atgggctatg | acgtgaatgg | tttgtacgcc | agcccggaaa | gcctgcttgg | ccaacccttg | 120 |
| ttcgatttcg | gcggcgagct | ggacagcatc | gaaatcgagg | gccgcagcta | cacctttccc | 180 |
| cgcagcatgc | atgtacacac | ctatttccat | tccgacttca | acaggatgt | cagcaaggaa | 240 |
| atcgaagagt | atcgggagaa | atgagccag | acgtgggcg | tgtccggccg | ctacaagttg | 300 |
| ttcagcgctt | cgctgagcgt | ggatttcacc | accacggacc | agcaactgac | cgagattacc | 360 |
| tacagctcca | cccgcgaagc | ccatgtgctg | tggtacatca | gcctgcctgg | cgcggccacg | 420 |
| ctgcgttcga | tgctgcgccg | cgatttccgc | gacgacctga | acaaccccaa | tatgccggcc | 480 |
| atggagctgt | tcaagcgcta | tggtccctac | tacatatcgg | aagcggcggt | gggcggccgg | 540 |
| ctggactaca | gcgcggccag | caagacccttg | aagatggaca | gcagccagtc | gctgtccacc | 600 |
| accgccgaaa | tgtcctacaa | ggcgctggtg | ggcgagatca | agatcgagca | tggctcggag | 660 |
| atggaaaagc | aggtcaacag | cttccgcagc | aactccacca | tccgtctcac | cgccaccggc | 720 |
| ggcaagccgg | gcatgaccga | tcgcatactg | cacggtccgg | attcgcagca | ggcgttctcg | 780 |
| caatgggcgg | aatcgctgct | cgactatgcg | acgctgatgg | acttttccac | cgaaaagcctg | 840 |
| caaccgatct | gggcgctggc | cgacaagccc | gagcgccgcg | tcgagcttga | ggacgccttc | 900 |
| cccgaattca | tgaagcagtc | gcagcagtcc | atccccaagg | tggacaaggt | gctgctgatg | 960 |
| gacgcgcggc | cgcctatggt | gaaggctggg | gaggatagcg | gctccggcgc | gtcggaggat | 1020 |
| ctggctgtgt | tcaatcccag | cacctccaat | ggctacaaga | tggttggcca | gttcggtcag | 1080 |
| cgcaaccatg | ccagcgtggc | ggatggccat | gcgccgattt | tcaaggatct | gttcgatctg | 1140 |
| ggcgtgctga | aggcgccggt | gggttggcag | cgggtgtggg | acgacgccgg | ctccggcaag | 1200 |
| tccaaggact | acgcgtgctg | gcgcgcgatt | ccgccgcagg | gctaccgcgc | gctgggcgat | 1260 |
| gtgatgatgc | tggccaccag | cggctataac | ccgccgaatc | tgccggacta | tgtttgcgtg | 1320 |
| catcaaagcc | tgtgcgcgga | tgtgcagacg | ctgcaaaact | tgtgtggtg | ggacaagggc | 1380 |
| accggcgcgc | gcaaggatgt | cagcctgtgg | caaccgggcg | cggccggcgc | ggtggcgtcc | 1440 |
| tcttgcttcg | ccggcgtgcc | taattacaac | aacccgccca | attccggcga | catcgagcgc | 1500 |
| ttgcgcggca | gcatcgcatg | cgtgaagacc | agcgcgatcg | cgtccatgca | ggaaatgaag | 1560 |
| tccatgctca | gccagcacca | aggcatggaa | gcgatgatgt | ccaagctgtg | a | 1611 |

<210> SEQ ID NO 41
<211> LENGTH: 536
<212> TYPE: PRT
<213> ORGANISM: Artificial Sequence
<220> FEATURE:
<223> OTHER INFORMATION: eAxmi205 #20 mutant

<400> SEQUENCE: 41

Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
        195                 200                 205

Leu Val Gly Glu Ile Lys Ile Glu His Gly Ser Glu Met Glu Lys Gln
210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
        275                 280                 285

Lys Pro Glu Arg Arg Val Glu Leu Glu Asp Ala Phe Pro Glu Phe Met
290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
                325                 330                 335

Ala Ser Glu Asp Leu Ala Val Phe Asn Pro Ser Thr Ser Asn Gly Tyr
            340                 345                 350

Lys Met Val Gly Gln Phe Gly Gln Arg Asn His Ala Ser Val Ala Asp
        355                 360                 365

Gly His Ala Pro Ile Phe Lys Asp Leu Phe Asp Leu Gly Val Leu Lys
370                 375                 380

Ala Pro Val Gly Trp Gln Arg Val Trp Asp Asp Ala Gly Ser Gly Lys
385                 390                 395                 400

Ser Lys Asp Tyr Ala Cys Trp Arg Ala Ile Pro Pro Gln Gly Tyr Arg
                405                 410                 415

```
Ala Leu Gly Asp Val Met Met Leu Ala Thr Ser Gly Tyr Asn Pro Pro
            420                 425                 430

Asn Leu Pro Asp Tyr Val Cys Val His Gln Ser Leu Cys Ala Asp Val
        435                 440                 445

Gln Thr Leu Gln Asn Arg Val Trp Trp Asp Lys Gly Thr Gly Ala Leu
    450                 455                 460

Lys Asp Val Ser Leu Trp Gln Pro Gly Ala Gly Ala Val Ala Ser
465                 470                 475                 480

Ser Cys Phe Ala Gly Val Pro Asn Tyr Asn Pro Pro Asn Ser Gly
                485                 490                 495

Asp Ile Glu Arg Leu Arg Gly Ser Ile Ala Cys Val Lys Thr Ser Ala
                500                 505                 510

Ile Ala Ser Met Gln Glu Met Lys Ser Met Leu Ser Gln His Gln Gly
            515                 520                 525

Met Glu Ala Met Met Ser Lys Leu
    530                 535

<210> SEQ ID NO 42
<211> LENGTH: 1611
<212> TYPE: DNA
<213> ORGANISM: Artificial Sequence
<220> FEATURE:
<223> OTHER INFORMATION: eAxmi205 #20 mutant

<400> SEQUENCE: 42
atggcatccg cagcaaatgc aggtcagctt ggcaacctcc ccggcgttac ttctatgggc      60
atgggctatg acgtgaatgg tttgtacgcc agcccggaaa gcctgcttgg ccaaccttg     120 ttcgatttcg gcggcgagct ggacagcatc gaaatcgagg ccgcagcta caccttccc     180 cgcagcatgc atgtacacac ctatttccat tccgacttca acaggatgt cagcaaggaa    240 atcgaagagt atcgggagaa aatgagccag acgtgggcg tgtccggccg ctacaagttg     300
ttcagcgctt cgctgagcgt ggatttcacc accacggacc agcaactgac cgagattacc    360
tacagctcca cccgcgaagc ccatgtgctg tggtacatca gcctgcctgg cgcggccacg    420
ctgcgttcga tgctgcgccg cgatttccgc gacgacctga caacccccaa tatgccggcc    480
atggagctgt tcaagcgcta tggtccctac tacatatcgg aagcggcggt gggcggccgg    540
ctggactaca gcgcggccag caagaccttg aagatggaca gcagccagtc gctgtccacc    600
accgccgaaa tgtcctacaa ggcgctggtg ggcgagatca agatcgagca tggctcggag    660
atggaaaagc aggtcaacag cttccgcagc aactccacca tccgtctcac cgccaccggc    720
ggcaagccgg gcatgaccga tcgcatactg cacggtccgg attcgcagca ggcgttctcg    780
caatgggcgg aatcgctgct cgactatgcg acgctgatgg actttccac cgaaaagcctg    840 caaccgatct gggcgctggc cgacaagccc gagcgccgcg tcgagcttga ggacgccttc    900
cccgaattca tgaagcagtc gcagcagtcc atccccaagg tggacaaggt gctgctgatg    960
gacgcgcggc cgcctatggt gaaggctggg gaggatagcg gctccggcgc gtcggaggat    1020
ctggctgtgt tcaatcccag cacctccaat ggctacaaga tggttggcca gttcggtcag    1080
cgcaaccatg ccagcgtggc ggatggccat gcgccgattt tcaaggatct gttcgatctg    1140
ggcgtgctga aggcgccggt gggttggcag cgggtgtggg acgacgccgg ctccggcaag    1200
tccaaggact acgcgtgctg gcgcgcgatt ccgccgcagg gctaccgcgc gctgggcgat    1260
gtgatgatgc tggccaccag cggctataac ccgccgaatc tgccggacta tgtttgcgtg    1320
```

```
catcaaagcc tgtgcgcgga tgtgcagacg ctgcaaaacc gggtgtggtg ggacaagggc    1380
accggcgcgc tgaaggatgt cagcctgtgg caaccgggcg cggccggcgc ggtggcgtcc    1440
tcttgcttcg ccggcgtgcc taattacaac aacccgccca attccggcga catcgagcgc    1500
ttgcgcggca gcatcgcatg cgtgaagacc agcgcgatcg cgtccatgca ggaaatgaag    1560
tccatgctca gccagcacca aggcatggaa gcgatgatgt ccaagctgtg a             1611
```

<210> SEQ ID NO 43
<211> LENGTH: 536
<212> TYPE: PRT
<213> ORGANISM: Artificial Sequence
<220> FEATURE:
<223> OTHER INFORMATION: eAxmi205 #21 mutant

<400> SEQUENCE: 43

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
    130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
        195                 200                 205

Leu Val Gly Glu Ile Lys Ile Glu His Gly Ser Glu Met Glu Lys Gln
    210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
        275                 280                 285

Lys Pro Glu Arg Arg Val Glu Leu Gly Asp Ala Phe Pro Glu Phe Met
    290                 295                 300

Lys Gln Ser Gln Gln Ser Ile Pro Lys Val Asp Lys Val Leu Leu Met
305                 310                 315                 320
```

Asp Ala Arg Pro Pro Met Val Lys Ala Gly Glu Asp Ser Gly Ser Gly
           325                 330                 335

Ala Ser Glu Asp Leu Ala Val Phe Asn Pro Ser Thr Ser Asn Gly Tyr
           340                 345                 350

Lys Met Val Gly Gln Phe Gly Gln Arg Asn His Ala Ser Val Ala Asp
           355                 360                 365

Gly His Ala Pro Ile Phe Lys Asp Leu Phe Asp Leu Gly Val Leu Lys
           370                 375                 380

Ala Pro Val Gly Trp Gln Arg Val Trp Asp Asp Ala Gly Ser Gly Lys
385                 390                 395                 400

Ser Lys Asp Tyr Ala Cys Trp Arg Ala Ile Pro Pro Gln Gly Tyr Arg
           405                 410                 415

Ala Leu Gly Asp Val Met Met Leu Ala Thr Ser Gly Tyr Asn Pro Pro
           420                 425                 430

Asn Leu Pro Asp Tyr Val Cys Val His Gln Ser Leu Cys Ala Asp Val
           435                 440                 445

Gln Thr Leu Gln Asn Arg Val Trp Trp Asp Lys Gly Thr Gly Ala Arg
           450                 455                 460

Lys Asp Val Ser Leu Trp Gln Pro Gly Ala Ala Gly Ala Val Ala Ser
465                 470                 475                 480

Ser Ser Phe Ala Gly Val Pro Asn Tyr Asn Asn Pro Pro Asn Ser Gly
           485                 490                 495

Asp Ile Glu Arg Leu Arg Gly Ser Ile Ala Cys Val Lys Thr Ser Ala
           500                 505                 510

Ile Ala Ser Met Gln Glu Met Lys Ser Met Leu Ser Gln His Gln Gly
           515                 520                 525

Met Glu Ala Met Met Ser Lys Leu
           530                 535

<210> SEQ ID NO 44
<211> LENGTH: 1611
<212> TYPE: DNA
<213> ORGANISM: Artificial Sequence
<220> FEATURE:
<223> OTHER INFORMATION: eAxmi205 #21 mutant

<400> SEQUENCE: 44
atggcatccg cagcaaatgc aggtcagctt ggcaacctcc ccggcgttac ttctatgggc      60
atgggctatg acgtgaatgg tttgtacgcc agcccggaaa gcctgcttgg ccaacccttg     120
ttcgatttcg gcggcgagct ggacagcatc gaaatcgagg ccgcagcta cacctttccc      180 cgcagcatgc atgtacacac ctatttccat tccgacttca acaggatgt cagcaaggaa      240 atcgaagagt tcggagaaa atgagccag cacgtgggcg tgtccggccg ctacaagttg       300
ttcagcgctt cgctgagcgt ggatttcacc accacggacc agcaactgac cgagattacc     360
tacagctcca cccgcgaagc ccatgtgctg tggtacatca gctgcctgg cgcggccacg      420 ctgcgttcga tgctgcgccg cgatttccgc gacgacctga caacccaa tatgccggcc      480 atggagctgt tcaagcgcta tggtccctac tacatatcgg aagcggcggt gggcggccgg     540
ctggactaca gcgcggccag caagaccttg aagatggaca gcagccagtc gctgtccacc     600
accgccgaaa tgtcctacaa ggcgctggtg ggcgagatca agatcgagca tggctcggag     660
atggaaaagc aggtcaacag cttccgcagc aactccacca tccgtctcac cgccaccggc     720
ggcaagccgg gcatgaccga tcgcatactg cacggtccgg attcgcagca ggcgttctcg     780

```
caatgggcgg aatcgctgct cgactatgcg acgctgatgg acttttccac cgaaagcctg    840
caaccgatct gggcgctggc cgacaagccc gagcgccgcg tcgagcttga ggacgccttc    900
cccgaattca tgaagcagtc gcagcagtcc atccccaagg tggacaaggt gctgctgatg    960
gacgcgcggc cgcctatggt gaaggctggg gaggatagcg gctccggcgc gtcggaggat    1020
ctggctgtgt tcaatcccag cacctccaat ggctacaaga tggttggcca gttcggtcag    1080
cgcaaccatg ccagcgtggc ggatggccat gcgccgattt tcaaggatct gttcgatctg    1140
ggcgtgctga aggcgccggt gggttggcag cgggtgtggg acgacgccgg ctccggcaag    1200
tccaaggact acgcgtgctg gcgcgcgatt ccgccgcagg gctaccgcgc gctgggcgat    1260
gtgatgatgc tggccaccag cggctataac ccgccgaatc tgccggacta tgtttgcgtg    1320
catcaaagcc tgtgcgcgga tgtgcagacg ctgcaaaacc gggtgtggtg ggacaagggc    1380
accggcgcgc gcaaggatgt cagcctgtgg caaccgggcg cggccggcgc ggtggcgtcc    1440
tctagcttcg ccggcgtgcc taattacaac aacccgccca attccggcga catcgagcgc    1500
ttgcgcggca gcatcgcatg cgtgaagacc agcgcgatcc gtccatgca ggaaatgaag    1560 tccatgctca gccagcacca aggcatggaa gcgatgatgt ccaagctgtg a           1611
```

<210> SEQ ID NO 45
<211> LENGTH: 536
<212> TYPE: PRT
<213> ORGANISM: Artificial Sequence
<220> FEATURE:
<223> OTHER INFORMATION: eAxmi205 #22 mutant

<400> SEQUENCE: 45

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
    130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
        195                 200                 205

Leu Val Gly Glu Ile Lys Ile Glu His Gly Ser Glu Met Glu Lys Gln
    210                 215                 220
```

```
Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
            245                 250                 255

Gln Ala Phe Ser Gln Trp Ala Glu Ser Leu Leu Asp Tyr Ala Thr Leu
        260                 265                 270

Met Asp Phe Ser Thr Glu Ser Leu Gln Pro Ile Trp Ala Leu Ala Asp
        275                 280                 285

Lys Pro Glu Arg Arg Val Glu Leu Glu Asp Ala Phe Pro Glu Phe Met
290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
                325                 330                 335

Ala Ser Glu Asp Leu Ala Val Phe Asn Pro Ser Thr Ser Asn Gly Tyr
            340                 345                 350

Lys Met Val Gly Gln Phe Gly Gln Arg Asn His Ala Ser Val Ala Asp
        355                 360                 365

Gly His Ala Pro Ile Phe Lys Asp Leu Phe Asp Leu Gly Val Leu Lys
370                 375                 380

Ala Pro Val Gly Trp Gln Arg Val Trp Asp Asp Ala Gly Ser Gly Lys
385                 390                 395                 400

Ser Lys Asp Tyr Ala Cys Trp Arg Ala Ile Pro Pro Gln Gly Tyr Arg
                405                 410                 415

Ala Leu Gly Asp Val Met Met Leu Ala Thr Ser Gly Tyr Asn Pro Pro
            420                 425                 430

Asn Leu Pro Asp Tyr Val Cys Val His Gln Ser Leu Cys Ala Asp Val
        435                 440                 445

Gln Thr Leu Gln Asn Arg Val Trp Trp Asp Lys Gly Thr Gly Ala Arg
450                 455                 460

Lys Asp Val Ser Leu Trp Gln Pro Gly Ala Ala Gly Ala Val Ala Ser
465                 470                 475                 480

Ser Leu Phe Ala Gly Val Pro Asn Tyr Asn Asn Pro Pro Asn Ser Gly
                485                 490                 495

Asp Ile Glu Arg Leu Arg Gly Ser Ile Ala Cys Val Lys Thr Ser Ala
            500                 505                 510

Ile Ala Ser Met Gln Glu Met Lys Ser Met Leu Ser Gln His Gln Gly
        515                 520                 525

Met Glu Ala Met Met Ser Lys Leu
530                 535

<210> SEQ ID NO 46
<211> LENGTH: 1611
<212> TYPE: DNA
<213> ORGANISM: Artificial Sequence
<220> FEATURE:
<223> OTHER INFORMATION: eAxmi205 #22 mutant

<400> SEQUENCE: 46
atggcatccg cagcaaatgc aggtcagctt ggcaacctcc ccggcgttac ttctatgggc      60
atgggctatg acgtgaatgg tttgtacgcc agcccggaaa gcctgcttgg ccaacccttg     120
ttcgatttcg gcggcgagct ggacagcatc gaaatcgagg ccgcagcta caccttttccc    180 cgcagcatgc atgtacacac ctatttccat tccgacttca acaggatgt cagcaaggaa     240
```

```
atcgaagagt atcgggagaa aatgagccag cacgtgggcg tgtccggccg ctacaagttg    300
ttcagcgctt cgctgagcgt ggatttcacc accacggacc agcaactgac cgagattacc    360
tacagctcca cccgcgaagc ccatgtgctg tggtacatca gcctgcctgg cgcggccacg    420
ctgcgttcga tgctgcgccg cgatttccgc gacgacctga acaacccaa  tatgccggcc    480 atggagctgt tcaagcgcta tggtccctac tacatatcgg aagcggcggt gggcggccgg    540
ctggactaca gcgcggccag caagaccttg aagatggaca gcagccagtc gctgtccacc    600
accgccgaaa tgtcctacaa ggcgctggtg ggcgagatca agatcgagca tggctcggag    660
atggaaaagc aggtcaacag cttccgcagc aactccacca tccgtctcac cgccaccggc    720
ggcaagccgg gcatgaccga tcgcatactg cacggtccgg attcgcagca ggcgttctcg    780
caatgggcgg aatcgctgct cgactatgcg acgctgatgg acttttccac cgaaagcctg    840
caaccgatct gggcgctggc cgacaagccc gagcgccgcg tcgagcttga ggacgccttc    900
cccgaattca tgaagcagtc gcagcagtcc atccccaagg tggacaaggt gctgctgatg    960
gacgcgcggc cgcctatggt gaaggctggg gaggatagcg gctccggcgc gtcggaggat    1020
ctggctgtgt tcaatcccag cacctccaat ggctacaaga tggttggcca gttcggtcag    1080
cgcaaccatg ccagcgtggc ggatggccat gcgccgattt tcaaggatct gttcgatctg    1140
ggcgtgctga aggcgccggt gggttggcag cgggtgtggg acgacgccgg ctccggcaag    1200
tccaaggact acgcgtgctg gcgcgcgatt ccgccgcagg gctaccgcgc gctgggcgat    1260
gtgatgatgc tggccaccag cggctataac ccgccgaatc tgccggacta tgtttgcgtg    1320
catcaaagcc tgtgcgcgga tgtgcagacg ctgcaaaacc gggtgtggtg ggacaagggc    1380
accggcgcgc gcaaggatgt cagcctgtgg caaccgggcg cggccggcgc ggtggcgtcc    1440
tctctgttcg ccggcgtgcc taattacaac aacccgccca attccggcga catcgagcgc    1500
ttgcgcggca gcatcgcatg cgtgaagacc agcgcgatcg cgtccatgca ggaaatgaag    1560
tccatgctca gccagcacca aggcatggaa gcgatgatgt ccaagctgtg a            1611
```

<210> SEQ ID NO 47
<211> LENGTH: 536
<212> TYPE: PRT
<213> ORGANISM: Artificial Sequence
<220> FEATURE:
<223> OTHER INFORMATION: eAxmi205 #23 mutant

<400> SEQUENCE: 47

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125
```

```
Val Leu Trp Tyr Ile Ser Leu Pro Gly Ala Ala Thr Leu Arg Ser Met
    130                 135                 140
Leu Arg Arg Asp Phe Arg Asp Asp Leu Asn Asn Pro Asn Met Pro Ala
145                 150                 155                 160
Met Glu Leu Phe Lys Arg Tyr Gly Pro Tyr Tyr Ile Ser Glu Ala Ala
                165                 170                 175
Val Gly Gly Arg Leu Asp Tyr Ser Ala Ala Ser Lys Thr Leu Lys Met
            180                 185                 190
Asp Ser Ser Gln Ser Leu Ser Thr Thr Ala Glu Met Ser Tyr Lys Ala
        195                 200                 205
Leu Val Gly Glu Ile Lys Ile Glu His Gly Ser Glu Met Glu Lys Gln
    210                 215                 220
Val Asn Ser Phe Arg Ser Asn Ser Thr Ile Arg Leu Thr Ala Thr Gly
225                 230                 235                 240
Gly Lys Pro Gly Met Thr Asp Arg Ile Leu His Gly Pro Asp Ser Gln
                245                 250                 255
Gln Ala Phe Ser Gln Trp Ala Glu Ser Leu Leu Asp Tyr Ala Thr Leu
            260                 265                 270
Met Asp Phe Ser Thr Glu Ser Leu Gln Pro Ile Trp Ala Leu Ala Asp
        275                 280                 285
Lys Pro Glu Arg Arg Val Glu Leu Glu Asp Ala Phe Pro Glu Phe Met
    290                 295                 300
Lys Gln Ser Gln Gln Ser Ile Pro Lys Val Asp Lys Val Leu Leu Met
305                 310                 315                 320
Asp Ala Arg Pro Pro Met Val Lys Ala Gly Glu Asp Ser Gly Ser Gly
                325                 330                 335
Ala Ser Glu Asp Leu Ala Val Phe Asn Pro Ser Thr Ser Asn Gly Tyr
            340                 345                 350
Lys Met Val Gly Gln Phe Gly Gln Arg Asn His Ala Ser Val Ala Asp
        355                 360                 365
Gly His Ala Pro Ile Phe Lys Asp Leu Phe Asp Leu Gly Val Leu Lys
    370                 375                 380
Ala Pro Val Gly Trp Gln Arg Val Trp Asp Asp Ala Gly Ser Gly Lys
385                 390                 395                 400
Ser Lys Asp Tyr Ala Cys Trp Arg Ala Ile Pro Pro Gln Gly Tyr Arg
                405                 410                 415
Ala Leu Gly Asp Val Met Met Leu Ala Thr Ser Gly Tyr Asn Pro Pro
            420                 425                 430
Asn Leu Pro Asp Tyr Val Cys Val His Gln Ser Leu Cys Ala Asp Val
        435                 440                 445
Gln Thr Leu Gln Asn Arg Val Trp Trp Asp Lys Gly Thr Gly Ala Arg
    450                 455                 460
Lys Asp Val Ser Leu Trp Gln Pro Gly Ala Gly Ala Val Ala Ser
465                 470                 475                 480
Ser Cys Phe Ala Gly Val Pro Asn Tyr Asn Pro Pro Asn Ser Gly
                485                 490                 495
Asp Ile Glu Arg Leu Arg Gly Ser Ile Ala Ser Val Lys Thr Ser Ala
            500                 505                 510
Ile Ala Ser Met Gln Glu Met Lys Ser Met Leu Ser Gln His Gln Gly
        515                 520                 525
Met Glu Ala Met Met Ser Lys Leu
    530                 535
```

<210> SEQ ID NO 48
<211> LENGTH: 1611
<212> TYPE: DNA
<213> ORGANISM: Artificial Sequence
<220> FEATURE:
<223> OTHER INFORMATION: eAxmi205 #23 mutant

<400> SEQUENCE: 48

```
atggcatccg cagcaaatgc aggtcagctt ggcaacctcc ccggcgttac ttctatgggc    60
atgggctatg acgtgaatgg tttgtacgcc agcccggaaa gcctgcttgg ccaacccttg   120
ttcgatttcg gcggcgagct ggacagcatc gaaatcgagg ccgcagcta caccttcccc    180
cgcagcatgc atgtacacac ctatttccat tccgacttca acaggatgt cagcaaggaa    240
atcgaagagt atcgggagaa atgagccag acgtgggcg tgtccggccg ctacaagttg     300
ttcagcgctt cgctgagcgt ggatttcacc accacggacc agcaactgac cgagattacc   360
tacagctcca cccgcgaagc ccatgtgctg tggtacatca gcctgcctgg cgcggccacg   420
ctgcgttcga tgctgcgccg cgattccgc gacgacctga caacccccaa tatgccggcc    480
atggagctgt tcaagcgcta tggtccctac tacatatcgg aagcggcggt gggcggccgg   540
ctggactaca gcgcggccag caagaccttg aagatggaca gcagccagtc gctgtccacc   600
accgccgaaa tgtcctacaa ggcgctggtg ggcgagatca agatcgagca tggctcggag   660
atggaaaagc aggtcaacag cttccgcagc aactccacca tccgtctcac cgccaccggc   720
ggcaagccgg gcatgaccga tcgcatactg cacggtccgg attcgcagca ggcgttctcg   780
caatgggcgg aatcgctgct cgactatgcg acgctgatgg acttttccac cgaaaagcctg  840
caaccgatct gggcgctggc cgacaagccc gagcgccgcg tcgagcttga ggacgccttc   900
cccgaattca tgaagcagtc gcagcagtcc atccccaagg tggacaaggt gctgctgatg   960
gacgcgcggc cgcctatggt gaaggctggg gaggatagcg gctccggcgc gtcggaggat  1020
ctggctgtgt tcaatcccag cacctccaat ggctacaaga tggttggcca gttcggtcag  1080
cgcaaccatg ccagcgtggc ggatggccat gcgccgattt tcaaggatct gttcgatctg  1140
ggcgtgctga aggcgccggt gggttggcag cgggtgtggg acgacgccgg ctccggcaag  1200
tccaaggact acgcgtgctg gcgcgcgatt ccgccgcagg gctaccgcgc gctgggcgat  1260
gtgatgatgc tggccaccag cggctataac ccgccgaatc tgccggacta tgtttgcgtg  1320
catcaaagcc tgtgcgcgga tgtgcagacg ctgcaaaacc gggtgtggtg ggacaagggc  1380
accggcgcgc gcaaggatgt cagcctgtgg caaccgggcg cggccggcgc ggtggcgtcc  1440
tcttgcttcg ccggcgtgcc taattacaac aacccgccca attccggcga catcgagcgc  1500
ttgcgcggca gcatcgcaag cgtgaagacc agcgcgatcg cgtccatgca ggaaatgaag  1560
tccatgctca gccagcacca aggcatggaa gcgatgatgt ccaagctgtg a            1611
```

<210> SEQ ID NO 49
<211> LENGTH: 536
<212> TYPE: PRT
<213> ORGANISM: Artificial Sequence
<220> FEATURE:
<223> OTHER INFORMATION: eAxmi205 #24 mutant

<400> SEQUENCE: 49

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30
```

```
Glu Ser Leu Leu Gly Gln Pro Leu Phe Asp Phe Gly Gly Glu Leu Asp
             35                  40                  45

Ser Ile Glu Ile Glu Gly Arg Ser Tyr Thr Phe Pro Arg Ser Met His
 50                      55                  60

Val His Thr Tyr Phe His Ser Asp Phe Lys Gln Asp Val Ser Lys Glu
 65              70                  75                      80

Ile Glu Glu Tyr Arg Glu Lys Met Ser Gln His Val Gly Val Ser Gly
                     85                  90                  95

Arg Tyr Lys Leu Phe Ser Ala Ser Leu Ser Val Asp Phe Thr Thr Thr
                100             105                 110

Asp Gln Gln Leu Thr Glu Ile Thr Tyr Ser Ser Thr Arg Glu Ala His
                115                 120                 125

Val Leu Trp Tyr Ile Ser Leu Pro Gly Ala Ala Thr Leu Arg Ser Met
        130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
                180                 185                 190

Asp Ser Ser Gln Ser Leu Ser Thr Thr Ala Glu Met Ser Tyr Lys Ala
                195                 200                 205

Leu Val Gly Glu Ile Lys Ile Glu His Gly Ser Glu Met Glu Lys Gln
        210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
                260                 265                 270

Met Asp Phe Ser Thr Glu Ser Leu Gln Pro Ile Trp Ala Leu Ala Asp
        275                 280                 285

Lys Pro Glu Arg Arg Val Glu Leu Glu Asp Ala Phe Pro Glu Phe Met
290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
                325                 330                 335

Ala Ser Glu Asp Leu Ala Val Phe Asn Pro Ser Thr Ser Asn Gly Tyr
                340                 345                 350

Lys Met Val Gly Gln Phe Gly Gln Arg Asn His Ala Ser Val Ala Asp
                355                 360                 365

Gly His Ala Pro Ile Phe Lys Asp Leu Phe Asp Leu Gly Val Leu Lys
        370                 375                 380

Ala Pro Val Gly Trp Gln Arg Val Trp Asp Asp Ala Gly Ser Gly Lys
385                 390                 395                 400

Ser Lys Asp Tyr Ala Ser Trp Arg Ala Ile Pro Pro Gln Gly Tyr Arg
                405                 410                 415

Ala Leu Gly Asp Val Met Met Leu Ala Thr Ser Gly Tyr Asn Pro Pro
                420                 425                 430

Asn Leu Pro Asp Tyr Val Ser Val His Gln Ser Leu Ser Ala Asp Val
                435                 440                 445
```

| | | | | | | | | | | | |
|---|---|---|---|---|---|---|---|---|---|---|---|
| Gln | Thr | Leu | Gln | Asn | Arg | Val | Trp | Trp | Asp | Lys | Gly | Thr | Gly | Ala | Arg |
| | 450 | | | | | 455 | | | | | 460 | | | | |

Lys Asp Val Ser Leu Trp Gln Pro Gly Ala Ala Gly Ala Val Ala Ser
465 470 475 480

Ser Ser Phe Ala Gly Val Pro Asn Tyr Asn Asn Pro Pro Asn Ser Gly
485 490 495

Asp Ile Glu Arg Leu Arg Gly Ser Ile Ala Ser Val Lys Thr Ser Ala
500 505 510

Ile Ala Ser Met Gln Glu Met Lys Ser Met Leu Ser Gln His Gln Gly
515 520 525

Met Glu Ala Met Met Ser Lys Leu
530 535

<210> SEQ ID NO 50
<211> LENGTH: 1611
<212> TYPE: DNA
<213> ORGANISM: Artificial Sequence
<220> FEATURE:
<223> OTHER INFORMATION: eAxmi205 #24 mutant

<400> SEQUENCE: 50

```
atggcatccg cagcaaatgc aggtcagctt ggcaaccctcc ccggcgttac ttctatgggc    60
atgggctatg acgtgaatgg tttgtacgcc agcccggaaa gcctgcttgg ccaacccttg   120
ttcgatttcg gcggcgagct ggacagcatc gaaatcgagg ccgcagcta cccttttccc    180
cgcagcatgc atgtacacac ctatttccat tccgacttca acaggatgt cagcaaggaa   240
atcgaagagt atcgggagaa aatgagccag cacgtgggcg tgtccggccg ctacaagttg   300
ttcagcgctt cgctgagcgt ggattcacc accacggacc agcaactgac cgagattacc   360
tacagctcca cccgcgaagc ccatgtgctg tggtacatca gcctgcctgg cgcggccacg   420
ctgcgttcga tgctgcgccg cgatttccgc gacgacctga caacccca tatgccggcc    480
atggagctgt tcaagcgcta tggtccctac tacatatcgg aagcggcggt gggcggccgg   540
ctggactaca gcgcggccag caagaccttg aagatggaca gcagccagtc gctgtccacc   600
accgccgaaa tgtcctacaa ggcgctggtg gcgagatca agatcgagca tggctcggag   660
atggaaaagc aggtcaacag cttccgcagc aactccacca tccgtctcac cgccaccggc   720
ggcaagccgg gcatgaccga tcgcatactg acggtccgg attcgcagca ggcgttctcg   780
caatgggcgg aatcgctgct cgactatgcg acgctgatgg actttccac cgaaagcctg   840
caaccgatct gggcgctggc cgacaagccc gagcgccgcg tcgagcttga ggacgccttc   900
cccgaattca tgaagcagtc gcagcagtcc atccccaagg tggacaaggt gctgctgatg   960
gacgcgcggc cgcctatggt gaaggctggg gaggatagcg gctccggcgc gtcggaggat  1020
ctggctgtgt tcaatcccag cacctccaat ggctacaaga tggttggcca gttcggtcag  1080
cgcaaccatg ccagcgtggc ggatggccat gcgccgattt tcaaggatct gttcgatctg  1140
ggcgtgctga aggcgccggt gggttggcag cgggtgtggg acgacgccgg ctccggcaag  1200
tccaaggact acgcgagctg gcgcgcgatt ccgccgcagg gctaccgcgc gctgggcgat  1260
gtgatgatgc tggccaccag cggctataac ccgccgaatc tgccggacta tgttagcgtg  1320
catcaaagcc tgagcgcgga tgtgcagacg ctgcaaaacc gggtgtggtg ggacaagggc  1380
accggcgcgc gcaaggatgt cagcctgtgg caaccgggcg cggccggcgc ggtggcgtcc  1440
tctagcttcg ccggcgtgcc taattacaac aacccgccca ttccggcga catcgagcgc  1500
ttgcgcggca gcatcgcaag cgtgaagacc agcgcgatcg cgtccatgca ggaaatgaag  1560
```
tccatgctca gccagcacca aggcatggaa gcgatgatgt ccaagctgtg a 1611

<210> SEQ ID NO 51
<211> LENGTH: 536
<212> TYPE: PRT
<213> ORGANISM: Artificial Sequence
<220> FEATURE:
<223> OTHER INFORMATION: eAxmi205 #25 mutant

<400> SEQUENCE: 51

Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
        195                 200                 205

Leu Val Gly Glu Ile Lys Ile Glu His Gly Ser Glu Met Glu Lys Gln
    210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Gly Ser Leu Leu Asp Tyr Ala Thr Leu
            260                 265                 270

Met Asp Phe Ser Thr Glu Ser Leu Gln Pro Ile Trp Ala Leu Ala Asp
        275                 280                 285

Lys Pro Glu Arg Arg Val Glu Leu Glu Asp Ala Phe Pro Glu Phe Met
    290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
                325                 330                 335

Ala Ser Glu Asp Leu Ala Val Phe Asn Pro Ser Thr Ser Asn Gly Tyr
            340                 345                 350

```
                Lys Met Val Gly Gln Phe Gly Gln Arg Asn His Ala Ser Val Ala Asp
                        355                 360                 365

Gly His Ala Pro Ile Phe Lys Asp Leu Leu Asp Leu Gly Val Leu Lys
                    370                 375                 380

Ala Pro Val Gly Trp Gln Arg Val Trp Asp Asp Ala Gly Ser Gly Lys
                385                 390                 395                 400

Ser Lys Asp Tyr Ala Cys Trp Arg Ala Ile Pro Pro Gln Gly Tyr Arg
                                405                 410                 415

Ala Leu Gly Asp Val Met Met Leu Ala Thr Ser Gly Tyr Asn Pro Pro
                            420                 425                 430

Asn Leu Pro Asp Tyr Val Cys Val His Gln Ser Leu Cys Ala Asp Val
                        435                 440                 445

Gln Thr Leu Gln Asn Arg Val Trp Trp Asp Lys Gly Thr Gly Ala Arg
                    450                 455                 460

Lys Asp Val Ser Leu Trp Gln Pro Gly Ala Ala Gly Ala Val Ala Ser
                465                 470                 475                 480

Ser Cys Phe Ala Gly Val Pro Asn Tyr Asn Pro Pro Asn Ser Gly
                                485                 490                 495

Asp Ile Glu Arg Leu Arg Gly Ser Ile Ala Cys Val Lys Thr Ser Ala
                            500                 505                 510

Ile Ala Ser Met Gln Glu Met Lys Ser Met Leu Ser Gln His Gln Gly
                        515                 520                 525

Met Glu Ala Met Met Ser Lys Leu
                    530                 535

<210> SEQ ID NO 52
<211> LENGTH: 1611
<212> TYPE: DNA
<213> ORGANISM: Artificial Sequence
<220> FEATURE:
<223> OTHER INFORMATION: eAxmi205 #25 mutant

<400> SEQUENCE: 52
atggcatccg cagcaaatgc aggtcagctt ggcaaccttc ccggcgttac ttctatgggc      60
atgggctatg acgtgaatgg tttgtacgcc agcccggaaa gcctgcttgg ccaacccttg     120
ttcgatttcg gcggcgagct ggacagcatc gaaatcgagg ccgcagcta caccctttcc     180 cgcagcatgc atgtacacac ctatttccat tccgacttca acaggatgt cagcaaggaa     240 atcgaagagt atcgggagaa aatgagccag cacgtgggcg tgtccggccg ctacaagttg     300
ttcagcgctt cgctgagcgt ggatttcacc accgcggacc agcaactgac cgagattacc     360
tacagctcca cccgcgaagc ccatgtgctg tggtacatca gcctgcctgg cgcggccacg     420
ctgcgttcga tgctgcgccg cgatttccgc gacgacctga caacccccaa tatgccggcc     480
atggagctgt tcaagcgcta tggtccctac tacatatcgg aagcggcggt gggcggccgg     540
ctggactaca gcgcggccag caagaccttg aagatggaca gcagccagtc gctgtccacc     600
accgccgaaa tgtcctacaa ggcgctggtg ggcgagatca agatcgagca tggctcggag     660
atggaaaagc aggtcaacag cttccgcagc aactccacca tccgtctcac cgccaccggc     720
ggcaagccgg gcatgaccga tcgcatactg cacggtccgg attcgcagca ggcgttctcg     780
caatgggcgg aatcgctgct cgactatgcg acgctgatgg acttttccac cgaaagcctg     840
caaccgatct gggcgctggc cgacaagccc gagcgccgcg tcgagcttga ggacgccttc     900
cccgaattca tgaagcagtc gcagcagtcc atccccaagg tggacaaggt gctgctgatg     960
gacgcgcggc cgcctatggt gaaggctggg gaggatagcg gctccggcgc gtcggaggat    1020
```

-continued

```
ctggctgtgt tcaatcccag cacctccaat ggctacaaga tggttggcca gttcggtcag    1080
cgcaaccatg ccagcgtggc ggatggccat gcgccgattt tcaaggatct gctggatctg    1140
ggcgtgctga aggcgccggt gggttggcag cgggtgtggg acgacgccgg ctccggcaag    1200
tccaaggact acgcgtgctg gcgcgcgatt ccgccgcagg gctaccgcgc gctgggcgat    1260
gtgatgatgc tggccaccag cggctataac ccgccgaatc tgccggacta tgtttgcgtg    1320
catcaaagcc tgtgcgcgga tgtgcagacg ctgcaaaacc gggtgtggtg ggacaagggc    1380
accggcgcgc gcaaggatgt cagcctgtgg caaccgggcg cggccggcgc ggtggcgtcc    1440
tcttgcttcg ccggcgtgcc taattacaac aacccgccca attccggcga catcgagcgc    1500
ttgcgcggca gcatcgcatg cgtgaagacc agcgcgatcg cgtccatgca ggaaatgaag    1560
tccatgctca gccagcacca aggcatggaa gcgatgatgt ccaagctgtg a             1611
```

<210> SEQ ID NO 53
<211> LENGTH: 536
<212> TYPE: PRT
<213> ORGANISM: Artificial Sequence
<220> FEATURE:
<223> OTHER INFORMATION: eAxmi205 #26 mutant

<400> SEQUENCE: 53

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
                20                  25                  30

Glu Ser Leu Leu Gly Gln Pro Leu Phe Asp Phe Gly Gly Glu Leu Asp
            35                  40                  45

Ser Ile Glu Ile Glu Gly Arg Ser Tyr Thr Phe Pro Arg Ser Met His
        50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
    130                 135                 140

Leu Arg Arg Asp Phe Arg Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
        195                 200                 205

Leu Val Gly Glu Ile Lys Ile Glu His Gly Ser Glu Met Glu Lys Gln
    210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255
```

Gln Ala Phe Ser Gln Trp Ala Glu Ser Leu Leu Asp Tyr Ala Thr Leu
                260                 265                 270

Met Asp Phe Ser Thr Glu Ser Leu Gln Pro Ile Trp Ala Leu Ala Asp
            275                 280                 285

Lys Pro Glu Arg Arg Val Glu Leu Glu Asp Ala Phe Pro Glu Phe Met
    290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
                325                 330                 335

Ala Ser Glu Asp Leu Ala Val Phe Asn Pro Ser Thr Ser Asn Gly Tyr
            340                 345                 350

Lys Met Val Gly Gln Phe Gly Gln Arg Asn His Ala Ser Val Ala Asp
                355                 360                 365

Gly His Ala Pro Ile Phe Lys Asp Leu Phe Asp Leu Gly Val Leu Lys
            370                 375                 380

Ala Pro Val Gly Trp Gln Arg Val Trp Asp Asp Ala Gly Ser Gly Lys
385                 390                 395                 400

Ser Lys Asp Tyr Ala Cys Trp Arg Ala Ile Pro Pro Gln Gly Tyr Arg
                405                 410                 415

Ala Leu Gly Asp Val Met Met Leu Ala Thr Ser Gly Tyr Asn Pro Pro
            420                 425                 430

Asn Leu Pro Asp Tyr Val Cys Val His Gln Ser Leu Cys Ala Asp Val
            435                 440                 445

Gln Thr Leu Gln Asn Arg Val Trp Trp Asp Lys Gly Thr Gly Ala Arg
    450                 455                 460

Lys Asp Val Ser Leu Trp Gln Pro Gly Ala Ala Gly Ala Val Ala Ser
465                 470                 475                 480

Ser Cys Phe Ala Gly Val Pro Asn Tyr Asn Asn Pro Pro Asn Leu Gly
                485                 490                 495

Asp Ile Glu Arg Leu Arg Gly Ser Ile Ala Cys Val Lys Thr Ser Ala
            500                 505                 510

Ile Ala Ser Met Gln Glu Met Lys Ser Met Leu Ser Gln His Gln Gly
            515                 520                 525

Met Glu Ala Met Met Ser Lys Leu
    530                 535

<210> SEQ ID NO 54
<211> LENGTH: 1611
<212> TYPE: DNA
<213> ORGANISM: Artificial Sequence
<220> FEATURE:
<223> OTHER INFORMATION: eAxmi205 #26 mutant

<400> SEQUENCE: 54
atggcatccg cagcaaatgc aggtcagctt ggcaacctcc ccggcgttac ttctatgggc      60
atgggctatg acgtgaatgg tttgtacgcc agcccggaaa gcctgcttgg ccaacccttg     120
ttcgatttcg gcggcgagct ggacagcatc gaaatcgagg ccgcagcta caccttccc      180 cgcagcatgc atgtacacac ctatttccat tccgacttca acaggatgt cagcaaggaa     240 atcgaagagt atcgggagaa atgagccag cacgtgggcg tgtccggccg ctacaagttg     300
ttcagcgctt cgctgagcgt ggatttcacc accacggacc agcaactgac cgagattacc     360
tacagctcca cccgcgaagc ccatgtgctg tggtacatca gctgcctggc gcggccacg     420 ctgcgttcga tgctgcgccg cgatttccgc gacgacctga caaccccaa tatgccggcc     480

```
atggagctgt tcaagcgcta tggtccctac tacatatcgg aagcggcggt gggcggccgg    540
ctggactaca gcgcggccag caagaccttg aagatggaca gcagccagtc gctgtccacc    600
accgccgaaa tgtcctacaa ggcgctggtg ggcgagatca agatcgagca tggctcggag    660
atggaaaagc aggtcaacag cttccgcagc aactccacca tccgtctcac cgccaccggc    720
ggcaagccgg gcatgaccga tcgcatactg cacggtccgg attcgcagca ggcgttctcg    780
caatgggcgg aatcgctgct cgactatgcg acgctgatgg acttttccac cgaaagcctg    840
caaccgatct gggcgctggc cgacaagccc gagcgccgcg tcgagcttga ggacgccttc    900
cccgaattca tgaagcagtc gcagcagtcc atccccaagg tggacaaggt gctgctgatg    960
gacgcgcggc cgcctatggt gaaggctggg gaggatagcg gctccggcgc gtcggaggat   1020
ctggctgtgt tcaatcccag cacctccaat ggctacaaga tggttggcca gttcggtcag   1080
cgcaaccatg ccagcgtggc ggatggccat cgccgatttt caaggatct gttcgatctg    1140 ggcgtgctga aggcgccggt gggttggcag cgggtgtggg acgacgccgg ctccggcaag   1200
tccaaggact acgcgtgctg gcgcgcgatt ccgccgcagg gctaccgcgc gctgggcgat   1260
gtgatgatgc tggccaccag cggctataac ccgccgaatc tgccggacta tgtttgcgtg   1320
catcaaagcc tgtgcgcgga tgtgcagacg ctgcaaaacc gggtgtggtg ggacaagggc   1380
accggcgcgc gcaaggatgt cagcctgtgg caaccgggcg cggccggcgc ggtggcgtcc   1440
tcttgcttcg ccggcgtgcc taattacaac aacccgccca atctgggcga catcgagcgc   1500
ttgcgcggca gcatcgcatg cgtgaagacc agcgcgatcg cgtccatgca ggaaatgaag   1560
tccatgctca gccagcacca aggcatggaa gcgatgatgt ccaagctgtg a             1611
```

<210> SEQ ID NO 55
<211> LENGTH: 536
<212> TYPE: PRT
<213> ORGANISM: Artificial Sequence
<220> FEATURE:
<223> OTHER INFORMATION: eAxmi205 #27 mutant

<400> SEQUENCE: 55

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
                20                  25                  30

Glu Ser Leu Leu Gly Gln Pro Leu Phe Asp Phe Gly Gly Glu Leu Asp
            35                  40                  45

Ser Ile Glu Ile Glu Gly Arg Ser Tyr Thr Phe Pro Arg Ser Met His
        50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
                100                 105                 110

Asp Gln Gln Leu Thr Glu Ile Thr Tyr Ser Ser Thr Arg Glu Ala His
            115                 120                 125

Val Leu Trp Tyr Ile Ser Leu Pro Gly Ala Ala Thr Leu Arg Ser Met
        130                 135                 140

Leu Arg Arg Asp Phe Arg Asp Asp Leu Asn Asn Pro Asn Met Pro Ala
145                 150                 155                 160
```

```
Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
        195                 200                 205

Leu Val Gly Glu Ile Lys Ile Glu His Gly Ser Glu Met Glu Lys Gln
    210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
        275                 280                 285

Lys Pro Glu Arg Arg Val Glu Leu Glu Asp Ala Phe Pro Glu Phe Met
    290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
                325                 330                 335

Ala Ser Glu Asp Leu Ala Val Phe Asn Pro Ser Thr Ser Asn Gly Tyr
            340                 345                 350

Lys Met Val Gly Gln Phe Gly Gln Arg Asn His Ala Ser Val Ala Asp
        355                 360                 365

Gly His Ala Pro Ile Phe Lys Asp Leu Phe Asp Leu Gly Val Leu Lys
    370                 375                 380

Ala Pro Val Gly Trp Gln Arg Val Trp Asp Asp Ala Gly Ser Gly Lys
385                 390                 395                 400

Ser Lys Asp Tyr Ala Cys Trp Arg Ala Ile Pro Pro Gln Gly Tyr Arg
                405                 410                 415

Ala Leu Gly Asp Val Met Met Leu Ala Thr Ser Gly Tyr Asn Pro Pro
            420                 425                 430

Asn Leu Pro Asp Tyr Val Cys Val His Gln Ser Leu Cys Ala Asp Val
        435                 440                 445

Gln Thr Leu Gln Asn Arg Val Trp Trp Asp Lys Gly Thr Gly Ala Arg
    450                 455                 460

Lys Asp Val Ser Leu Trp Gln Pro Gly Ala Ala Gly Ala Val Ala Ser
465                 470                 475                 480

Ser Cys Phe Ala Gly Val Pro Asn Tyr Asn Asn Pro Asn Ser Leu
                485                 490                 495

Asp Ile Glu Arg Leu Arg Gly Ser Ile Ala Cys Val Lys Thr Ser Ala
            500                 505                 510

Ile Ala Ser Met Gln Glu Met Lys Ser Met Leu Ser Gln His Gln Gly
        515                 520                 525

Met Glu Ala Met Met Ser Lys Leu
    530                 535

<210> SEQ ID NO 56
<211> LENGTH: 1611
<212> TYPE: DNA
<213> ORGANISM: Artificial Sequence
<220> FEATURE:
<223> OTHER INFORMATION: eAxmi205 #27 mutant
```

<400> SEQUENCE: 56

```
atggcatccg cagcaaatgc aggtcagctt ggcaacctcc ccggcgttac ttctatgggc      60
atgggctatg acgtgaatgg tttgtacgcc agcccggaaa gcctgcttgg ccaacccttg     120
ttcgatttcg gcggcgagct ggacagcatc gaaatcgagg ccgcagcta cacctttccc     180
cgcagcatgc atgtacacac ctatttccat tccgacttca acaggatgt cagcaaggaa     240
atcgaagagt atcgggagaa atgagccag acgtgggcg tgtccggccg ctacaagttg      300
ttcagcgctt cgctgagcgt ggatttcacc accacggacc agcaactgac cgagattacc     360
tacagctcca cccgcgaagc ccatgtgctg tggtacatca gcctgcctgg cgcggccacg     420
ctgcgttcga tgctgcgccg cgatttccgc gacgacctga caaccccaa tatgccggcc      480
atggagctgt tcaagcgcta tggtccctac tacatatcgg aagcggcggt gggcggccgg     540
ctggactaca gcgcggccag caagaccttg aagatggaca gcagccagtc gctgtccacc     600
accgccgaaa tgtcctacaa ggcgctggtg gcgagatca agatcgagca tggctcggag      660
atggaaaagc aggtcaacag cttccgcagc aactccacca tccgtctcac cgccaccggc     720
ggcaagccgg gcatgaccga tcgcatactg acggtccgg attcgcagca ggcgttctcg      780
caatgggcgg aatcgctgct cgactatgcg acgctgatgg acttttccac cgaaagcctg     840
caaccgatct gggcgctggc cgacaagccc gagcgccgcg tcgagcttga ggacgccttc     900
cccgaattca tgaagcagtc gcagcagtcc atccccaagg tggacaaggt gctgctgatg     960
gacgcgcggc cgcctatggt gaaggctggg gaggatagcg gctccggcgc gtcggaggat    1020
ctggctgtgt tcaatcccag cacctccaat ggctacaaga tggttggcca gttcggtcag    1080
cgcaaccatg ccagcgtggc ggatggccat gcgccgattt tcaaggatct gttcgatctg    1140
ggcgtgctga aggcgccggt gggttggcag cgggtgtggg acgacgccgg ctccggcaag    1200
tccaaggact acgcgtgctg gcgcgcgatt ccgccgcagg gctaccgcgc gctgggcgat    1260
gtgatgatgc tggccaccag cggctataac cgccgaatc tgccggacta tgtttgcgtg    1320
catcaaagcc tgtgcgcgga tgtgcagacg ctgcaaaacc gggtgtggtg ggacaagggc    1380
accggcgcgc gcaaggatgt cagcctgtgg caacgggcg cggccggcgc ggtggcgtcc    1440
tcttgcttcg ccggcgtgcc taattacaac aacccgccca attccctgga catcgagcgc    1500
ttgcgcggca gcatcgcatg cgtgaagacc agcgcgatcg cgtccatgca ggaaatgaag    1560
tccatgctca gccagcacca aggcatggaa gcgatgatgt ccaagctgtg a             1611
```

<210> SEQ ID NO 57
<211> LENGTH: 536
<212> TYPE: PRT
<213> ORGANISM: Artificial Sequence
<220> FEATURE:
<223> OTHER INFORMATION: eAxmi205 #28 mutant

<400> SEQUENCE: 57

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60
```

```
Val His Thr Tyr Phe His Ser Asp Phe Lys Gln Asp Val Ser Lys Glu
 65                  70                  75                  80

Ile Glu Glu Tyr Arg Glu Lys Met Ser Gln His Val Gly Val Ser Gly
                 85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
            115                 120                 125

Val Leu Trp Tyr Ile Ser Leu Pro Gly Ala Ala Thr Leu Arg Ser Met
130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
            195                 200                 205

Leu Val Gly Glu Ile Lys Ile Glu His Gly Ser Glu Met Glu Lys Gln
210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
            275                 280                 285

Lys Pro Glu Arg Arg Val Glu Leu Glu Asp Ala Phe Pro Glu Phe Met
290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
                325                 330                 335

Ala Ser Glu Asp Leu Ala Val Phe Asn Pro Ser Thr Ser Asn Gly Tyr
            340                 345                 350

Lys Met Val Gly Gln Phe Gly Gln Arg Asn His Ala Ser Val Ala Asp
            355                 360                 365

Gly His Ala Pro Ile Phe Lys Asp Leu Phe Asp Leu Gly Val Leu Lys
370                 375                 380

Ala Pro Val Gly Trp Gln Arg Val Trp Asp Asp Ala Gly Ser Gly Lys
385                 390                 395                 400

Ser Lys Asp Tyr Ala Cys Trp Arg Ala Ile Pro Pro Gln Gly Tyr Arg
                405                 410                 415

Ala Leu Gly Asp Val Ser Leu Leu Ala Thr Ser Gly Tyr Asn Pro Pro
            420                 425                 430

Asn Leu Pro Asp Tyr Val Cys Val His Gln Ser Leu Cys Ala Asp Val
            435                 440                 445

Gln Thr Leu Gln Asn Arg Val Trp Trp Asp Lys Gly Thr Gly Ala Arg
            450                 455                 460

Lys Asp Val Ser Leu Trp Gln Pro Gly Ala Ala Gly Ala Val Ala Ser
465                 470                 475                 480

Ser Cys Phe Ala Gly Val Pro Asn Tyr Asn Asn Pro Pro Asn Ser Gly
```

485                 490                 495
Asp Ile Glu Arg Leu Arg Gly Ser Ile Ala Cys Val Lys Thr Ser Ala
              500                 505                 510

Ile Ala Ser Met Gln Glu Met Lys Ser Met Leu Ser Gln His Gln Gly
          515                 520                 525

Met Glu Ala Met Met Ser Lys Leu
      530                 535

<210> SEQ ID NO 58
<211> LENGTH: 1611
<212> TYPE: DNA
<213> ORGANISM: Artificial Sequence
<220> FEATURE:
<223> OTHER INFORMATION: eAxmi205 #28 mutant

<400> SEQUENCE: 58

| | | | | | | |
|---|---|---|---|---|---|---|
| atggcatccg | cagcaaatgc | aggtcagctt | ggcaaccctcc | ccggcgttac | ttctatgggc | 60 |
| atgggctatg | acgtgaatgg | tttgtacgcc | agcccggaaa | gcctgcttgg | ccaacccttg | 120 |
| ttcgatttcg | gcggcgagct | ggacagcatc | gaaatcgagg | gccgcagcta | cacctttccc | 180 |
| cgcagcatgc | atgtacacac | ctatttccat | tccgacttca | acaggatgt | cagcaaggaa | 240 |
| atcgaagagt | atcgggagaa | aatgagccag | cacgtgggcg | tgtccggccg | ctacaagttg | 300 |
| ttcagcgctt | cgctgagcgt | ggatttcacc | accacggacc | agcaactgac | cgagattacc | 360 |
| tacagctcca | cccgcgaagc | ccatgtgctg | tggtacatca | gcctgcctgg | cgcggccacg | 420 |
| ctgcgttcga | tgctgcgccg | cgatttccgc | gacgacctga | caacccaa | tatgccggcc | 480 |
| atggagctgt | tcaagcgcta | tggtccctac | tacatatcgg | aagcggcggt | gggcggccgg | 540 |
| ctggactaca | gcgcggccag | caagaccttg | aagatggaca | gcagccagtc | gctgtccacc | 600 |
| accgccgaaa | tgtcctacaa | ggcgctggtg | ggcgagatca | agatcgagca | tggctcggag | 660 |
| atggaaaagc | aggtcaacag | cttccgcagc | aactccacca | tccgtctcac | cgccaccggc | 720 |
| ggcaagccgg | gcatgaccga | tcgcatactg | cacggtccgg | attcgcagca | ggcgttctcg | 780 |
| caatgggcgg | aatcgctgct | cgactatgcg | acgctgatgg | acttttccac | cgaaagcctg | 840 |
| caaccgatct | gggcgctggc | cgacaagccc | gagcgccgcg | tcgagcttga | ggacgccttc | 900 |
| cccgaattca | tgaagcagtc | gcagcagtcc | atccccaagg | tggacaaggt | gctgctgatg | 960 |
| gacgcgcggc | cgcctatggt | gaaggctggg | gaggatagcg | gctccggcgc | gtcggaggat | 1020 |
| ctggctgtgt | tcaatcccag | cacctccaat | ggctacaaga | tggttggcca | gttcggtcag | 1080 |
| cgcaaccatg | ccagcgtggc | ggatggccat | gcgccgattt | tcaaggatct | gttcgatctg | 1140 |
| ggcgtgctga | aggcgccggt | gggttggcag | cgggtgtggg | acgacgccgg | ctccggcaag | 1200 |
| tccaaggact | acgcgtgctg | gcgcgcgatt | ccgccgcagg | gctaccgcgc | gctgggcgat | 1260 |
| gtgagcctgc | tggccaccag | cggctataac | ccgccgaatc | tgccggacta | tgtttgcgtg | 1320 |
| catcaaagcc | tgtgcgcgga | tgtgcagacg | ctgcaaaacc | gggtgtggtg | ggacaagggc | 1380 |
| accggcgcgc | gcaaggatgt | cagcctgtgg | caaccgggcg | cggccggcgc | ggtggcgtcc | 1440 |
| tcttgcttcg | ccggcgtgcc | taattacaac | aacccgccca | attccggcga | catcgagcgc | 1500 |
| ttgcgcggca | gcatcgcatg | cgtgaagacc | agcgcgatcg | cgtccatgca | ggaaatgaag | 1560 |
| tccatgctca | gccagcacca | aggcatggaa | gcgatgatgt | ccaagctgtg | a | 1611 |

<210> SEQ ID NO 59
<211> LENGTH: 536
<212> TYPE: PRT

<213> ORGANISM: Artificial Sequence
<220> FEATURE:
<223> OTHER INFORMATION: eAxmi205 #29 mutant

<400> SEQUENCE: 59

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Glu Leu Asp
        35                  40                  45

Ser Ile Glu Ile Glu Gly Arg Ser Tyr Thr Phe Pro Arg Ser Met His
50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
130                 135                 140

Leu Arg Arg Asp Phe Arg Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
        195                 200                 205

Leu Val Gly Glu Ile Lys Ile Glu His Gly Ser Glu Met Glu Lys Gln
210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
        275                 280                 285

Lys Pro Glu Arg Arg Val Glu Leu Glu Asp Ala Phe Pro Glu Phe Met
290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
                325                 330                 335

Ala Ser Glu Asp Leu Ala Val Phe Asn Pro Ser Thr Ser Asn Gly Tyr
            340                 345                 350

Lys Met Val Gly Gln Phe Gly Gln Arg Asn His Ala Ser Val Ala Asp
        355                 360                 365

Gly His Ala Pro Ile Phe Lys Asp Leu Phe Asp Leu Gly Val Leu Lys
370                 375                 380

Ala Pro Val Gly Trp Gln Arg Val Trp Asp Asp Ala Gly Ser Gly Lys
```

```
            385                 390                 395                 400
Ser Lys Asp Tyr Ala Cys Trp Arg Ala Ile Pro Pro Gln Gly Tyr Arg
                    405                 410                 415

Ala Leu Gly Asp Val Met Met Leu Ala Thr Ser Gly Tyr Asn Pro Pro
                420                 425                 430

Asn Leu Pro Asp Tyr Val Cys Val His Gln Ser Leu Cys Ala Asp Val
            435                 440                 445

Gln Thr Leu Gln Asn Arg Val Trp Trp Asp Lys Gly Thr Gly Ala Arg
        450                 455                 460

Lys Asp Ser Leu Leu Trp Gln Pro Gly Ala Ala Gly Ala Val Ala Ser
465                 470                 475                 480

Ser Cys Phe Ala Gly Val Pro Asn Tyr Asn Asn Pro Pro Asn Ser Gly
                485                 490                 495

Asp Ile Glu Arg Leu Arg Gly Ser Ile Ala Cys Val Lys Thr Ser Ala
            500                 505                 510

Ile Ala Ser Met Gln Glu Met Lys Ser Met Leu Ser Gln His Gln Gly
        515                 520                 525

Met Glu Ala Met Met Ser Lys Leu
    530                 535

<210> SEQ ID NO 60
<211> LENGTH: 1611
<212> TYPE: DNA
<213> ORGANISM: Artificial Sequence
<220> FEATURE:
<223> OTHER INFORMATION: eAxmi205 #29 mutant

<400> SEQUENCE: 60
atggcatccg cagcaaatgc aggtcagctt ggcaacctcc ccggcgttac ttctatgggc      60
atgggctatg acgtgaatgg tttgtacgcc agcccggaaa gcctgcttgg ccaacccttg     120
ttcgatttcg gcggcgagct ggacagcatc gaaatcgagg ccgcagcta caccttcc        180 cgcagcatgc atgtacacac ctatttccat tccgacttca acaggatgt cagcaaggaa      240 atcgaagagt atcgggagaa atgagccag cacgtgggcg tgtccggccg ctacaagttg      300
ttcagcgctt cgctgagcgt ggatttcacc accacgacc agcaactgac cgagattacc      360
tacagctcca cccgcgaagc ccatgtgctg tggtacatca gcctgcctgg cgcggccacg      420
ctgcgttcga tgctgcgccg cgatttccgc gacgacctga caaccccaa tatgccggcc      480 atggagctgt tcaagcgcta tggtccctac tacatatcgg aagcggcggt gggcggccgg     540
ctggactaca gcgcggccag caagaccttg aagatggaca gcagccagtc gctgtccacc      600
accgccgaaa tgtcctacaa ggcgctggtg ggcgagatca gatcgagca tggctcggag      660 atggaaaagc aggtcaacag cttccgcagc aactccacca tccgtctcac cgccaccggc      720
ggcaagccgg gcatgaccga tcgcatactg cacggtccgg attcgcagca ggcgttctcg      780
caatgggcgg aatcgctgct cgactatgcg acgctgatgg acttttccac cgaaaagcctg     840 caaccgatct gggcgctggc cgacaagccc gagcgccgcg tcgagcttga ggacgccttc      900
cccgaattca tgaagcagtc gcagcagtcc atccccaagg tggacaaggt gctgctgatg      960
gacgcgcggc cgcctatggt gaaggctggg aggatagcg ctccggcgc gtcggaggat      1020 ctggctgtgt tcaatcccag cacctccaat ggctacaaga tggttggcca gttcggtcag     1080
cgcaaccatg ccagcgtggc cggatggccat gcgccgattt tcaaggatct gttcgatctg     1140
ggcgtgctga aggcgccggt gggttggcag cgggtgtggg acgacgccgg ctccggcaag     1200
```

```
tccaaggact acgcgtgctg gcgcgcgatt ccgccgcagg gctaccgcgc gctgggcgat    1260
gtgatgatgc tggccaccag cggctataac ccgccgaatc tgccggacta tgtttgcgtg    1320
catcaaagcc tgtgcgcgga tgtgcagacg ctgcaaaacc gggtgtggtg ggacaagggc    1380
accggcgcgc gcaaggatag cctgctgtgg caaccgggcg cggccggcgc ggtggcgtcc    1440
tcttgcttcg ccggcgtgcc taattacaac aacccgccca attccggcga catcgagcgc    1500
ttgcgcggca gcatcgcatg cgtgaagacc agcgcgatcg cgtccatgca ggaaatgaag    1560
tccatgctca gccagcacca aggcatggaa gcgatgatgt ccaagctgtg a             1611
```

<210> SEQ ID NO 61
<211> LENGTH: 536
<212> TYPE: PRT
<213> ORGANISM: Artificial Sequence
<220> FEATURE:
<223> OTHER INFORMATION: eAxmi205 #30 mutant

<400> SEQUENCE: 61

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
    130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
        195                 200                 205

Leu Val Gly Glu Ile Lys Ile Glu His Gly Ser Glu Met Glu Lys Gln
    210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
        275                 280                 285

Lys Pro Glu Arg Arg Val Glu Leu Glu Asp Ala Phe Pro Glu Phe Met
```

```
        290                     295                     300
Lys Gln Ser Gln Gln Ser Ile Pro Lys Val Asp Lys Val Leu Leu Met
305                     310                     315                 320

Asp Ala Arg Pro Pro Met Val Lys Ala Gly Glu Asp Ser Gly Ser Gly
                325                     330                     335

Ala Ser Glu Asp Leu Ala Val Phe Asn Pro Ser Thr Ser Asn Gly Tyr
            340                     345                     350

Lys Met Val Gly Gln Phe Gly Gln Arg Asn His Ala Ser Val Ala Asp
        355                     360                     365

Gly His Ala Pro Ile Phe Lys Asp Leu Phe Asp Leu Gly Val Leu Lys
    370                     375                     380

Ala Pro Val Gly Trp Gln Arg Val Trp Asp Asp Ala Gly Ser Gly Lys
385                     390                     395                 400

Ser Lys Asp Tyr Ala Cys Trp Arg Ala Ile Pro Pro Gln Gly Tyr Arg
                405                     410                     415

Ala Leu Gly Asp Val Met Met Leu Ala Thr Ser Gly Tyr Asn Pro Pro
            420                     425                     430

Asn Leu Pro Asp Tyr Val Cys Val His Gln Ser Leu Cys Ala Asp Val
        435                     440                     445

Gln Thr Leu Gln Asn Arg Val Trp Trp Asp Lys Gly Thr Gly Ala Arg
    450                     455                     460

Lys Asp Ser Leu Leu Gly Gln Pro Gly Ala Ala Gly Val Ala Ser
465                     470                     475                 480

Ser Cys Phe Ala Gly Val Pro Asn Tyr Asn Asn Pro Asn Ser Gly
                485                     490                     495

Asp Ile Glu Arg Leu Arg Gly Ser Ile Ala Cys Val Lys Thr Ser Ala
            500                     505                     510

Ile Ala Ser Met Gln Glu Met Lys Ser Met Leu Ser Gln His Gln Gly
        515                     520                     525

Met Glu Ala Met Met Ser Lys Leu
    530                     535

<210> SEQ ID NO 62
<211> LENGTH: 1611
<212> TYPE: DNA
<213> ORGANISM: Artificial Sequence
<220> FEATURE:
<223> OTHER INFORMATION: eAxmi205 #30 mutant

<400> SEQUENCE: 62
atggcatccg cagcaaatgc aggtcagctt ggcaacctcc ccggcgttac ttctatgggc      60
atgggctatg acgtgaatgg tttgtacgcc agcccggaaa gcctgcttgg ccaacccttg     120
ttcgatttcg gcggcgagct ggacagcatc gaaatcgagg ccgcagcta cacctttccc      180 cgcagcatgc atgtacacac ctatttccat tccgacttca acaggatgt cagcaaggaa      240 atcgaagagt atcgggagaa aatgagccag cacgtgggcg tgtccggccg ctacaagttg     300
ttcagcgctt cgctgagcgt ggatttcacc accacggacc agcaactgac cgagattacc     360
tacagctcca cccgcgaagc ccatgtgctc tggtacatca gcctgcctgg cgcggccacg     420
ctgcgttcga tgctgcgccg cgattccgc gacgacctga caaccccaa tatgccggcc       480 atggagctgt tcaagcgcta tggtccctac tacatatcgg aagcggcggt gggcggccgg    540
ctggactaca gcgcggccag caagaccttg aagatggaca gcagccagtc gctgtccacc    600
accgccgaaa tgtcctacaa ggcgctggtg ggcgagatca agatcgagca tggctcggag    660
```

```
atggaaaagc aggtcaacag cttccgcagc aactccacca tccgtctcac cgccaccggc    720
ggcaagccgg gcatgaccga tcgcatactg cacggtccgg attcgcagca ggcgttctcg    780
caatgggcgg aatcgctgct cgactatgcg acgctgatgg acttttccac cgaaagcctg    840
caaccgatct gggcgctggc cgacaagccc gagcgccgcg tcgagcttga ggacgccttc    900
cccgaattca tgaagcagtc gcagcagtcc atccccaagg tggacaaggt gctgctgatg    960
gacgcgcggc cgcctatggt gaaggctggg gaggatagcg gctccggcgc gtcggaggat   1020
ctggctgtgt tcaatcccag cacctccaat ggctacaaga tggttggcca gttcggtcag   1080
cgcaaccatg ccagcgtggc ggatggccat gcgccgattt tcaaggatct gttcgatctg   1140
ggcgtgctga aggcgccggt gggttggcag cgggtgtggg acgacgccgg ctccggcaag   1200
tccaaggact acgcgtgctg gcgcgcgatt ccgccgcagg gctaccgcgc gctgggcgat   1260
gtgatgatgc tggccaccag cggctataac ccgccgaatc tgccggacta tgtttgcgtg   1320
catcaaagcc tgtgcgcgga tgtgcagacg ctgcaaaacc gggtgtggtg ggacaagggc   1380
accggcgcgc gcaaggatag cctgctgggc caaccgggcg cggccggcgc ggtggcgtcc   1440
tcttgcttcg ccggcgtgcc taattacaac aacccgccca attccggcga catcgagcgc   1500
ttgcgcggca gcatcgcatg cgtgaagacc agcgcgatcg cgtccatgca ggaaatgaag   1560
tccatgctca gccagcacca aggcatggaa gcgatgatgt ccaagctgtg a             1611
```

<210> SEQ ID NO 63  
<211> LENGTH: 537  
<212> TYPE: PRT  
<213> ORGANISM: Artificial Sequence  
<220> FEATURE:  
<223> OTHER INFORMATION: eAxmi205 #31 mutant

<400> SEQUENCE: 63

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
    130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
```

```
                195                 200                 205
Leu Val Gly Glu Ile Lys Ile Glu His Gly Ser Glu Met Glu Lys Gln
    210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
        275                 280                 285

Lys Pro Glu Arg Arg Val Glu Leu Glu Asp Ala Phe Pro Glu Phe Met
290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
                325                 330                 335

Ala Ser Glu Asp Leu Ala Val Phe Asn Pro Ser Thr Ser Asn Gly Tyr
            340                 345                 350

Lys Met Val Gly Gln Phe Gly Gln Arg Asn His Ala Ser Val Ala Asp
        355                 360                 365

Gly His Ala Pro Ile Phe Lys Asp Leu Phe Asp Leu Gly Val Leu Lys
370                 375                 380

Ala Pro Val Gly Trp Gln Arg Val Trp Asp Asp Ala Leu Gly Ser Gly
385                 390                 395                 400

Lys Ser Lys Asp Tyr Ala Cys Trp Arg Ala Ile Pro Pro Gln Gly Tyr
                405                 410                 415

Arg Ala Leu Gly Asp Val Met Met Leu Ala Thr Ser Gly Tyr Asn Pro
            420                 425                 430

Pro Asn Leu Pro Asp Tyr Val Cys Val His Gln Ser Leu Cys Ala Asp
        435                 440                 445

Val Gln Thr Leu Gln Asn Arg Val Trp Trp Asp Lys Gly Thr Gly Ala
450                 455                 460

Arg Lys Asp Val Ser Leu Trp Gln Pro Gly Ala Ala Gly Ala Val Ala
465                 470                 475                 480

Ser Ser Cys Phe Ala Gly Val Pro Asn Tyr Asn Asn Pro Pro Asn Ser
                485                 490                 495

Gly Asp Ile Glu Arg Leu Arg Gly Ser Ile Ala Cys Val Lys Thr Ser
            500                 505                 510

Ala Ile Ala Ser Met Gln Glu Met Lys Ser Met Leu Ser Gln His Gln
        515                 520                 525

Gly Met Glu Ala Met Met Ser Lys Leu
    530                 535
```

<210> SEQ ID NO 64
<211> LENGTH: 1614
<212> TYPE: DNA
<213> ORGANISM: Artificial Sequence
<220> FEATURE:
<223> OTHER INFORMATION: eAxmi205 #31 mutant

<400> SEQUENCE: 64
atggcatccg cagcaaatgc aggtcagctt ggcaacctcc ccggcgttac ttctatgggc    60
atgggctatg acgtgaatgg tttgtacgcc agcccggaaa gcctgcttgg ccaacccttg   120

```
ttcgatttcg gcggcgagct ggacagcatc gaaatcgagg gccgcagcta cacctttccc    180
cgcagcatgc atgtacacac ctatttccat tccgacttca acaggatgt cagcaaggaa     240
atcgaagagt atcgggagaa atgagccag cacgtgggcg tgtccggccg ctacaagttg     300
ttcagcgctt cgctgagcgt ggatttcacc accacggacc agcaactgac cgagattacc    360
tacagctcca cccgcgaagc ccatgtgctg tggtacatca gcctgcctgg cgcggccacg    420
ctgcgttcga tgctgcgccg cgatttccgc gacgacctga caacccaa tatgccggcc      480
atggagctgt tcaagcgcta tggtccctac tacatatcgg aagcggcggt gggcggccgg    540
ctggactaca gcgcggccag caagaccttg aagatggaca gcagccagtc gctgtccacc    600
accgccgaaa tgtcctacaa ggcgctggtg ggcgagatca agatcgagca tggctcggag    660
atggaaaagc aggtcaacag cttccgcagc aactccacca tccgtctcac cgccaccggc    720
ggcaagccgg gcatgaccga tcgcatactg cacggtccgg attcgcagca ggcgttctcg    780
caatgggcgg aatcgctgct cgactatgcg acgctgatgg acttttccac cgaaagcctg    840
caaccgatct gggcgctggc cgacaagccc gagcgccgcg tcgagcttga ggacgccttc    900
cccgaattca tgaagcagtc gcagcagtcc atccccaagg tggacaaggt gctgctgatg    960
gacgcgcggc cgcctatggt gaaggctggg gaggatagcg gctccggcgc gtcggaggat   1020
ctggctgtgt tcaatcccag cacctccaat ggctacaaga tggttggcca gttcggtcag   1080
cgcaaccatg ccagcgtggc ggatggccat gcgccgattt tcaaggatct gttcgatctg   1140
ggcgtgctga aggcgccggt gggttggcag cgggtgtggg acgacgccct gggctccggc   1200
aagtccaagg actacgcgtg ctggcgcgcg attccgccgc agggctaccg cgcgctgggc   1260
gatgtgatga tgctggccac cagcggctat aacccgccga atctgccgga ctatgtttgc   1320
gtgcatcaaa gcctgtgcgc ggatgtgcag acgctgcaaa accgggtgtg gtgggacaag   1380
ggcaccggcg cgcgcaagga tgtcagcctg tgcaaccgg gcgcggccgg cgcggtggcg    1440
tcctcttgct cgccggcgt gcctaattac aacaacccgc ccaattccgg cgacatcgag    1500
cgcttgcgcg gcagcatcgc atgcgtgaag accagcgcga tcgcgtccat gcaggaaatg   1560
aagtccatgc tcagccagca ccaaggcatg gaagcgatga tgtccaagct gtga          1614
```

<210> SEQ ID NO 65
<211> LENGTH: 537
<212> TYPE: PRT
<213> ORGANISM: Artificial Sequence
<220> FEATURE:
<223> OTHER INFORMATION: eAxmi205 #32 mutant

<400> SEQUENCE: 65

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
```

```
            100                 105                 110
Asp Gln Gln Leu Thr Glu Ile Thr Tyr Ser Ser Thr Arg Glu Ala His
            115                 120                 125

Val Leu Trp Tyr Ile Ser Leu Pro Gly Ala Ala Thr Leu Arg Ser Met
            130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
            165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
            195                 200                 205

Leu Val Gly Glu Ile Lys Ile Glu His Gly Ser Glu Met Glu Lys Gln
            210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
            245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
            275                 280                 285

Lys Pro Glu Arg Arg Val Glu Leu Glu Asp Ala Phe Pro Glu Phe Met
            290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Leu Glu Asp Ser Gly Ser
            325                 330                 335

Gly Ala Ser Glu Asp Leu Ala Val Phe Asn Pro Ser Thr Ser Asn Gly
            340                 345                 350

Tyr Lys Met Val Gly Gln Phe Gly Gln Arg Asn His Ala Ser Val Ala
            355                 360                 365

Asp Gly His Ala Pro Ile Phe Lys Asp Leu Phe Asp Leu Gly Val Leu
            370                 375                 380

Lys Ala Pro Val Gly Trp Gln Arg Val Trp Asp Asp Ala Gly Ser Gly
385                 390                 395                 400

Lys Ser Lys Asp Tyr Ala Cys Trp Arg Ala Ile Pro Pro Gln Gly Tyr
            405                 410                 415

Arg Ala Leu Gly Asp Val Met Met Leu Ala Thr Ser Gly Tyr Asn Pro
            420                 425                 430

Pro Asn Leu Pro Asp Tyr Val Cys Val His Gln Ser Leu Cys Ala Asp
            435                 440                 445

Val Gln Thr Leu Gln Asn Arg Val Trp Trp Asp Lys Gly Thr Gly Ala
            450                 455                 460

Arg Lys Asp Val Ser Leu Trp Gln Pro Gly Ala Ala Gly Ala Val Ala
465                 470                 475                 480

Ser Ser Cys Phe Ala Gly Val Pro Asn Tyr Asn Asn Pro Pro Asn Ser
            485                 490                 495

Gly Asp Ile Glu Arg Leu Arg Gly Ser Ile Ala Cys Val Lys Thr Ser
            500                 505                 510

Ala Ile Ala Ser Met Gln Glu Met Lys Ser Met Leu Ser Gln His Gln
            515                 520                 525
```

Gly Met Glu Ala Met Met Ser Lys Leu
        530                 535

<210> SEQ ID NO 66
<211> LENGTH: 1614
<212> TYPE: DNA
<213> ORGANISM: Artificial Sequence
<220> FEATURE:
<223> OTHER INFORMATION: eAxmi205 #32 mutant

<400> SEQUENCE: 66

```
atggcatccg cagcaaatgc aggtcagctt ggcaacctcc ccggcgttac ttctatgggc      60
atgggctatg acgtgaatgg tttgtacgcc agcccggaaa gcctgcttgg ccaacccttg     120
ttcgatttcg gcggcgagct ggacagcatc gaaatcgagg gccgcagcta cacctttccc     180
cgcagcatgc atgtacacac ctatttccat tccgacttca acaggatgt cagcaaggaa      240
atcgaagagt atcgggagaa atgagccag cacgtgggcg tgtccggccg ctacaagttg      300
ttcagcgctt cgctgagcgt ggatttcacc accacgacc agcaactgac cgagattacc      360
tacagctcca cccgcgaagc ccatgtgctg tggtacatca gcctgcctgg cgcggccacg      420
ctgcgttcga tgctgcgccg cgattccgc gacgacctga caaccccaa tatgccggcc       480
atggagctgt tcaagcgcta tggtccctac tacatatcgg aagcggcggt gggcggccgg     540
ctggactaca gcgcggccag caagaccttg aagatggaca cagccagtc gctgtccacc     600
accgccgaaa tgtcctacaa ggcgctggtg ggcgagatca agatcgagca tggctcggag     660
atggaaaagc aggtcaacag cttccgcagc aactccacca tccgtctcac cgccaccggc     720
ggcaagccgg gcatgaccga tcgcatactg cacggtccgg attcgcagca ggcgttctcg     780
caatgggcg aatcgctgct cgactatgcg acgctgatgg acttttccac cgaaagcctg      840
caaccgatct gggcgctggc cgacaagccc gagcgccgcg tcgagcttga ggacgccttc     900
cccgaattca tgaagcagtc gcagcagtcc atccccaagg tggacaaggt gctgctgatg     960
gacgcgcggc cgcctatggt gaaggctggg ctggaggata gcggctccgg cgcgtcggag    1020
gatctggctg tgttcaatcc cagcacctcc aatggctaca agatggttgg ccagttcggt    1080
cagcgcaacc atgccagcgt ggcggatggc catgcgccga ttttcaagga tctgttcgat    1140
ctgggcgtgc tgaaggcgcc ggtgggttgg cagcgggtgt gggacgacgc cggctccggc    1200
aagtccaagg actacgcgtg ctggcgcgcg attccgccgc agggctaccg cgcgctgggc    1260
gatgtgatga tgctggccac cagcggctat aacccgccga tctgccggaa ctatgtttgc    1320
gtgcatcaaa gcctgtgcgc ggatgtgcag acgctgcaaa accgggtgtg gtgggacaag    1380
ggcaccggcg cgcgcaagga tgtcagcctg tggcaaccgg gcgcggccgg cgcggtggcg    1440
tcctcttgct tcgccggcgt gcctaattac aacaacccgc ccaattccgg cgacatcgag    1500
cgcttgcgcg gcagcatcgc atgcgtgaag accagcgcga tcgcgtccat gcaggaaatg    1560
aagtccatgc tcagccagca ccaaggcatg gaagcgatga tgtccaagct gtga          1614
```

<210> SEQ ID NO 67
<211> LENGTH: 537
<212> TYPE: PRT
<213> ORGANISM: Artificial Sequence
<220> FEATURE:
<223> OTHER INFORMATION: eAxmi205 #33 mutant

<400> SEQUENCE: 67

Met Ala Ser Ala Ala Asn Ala Gly Gln Leu Gly Asn Leu Pro Gly Val

-continued

```
1               5                   10                  15
Thr Ser Met Gly Met Gly Tyr Asp Val Asn Gly Leu Tyr Ala Ser Pro
                20                  25                  30
Glu Ser Leu Leu Gly Gln Pro Leu Phe Asp Phe Gly Gly Glu Leu Asp
                35                  40                  45
Ser Ile Glu Ile Glu Gly Arg Ser Tyr Thr Phe Pro Arg Ser Met His
            50                  55                  60
Val His Thr Tyr Phe His Ser Asp Phe Lys Gln Asp Val Ser Lys Glu
65                  70                  75                  80
Ile Glu Glu Tyr Arg Glu Lys Met Ser Gln His Val Gly Val Ser Gly
                85                  90                  95
Arg Tyr Lys Leu Phe Ser Ala Ser Leu Ser Val Asp Phe Thr Thr Thr
                100                 105                 110
Asp Gln Gln Leu Thr Glu Ile Thr Tyr Ser Ser Thr Arg Glu Ala His
                115                 120                 125
Val Leu Trp Tyr Ile Ser Leu Pro Gly Ala Ala Thr Leu Arg Ser Met
                130                 135                 140
Leu Arg Arg Asp Phe Arg Asp Asp Leu Asn Asn Pro Asn Met Pro Ala
145                 150                 155                 160
Met Glu Leu Phe Lys Arg Tyr Gly Pro Tyr Tyr Ile Ser Glu Ala Ala
                165                 170                 175
Val Gly Gly Arg Leu Asp Tyr Ser Ala Ala Ser Lys Thr Leu Lys Met
                180                 185                 190
Asp Ser Ser Gln Ser Leu Ser Thr Thr Ala Glu Met Ser Tyr Lys Ala
                195                 200                 205
Leu Val Gly Glu Ile Lys Ile Glu His Gly Ser Glu Met Glu Lys Gln
                210                 215                 220
Val Asn Ser Phe Arg Ser Asn Ser Thr Ile Arg Leu Thr Ala Thr Gly
225                 230                 235                 240
Gly Lys Pro Gly Met Thr Asp Arg Ile Leu His Gly Pro Asp Ser Gln
                245                 250                 255
Gln Ala Phe Ser Gln Trp Ala Glu Ser Leu Leu Asp Tyr Ala Thr Leu
                260                 265                 270
Met Asp Phe Ser Thr Glu Ser Leu Gln Pro Ile Trp Ala Leu Ala Asp
                275                 280                 285
Lys Pro Glu Arg Arg Val Glu Leu Glu Asp Ala Phe Pro Glu Phe Met
                290                 295                 300
Lys Gln Ser Gln Gln Ser Ile Pro Lys Val Asp Lys Val Leu Leu Met
305                 310                 315                 320
Asp Ala Arg Pro Pro Met Val Lys Ala Gly Glu Asp Ser Gly Ser Gly
                325                 330                 335
Ala Ser Glu Asp Leu Ala Val Phe Asn Pro Ser Thr Ser Asn Gly Tyr
                340                 345                 350
Lys Met Val Gly Gln Phe Gly Gln Arg Asn His Ala Ser Val Ala Asp
                355                 360                 365
Gly His Ala Pro Ile Phe Lys Asp Leu Phe Asp Leu Gly Val Leu Lys
                370                 375                 380
Ala Pro Val Gly Trp Gln Arg Val Trp Asp Asp Ala Gly Ser Gly Lys
385                 390                 395                 400
Ser Lys Asp Tyr Ala Cys Trp Arg Ala Ile Pro Pro Gln Gly Tyr Arg
                405                 410                 415
Ala Leu Gly Asp Val Met Met Leu Ala Thr Ser Gly Tyr Asn Pro Pro
                420                 425                 430
```

```
Asn Leu Pro Asp Tyr Val Cys Val His Gln Ser Leu Cys Ala Asp Val
        435                 440                 445
Gln Thr Leu Gln Asn Arg Val Trp Leu Trp Asp Lys Gly Thr Gly Ala
    450                 455                 460
Arg Lys Asp Val Ser Leu Trp Gln Pro Gly Ala Ala Gly Ala Val Ala
465                 470                 475                 480
Ser Ser Cys Phe Ala Gly Val Pro Asn Tyr Asn Asn Pro Pro Asn Ser
            485                 490                 495
Gly Asp Ile Glu Arg Leu Arg Gly Ser Ile Ala Cys Val Lys Thr Ser
        500                 505                 510
Ala Ile Ala Ser Met Gln Glu Met Lys Ser Met Leu Ser Gln His Gln
    515                 520                 525
Gly Met Glu Ala Met Met Ser Lys Leu
    530                 535
```

<210> SEQ ID NO 68
<211> LENGTH: 1614
<212> TYPE: DNA
<213> ORGANISM: Artificial Sequence
<220> FEATURE:
<223> OTHER INFORMATION: eAxmi205 #33 mutant

<400> SEQUENCE: 68

```
atggcatccg cagcaaatgc aggtcagctt ggcaacctcc ccggcgttac ttctatgggc      60
atgggctatg acgtgaatgg tttgtacgcc agcccggaaa gcctgcttgg ccaacccttg     120
ttcgatttcg gcggcgagct ggacagcatc gaaatcgagg ccgcagcta caccttttccc     180
cgcagcatgc atgtacacac ctatttccat tccgacttca acaggatgt cagcaaggaa     240
atcgaagagt atcgggagaa aatgagccag cacgtgggcg tgtccggccg ctacaagttg     300
ttcagcgctt cgctgagcgt ggatttcacc accacggacc agcaactgac cgagattacc     360
tacagctcca cccgcgaagc ccatgtgctg tggtacatca gcctgcctgg cgcggccacg     420
ctgcgttcga tgctgcgccg cgatttccgc gacgacctga caaccccaa tatgccggcc     480
atggagctgt tcaagcgcta tggtccctac tacatatcgg aagcggcggt gggcggccgg     540
ctggactaca gcgcggccag caagaccttg aagatggaca gccagccagtc gctgtccacc     600
accgccgaaa tgtcctacaa ggcgctggtg gcgagatca agatcgagca tggctcggag     660
atggaaaagc aggtcaacag cttccgcagc aactccacca tccgtctcac cgccaccggc     720
ggcaagccgg gcatgaccga tcgcatactg cacggtccgg attcgcagca ggcgttctcg     780
caatgggcgg aatcgctgct cgactatgcg acgctgatgg acttttccac cgaaaagcctg     840
caaccgatct gggcgctggc cgacaagccc gagcgccgcg tcgagcttga ggacgccttc     900
cccgaattca tgaagcagtc gcagcagtcc atccccaagg tggacaaggt gctgctgatg     960
gacgcgcggc cgcctatggt gaaggctggg gaggatagcg gctccggcgc gtcggaggat    1020
ctggctgtgt tcaatcccag cacctccaat ggctacaaga tggttggcca gttcggtcag    1080
cgcaaccatg ccagcgtggc ggatggccat gcgccgattt tcaaggatct gttcgatctg    1140
ggcgtgctga aggcgccggt gggttggcag cgggtgtggg acgacgccgg ctccggcaag    1200
tccaaggact acgcgtgctg gcgcgcgatt ccgccgcagg gctaccgcgc gctgggcgat    1260
gtgatgatgc tggccaccag cggctataac ccgccgaatc tgccggacta tgtttgcgtg    1320
catcaaagcc tgtgcgcgga tgtgcagacg ctgcaaaacc gggtgtggct gtgggacaag    1380
ggcaccggcg cgcgcaagga tgtcagcctg tggcaaccgg gcgcggccgg cgcggtggcg    1440
```

```
tcctcttgct cgccggcgt gcctaattac aacaacccgc ccaattccgg cgacatcgag    1500
cgcttgcgcg gcagcatcgc atgcgtgaag accagcgcga tcgcgtccat gcaggaaatg    1560
aagtccatgc tcagccagca ccaaggcatg gaagcgatga tgtccaagct gtga          1614
```

<210> SEQ ID NO 69
<211> LENGTH: 537
<212> TYPE: PRT
<213> ORGANISM: Artificial Sequence
<220> FEATURE:
<223> OTHER INFORMATION: eAxmi205 #34 mutant

<400> SEQUENCE: 69

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
    130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
        195                 200                 205

Leu Val Gly Glu Ile Lys Ile Glu His Gly Ser Glu Met Glu Lys Gln
    210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
        275                 280                 285

Lys Pro Glu Arg Arg Val Glu Leu Glu Asp Ala Phe Pro Glu Phe Met
    290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
                325                 330                 335
```

Ala Ser Glu Asp Leu Ala Val Phe Asn Pro Ser Thr Ser Asn Gly Tyr
            340                 345                 350

Lys Met Val Gly Gln Phe Gly Gln Arg Asn His Ala Ser Val Ala Asp
            355                 360                 365

Gly His Ala Pro Ile Phe Lys Asp Leu Phe Asp Leu Gly Val Leu Lys
        370                 375                 380

Ala Pro Val Gly Trp Gln Arg Val Trp Asp Ala Gly Ser Gly Lys
385                 390                 395                 400

Ser Lys Asp Tyr Ala Cys Trp Arg Ala Ile Pro Pro Gln Gly Tyr Arg
                405                 410                 415

Ala Leu Gly Asp Val Met Met Leu Ala Thr Ser Gly Tyr Asn Pro Pro
            420                 425                 430

Asn Leu Pro Asp Tyr Val Cys Val His Gln Ser Leu Cys Ala Asp Val
            435                 440                 445

Gln Thr Leu Gln Asn Arg Val Trp Trp Asp Lys Gly Thr Gly Ala Arg
        450                 455                 460

Lys Asp Val Ser Leu Trp Gln Pro Gly Ala Ala Leu Gly Ala Val Ala
465                 470                 475                 480

Ser Ser Cys Phe Ala Gly Val Pro Asn Tyr Asn Asn Pro Pro Asn Ser
                485                 490                 495

Gly Asp Ile Glu Arg Leu Arg Gly Ser Ile Ala Cys Val Lys Thr Ser
            500                 505                 510

Ala Ile Ala Ser Met Gln Glu Met Lys Ser Met Leu Ser Gln His Gln
            515                 520                 525

Gly Met Glu Ala Met Met Ser Lys Leu
        530                 535

<210> SEQ ID NO 70
<211> LENGTH: 1614
<212> TYPE: DNA
<213> ORGANISM: Artificial Sequence
<220> FEATURE:
<223> OTHER INFORMATION: eAxmi205 #34 mutant

<400> SEQUENCE: 70
atggcatccg cagcaaatgc aggtcagctt ggcaaccttc ccggcgttac ttctatgggc    60
atgggctatg acgtgaatgg tttgtacgcc agcccggaaa gcctgcttgg ccaacccttg   120
ttcgatttcg gcggcgagct ggacagcatc gaaatcgagg ccgcagcta caccttcc     180 cgcagcatgc atgtacacac ctatttccat tccgacttca acaggatgt cagcaaggaa    240 atcgaagagt atcgggagaa atgagccag cacgtgggcg tgtccggccg ctacaagttg    300
ttcagcgctt cgctgagcgt ggatttcacc accacggacc agcaactgac cgagattacc    360
tacagctcca cccgcgaagc ccatgtgctg tggtacatca gcctgcctgg cgcggccacg    420
ctgcgttcga tgctgcgccg cgatttccgc gacgacctga caaccccaa tatgccggcc    480 atggagctgt tcaagcgcta tggtccctac tacatatcgg aagcggcggt gggcggccgg    540
ctggactaca gcgcggccag caagaccttg aagatggaca gcagccagtc gctgtccacc    600
accgccgaaa tgtcctacaa ggcgctggtg ggcgagatca gatcgagca tggctcggag    660 atggaaaagc aggtcaacag cttccgcagc aactccacca tccgtctcac cgccaccggc    720
ggcaagccgg gcatgaccga tcgcatactg cacggtccgg attcgcagca ggcgttctcg    780
caatgggcgg aatcgctgct cgactatgcg acgctgatgg acttttccac cgaaagcctg    840
caaccgatct gggcgctggc cgacaagccc gagcgccgcg tcgagcttga ggacgccttc    900

```
cccgaattca tgaagcagtc gcagcagtcc atccccaagg tggacaaggt gctgctgatg    960
gacgcgcggc cgcctatggt gaaggctggg gaggatagcg gctccggcgc gtcggaggat   1020
ctggctgtgt tcaatcccag cacctccaat ggctacaaga tggttggcca gttcggtcag   1080
cgcaaccatg ccagcgtggc ggatggccat gcgccgattt tcaaggatct gttcgatctg   1140
ggcgtgctga aggcgccggt gggttggcag cgggtgtggg acgacgccgg ctccggcaag   1200
tccaaggact acgcgtgctg gcgcgcgatt ccgccgcagg gctaccgcgc gctgggcgat   1260
gtgatgatgc tggccaccag cggctataac ccgccgaatc tgccggacta tgtttgcgtg   1320
catcaaagcc tgtgcgcgga tgtgcagacg ctgcaaaaacc gggtgtggtg ggacaagggc   1380
accggcgcgc gcaaggatgt cagcctgtgg caaccgggcg cggccctggg cgcggtggcg   1440
tcctcttgct cgccggcgt gcctaattac aacaacccgc ccaattccgg cgacatcgag   1500
cgcttgcgcg gcagcatcgc atgcgtgaag accagcgcga tcgcgtccat gcaggaaatg   1560
aagtccatgc tcagccagca ccaaggcatg gaagcgatga tgtccaagct gtga          1614
```

<210> SEQ ID NO 71
<211> LENGTH: 537
<212> TYPE: PRT
<213> ORGANISM: Artificial Sequence
<220> FEATURE:
<223> OTHER INFORMATION: eAxmi205 #35 mutant

<400> SEQUENCE: 71

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
    130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
        195                 200                 205

Leu Val Gly Glu Ile Lys Ile Glu His Gly Ser Glu Met Glu Lys Gln
    210                 215                 220

Val Asn Ser Phe Arg Ser Asn Ser Thr Ile Arg Leu Thr Ala Thr Gly
225                 230                 235                 240
```

```
Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
        275                 280                 285

Lys Pro Glu Arg Arg Val Glu Leu Gly Asp Ala Phe Pro Glu Phe Met
    290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
                325                 330                 335

Ala Ser Glu Asp Leu Ala Val Phe Asn Pro Ser Thr Ser Asn Gly Tyr
            340                 345                 350

Lys Met Val Gly Gln Phe Gly Gln Arg Asn His Ala Ser Val Ala Leu
        355                 360                 365

Asp Gly His Ala Pro Ile Phe Lys Asp Leu Phe Asp Leu Gly Val Leu
    370                 375                 380

Lys Ala Pro Val Gly Trp Gln Arg Val Trp Asp Asp Ala Gly Ser Gly
385                 390                 395                 400

Lys Ser Lys Asp Tyr Ala Cys Trp Arg Ala Ile Pro Pro Gln Gly Tyr
                405                 410                 415

Arg Ala Leu Gly Asp Val Met Met Leu Ala Thr Ser Gly Tyr Asn Pro
            420                 425                 430

Pro Asn Leu Pro Asp Tyr Val Cys Val His Gln Ser Leu Cys Ala Asp
        435                 440                 445

Val Gln Thr Leu Gln Asn Arg Val Trp Trp Asp Lys Gly Thr Gly Ala
    450                 455                 460

Arg Lys Asp Val Ser Leu Trp Gln Pro Gly Ala Ala Gly Ala Val Ala
465                 470                 475                 480

Ser Ser Cys Phe Ala Gly Val Pro Asn Tyr Asn Asn Pro Pro Asn Ser
                485                 490                 495

Gly Asp Ile Glu Arg Leu Arg Gly Ser Ile Ala Cys Val Lys Thr Ser
            500                 505                 510

Ala Ile Ala Ser Met Gln Glu Met Lys Ser Met Leu Ser Gln His Gln
        515                 520                 525

Gly Met Glu Ala Met Met Ser Lys Leu
    530                 535

<210> SEQ ID NO 72
<211> LENGTH: 1614
<212> TYPE: DNA
<213> ORGANISM: Artificial Sequence
<220> FEATURE:
<223> OTHER INFORMATION: eAxmi205 #35 mutant

<400> SEQUENCE: 72
atggcatccg cagcaaatgc aggtcagctt ggcaaccctc ccggcgttac ttctatgggc    60
atgggctatg acgtgaatgg tttgtacgcc agcccggaaa gcctgcttgg ccaacccttg   120
ttcgatttcg gcggcgagct ggacagcatc gaaatcgagg ccgcagcta cacctttccc    180 cgcagcatgc atgtacacac ctatttccat tccgacttca acaggatgt cagcaaggaa    240 atcgaagagt atcgggagaa aatgagccag cacgtgggcg tgtccggccg ctacaagttg   300
ttcagcgctt cgctgagcgt ggatttcacc accacggacc agcaactgac cgagattacc   360
```

```
tacagctcca cccgcgaagc ccatgtgctg tggtacatca gcctgcctgg cgcggccacg    420
ctgcgttcga tgctgcgccg cgatttccgc gacgacctga caacccccaa tatgccggcc    480
atggagctgt tcaagcgcta tggtccctac tacatatcgg aagcggcggt gggcggccgg    540
ctggactaca gcgcggccag caagaccttg aagatggaca gcagccagtc gctgtccacc    600
accgccgaaa tgtcctacaa ggcgctggtg ggcgagatca agatcgagca tggctcggag    660
atggaaaagc aggtcaacag cttccgcagc aactccacca tccgtctcac cgccaccggc    720
ggcaagccgg gcatgaccga tcgcatactg cacggtccgg attcgcagca ggcgttctcg    780
caatgggcga atcgctgctc gactatgcga cgctgatgg acttttccac cgaaagcctg    840
caaccgatct gggcgctggc cgacaagccc gagcgccgcg tcgagcttga ggacgccttc    900
cccgaattca tgaagcagtc gcagcagtcc atccccaagg tggacaaggt gctgctgatg    960
gacgcgcggc cgcctatggt gaaggctggg gaggatagcg gctccggcgc gtcggaggat   1020
ctggctgtgt tcaatcccag cacctccaat ggctacaaga tggttggcca gttcggtcag   1080
cgcaaccatg ccagcgtggc gctggatggc catgcgccga ttttcaagga tctgttcgat   1140
ctgggcgtgc tgaaggcgcc ggtgggttgg cagcgggtgt gggacgacgc cggctccggc   1200
aagtccaagg actacgcgtg ctggcgcgcg attccgccgc agggctaccg cgcgctgggc   1260
gatgtgatga tgctggccac cagcggctat aacccgccga atctgccgga ctatgtttgc   1320
gtgcatcaaa gcctgtgcgc ggatgtgcag acgctgcaaa accgggtgtg gtgggacaag   1380
ggcaccggcg cgcgcaagga tgtcagcctg tggcaaccgg gcgcggccgg cgcggtggcg   1440
tcctcttgct tcgccggcgt gcctaattac aacaacccgc ccaattccgg cgacatcgag   1500
cgcttgcgcg gcagcatcgc atgcgtgaag accagcgcga tcgcgtccat gcaggaaatg   1560
aagtccatgc tcagccagca ccaaggcatg gaagcgatga tgtccaagct gtga          1614
```

<210> SEQ ID NO 73
<211> LENGTH: 537
<212> TYPE: PRT
<213> ORGANISM: Artificial Sequence
<220> FEATURE:
<223> OTHER INFORMATION: eAxmi205 #36 mutant

<400> SEQUENCE: 73

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
    130                 135                 140
```

Leu Arg Arg Asp Phe Arg Asp Leu Asn Asn Pro Asn Met Pro Ala
145                 150                 155                 160

Met Glu Leu Phe Lys Arg Tyr Gly Pro Tyr Tyr Ile Ser Glu Ala Ala
            165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
            195                 200                 205

Leu Val Gly Glu Ile Lys Ile Glu His Gly Ser Glu Met Glu Lys Gln
210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
            245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
            275                 280                 285

Lys Pro Glu Arg Arg Val Glu Leu Glu Asp Ala Phe Pro Glu Phe Met
290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
            325                 330                 335

Ala Ser Glu Asp Leu Ala Val Phe Asn Pro Ser Thr Ser Asn Gly Tyr
            340                 345                 350

Lys Met Val Gly Gln Phe Gly Gln Arg Asn His Ala Ser Val Ala Asp
            355                 360                 365

Gly His Ala Pro Ile Phe Lys Asp Leu Phe Asp Leu Gly Val Leu Lys
370                 375                 380

Ala Pro Val Gly Trp Gln Arg Val Trp Asp Asp Ala Gly Ser Gly Lys
385                 390                 395                 400

Ser Lys Asp Tyr Ala Cys Trp Arg Ala Ile Pro Pro Gln Gly Tyr Arg
            405                 410                 415

Ala Leu Gly Asp Val Met Met Leu Ala Thr Ser Gly Tyr Asn Pro Pro
            420                 425                 430

Asn Leu Pro Asp Tyr Val Cys Val His Gln Ser Leu Cys Ala Asp Val
            435                 440                 445

Gln Thr Leu Gln Asn Arg Val Trp Trp Asp Lys Gly Thr Gly Ala Arg
450                 455                 460

Lys Asp Val Ser Leu Trp Gln Pro Gly Ala Ala Gly Ala Val Ala Ser
465                 470                 475                 480

Ser Cys Phe Ala Gly Val Pro Asn Tyr Asn Asn Pro Asn Ser Gly
            485                 490                 495

Leu Asp Ile Glu Arg Leu Arg Gly Ser Ile Ala Cys Val Lys Thr Ser
            500                 505                 510

Ala Ile Ala Ser Met Gln Glu Met Lys Ser Met Leu Ser Gln His Gln
            515                 520                 525

Gly Met Glu Ala Met Met Ser Lys Leu
            530                 535

<210> SEQ ID NO 74
<211> LENGTH: 1614

<212> TYPE: DNA
<213> ORGANISM: Artificial Sequence
<220> FEATURE:
<223> OTHER INFORMATION: eAxmi205 #36 mutant

<400> SEQUENCE: 74

| | | | | | |
|---|---|---|---|---|---|
| atggcatccg | cagcaaatgc | aggtcagctt | ggcaacctcc | ccggcgttac | ttctatgggc | 60 |
| atgggctatg | acgtgaatgg | tttgtacgcc | agcccggaaa | gcctgcttgg | ccaacccttg | 120 |
| ttcgatttcg | gcggcgagct | ggacagcatc | gaaatcgagg | gccgcagcta | cacctttccc | 180 |
| cgcagcatgc | atgtacacac | ctatttccat | tccgacttca | acaggatgt | cagcaaggaa | 240 |
| atcgaagagt | atcgggagaa | aatgagccag | acgtgggcg | tgtccggccg | ctacaagttg | 300 |
| ttcagcgctt | cgctgagcgt | ggatttcacc | accacggacc | agcaactgac | cgagattacc | 360 |
| tacagctcca | cccgcgaagc | ccatgtgctg | tggtacatca | gctgcctgg | cgcggccacg | 420 |
| ctgcgttcga | tgctgcgccg | cgatttccgc | gacgacctga | caacccaa | tatgccggcc | 480 |
| atggagctgt | tcaagcgcta | tggtccctac | tacatatcgg | aagcggcggt | gggcggccgg | 540 |
| ctggactaca | gcgcggccag | caagaccttg | aagatggaca | gcagccagtc | gctgtccacc | 600 |
| accgccgaaa | tgtcctacaa | ggcgctggtg | gcgagatca | agatcgagca | tggctcggag | 660 |
| atggaaaagc | aggtcaacag | cttccgcagc | aactccacca | tccgtctcac | cgccaccggc | 720 |
| ggcaagccgg | gcatgaccga | tcgcatactg | cacggtccgg | attcgcagca | ggcgttctcg | 780 |
| caatgggcgg | aatcgctgct | cgactatgcg | acgctgatgg | acttttccac | cgaaagcctg | 840 |
| caaccgatct | gggcgctggc | cgacaagccc | gagcgccgcg | tcgagcttga | ggacgccttc | 900 |
| cccgaattca | tgaagcagtc | gcagcagtcc | atccccaagg | tggacaaggt | gctgctgatg | 960 |
| gacgcgcggc | cgcctatggt | gaaggctggg | gaggatagcg | gctccggcgc | gtcggaggat | 1020 |
| ctggctgtgt | tcaatcccag | cacctccaat | ggctacaaga | tggttggcca | gttcggtcag | 1080 |
| cgcaaccatg | ccagcgtggc | ggatggccat | gcgccgattt | tcaaggatct | gttcgatctg | 1140 |
| ggcgtgctga | aggcgccggt | gggttggcag | cgggtgtggg | acgacgccgg | ctccggcaag | 1200 |
| tccaaggact | acgcgtgctg | gcgcgcgatt | ccgccgcagg | gctaccgcgc | gctgggcgat | 1260 |
| gtgatgatgc | tggccaccag | cggctataac | cgccgaatc | tgccggacta | tgtttgcgtg | 1320 |
| catcaaagcc | tgtgcgcgga | tgtgcagacg | ctgcaaaacc | gggtgtggtg | gacaagggc | 1380 |
| accggcgcgc | gcaaggatgt | cagcctgtgg | caaccgggcg | cggccggcgc | ggtggcgtcc | 1440 |
| tcttgcttcg | ccggcgtgcc | taattacaac | aacccgccca | attccggcct | ggacatcgag | 1500 |
| cgcttgcgcg | gcagcatcgc | atgcgtgaag | accagcgcga | tcgcgtccat | gcaggaaatg | 1560 |
| aagtccatgc | tcagccagca | ccaaggcatg | gaagcgatga | tgtccaagct | gtga | 1614 |

<210> SEQ ID NO 75
<211> LENGTH: 1614
<212> TYPE: DNA
<213> ORGANISM: Artificial Sequence
<220> FEATURE:
<223> OTHER INFORMATION: Maize optimized eAxmi205 #23 mutant

<400> SEQUENCE: 75

| | | | | | |
|---|---|---|---|---|---|
| atggcctctg | ctgccaacgc | tggacaactc | ggcaacctac | caggtgtgac | ttccatgggc | 60 |
| atgggatacg | acgtaaatgg | cctttatgct | tctcctgaga | gcttgctggg | gcagccgctc | 120 |
| tttgacttcg | gcggcgaatt | ggattcaatc | gagatagaag | gaagaagcta | cacctttcca | 180 |
| agaagcatgc | atgttcacac | ctacttccat | tcagatttca | gcaagatgt | cagcaaagaa | 240 |

```
attgaggaat atcgagaaaa aatgagccag catgttggag tttctggaag atacaagctc      300
ttctccgcct ccctctccgt ggacttcacc accactgatc agcagctgac agagatcacc      360
tacagctcaa caagagaagc tcatgttctc tggtacatct cattgccagg agctgctacc      420
ttgcgatcaa tgctgcgccg cgacttcaga gatgatctca acaacccaa catgccggcc       480 atggagctct tcaagagata tggcccctac tacatctcag aagctgctgt tggaggaagg      540
ctggactaca gcgccgccag caagaccttg aagatggaca gcagccaaag cctctccacc      600
accgccgaga tgagctataa agctttggtg ggagagatca agattgagca tggatcagag      660
atggagaagc aggtgaacag cttcagatca aattcaacca ttcgattgac ggccactgga      720
ggaaagccag ggatgacaga caggatcctt cacggcccgg actcacagca ggctttctcc      780
caatgggcgg agagcttgct ggattatgcc accttgatgg acttctcaac agaaagcctc      840
cagcccatct gggcgctcgc cgacaagcca gaaagaaggg tggagctgga ggatgccttc      900
cctgagttca tgaagcaaag tcagcagagc atccccaagg tggacaaggt gttgttgatg      960
gatgcacgac caccaatggt taaagccggc gaggactcag gctctggcgc gtcagaggac     1020
ttggcggtgt tcaaccccte caccagcaat ggctacaaga tggtgggcca gtttggccaa     1080
cgaaatcacg cgagcgtcgc tgacggccat gctccaatct tcaaagatct ctttgacttg     1140
ggagtcctga aagcgccagt cggatggcag cgcgtctggg atgatgctgg atcagggaag     1200
agcaaggatt atgcttgctg gagggccatc cctcctcaag gctacagagc tcttggagat     1260
gtcatgatgc tggccaccte aggctacaac cctccaaatc ttccagatta tgtttgtgtt     1320
catcaaagcc tctgtgctga tgttcaaacc ctccagaaca gggtttggtg ggacaaagga     1380
actggagcaa ggaaggatgt cagcttgtgg cagcctggag ctgctggagc tgtagcaagc     1440
agctgctttg ctggagttcc aaactacaac aaccctccaa actcaggaga cattgagagg     1500
ctgagaggaa gcattgccag cgtcaagacc tccgccatcg cgtcaatgca ggagatgaag     1560
tcaatgctct cccagcatca agggatggag gccatgatga gcaagctgta gtaa           1614
```

<210> SEQ ID NO 76
<211> LENGTH: 1614
<212> TYPE: DNA
<213> ORGANISM: Artificial Sequence
<220> FEATURE:
<223> OTHER INFORMATION: Maize optimized eAxmi205 #28 mutant

<400> SEQUENCE: 76

```
atggcctctg ctgccaacgc tggacaactc ggcaacctac caggtgtgac ttccatgggc       60
atgggatacg acgtaaatgg cctttatgct tctcctgaga gcttgctggg gcagccgctc      120
tttgacttcg gcggcgaatt ggattcaatc gagatagaag gaagaagcta caccttccca      180
agaagcatgc atgttcacac ctacttccat tcagatttca agcaagatgt cagcaaagaa      240
attgaggaat atcgagaaaa aatgagccag catgttggag tttctggaag atacaagctc      300
ttctccgcct ccctctccgt ggacttcacc accactgatc agcagctgac agagatcacc      360
tacagctcaa caagagaagc tcatgttctc tggtacatct cattgccagg agctgctacc      420
ttgcgatcaa tgctgcgccg cgacttcaga gatgatctca acaacccaa catgccggcc       480 atggagctct tcaagagata tggcccctac tacatctcag aagctgctgt tggaggaagg      540
ctggactaca gcgccgccag caagaccttg aagatggaca gcagccaaag cctctccacc      600
accgccgaga tgagctataa agctttggtg ggagagatca agattgagca tggatcagag      660
atggagaagc aggtgaacag cttcagatca aattcaacca ttcgattgac ggccactgga      720
```

```
ggaaagccag ggatgacaga caggatcctt cacggcccgg actcacagca ggctttctcc    780
caatgggcgg agagcttgct ggattatgcc accttgatgg acttctcaac agaaagcctc    840
cagcccatct gggcgctcgc cgacaagcca gaaagaaggg tggagctgga ggatgccttc    900
cctgagttca tgaagcaaag tcagcagagc atccccaagg tggacaaggt gttgttgatg    960
gatgcacgac caccaatggt taaagccggc gaggactcag gctctggcgc gtcagaggac   1020
ttggcggtgt tcaaccccctc caccagcaat ggctacaaga tggtgggcca gtttggccaa   1080
cgaaatcacg cgagcgtcgc tgacggccat gctccaatct tcaaagatct ctttgacttg   1140
ggagtcctga agcgccagt cggatggcag cgcgtctggg atgatgctgg atcagggaag   1200
agcaaggatt atgcttgctg gagggccatc cctcctcaag gctacagagc tcttggagat   1260
gtcagcttgc tggccaccct aggctacaac cctccaaatc ttccagatta tgtttgtgtt   1320
catcaaagcc tctgtgctga tgttcaaacc ctccagaaca gggtttggtg gacaaagga   1380 actggagcaa ggaaggatgt cagcttgtgg cagcctggag ctgctggagc tgtagcaagc   1440
agctgctttg ctggagttcc aaactacaac aaccctccaa actcaggaga cattgagagg   1500
ctgagaggaa gcattgcctg cgtcaagacc tccgccatcg cgtcaatgca ggagatgaag   1560
tcaatgctct cccagcatca agggatggag gccatgatga gcaagctgta gtaa         1614
```

<210> SEQ ID NO 77
<211> LENGTH: 1617
<212> TYPE: DNA
<213> ORGANISM: Artificial Sequence
<220> FEATURE:
<223> OTHER INFORMATION: Maize optimized eAxmi205 #34 mutant

<400> SEQUENCE: 77

```
atggcctctg ctgccaacgc tggacaactc ggcaacctac caggtgtgac ttccatgggc     60
atgggatacg acgtaaatgg cctttatgct tctcctgaga gcttgctggg gcagccgctc    120
tttgacttcg gcggcgaatt ggattcaatc gagatagaag gaagaagcta caccttccca    180
agaagcatgc atgttcacac ctacttccat tcagatttca gcaagatgt cagcaaagaa    240 attgaggaat atcgagaaaa aatgagccag catgttggag tttctggaag atacaagctc    300
ttctccgcct ccctctccgt ggacttcacc accactgatc agcagctgac agagatcacc    360
tacagctcaa caagagaagc tcatgttctc tggtacatct cattgccagg agctgctacc    420
ttgcgatcaa tgctgcgccg cgacttcaga gatgatctca acaaccccaa catgccggcc    480
atggagctct tcaagagata tggcccctac tacatctcag aagctgctgt tggaggaagg    540
ctggactaca gcgccgccag caagaccttg aagatggaca gcagccaaag cctctccacc    600
accgccgaga tgagctataa agcttttggtg ggagagatca agattgagca tggatcagag    660
atggagaagc aggtgaacag cttcagatca aattcaacca ttcgattgac ggccactgga    720
ggaaagccag ggatgacaga caggatcctt cacggcccgg actcacagca ggctttctcc    780
caatgggcgg agagcttgct ggattatgcc accttgatgg acttctcaac agaaagcctc    840
cagcccatct gggcgctcgc cgacaagcca gaaagaaggg tggagctgga ggatgccttc    900
cctgagttca tgaagcaaag tcagcagagc atccccaagg tggacaaggt gttgttgatg    960
gatgcacgac caccaatggt taaagccggc gaggactcag gctctggcgc gtcagaggac   1020
ttggcggtgt tcaaccccctc caccagcaat ggctacaaga tggtgggcca gtttggccaa   1080
cgaaatcacg cgagcgtcgc tgacggccat gctccaatct tcaaagatct ctttgacttg   1140
```

```
ggagtcctga aagcgccagt cggatggcag cgcgtctggg atgatgctgg atcagggaag    1200
agcaaggatt atgcttgctg gagggccatc cctcctcaag gctacagagc tcttggagat    1260
gtcatgatgc tggccacctc aggctacaac cctccaaatc ttccagatta tgtttgtgtt    1320
catcaaagcc tctgtgctga tgttcaaacc ctccagaaca gggtttggtg ggacaaagga    1380
actggagcaa ggaaggatgt cagcttgtgg cagcctggag ctgctctggg agctgtagca    1440
agcagctgct ttgctggagt tccaaactac aacaaccctc caaactcagg agacattgag    1500
aggctgagag aagcattgc ctgcgtcaag acctccgcca tcgcgtcaat gcaggagatg    1560
aagtcaatgc tctcccagca tcaagggatg gaggccatga tgagcaagct gtagtaa        1617
```

```
<210> SEQ ID NO 78
<211> LENGTH: 1611
<212> TYPE: DNA
<213> ORGANISM: Artificial Sequence
<220> FEATURE:
<223> OTHER INFORMATION: eAxmi205 #5D

<400> SEQUENCE: 78
```

```
atggcatccg cagcaaatgc aggtcagctt ggcaacctcc ccggcgttac ttctatgggc     60
atgggctatg acgtgaatgg tttgtacgcc agcccggaaa gctgcttgg ccaacccttg     120 ttcgatttcg gcggcgagct ggacagcatc gaaatcgagg ccgcagcta cacctttccc     180 cgcagcatgc atgtacacac ctatttccat tccgacttca acaggatgt cagcaaggaa    240 atcgaagagt atcgggagaa atgagccag cacgtgggcg tgtccggccg ctacaagttg     300
ttcagcgctt cgctgagcgt ggatttcacc accacgggacc agcaactgac cgagattacc    360
tacagctcca cccgcgaagc ccatgtgctg tggtacatca gcctgcctgg cgcggccacg    420
ctgcgttcga tgctgcgccg cgatttccgc gacgacctga caacccccaa tatgccggcc    480
atggagctgt tcaagcgcta tggtccctac tacatatcgg aagcggcggt gggcggccgg    540
ctggactaca gcgcggccag caagaccttg aagatggaca gcagccagtc gctgtccacc    600
accgccgaaa tgtcctacaa ggcgctggtg gcgagatca agatcgagca tggctcggag    660
atggaaaagc aggtcaacag cttccgcagc aactccacca tccgtctcac cgccaccggc    720
ggcaagccgg gcatgaccga tcgcatactg cacggtccgg attcgcagca ggcgttctcg    780
caatgggcga atcgctgctc gactatgcg acgctgatgg acttttccac cgaaaagcctg    840 caaccgatct gggcgctggc cgacaagccc gagcgccgcg tcgagcttga ggacgccttc    900
cccgaattca tgaagcagtc gcagcagtcc atccccaagg tggacaaggt gctgctgatg    960
gacgcgcggc cgcctatggt gaaggctggg gaggatagcg gctccggcgc gtcggaggat    1020
ctggctgtgt tcaatcccag cacctccaat ggctacaaga tggttggcca gttcggtcag    1080
cgcaaccatg ccagcgtggc ggatggccat gcgccgattt tcaaggatct gttcgatctg    1140
ggcgtgctga ggcgccggt gggttggcag cgggtgtggg acgacgccgg ctccggcaag    1200 tccttgact acgcgtgctg gcgcgcgatt ccgccgcagg gctaccgcgc gctgggcgat    1260
gtgatgatgc tggccaccag cggctataac ccgccgaatc tgccggacta tgtttgcgtg    1320
catcaaagcc tgtgcgcgga tgtgcagacg ctgcaaaacc gggtgtggtg gacaagggc    1380 accggcgcgc gcaaggatgt cagcctgtgg caaccgggcg cggccggcgc ggtggcgtcc    1440
tcttgcttcg ccggcgtgcc taattacaac aacccgccca attccggcga catcgagcgc    1500
ttgcgcggca gcatcgcatg cgtgaagacc agcgcgatcg cgtccatgca ggaaatgaag    1560
tccatgctca gccagcacca aggcatggaa gcgatgatgt ccaagctgtg a               1611
```

<210> SEQ ID NO 79
<211> LENGTH: 536
<212> TYPE: PRT
<213> ORGANISM: Artificial Sequence
<220> FEATURE:
<223> OTHER INFORMATION: eAxmi205 #5D Protein

<400> SEQUENCE: 79

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
    130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
        195                 200                 205

Leu Val Gly Glu Ile Lys Ile Glu His Gly Ser Glu Met Glu Lys Gln
    210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
        275                 280                 285

Lys Pro Glu Arg Arg Val Glu Leu Glu Asp Ala Phe Pro Glu Phe Met
    290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
                325                 330                 335

Ala Ser Glu Asp Leu Ala Val Phe Asn Pro Ser Thr Ser Asn Gly Tyr
            340                 345                 350

Lys Met Val Gly Gln Phe Gly Gln Arg Asn His Ala Ser Val Ala Asp
        355                 360                 365
```

```
Gly His Ala Pro Ile Phe Lys Asp Leu Phe Asp Leu Gly Val Leu Lys
    370                 375                 380

Ala Pro Val Gly Trp Gln Arg Val Trp Asp Asp Ala Gly Ser Gly Lys
385                 390                 395                 400

Ser Asp Asp Tyr Ala Cys Trp Arg Ala Ile Pro Pro Gln Gly Tyr Arg
                405                 410                 415

Ala Leu Gly Asp Val Met Met Leu Ala Thr Ser Gly Tyr Asn Pro Pro
            420                 425                 430

Asn Leu Pro Asp Tyr Val Cys Val His Gln Ser Leu Cys Ala Asp Val
        435                 440                 445

Gln Thr Leu Gln Asn Arg Val Trp Trp Asp Lys Gly Thr Gly Ala Arg
    450                 455                 460

Lys Asp Val Ser Leu Trp Gln Pro Gly Ala Ala Gly Ala Val Ala Ser
465                 470                 475                 480

Ser Cys Phe Ala Gly Val Pro Asn Tyr Asn Asn Pro Pro Asn Ser Gly
                485                 490                 495

Asp Ile Glu Arg Leu Arg Gly Ser Ile Ala Cys Val Lys Thr Ser Ala
            500                 505                 510

Ile Ala Ser Met Gln Glu Met Lys Ser Met Leu Ser Gln His Gln Gly
        515                 520                 525

Met Glu Ala Met Met Ser Lys Leu
    530                 535
```

<210> SEQ ID NO 80
<211> LENGTH: 1611
<212> TYPE: DNA
<213> ORGANISM: Artificial Sequence
<220> FEATURE:
<223> OTHER INFORMATION: eAxmi205 #21F

<400> SEQUENCE: 80

```
atggcatccg cagcaaatgc aggtcagctt ggcaacctcc ccggcgttac ttctatgggc      60
atgggctatg acgtgaatgg tttgtacgcc agcccggaaa gcctgcttgg ccaacccttg     120
ttcgatttcg gcggcgagct ggacagcatc gaaatcgagg ccgcagcta caccttccc      180
cgcagcatgc atgtacacac ctatttccat tccgacttca acaggatgt cagcaaggaa     240
atcgaagagt atcgggagaa aatgagccag cacgtgggcg tgtccggccg ctacaagttg     300
ttcagcgctt cgctgagcgt ggatttcacc accacggacc agcaactgac cgagattacc     360
tacagctcca cccgcgaagc ccatgtgctg tggtacatca gcctgcctgg cgcggccacg     420
ctgcgttcga tgctgcgccg cgatttccgc gacgacctga caaccccaa tatgccggcc     480
atggagctgt tcaagcgcta tggtccctac tacatatcgg aagcggcggt gggcggccgg     540
ctggactaca gcgcggccag caagaccttg aagatggaca gcagccagtc gctgtccacc     600
accgccgaaa tgtcctacaa ggcgctggtg ggcgagatca agatcgagca tggctcggag     660
atggaaaagc aggtcaacag cttccgcagc aactccacca tccgtctcac cgccaccggc     720
ggcaagccgg gcatgaccga tcgcatactg cacggtccgg attcgcagca ggcgttctcg     780
caatgggcgg aatcgctgct cgactatgcg acgctgatgg acttttccac cgaaagcctg     840
caaccgatct gggcgctggc cgacaagccc gagcgccgcg tcgagcttga ggacgccttc     900
cccgaattca tgaagcagtc gcagcagtcc atccccaagg tggacaaggt gctgctgatg     960
gacgcgcggc cgcctatggt gaaggctggg gaggatagcg gctccggcgc gtcgaggat    1020
ctggctgtgt tcaatcccag cacctccaat ggctacaaga tggttggcca gttcggtcag    1080
```

```
cgcaaccatg ccagcgtggc ggatggccat gcgccgattt tcaaggatct gttcgatctg    1140
ggcgtgctga aggcgccggt gggttggcag cgggtgtggg acgacgccgg ctccggcaag    1200
tccaaggact acgcgtgctg gcgcgcgatt ccgccgcagg gctaccgcgc gctgggcgat    1260
gtgatgatgc tggccaccag cggctataac ccgccgaatc tgccggacta tgtttgcgtg    1320
catcaaagcc tgtgcgcgga tgtgcagacg ctgcaaaacc gggtgtggtg ggacaagggc    1380
accggcgcgc gcaaggatgt cagcctgtgg caacccgggcg cggccggcgc ggtggcgtcc    1440 tctttttttcg ccggcgtgcc taattacaac aacccgccca attccggcga catcgagcgc    1500
ttgcgcggca gcatcgcatg cgtgaagacc agcgcgatcg cgtccatgca ggaaatgaag    1560
tccatgctca gccagcacca aggcatggaa gcgatgatgt ccaagctgtg a             1611
```

<210> SEQ ID NO 81
<211> LENGTH: 536
<212> TYPE: PRT
<213> ORGANISM: Artificial Sequence
<220> FEATURE:
<223> OTHER INFORMATION: eAxmi205 #21F Protein

<400> SEQUENCE: 81

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
    130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
        195                 200                 205

Leu Val Gly Glu Ile Lys Ile Glu His Gly Ser Glu Met Glu Lys Gln
    210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
            260                 265                 270
```

Met Asp Phe Ser Thr Glu Ser Leu Gln Pro Ile Trp Ala Leu Ala Asp
        275                 280                 285

Lys Pro Glu Arg Arg Val Glu Leu Glu Asp Ala Phe Pro Glu Phe Met
    290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
            325                 330                 335

Ala Ser Glu Asp Leu Ala Val Phe Asn Pro Ser Thr Ser Asn Gly Tyr
        340                 345                 350

Lys Met Val Gly Gln Phe Gly Gln Arg Asn His Ala Ser Val Ala Asp
        355                 360                 365

Gly His Ala Pro Ile Phe Lys Asp Leu Phe Asp Leu Gly Val Leu Lys
    370                 375                 380

Ala Pro Val Gly Trp Gln Arg Val Trp Asp Asp Ala Gly Ser Gly Lys
385                 390                 395                 400

Ser Lys Asp Tyr Ala Cys Trp Arg Ala Ile Pro Pro Gln Gly Tyr Arg
            405                 410                 415

Ala Leu Gly Asp Val Met Met Leu Ala Thr Ser Gly Tyr Asn Pro Pro
        420                 425                 430

Asn Leu Pro Asp Tyr Val Cys Val His Gln Ser Leu Cys Ala Asp Val
        435                 440                 445

Gln Thr Leu Gln Asn Arg Val Trp Trp Asp Lys Gly Thr Gly Ala Arg
    450                 455                 460

Lys Asp Val Ser Leu Trp Gln Pro Gly Ala Gly Ala Val Ala Ser
465                 470                 475                 480

Ser Phe Phe Ala Gly Val Pro Asn Tyr Asn Asn Pro Pro Asn Ser Gly
            485                 490                 495

Asp Ile Glu Arg Leu Arg Gly Ser Ile Ala Cys Val Lys Thr Ser Ala
        500                 505                 510

Ile Ala Ser Met Gln Glu Met Lys Ser Met Leu Ser Gln His Gln Gly
        515                 520                 525

Met Glu Ala Met Met Ser Lys Leu
    530                 535

<210> SEQ ID NO 82
<211> LENGTH: 1611
<212> TYPE: DNA
<213> ORGANISM: Artificial Sequence
<220> FEATURE:
<223> OTHER INFORMATION: eAxmi205 #21D

<400> SEQUENCE: 82
atggcatccg cagcaaatgc aggtcagctt ggcaacctcc ccggcgttac ttctatgggc      60
atgggctatg acgtgaatgg tttgtacgcc agcccggaaa gcctgcttgg ccaacccttg     120
ttcgatttcg gcggcgagct ggacagcatc gaaatcgagg ccgcagctac cacctttccc     180
cgcagcatgc atgtacacac ctatttccat tccgacttca acaggatgtg cagcaaggaa     240
atcgaagagt atcgggagaa aatgagccag cacgtgggcg tgtccggccg ctacaagttg     300
ttcagcgctt cgctgagcgt ggatttcacc accacggacc agcaactgac cgagattacc     360
tacagctcca cccgcgaagc ccatgtgctg tggtacatca gcctgcctgg cgcggccacg     420
ctgcgttcga tgctgcgccg cgattccgc gacgacctga caacccccaa tatgccggcc     480
atggagctgt tcaagcgcta tggtccctac tacatatcgg aagcggcggt gggcggccgg     540

```
ctggactaca gcgcggccag caagaccttg aagatggaca gcagccagtc gctgtccacc      600
accgccgaaa tgtcctacaa ggcgctggtg ggcgagatca agatcgagca tggctcggag      660
atggaaaagc aggtcaacag cttccgcagc aactccacca tccgtctcac cgccaccggc      720
ggcaagccgg gcatgaccga tcgcatactg cacggtccgg attcgcagca ggcgttctcg      780
caatgggcgg aatcgctgct cgactatgcg acgctgatgg acttttccac cgaaagcctg      840
caaccgatct gggcgctggc cgacaagccc gagcgccgcg tcgagcttga ggacgccttc      900
cccgaattca tgaagcagtc gcagcagtcc atccccaagg tggacaaggt gctgctgatg      960
gacgcgcggc cgcctatggt gaaggctggg gaggatagcg gctccggcgc gtcggaggat     1020
ctggctgtgt tcaatcccag cacctccaat ggctacaaga tggttggcca gttcggtcag     1080
cgcaaccatg ccagcgtggc ggatggccat gcgccgattt tcaaggatct gttcgatctg     1140
ggcgtgctga aggcgccggt gggttggcag cgggtgtggg acgacgccgg ctccggcaag     1200
tccaaggact acgcgtgctg gcgcgcgatt ccgccgcagg gctaccgcgc gctgggcgat     1260
gtgatgatgc tggccaccag cggctataac ccgccgaatc tgccggacta tgtttgcgtg     1320
catcaaagcc tgtgcgcgga tgtgcagacg ctgcaaaacc gggtgtggtg ggacaagggc     1380
accggcgcgc gcaaggatgt cagcctgtgg caaccgggcg cggccggcgc ggtggcgtcc     1440
tctgatttcg ccggcgtgcc taattacaac aacccgccca attccggcga catcgagcgc     1500
ttgcgcggca gcatcgcatg cgtgaagacc agcgcgatcg cgtccatgca ggaaatgaag     1560
tccatgctca gccagcacca aggcatggaa gcgatgatgt ccaagctgtg a              1611
```

<210> SEQ ID NO 83
<211> LENGTH: 536
<212> TYPE: PRT
<213> ORGANISM: Artificial Sequence
<220> FEATURE:
<223> OTHER INFORMATION: eAxmi205 #21D Protein

<400> SEQUENCE: 83

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
    130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175
```

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
        195                 200                 205

Leu Val Gly Glu Ile Lys Ile Glu His Gly Ser Glu Met Glu Lys Gln
    210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
        275                 280                 285

Lys Pro Glu Arg Arg Val Glu Leu Glu Asp Ala Phe Pro Glu Phe Met
    290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
                325                 330                 335

Ala Ser Glu Asp Leu Ala Val Phe Asn Pro Ser Thr Ser Asn Gly Tyr
            340                 345                 350

Lys Met Val Gly Gln Phe Gly Gln Arg Asn His Ala Ser Val Ala Asp
        355                 360                 365

Gly His Ala Pro Ile Phe Lys Asp Leu Phe Asp Leu Gly Val Leu Lys
    370                 375                 380

Ala Pro Val Gly Trp Gln Arg Val Trp Asp Asp Ala Gly Ser Gly Lys
385                 390                 395                 400

Ser Lys Asp Tyr Ala Cys Trp Arg Ala Ile Pro Pro Gln Gly Tyr Arg
                405                 410                 415

Ala Leu Gly Asp Val Met Met Leu Ala Thr Ser Gly Tyr Asn Pro Pro
            420                 425                 430

Asn Leu Pro Asp Tyr Val Cys Val His Gln Ser Leu Cys Ala Asp Val
        435                 440                 445

Gln Thr Leu Gln Asn Arg Val Trp Trp Asp Lys Gly Thr Gly Ala Arg
    450                 455                 460

Lys Asp Val Ser Leu Trp Gln Pro Gly Ala Gly Ala Val Ala Ser
465                 470                 475                 480

Ser Asp Phe Ala Gly Val Pro Asn Tyr Asn Pro Asn Ser Gly
                485                 490                 495

Asp Ile Glu Arg Leu Arg Gly Ser Ile Ala Cys Val Lys Thr Ser Ala
            500                 505                 510

Ile Ala Ser Met Gln Glu Met Lys Ser Met Leu Ser Gln His Gln Gly
        515                 520                 525

Met Glu Ala Met Met Ser Lys Leu
    530                 535

<210> SEQ ID NO 84
<211> LENGTH: 1611
<212> TYPE: DNA
<213> ORGANISM: Artificial Sequence
<220> FEATURE:
<223> OTHER INFORMATION: eAxmi205 #23L

<400> SEQUENCE: 84

```
atggcatccg cagcaaatgc aggtcagctt ggcaaccttcc ccggcgttac ttctatgggc    60
atgggctatg acgtgaatgg tttgtacgcc agcccggaaa gcctgcttgg ccaacccttg   120
ttcgatttcg gcggcgagct ggacagcatc gaaatcgagg ccgcagcta caccttccc    180
cgcagcatgc atgtacacac ctatttccat tccgacttca acaggatgt cagcaaggaa   240
atcgaagagt atcgggagaa atgagccag cacgtgggcg tgtccggccg ctacaagttg   300
ttcagcgctt cgctgagcgt ggatttcacc accacggacc agcaactgac cgagattacc   360
tacagctcca cccgcgaagc ccatgtgctg tggtacatca gcctgcctgg cgcggccacg   420
ctgcgttcga tgctgcgccg cgattccgc gacgacctga caaccccaa tatgccggcc   480
atggagctgt tcaagcgcta tggtccctac tacatatcgg aagcggcggt gggcggccgg   540
ctggactaca gcgcggccag caagaccttg aagatggaca gcagccagtc gctgtccacc   600
accgccgaaa tgtcctacaa ggcgctggtg ggcgagatca agatcgagca tggctcggag   660
atggaaaagc aggtcaacag cttccgcagc aactccacca tccgtctcac cgccaccggc   720
ggcaagccgg gcatgaccga tcgcatactg cacggtccgg attcgcagca ggcgttctcg   780
caatgggcg aatcgctgct cgactatgcg acgctgatgg acttttccac cgaaaagcctg   840
caaccgatct gggcgctggc cgacaagccc gagcgccgcg tcgagcttga ggacgccttc   900
cccgaattca tgaagcagtc gcagcagtcc atccccaagg tggacaaggt gctgctgatg   960
gacgcgcggc cgcctatggt gaaggctggg gaggatagcg gctccggcgc gtcggaggat  1020
ctggctgtgt tcaatcccag cacctccaat ggctacaaga tggttggcca gttcggtcag  1080
cgcaaccatg ccagcgtggc ggatggccat gcgccgattt tcaaggatct gttcgatctg  1140
ggcgtgctga aggcgccggt gggttggcag cgggtgtggg acgacgccgg ctccggcaag  1200
tccaaggact acgcgtgctg gcgcgcgatt ccgccgcagg gctaccgcgc gctgggcgat  1260
gtgatgatgc tggccaccag cggctataac ccgccgaatc tgccggacta tgtttgcgtg  1320
catcaaagcc tgtgcgcgga tgtgcagacg ctgcaaaacc gggtgtggtg ggacaagggc  1380
accggcgcgc gcaaggatgt cagcctgtgg caaccgggcg cggccggcgc ggtggcgtcc  1440
tcttgcttcg ccggcgtgcc taattacaac aacccgccca attccggcga catcgagcgc  1500
ttgcgcggca gcatcgcact ggtgaagacc agcgcgatcg cgtccatgca ggaaatgaag  1560
tccatgctca gccagcacca aggcatggaa gcgatgatgt ccaagctgtg a           1611
```

<210> SEQ ID NO 85
<211> LENGTH: 536
<212> TYPE: PRT
<213> ORGANISM: Artificial Sequence
<220> FEATURE:
<223> OTHER INFORMATION: eAxmi205 #23L

<400> SEQUENCE: 85

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80
```

-continued

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
        195                 200                 205

Leu Val Gly Glu Ile Lys Ile Glu His Gly Ser Glu Met Glu Lys Gln
210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
        275                 280                 285

Lys Pro Glu Arg Arg Val Glu Leu Glu Asp Ala Phe Pro Glu Phe Met
290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
                325                 330                 335

Ala Ser Glu Asp Leu Ala Val Phe Asn Pro Ser Thr Ser Asn Gly Tyr
            340                 345                 350

Lys Met Val Gly Gln Phe Gly Gln Arg Asn His Ala Ser Val Ala Asp
        355                 360                 365

Gly His Ala Pro Ile Phe Lys Asp Leu Phe Asp Leu Gly Val Leu Lys
370                 375                 380

Ala Pro Val Gly Trp Gln Arg Val Trp Asp Ala Gly Ser Gly Lys
385                 390                 395                 400

Ser Lys Asp Tyr Ala Cys Trp Arg Ala Ile Pro Pro Gln Gly Tyr Arg
                405                 410                 415

Ala Leu Gly Asp Val Met Met Leu Ala Thr Ser Gly Tyr Asn Pro Pro
            420                 425                 430

Asn Leu Pro Asp Tyr Val Cys Val His Gln Ser Leu Cys Ala Asp Val
        435                 440                 445

Gln Thr Leu Gln Asn Arg Val Trp Trp Asp Lys Gly Thr Gly Ala Arg
450                 455                 460

Lys Asp Val Ser Leu Trp Gln Pro Gly Ala Gly Ala Val Ala Ser
465                 470                 475                 480

Ser Cys Phe Ala Gly Val Pro Asn Tyr Asn Asn Pro Pro Asn Ser Gly
                485                 490                 495

```
Asp Ile Glu Arg Leu Arg Gly Ser Ile Ala Leu Val Lys Thr Ser Ala
        500                 505                 510

Ile Ala Ser Met Gln Glu Met Lys Ser Met Leu Ser Gln His Gln Gly
    515                 520                 525

Met Glu Ala Met Met Ser Lys Leu
    530                 535

<210> SEQ ID NO 86
<211> LENGTH: 1611
<212> TYPE: DNA
<213> ORGANISM: Artificial Sequence
<220> FEATURE:
<223> OTHER INFORMATION: eAxmi205 #23A

<400> SEQUENCE: 86
atggcatccg cagcaaatgc aggtcagctt ggcaacctcc ccggcgttac ttctatgggc      60
atgggctatg acgtgaatgg tttgtacgcc agcccggaaa gcctgcttgg ccaacccttg     120
ttcgatttcg gcggcgagct ggacagcatc gaaatcgagg ccgcagcta  cacctttccc     180
cgcagcatgc atgtacacac ctatttccat tccgacttca acaggatgt  cagcaaggaa     240
atcgaagagt atcgggagaa aatgagccag acgtgggcg  tgtccggccg ctacaagttg     300
ttcagcgctt cgctgagcgt ggatttcacc accacggacc agcaactgac cgagattacc     360
tacagctcca cccgcgaagc ccatgtgctg tggtacatca gcctgcctgg cgcggccacg     420
ctgcgttcga tgctgcgccg cgatttccgc gacgacctga caaccccaa  tatgccggcc     480
atggagctgt tcaagcgcta tggtccctac tacatatcgg aagcggcggt gggcggccgg     540
ctggactaca gcgcggccag caagaccttg aagatggaca gcagccagtc gctgtccacc     600
accgccgaaa tgtcctacaa ggcgctggtg gcgagatca  agatcgagca tggctcggag     660
atggaaaagc aggtcaacag cttccgcagc aactccacca tccgtctcac cgccaccggc     720
ggcaagccgg gcatgaccga tcgcatactg acggtccgg  attcgcagca ggcgttctcg     780
caatgggcgg aatcgctgct cgactatgcg acgctgatgg acttttccac cgaaagcctg     840
caaccgatct gggcgctggc cgacaagccc gagcgccgcg tcgagcttga ggacgccttc     900
cccgaattca tgaagcagtc gcagcagtcc atccccaagg tggacaaggt gctgctgatg     960
gacgcgcggc cgcctatggt gaaggctggg gaggatagcg gctccggcgc gtcggaggat    1020
ctggctgtgt tcaatcccag cacctccaat ggctacaaga tggttggcca gttcggtcag    1080
cgcaaccatg ccagcgtggc ggatggccat gcgccgattt tcaaggatct gttcgatctg    1140
ggcgtgctga aggcgccggt gggttggcag cgggtgtggg acgacgccgg ctccggcaag    1200
tccaaggact acgcgtgctg gcgcgcgatt ccgccgcagg gctaccgcgc gctgggcgat    1260
gtgatgatgc tggccaccag cggctataac cgccgaatc  tgccggacta tgtttgcgtg    1320
catcaaagcc tgtgcgcgga tgtgcagacg ctgcaaaacc gggtgtggtg gacaagggc     1380
accggcgcgc gcaaggatgt cagcctgtgg caaccgggcg cggccggcgc ggtggcgtcc    1440
tcttgcttcg ccggcgtgcc taattacaac aacccgccca ttccggcga  catcgagcgc    1500
ttgcgcggca gcatcgcagc ggtgaagacc agcgcgatcg cgtccatgca ggaaatgaag    1560
tccatgctca gccagcacca aggcatggaa gcgatgatgt ccaagctgtg a             1611

<210> SEQ ID NO 87
<211> LENGTH: 536
<212> TYPE: PRT
<213> ORGANISM: Artificial Sequence
<220> FEATURE:
```

<223> OTHER INFORMATION: eAxmi205 #23A Protein

<400> SEQUENCE: 87

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
    130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
        195                 200                 205

Leu Val Gly Glu Ile Lys Ile Glu His Gly Ser Glu Met Leu Lys Gln
    210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
        275                 280                 285

Lys Pro Glu Arg Arg Val Glu Leu Glu Asp Ala Phe Pro Glu Phe Met
    290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
                325                 330                 335

Ala Ser Glu Asp Leu Ala Val Phe Asn Pro Ser Thr Ser Asn Gly Tyr
            340                 345                 350

Lys Met Val Gly Gln Phe Gly Gln Arg Asn His Ala Ser Val Ala Asp
        355                 360                 365

Gly His Ala Pro Ile Phe Lys Asp Leu Phe Asp Leu Gly Val Leu Lys
    370                 375                 380

Ala Pro Val Gly Trp Gln Arg Val Trp Asp Asp Ala Gly Ser Gly Lys
385                 390                 395                 400
```

Ser Lys Asp Tyr Ala Cys Trp Arg Ala Ile Pro Pro Gln Gly Tyr Arg
            405                 410                 415

Ala Leu Gly Asp Val Met Met Leu Ala Thr Ser Gly Tyr Asn Pro Pro
        420                 425                 430

Asn Leu Pro Asp Tyr Val Cys Val His Gln Ser Leu Cys Ala Asp Val
        435                 440                 445

Gln Thr Leu Gln Asn Arg Val Trp Trp Asp Lys Gly Thr Gly Ala Arg
    450                 455                 460

Lys Asp Val Ser Leu Trp Gln Pro Gly Ala Gly Ala Val Ala Ser
465                 470                 475                 480

Ser Cys Phe Ala Gly Val Pro Asn Tyr Asn Asn Pro Pro Asn Ser Gly
                485                 490                 495

Asp Ile Glu Arg Leu Arg Gly Ser Ile Ala Ala Val Lys Thr Ser Ala
            500                 505                 510

Ile Ala Ser Met Gln Glu Met Lys Ser Met Leu Ser Gln His Gln Gly
        515                 520                 525

Met Glu Ala Met Met Ser Lys Leu
    530                 535

<210> SEQ ID NO 88
<211> LENGTH: 1611
<212> TYPE: DNA
<213> ORGANISM: Artificial Sequence
<220> FEATURE:
<223> OTHER INFORMATION: eAxmi205 #23F

<400> SEQUENCE: 88

| | | |
|---|---|---|
| atggcatccg cagcaaatgc aggtcagctt ggcaaccctcc ccggcgttac ttctatgggc | 60 |
| atgggctatg acgtgaatgg tttgtacgcc agcccggaaa gcctgcttgg ccaacccttg | 120 |
| ttcgatttcg gcggcgagct ggacagcatc gaaatcgagg ccgcagcta cacctttccc | 180 |
| cgcagcatgc atgtacacac ctatttccat tccgacttca acaggatgt cagcaaggaa | 240 |
| atcgaagagt atcgggagaa atgagccag cacgtgggcg tgtccggccg ctacaagttg | 300 |
| ttcagcgctt cgctgagcgt ggatttcacc accacggacc agcaactgac cgagattacc | 360 |
| tacagctcca cccgcgaagc ccatgtgctg tggtacatca gcctgcctgg cgcggccacg | 420 |
| ctgcgttcga tgctgcgccg cgatttccgc gacgacctga caacccccaa tatgccggcc | 480 |
| atggagctgt tcaagcgcta tggtccctac tacatatcgg aagcggcggt gggcggccgg | 540 |
| ctggactaca gcgcggccag caagaccttg aagatggaca gcagccagtc gctgtccacc | 600 |
| accgccgaaa tgtcctacaa ggcgctggtg gcgagatca agatcgagca tggctcggag | 660 |
| atggaaaagc aggtcaacag cttccgcagc aactccacca tccgtctcac cgccaccggc | 720 |
| ggcaagccgg gcatgaccga tcgcatactg acggtccgg attcgcagca ggcgttctcg | 780 |
| caatgggcgg aatcgctgct cgactatgcg acgctgatgg acttttccac cgaaagcctg | 840 |
| caaccgatct gggcgctggc cgacaagccc gagcgccgcg tcgagcttga ggacgccttc | 900 |
| cccgaattca tgaagcagtc gcagcagtcc atccccaagg tggacaaggt gctgctgatg | 960 |
| gacgcgcggc cgcctatggt gaaggctggg gaggatagcg gctccggcgc gtcggaggat | 1020 |
| ctggctgtgt tcaatcccag cacctccaat ggctacaaga tggttggcca gttcggtcag | 1080 |
| cgcaaccatg ccagcgtggc ggatggccat gcgccgattt tcaaggatct gttcgatctg | 1140 |
| ggcgtgctga aggcgccggt gggttggcag cgggtgtggg acgacgccgg ctccggcaag | 1200 |
| tccaaggact acgcgtgctg gcgcgcgatt ccgccgcagg gctaccgcgc gctgggcgat | 1260 |

-continued

```
gtgatgatgc tggccaccag cggctataac ccgccgaatc tgccggacta tgtttgcgtg     1320
catcaaagcc tgtgcgcgga tgtgcagacg ctgcaaaacc gggtgtggtg ggacaagggc     1380
accggcgcgc gcaaggatgt cagcctgtgg caaccgggcg cggccggcgc ggtggcgtcc     1440
tcttgcttcg ccggcgtgcc taattacaac aacccgccca attccggcga catcgagcgc     1500
ttgcgcggca gcatcgcatt tgtgaagacc agcgcgatcg cgtccatgca ggaaatgaag     1560
tccatgctca gccagcacca aggcatggaa gcgatgatgt ccaagctgtg a                1611
```

```
<210> SEQ ID NO 89
<211> LENGTH: 536
<212> TYPE: PRT
<213> ORGANISM: Artificial Sequence
<220> FEATURE:
<223> OTHER INFORMATION: eAxmi205 #23F Protein

<400> SEQUENCE: 89
```

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
    130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
        195                 200                 205

Leu Val Gly Glu Ile Lys Ile Glu His Gly Ser Glu Met Glu Lys Gln
    210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
        275                 280                 285

Lys Pro Glu Arg Arg Val Glu Leu Glu Asp Ala Phe Pro Glu Phe Met
    290                 295                 300
```

| | | | | | | | | | | | | |
|---|---|---|---|---|---|---|---|---|---|---|---|---|
| Lys | Gln | Ser | Gln | Gln | Ser | Ile | Pro | Lys | Val | Asp | Lys | Val | Leu | Leu | Met |
| 305 | | | | 310 | | | | | 315 | | | | | 320 | |
| Asp | Ala | Arg | Pro | Pro | Met | Val | Lys | Ala | Gly | Glu | Asp | Ser | Gly | Ser | Gly |
| | | | 325 | | | | | 330 | | | | | 335 | | |
| Ala | Ser | Glu | Asp | Leu | Ala | Val | Phe | Asn | Pro | Ser | Thr | Ser | Asn | Gly | Tyr |
| | | | 340 | | | | | 345 | | | | | 350 | | |
| Lys | Met | Val | Gly | Gln | Phe | Gly | Gln | Arg | Asn | His | Ala | Ser | Val | Ala | Asp |
| | | | 355 | | | | | 360 | | | | | 365 | | |
| Gly | His | Ala | Pro | Ile | Phe | Lys | Asp | Leu | Phe | Asp | Leu | Gly | Val | Leu | Lys |
| | 370 | | | | | 375 | | | | | 380 | | | | |
| Ala | Pro | Val | Gly | Trp | Gln | Arg | Val | Trp | Asp | Asp | Ala | Gly | Ser | Gly | Lys |
| 385 | | | | | 390 | | | | | 395 | | | | | 400 |
| Ser | Lys | Asp | Tyr | Ala | Cys | Trp | Arg | Ala | Ile | Pro | Pro | Gln | Gly | Tyr | Arg |
| | | | | 405 | | | | | 410 | | | | | 415 | |
| Ala | Leu | Gly | Asp | Val | Met | Met | Leu | Ala | Thr | Ser | Gly | Tyr | Asn | Pro | Pro |
| | | | 420 | | | | | 425 | | | | | 430 | | |
| Asn | Leu | Pro | Asp | Tyr | Val | Cys | Val | His | Gln | Ser | Leu | Cys | Ala | Asp | Val |
| | | | 435 | | | | | 440 | | | | | 445 | | |
| Gln | Thr | Leu | Gln | Asn | Arg | Val | Trp | Trp | Asp | Lys | Gly | Thr | Gly | Ala | Arg |
| | 450 | | | | | 455 | | | | | 460 | | | | |
| Lys | Asp | Val | Ser | Leu | Trp | Gln | Pro | Gly | Ala | Ala | Gly | Ala | Val | Ala | Ser |
| 465 | | | | | 470 | | | | | 475 | | | | | 480 |
| Ser | Cys | Phe | Ala | Gly | Val | Pro | Asn | Tyr | Asn | Asn | Pro | Asn | Ser | Gly | |
| | | | | 485 | | | | | 490 | | | | | 495 | |
| Asp | Ile | Glu | Arg | Leu | Arg | Gly | Ser | Ile | Ala | Phe | Val | Lys | Thr | Ser | Ala |
| | | | 500 | | | | | 505 | | | | | 510 | | |
| Ile | Ala | Ser | Met | Gln | Glu | Met | Lys | Ser | Met | Leu | Ser | Gln | His | Gln | Gly |
| | | 515 | | | | | 520 | | | | | 525 | | | |
| Met | Glu | Ala | Met | Met | Ser | Lys | Leu | | | | | | | | |
| | 530 | | | | | 535 | | | | | | | | | |

<210> SEQ ID NO 90
<211> LENGTH: 1611
<212> TYPE: DNA
<213> ORGANISM: Artificial Sequence
<220> FEATURE:
<223> OTHER INFORMATION: eAxmi205 #23D

<400> SEQUENCE: 90

```
atggcatccg cagcaaatgc aggtcagctt ggcaacctcc ccggcgttac ttctatgggc      60
atgggctatg acgtgaatgg tttgtacgcc agcccggaaa gctgcttgg ccaacccttg     120
ttcgatttcg cggcgagct ggacagcatc gaaatcgagg ccgcagcta cactttccc      180
cgcagcatgc atgtacacac ctatttccat tccgacttca acaggatgt cagcaaggaa     240
atcgaagagt atcgggagaa aatgagccag cacgtgggcg tgtccggccg ctacaagttg     300
ttcagcgctt cgctgagcgt ggatttcacc accgcgacc agcaactgac cgagattacc     360
tacagctcca cccgcgaagc ccatgtgctg tggtacatca gcctgcctgg cgcggccacg     420
ctgcgttcga tgctgcgccg cgatttccgc gacgacctga acaaccccaa tatgccggcc     480
atggagctgt tcaagcgcta tggtccctac tacatatcgg aagcggcggt gggcggccgg     540
ctggactaca gcgcggccag caagaccttg aagatggaca gcagccagtc gctgtccacc     600
accgccgaaa tgtcctacaa ggcgctggtg gcgagatca agatcgagca tggctcggag     660
atggaaaagc aggtcaacag cttccgcagc aactccacca tccgtctcac cgccaccggc     720
```

```
ggcaagccgg gcatgaccga tcgcatactg cacggtccgg attcgcagca ggcgttctcg    780
caatgggcgg aatcgctgct cgactatgcg acgctgatgg acttttccac cgaaagcctg    840
caaccgatct gggcgctggc cgacaagccc gagcgccgcg tcgagcttga ggacgccttc    900
cccgaattca tgaagcagtc gcagcagtcc atccccaagg tggacaaggt gctgctgatg    960
gacgcgcggc cgcctatggt gaaggctggg gaggatagcg gctccggcgc gtcggaggat   1020
ctggctgtgt tcaatcccag cacctccaat ggctacaaga tggttggcca gttcggtcag   1080
cgcaaccatg ccagcgtggc ggatggccat gcgccgattt tcaaggatct gttcgatctg   1140
ggcgtgctga aggcgccggt gggttggcag cgggtgtggg acgacgccgg ctccggcaag   1200
tccaaggact acgcgtgctg cgcgcgcgatt ccgccgcagg gctaccgcgc gctgggcgat   1260
gtgatgatgc tggccaccag cggctataac ccgccgaatc tgccggacta tgtttgcgtg   1320
catcaaagcc tgtgcgcgga tgtgcagacg ctgcaaaacc gggtgtggtg ggacaagggc   1380
accggcgcgc gcaaggatgt cagcctgtgg caaccgggcg cggccggcgc ggtggcgtcc   1440
tcttgcttcg ccggcgtgcc taattacaac aacccgccca attccggcga catcgagcgc   1500
ttgcgcggca gcatcgcaga tgtgaagacc agcgcgatcg cgtccatgca ggaaatgaag   1560
tccatgctca gccagcacca aggcatggaa gcgatgatgt ccaagctgtg a             1611
```

<210> SEQ ID NO 91
<211> LENGTH: 536
<212> TYPE: PRT
<213> ORGANISM: Artificial Sequence
<220> FEATURE:
<223> OTHER INFORMATION: eAxmi205 #23D Protein

<400> SEQUENCE: 91

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
    130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
        195                 200                 205
```

-continued

```
Leu Val Gly Glu Ile Lys Ile Glu His Gly Ser Glu Met Glu Lys Gln
    210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
        275                 280                 285

Lys Pro Glu Arg Arg Val Glu Leu Glu Asp Ala Phe Pro Glu Phe Met
290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
                325                 330                 335

Ala Ser Glu Asp Leu Ala Val Phe Asn Pro Ser Thr Ser Asn Gly Tyr
            340                 345                 350

Lys Met Val Gly Gln Phe Gly Gln Arg Asn His Ala Ser Val Ala Asp
        355                 360                 365

Gly His Ala Pro Ile Phe Lys Asp Leu Phe Asp Leu Gly Val Leu Lys
    370                 375                 380

Ala Pro Val Gly Trp Gln Arg Val Trp Asp Ala Gly Ser Gly Lys
385                 390                 395                 400

Ser Lys Asp Tyr Ala Cys Trp Arg Ala Ile Pro Pro Gln Gly Tyr Arg
                405                 410                 415

Ala Leu Gly Asp Val Met Met Leu Ala Thr Ser Gly Tyr Asn Pro Pro
            420                 425                 430

Asn Leu Pro Asp Tyr Val Cys Val His Gln Ser Leu Cys Ala Asp Val
        435                 440                 445

Gln Thr Leu Gln Asn Arg Val Trp Trp Asp Lys Gly Thr Gly Ala Arg
    450                 455                 460

Lys Asp Val Ser Leu Trp Gln Pro Gly Ala Ala Gly Ala Val Ala Ser
465                 470                 475                 480

Ser Cys Phe Ala Gly Val Pro Asn Tyr Asn Pro Pro Asn Ser Gly
                485                 490                 495

Asp Ile Glu Arg Leu Arg Gly Ser Ile Ala Asp Val Lys Thr Ser Ala
            500                 505                 510

Ile Ala Ser Met Gln Glu Met Lys Ser Met Leu Ser Gln His Gln Gly
        515                 520                 525

Met Glu Ala Met Met Ser Lys Leu
    530                 535
```

<210> SEQ ID NO 92
<211> LENGTH: 1611
<212> TYPE: DNA
<213> ORGANISM: Artificial Sequence
<220> FEATURE:
<223> OTHER INFORMATION: eAxmi205 #23R

<400> SEQUENCE: 92

```
atggcatccg cagcaaatgc aggtcagctt ggcaaccctc ccggcgttac ttctatgggc    60
atgggctatg acgtgaatgg tttgtacgcc agcccggaaa gcctgcttgg ccaacccttg   120
ttcgatttcg gcggcgagct ggacagcatc gaaatcgagg ccgcagcta caccttcc     180
```

```
cgcagcatgc atgtacacac ctatttccat tccgacttca acaggatgtc agcaaggaa    240
atcgaagagt atcgggagaa aatgagccag cacgtgggcg tgtccggccg ctacaagttg    300
ttcagcgctt cgctgagcgt ggatttcacc accacggacc agcaactgac cgagattacc    360
tacagctcca cccgcgaagc ccatgtgctg tggtacatca gcctgcctgg cgcggccacg    420
ctgcgttcga tgctgcgccg cgatttccgc gacgacctga caaccccaa tatgccggcc    480
atggagctgt tcaagcgcta tggtccctac tacatatcgg aagcggcggt gggcggccgg    540
ctggactaca gcgcggccag caagaccttg aagatggaca gcagccagtc gctgtccacc    600
accgccgaaa tgtcctacaa ggcgctggtg ggcgagatca agatcgagca tggctcggag    660
atggaaaagc aggtcaacag cttccgcagc aactccacca tccgtctcac cgccaccggc    720
ggcaagccgg gcatgaccga tcgcatactg cacggtccgg attcgcagca ggcgttctcg    780
caatgggcgg aatcgctgct cgactatgcg acgctgatgg actttcca cgaaagcctg    840
caaccgatct gggcgctggc cgacaagccc gagcgccgcg tcgagcttga ggacgccttc    900
cccgaattca tgaagcagtc gcagcagtcc atccccaagg tggacaaggt gctgctgatg    960
gacgcgcggc cgcctatggt gaaggctggg gaggatagcg gctccggcgc gtcggaggat   1020
ctggctgtgt tcaatcccag cacctccaat ggctacaaga tggttggcca gttcggtcag   1080
cgcaaccatg ccagcgtggc ggatggccat gcgccgattt tcaaggatct gttcgatctg   1140
ggcgtgctga aggcgccggt gggttggcag cgggtgtggg acgacgccgg ctccggcaag   1200
tccaaggact acgcgtgctg gcgcgcgatt ccgccgcagg gctaccgcgc gctgggcgat   1260
gtgatgatgc tggccaccag cggctataac cgccgaatc tgccggacta tgtttgcgtg   1320
catcaaagcc tgtgcgcgga tgtgcagacg ctgcaaaacc gggtgtggtg gacaagggc    1380
accggcgcgc gcaaggatgt cagcctgtgg caaccgggcg cggccggcgc ggtggcgtcc   1440
tcttgcttcg ccggcgtgcc taattacaac aacccgccca attccggcga catcgagcgc   1500
ttgcgcggca gcatcgcacg tgtgaagacc agcgcgatcg cgtccatgca ggaaatgaag   1560
tccatgctca gccagcacca aggcatggaa gcgatgatgt ccaagctgtg a            1611
```

<210> SEQ ID NO 93
<211> LENGTH: 536
<212> TYPE: PRT
<213> ORGANISM: Artificial Sequence
<220> FEATURE:
<223> OTHER INFORMATION: eAxmi205 #23R Protein

<400> SEQUENCE: 93

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110
```

```
Asp Gln Gln Leu Thr Glu Ile Thr Tyr Ser Ser Thr Arg Glu Ala His
            115                 120                 125

Val Leu Trp Tyr Ile Ser Leu Pro Gly Ala Ala Thr Leu Arg Ser Met
130                 135                 140

Leu Arg Arg Asp Phe Arg Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ser Lys Thr Leu Lys Met
                180                 185                 190

Asp Ser Ser Gln Ser Leu Ser Thr Thr Ala Glu Met Ser Tyr Lys Ala
            195                 200                 205

Leu Val Gly Glu Ile Lys Ile Glu His Gly Ser Glu Met Glu Lys Gln
210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
            275                 280                 285

Lys Pro Glu Arg Arg Val Glu Leu Glu Asp Ala Phe Pro Glu Phe Met
            290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
                325                 330                 335

Ala Ser Glu Asp Leu Ala Val Phe Asn Pro Ser Thr Ser Asn Gly Tyr
                340                 345                 350

Lys Met Val Gly Gln Phe Gly Gln Arg Asn His Ala Ser Val Ala Asp
            355                 360                 365

Gly His Ala Pro Ile Phe Lys Asp Leu Phe Asp Leu Gly Val Leu Lys
370                 375                 380

Ala Pro Val Gly Trp Gln Arg Val Trp Asp Asp Ala Gly Ser Gly Lys
385                 390                 395                 400

Ser Lys Asp Tyr Ala Cys Trp Arg Ala Ile Pro Pro Gln Gly Tyr Arg
                405                 410                 415

Ala Leu Gly Asp Val Met Met Leu Ala Thr Ser Gly Tyr Asn Pro Pro
                420                 425                 430

Asn Leu Pro Asp Tyr Val Cys Val His Gln Ser Leu Cys Ala Asp Val
            435                 440                 445

Gln Thr Leu Gln Asn Arg Val Trp Trp Asp Lys Gly Thr Gly Ala Arg
            450                 455                 460

Lys Asp Val Ser Leu Trp Gln Pro Gly Ala Ala Gly Ala Val Ala Ser
465                 470                 475                 480

Ser Cys Phe Ala Gly Val Pro Asn Tyr Asn Asn Pro Asn Ser Gly
                485                 490                 495

Asp Ile Glu Arg Leu Arg Gly Ser Ile Ala Arg Val Lys Thr Ser Ala
                500                 505                 510

Ile Ala Ser Met Gln Glu Met Lys Ser Met Leu Ser Gln His Gln Gly
            515                 520                 525

Met Glu Ala Met Met Ser Lys Leu
```

530          535

<210> SEQ ID NO 94
<211> LENGTH: 1611
<212> TYPE: DNA
<213> ORGANISM: Artificial Sequence
<220> FEATURE:
<223> OTHER INFORMATION: eAxmi205 #28TF

<400> SEQUENCE: 94

| | | | | | |
|---|---|---|---|---|---|
| atggcatccg | cagcaaatgc | aggtcagctt | ggcaaccctcc | ccggcgttac | ttctatgggc | 60 |
| atgggctatg | acgtgaatgg | tttgtacgcc | agcccggaaa | gcctgcttgg | ccaacccttg | 120 |
| ttcgatttcg | gcggcgagct | ggacagcatc | gaaatcgagg | gccgcagcta | cacctttccc | 180 |
| cgcagcatgc | atgtacacac | ctatttccat | ccgacttca | aacaggatgt | cagcaaggaa | 240 |
| atcgaagagt | atcgggagaa | aatgagccag | cacgtgggcg | tgtccggccg | ctacaagttg | 300 |
| ttcagcgctt | cgctgagcgt | ggatttcacc | accacggacc | agcaactgac | cgagattacc | 360 |
| tacagctcca | cccgcgaagc | ccatgtgctg | tggtacatca | gcctgcctgg | cgcggccacg | 420 |
| ctgcgttcga | tgctgcgccg | cgatttccgc | gacgacctga | acaaccccaa | tatgccggcc | 480 |
| atggagctgt | tcaagcgcta | tggtccctac | tacatatcgg | aagcggcggt | gggcggccgg | 540 |
| ctggactaca | gcgcggccag | caagaccttg | aagatggaca | gcagccagtc | gctgtccacc | 600 |
| accgccgaaa | tgtcctacaa | ggcgctggtg | gcgagatca | agatcgagca | tggctcggag | 660 |
| atggaaaagc | aggtcaacag | cttccgcagc | aactccacca | tccgtctcac | cgccaccggc | 720 |
| ggcaagccgg | gcatgaccga | tcgcatactg | cacggtccgg | attcgcagca | ggcgttctcg | 780 |
| caatgggcgg | aatcgctgct | cgactatgcg | acgctgatgg | acttttccac | cgaaagcctg | 840 |
| caaccgatct | gggcgctggc | cgacaagccc | gagcgccgcg | tcgagcttga | ggacgccttc | 900 |
| cccgaattca | tgaagcagtc | gcagcagtcc | atccccaagg | tggacaaggt | gctgctgatg | 960 |
| gacgcgcggc | cgcctatggt | gaaggctggg | gaggatagcg | gctccggcgc | gtcggaggat | 1020 |
| ctggctgtgt | tcaatcccag | cacctccaat | ggctacaaga | tggttggcca | gttcggtcag | 1080 |
| cgcaaccatg | ccagcgtggc | ggatggccat | gcgccgattt | tcaaggatct | gttcgatctg | 1140 |
| ggcgtgctga | aggcgccggt | gggttggcag | cgggtgtggg | acgacgccgg | ctccggcaag | 1200 |
| tccaaggact | acgcgtgctg | gcgcgcgatt | ccgccgcagg | gctaccgcgc | gctgggcgat | 1260 |
| gtgacctttc | tggccaccag | cggctataac | ccgccgaatc | tgccggacta | tgtttgcgtg | 1320 |
| catcaaagcc | tgtgcgcgga | tgtgcagacg | ctgcaaaacc | gggtgtggtg | gacaagggc | 1380 |
| accggcgcgc | gcaaggatgt | cagcctgtgg | caaccgggcg | cggccggcgc | ggtggcgtcc | 1440 |
| tcttgcttcg | ccggcgtgcc | taattacaac | aacccgccca | attccggcga | catcgagcgc | 1500 |
| ttgcgcggca | gcatcgcatg | cgtgaagacc | agcgcgatcg | cgtccatgca | ggaaatgaag | 1560 |
| tccatgctca | gccagcacca | aggcatggaa | gcgatgatgt | ccaagctgtg | a | 1611 |

<210> SEQ ID NO 95
<211> LENGTH: 536
<212> TYPE: PRT
<213> ORGANISM: Artificial Sequence
<220> FEATURE:
<223> OTHER INFORMATION: eAxmi205 #28TF Protein

<400> SEQUENCE: 95

Met Ala Ser Ala Ala Asn Ala Gly Gln Leu Gly Asn Leu Pro Gly Val
1               5                   10                  15

```
Thr Ser Met Gly Met Gly Tyr Asp Val Asn Gly Leu Tyr Ala Ser Pro
            20                  25                  30
Glu Ser Leu Leu Gly Gln Pro Leu Phe Asp Phe Gly Gly Glu Leu Asp
        35                  40                  45
Ser Ile Glu Ile Glu Gly Arg Ser Tyr Thr Phe Pro Arg Ser Met His
    50                  55                  60
Val His Thr Tyr Phe His Ser Asp Phe Lys Gln Asp Val Ser Lys Glu
65                  70                  75                  80
Ile Glu Glu Tyr Arg Glu Lys Met Ser Gln His Val Gly Val Ser Gly
                85                  90                  95
Arg Tyr Lys Leu Phe Ser Ala Ser Leu Ser Val Asp Phe Thr Thr Thr
            100                 105                 110
Asp Gln Gln Leu Thr Glu Ile Thr Tyr Ser Ser Thr Arg Glu Ala His
        115                 120                 125
Val Leu Trp Tyr Ile Ser Leu Pro Gly Ala Ala Thr Leu Arg Ser Met
    130                 135                 140
Leu Arg Arg Asp Phe Arg Asp Asp Leu Asn Asn Pro Asn Met Pro Ala
145                 150                 155                 160
Met Glu Leu Phe Lys Arg Tyr Gly Pro Tyr Tyr Ile Ser Glu Ala Ala
                165                 170                 175
Val Gly Gly Arg Leu Asp Tyr Ser Ala Ala Ser Lys Thr Leu Lys Met
            180                 185                 190
Asp Ser Ser Gln Ser Leu Ser Thr Thr Ala Glu Met Ser Tyr Lys Ala
        195                 200                 205
Leu Val Gly Glu Ile Lys Ile Glu His Gly Ser Glu Met Glu Lys Gln
    210                 215                 220
Val Asn Ser Phe Arg Ser Asn Ser Thr Ile Arg Leu Thr Ala Thr Gly
225                 230                 235                 240
Gly Lys Pro Gly Met Thr Asp Arg Ile Leu His Gly Pro Asp Ser Gln
                245                 250                 255
Gln Ala Phe Ser Gln Trp Ala Glu Ser Leu Leu Asp Tyr Ala Thr Leu
            260                 265                 270
Met Asp Phe Ser Thr Glu Ser Leu Gln Pro Ile Trp Ala Leu Ala Asp
        275                 280                 285
Lys Pro Glu Arg Arg Val Glu Leu Glu Asp Ala Phe Pro Glu Phe Met
    290                 295                 300
Lys Gln Ser Gln Gln Ser Ile Pro Lys Val Asp Lys Val Leu Leu Met
305                 310                 315                 320
Asp Ala Arg Pro Pro Met Val Lys Ala Gly Glu Asp Ser Gly Ser Gly
                325                 330                 335
Ala Ser Glu Asp Leu Ala Val Phe Asn Pro Ser Thr Ser Asn Gly Tyr
            340                 345                 350
Lys Met Val Gly Gln Phe Gly Gln Arg Asn His Ala Ser Val Ala Asp
        355                 360                 365
Gly His Ala Pro Ile Phe Lys Asp Leu Phe Asp Leu Gly Val Leu Lys
    370                 375                 380
Ala Pro Val Gly Trp Gln Arg Val Trp Asp Asp Ala Gly Ser Gly Lys
385                 390                 395                 400
Ser Lys Asp Tyr Ala Cys Trp Arg Ala Ile Pro Pro Gln Gly Tyr Arg
                405                 410                 415
Ala Leu Gly Asp Val Thr Phe Leu Ala Thr Ser Gly Tyr Asn Pro Pro
            420                 425                 430
Asn Leu Pro Asp Tyr Val Cys Val His Gln Ser Leu Cys Ala Asp Val
```

|  |  | 435 |  |  | 440 |  |  | 445 |  |  |  |
|---|---|---|---|---|---|---|---|---|---|---|---|

Gln Thr Leu Gln Asn Arg Val Trp Trp Asp Lys Gly Thr Gly Ala Arg
  450                        455                    460

Lys Asp Val Ser Leu Trp Gln Pro Gly Ala Ala Gly Ala Val Ala Ser
465                        470                    475                480

Ser Cys Phe Ala Gly Val Pro Asn Tyr Asn Asn Pro Pro Asn Ser Gly
                          485                    490                    495

Asp Ile Glu Arg Leu Arg Gly Ser Ile Ala Cys Val Lys Thr Ser Ala
            500                    505                    510

Ile Ala Ser Met Gln Glu Met Lys Ser Met Leu Ser Gln His Gln Gly
        515                    520                    525

Met Glu Ala Met Met Ser Lys Leu
  530                        535

<210> SEQ ID NO 96
<211> LENGTH: 1611
<212> TYPE: DNA
<213> ORGANISM: Artificial Sequence
<220> FEATURE:
<223> OTHER INFORMATION: eAxmi205 #28DE

<400> SEQUENCE: 96

```
atggcatccg cagcaaatgc aggtcagctt ggcaacctcc ccggcgttac ttctatgggc      60
atgggctatg acgtgaatgg tttgtacgcc agcccggaaa gcctgcttgg ccaacccttg     120
ttcgatttcg gcggcgagct ggacagcatc gaaatcgagg ccgcagcta caccttccc      180
cgcagcatgc atgtacacac ctatttccat tccgacttca acaggatgt cagcaaggaa     240
atcgaagagt atcgggagaa atgagccag cacgtgggcg tgtccggccg ctacaagttg     300
ttcagcgctt cgctgagcgt ggatttcacc accacggacc agcaactgac cgagattacc     360
tacagctcca cccgcgaagc ccatgtgctg tggtacatca gcctgcctgg cgcggccacg     420
ctgcgttcga tgctgcgccg cgattccgc gacgacctga caacccccaa tatgccggcc     480
atggagctgt tcaagcgcta tggtccctac tacatatcgg aagcggcggt gggcggccgg     540
ctggactaca gcgcggccag caagaccttg aagatggaca gcagccagtc gctgtccacc     600
accgccgaaa tgtcctacaa ggcgctggtg gcgagatca agatcgagca tggctcggag     660
atggaaaagc aggtcaacag cttccgcagc aactccacca tccgtctcac cgccaccggc     720
ggcaagccgg gcatgaccga tcgcatactg cacggtccgg attcgcagca ggcgttctcg     780
caatgggcgg aatcgctgct cgactatgcg acgctgatgg actttccac gaaaagcctg     840
caaccgatct gggcgctggc cgacaagccc gagcgccgcg tcgagcttga ggacgccttc     900
cccgaattca tgaagcagtc gcagcagtcc atccccaagg tggacaaggt gctgctgatg     960
gacgcgcggc cgcctatggt gaaggctggg gaggatagcg gctccggcgc gtcggaggat    1020
ctggctgtgt tcaatcccag cacctccaat ggctacaaga tggttggcca gttcggtcag    1080
cgcaaccatg ccagcgtggc ggatggccat gcgccgattt tcaaggatct gttcgatctg    1140
ggcgtgctga aggcgccggt gggttggcag cgggtgtggg acgacgccgg ctccggcaag    1200
tccaaggact acgcgtgctg gcgcgcgatt ccgccgcagg gctaccgcgc gctgggcgat    1260
gtggatgaac tggccaccag cggctataac ccgccgaatc tgccggacta tgtttgcgtg    1320
catcaaagcc tgtgcgcgga tgtgcagacg ctgcaaaacc gggtgtggtg gacaagggc    1380
accggcgcgc gcaaggatgt cagcctgtgg caaccgggcg cggccggcgc ggtggcgtcc    1440
tcttgcttcg ccggcgtgcc taattacaac aacccgccca ttccggcga catcgagcgc    1500
```

-continued

```
ttgcgcggca gcatcgcatg cgtgaagacc agcgcgatcg cgtccatgca ggaaatgaag    1560
tccatgctca gccagcacca aggcatggaa gcgatgatgt ccaagctgtg a              1611

<210> SEQ ID NO 97
<211> LENGTH: 536
<212> TYPE: PRT
<213> ORGANISM: Artificial Sequence
<220> FEATURE:
<223> OTHER INFORMATION: eAxmi205 #28DE Protein

<400> SEQUENCE: 97
```

Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
    130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
        195                 200                 205

Leu Val Gly Glu Ile Lys Ile Glu His Gly Ser Glu Met Glu Lys Gln
    210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
        275                 280                 285

Lys Pro Glu Arg Arg Val Glu Leu Glu Asp Ala Phe Pro Glu Phe Met
    290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
                325                 330                 335

Ala Ser Glu Asp Leu Ala Val Phe Asn Pro Ser Thr Ser Asn Gly Tyr

```
              340                 345                 350
Lys Met Val Gly Gln Phe Gly Gln Arg Asn His Ala Ser Val Ala Asp
            355                 360                 365
Gly His Ala Pro Ile Phe Lys Asp Leu Phe Asp Leu Gly Val Leu Lys
        370                 375                 380
Ala Pro Val Gly Trp Gln Arg Val Trp Asp Asp Ala Gly Ser Gly Lys
385                 390                 395                 400
Ser Lys Asp Tyr Ala Cys Trp Arg Ala Ile Pro Pro Gln Gly Tyr Arg
                405                 410                 415
Ala Leu Gly Asp Val Asp Glu Leu Ala Thr Ser Gly Tyr Asn Pro Pro
            420                 425                 430
Asn Leu Pro Asp Tyr Val Cys Val His Gln Ser Leu Cys Ala Asp Val
        435                 440                 445
Gln Thr Leu Gln Asn Arg Val Trp Trp Asp Lys Gly Thr Gly Ala Arg
    450                 455                 460
Lys Asp Val Ser Leu Trp Gln Pro Gly Ala Ala Gly Ala Val Ala Ser
465                 470                 475                 480
Ser Cys Phe Ala Gly Val Pro Asn Tyr Asn Asn Pro Pro Asn Ser Gly
                485                 490                 495
Asp Ile Glu Arg Leu Arg Gly Ser Ile Ala Cys Val Lys Thr Ser Ala
            500                 505                 510
Ile Ala Ser Met Gln Glu Met Lys Ser Met Leu Ser Gln His Gln Gly
        515                 520                 525
Met Glu Ala Met Met Ser Lys Leu
    530                 535

<210> SEQ ID NO 98
<211> LENGTH: 1611
<212> TYPE: DNA
<213> ORGANISM: Artificial Sequence
<220> FEATURE:
<223> OTHER INFORMATION: eAxmi205 #28KR

<400> SEQUENCE: 98
atggcatccg cagcaaatgc aggtcagctt ggcaacctcc ccggcgttac ttctatgggc     60
atgggctatg acgtgaatgg tttgtacgcc agcccggaaa gcctgcttgg ccaacccttg    120
ttcgatttcg gcggcgagct ggacagcatc gaaatcgagg ccgcagcta  cacctttccc    180
cgcagcatgc atgtacacac ctatttccat tccgacttca acaggatgt  cagcaaggaa    240
atcgaagagt atcgggagaa aatgagccag cacgtgggcg tgtccggccg ctacaagttg    300
ttcagcgctt cgctgagcgt ggatttcacc accacggacc agcaactgac cgagattacc    360
tacagctcca cccgcgaagc ccatgtgctg tggtacatca gcctgcctgg cgcggccacg    420
ctgcgttcga tgctgcgccg cgatttccgc gacgacctga caaccccaa  tatgccggcc    480
atggagctgt tcaagcgcta tggtccctac tacatatcgg aagcggcggt gggcggccgg    540
ctggactaca gcgcggccag caagaccttg aagatggaca gcagccagtc gctgtccacc    600
accgccgaaa tgtcctacaa ggcgctggtg gcgagatca  agatcgagca tggctcggag    660
atggaaaagc aggtcaacag cttccgcagc aactccacca tccgtctcac cgccaccggc    720
ggcaagccgg gcatgaccga tcgcatactg cacggtccgg attcgcagca ggcgttctcg    780
caatgggcgg aatcgctgct cgactatgcg acgctgatgg acttttccac cgaaagcctg    840
caaccgatct gggcgctggc cgacaagccc gagcgccgcg tcgagcttga ggacgccttc    900
cccgaattca tgaagcagtc gcagcagtcc atccccaagg tggacaaggt gctgctgatg    960
```

```
gacgcgcggc cgcctatggt gaaggctggg gaggatagcg gctccggcgc gtcggaggat    1020
ctggctgtgt tcaatcccag cacctccaat ggctacaaga tggttggcca gttcggtcag    1080
cgcaaccatg ccagcgtggc ggatggccat gcgccgattt tcaaggatct gttcgatctg    1140
ggcgtgctga aggcgccggt gggttggcag cgggtgtggg acgacgccgg ctccggcaag    1200
tccaaggact acgcgtgctg gcgcgcgatt ccgccgcagg gctaccgcgc gctgggcgat    1260
gtgaaacgtc tggccaccag cggctataac cgccgaatc tgccggacta tgtttgcgtg    1320
catcaaagcc tgtgcgcgga tgtgcagacg ctgcaaaacc gggtgtggtg ggacaagggc    1380
accggcgcgc gcaaggatgt cagcctgtgg caacccgggcg cggccggcgc ggtggcgtcc    1440
tcttgcttcg ccggcgtgcc taattacaac aacccgccca attccggcga catcgagcgc    1500
ttgcgcggca gcatcgcatg cgtgaagacc agcgcgatcg cgtccatgca ggaaatgaag    1560
tccatgctca gccagcacca aggcatggaa gcgatgatgt ccaagctgtg a             1611
```

<210> SEQ ID NO 99
<211> LENGTH: 536
<212> TYPE: PRT
<213> ORGANISM: Artificial Sequence
<220> FEATURE:
<223> OTHER INFORMATION: eAxmi205 #28KR

<400> SEQUENCE: 99

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
    130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
        195                 200                 205

Leu Val Gly Glu Ile Lys Ile Glu His Gly Ser Glu Met Glu Lys Gln
    210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
```

```
                    245                 250                 255
Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
        275                 280                 285

Lys Pro Glu Arg Arg Val Glu Leu Glu Asp Ala Phe Pro Glu Phe Met
    290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
                325                 330                 335

Ala Ser Glu Asp Leu Ala Val Phe Asn Pro Ser Thr Ser Asn Gly Tyr
            340                 345                 350

Lys Met Val Gly Gln Phe Gly Gln Arg Asn His Ala Ser Val Ala Asp
        355                 360                 365

Gly His Ala Pro Ile Phe Lys Asp Leu Phe Asp Leu Gly Val Leu Lys
    370                 375                 380

Ala Pro Val Gly Trp Gln Arg Val Trp Asp Asp Ala Gly Ser Gly Lys
385                 390                 395                 400

Ser Lys Asp Tyr Ala Cys Trp Arg Ala Ile Pro Pro Gln Gly Tyr Arg
                405                 410                 415

Ala Leu Gly Asp Val Lys Arg Leu Ala Thr Ser Gly Tyr Asn Pro Pro
            420                 425                 430

Asn Leu Pro Asp Tyr Val Cys Val His Gln Ser Leu Cys Ala Asp Val
        435                 440                 445

Gln Thr Leu Gln Asn Arg Val Trp Trp Asp Lys Gly Thr Gly Ala Arg
    450                 455                 460

Lys Asp Val Ser Leu Trp Gln Pro Gly Ala Ala Gly Ala Val Ala Ser
465                 470                 475                 480

Ser Cys Phe Ala Gly Val Pro Asn Tyr Asn Asn Pro Pro Asn Ser Gly
                485                 490                 495

Asp Ile Glu Arg Leu Arg Gly Ser Ile Ala Cys Val Lys Thr Ser Ala
            500                 505                 510

Ile Ala Ser Met Gln Glu Met Lys Ser Met Leu Ser Gln His Gln Gly
        515                 520                 525

Met Glu Ala Met Met Ser Lys Leu
    530                 535

<210> SEQ ID NO 100
<211> LENGTH: 1611
<212> TYPE: DNA
<213> ORGANISM: Artificial Sequence
<220> FEATURE:
<223> OTHER INFORMATION: eAxmi205 #28SE

<400> SEQUENCE: 100
atggcatccg cagcaaatgc aggtcagctt ggcaacctcc ccggcgttac ttctatgggc    60
atgggctatg acgtgaatgg tttgtacgcc agcccggaaa gcctgcttgg ccaacccttg   120
ttcgatttcg gcggcgagct ggacagcatc gaaatcgagg ccgcagcta caccttttccc   180 cgcagcatgc atgtacacac ctatttccat tccgacttca acaggatgt cagcaaggaa   240 atcgaagagt atcgggagaa aatgagccag cacgtgggcg tgtccggccg ctacaagttg   300
ttcagcgctt cgctgagcgt ggatttcacc accacggacc agcaactgac cgagattacc   360
tacagctcca cccgcgaagc ccatgtgctg tggtacatca gcctgcctgg cgcggccacg   420
```

```
ctgcgttcga tgctgcgccg cgatttccgc gacgacctga acaacccaa tatgccggcc    480 atggagctgt tcaagcgcta tggtccctac tacatatcgg aagcggcggt gggcggccgg    540
ctggactaca gcgcggccag caagaccttg aagatggaca gcagccagtc gctgtccacc    600
accgccgaaa tgtcctacaa ggcgctggtg ggcgagatca agatcgagca tggctcggag    660
atggaaaagc aggtcaacag cttccgcagc aactccacca tccgtctcac cgccaccggc    720
ggcaagccgg gcatgaccga tcgcatactg acggtccggg attcgcagca ggcgttctcg    780
caatgggcgg aatcgctgct cgactatgcg acgctgatgg acttttccac cgaaagcctg    840
caaccgatct gggcgctggc cgacaagccc gagcgccgcg tcgagcttga ggacgccttc    900
cccgaattca tgaagcagtc gcagcagtcc atccccaagg tggacaaggt gctgctgatg    960
gacgcgcggc cgcctatggt gaaggctggg gaggatagcg gctccggcgc gtcggaggat   1020
ctggctgtgt tcaatcccag cacctccaat ggctacaaga tggttggcca gttcggtcag   1080
cgcaaccatg ccagcgtggc ggatggccat gcgccgattt tcaaggatct gttcgatctg   1140
ggcgtgctga aggcgccggt gggttggcag cgggtgtggg acgacgccgg ctccggcaag   1200
tccaaggact acgcgtgctg gcgcgcgatt ccgccgcagg gctaccgcgc gctgggcgat   1260
gtgagcgaac tggccaccag cggctataac ccgccgaatc tgccggacta tgtttgcgtg   1320
catcaaagcc tgtgcgcgga tgtgcagacg ctgcaaaacc gggtgtggtg ggacaagggc   1380
accggcgcgc gcaaggatgt cagcctgtgg caaccgggcg cggccggcgc ggtggcgtcc   1440
tcttgcttcg ccggcgtgcc taattacaac aacccgccca attccggcga catcgagcgc   1500
ttgcgcggca gcatcgcatg cgtgaagacc agcgcgatcg cgtccatgca ggaaatgaag   1560
tccatgctca gccagcacca aggcatggaa gcgatgatgt ccaagctgtg a              1611
```

<210> SEQ ID NO 101
<211> LENGTH: 536
<212> TYPE: PRT
<213> ORGANISM: Artificial Sequence
<220> FEATURE:
<223> OTHER INFORMATION: eAxmi205 #28SE Protein

<400> SEQUENCE: 101

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
    130                 135                 140

Leu Arg Arg Asp Phe Arg Asp Asp Leu Asn Asn Pro Asn Met Pro Ala
```

```
            145                 150                 155                 160
Met Glu Leu Phe Lys Arg Tyr Gly Tyr Tyr Ile Ser Glu Ala Ala
                165                 170                 175

Val Gly Gly Arg Leu Asp Tyr Ser Ala Ala Ser Lys Thr Leu Lys Met
            180                 185                 190

Asp Ser Gln Ser Leu Ser Thr Thr Ala Glu Met Ser Tyr Lys Ala
            195                 200                 205

Leu Val Gly Glu Ile Lys Ile Glu His Gly Ser Glu Met Glu Lys Gln
            210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
            275                 280                 285

Lys Pro Glu Arg Arg Val Glu Leu Glu Asp Ala Phe Pro Glu Phe Met
            290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
                325                 330                 335

Ala Ser Glu Asp Leu Ala Val Phe Asn Pro Ser Thr Ser Asn Gly Tyr
            340                 345                 350

Lys Met Val Gly Gln Phe Gly Gln Arg Asn His Ala Ser Val Ala Asp
            355                 360                 365

Gly His Ala Pro Ile Phe Lys Asp Leu Phe Asp Leu Gly Val Leu Lys
            370                 375                 380

Ala Pro Val Gly Trp Gln Arg Val Trp Asp Asp Ala Gly Ser Gly Lys
385                 390                 395                 400

Ser Lys Asp Tyr Ala Cys Trp Arg Ala Ile Pro Pro Gln Gly Tyr Arg
                405                 410                 415

Ala Leu Gly Asp Val Ser Glu Leu Ala Thr Ser Gly Tyr Asn Pro Pro
            420                 425                 430

Asn Leu Pro Asp Tyr Val Cys Val His Gln Ser Leu Cys Ala Asp Val
            435                 440                 445

Gln Thr Leu Gln Asn Arg Val Trp Trp Asp Lys Gly Thr Gly Ala Arg
        450                 455                 460

Lys Asp Val Ser Leu Trp Gln Pro Gly Ala Ala Gly Ala Val Ala Ser
465                 470                 475                 480

Ser Cys Phe Ala Gly Val Pro Asn Tyr Asn Asn Pro Asn Ser Gly
                485                 490                 495

Asp Ile Glu Arg Leu Arg Gly Ser Ile Ala Cys Val Lys Thr Ser Ala
            500                 505                 510

Ile Ala Ser Met Gln Glu Met Lys Ser Met Leu Ser Gln His Gln Gly
            515                 520                 525

Met Glu Ala Met Met Ser Lys Leu
        530                 535

<210> SEQ ID NO 102
<211> LENGTH: 1611
<212> TYPE: DNA
<213> ORGANISM: Artificial Sequence
```

<220> FEATURE:
<223> OTHER INFORMATION: eAxmi205 #28KF

<400> SEQUENCE: 102

```
atggcatccg cagcaaatgc aggtcagctt ggcaacctcc ccggcgttac ttctatgggc      60
atgggctatg acgtgaatgg tttgtacgcc agcccggaaa gctgcttgg ccaacccttg     120
ttcgatttcg gcggcgagct ggacagcatc gaaatcgagg ccgcagcta cccttttccc     180
cgcagcatgc atgtacacac ctatttccat tccgacttca acaggatgt cagcaaggaa     240
atcgaagagt atcgggagaa atgagccag cacgtgggcg tgtccggccg ctacaagttg     300
ttcagcgctt cgctgagcgt ggatttcacc accacggacc agcaactgac cgagattacc     360
tacagctcca cccgcgaagc ccatgtgctg tggtacatca gcctgcctgg cgcggccacg     420
ctgcgttcga tgctgcgccg cgatttccgc gacgacctga caaccccaa tatgccggcc     480
atggagctgt tcaagcgcta tggtccctac tacatatcgg aagcggcggt gggcggccgg     540
ctggactaca gcgcggccag caagaccttg aagatggaca gcagccagtc gctgtccacc     600
accgccgaaa tgtcctacaa ggcgctggtg gcgagatca agatcgagca tggctcggag     660
atggaaaagc aggtcaacag cttccgcagc aactccacca tccgtctcac cgccaccggc     720
ggcaagccgg gcatgaccga tcgcatactg cacggtccgg attcgcagca ggcgttctcg     780
caatgggcgg aatcgctgct cgactatgcg acgctgatgg acttttccac cgaaagcctg     840
caaccgatct gggcgctggc cgacaagccc gagcgccgcg tcgagcttga ggacgccttc     900
cccgaattca tgaagcagtc gcagcagtcc atccccaagg tggacaaggt gctgctgatg     960
gacgcgcggc cgcctatggt gaaggctggg gaggatagcg gctccggcgc gtcggaggat    1020
ctggctgtgt tcaatcccag cacctccaat ggctacaaga tggttggcca gttcggtcag    1080
cgcaaccatg ccagcgtggc ggatggccat gcgccgattt tcaaggatct gttcgatctg    1140
ggcgtgctga ggcgccggt gggttggcag cgggtgtggg acgacgccgg ctccggcaag    1200
tccaaggact acgcgtgctg gcgcgcgatt ccgccgcagg gctaccgcgc gctgggcgat    1260
gtgaaatttc tggccaccag cggctataac ccgccgaatc tgccggacta tgtttgcgtg    1320
catcaaagcc tgtgcgcgga tgtgcagacg ctgcaaaacc gggtgtggtg ggacaagggc    1380
accggcgcgc gcaaggatgt cagcctgtgg caaccgggcg cggccggcgc ggtggcgtcc    1440
tcttgcttcg ccggcgtgcc taattacaac aacccgccca ttccggcga catcgagcgc    1500
ttgcgcggca gcatcgcatg cgtgaagacc agcgcgatcg cgtccatgca ggaaatgaag    1560
tccatgctca gccagcacca aggcatggaa gcgatgatgt ccaagctgtg a            1611
```

<210> SEQ ID NO 103
<211> LENGTH: 536
<212> TYPE: PRT
<213> ORGANISM: Artificial Sequence
<220> FEATURE:
<223> OTHER INFORMATION: eAxmi205 #28KF Protein

<400> SEQUENCE: 103

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
```

-continued

```
            50                  55                  60
Val His Thr Tyr Phe His Ser Asp Phe Lys Gln Asp Val Ser Lys Glu
 65                  70                  75                  80

Ile Glu Glu Tyr Arg Glu Lys Met Ser Gln His Val Gly Val Ser Gly
                 85                  90                  95

Arg Tyr Lys Leu Phe Ser Ala Ser Leu Ser Val Asp Phe Thr Thr Thr
                100                 105                 110

Asp Gln Gln Leu Thr Glu Ile Thr Tyr Ser Ser Thr Arg Glu Ala His
                115                 120                 125

Val Leu Trp Tyr Ile Ser Leu Pro Gly Ala Ala Thr Leu Arg Ser Met
130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
                180                 185                 190

Asp Ser Ser Gln Ser Leu Ser Thr Thr Ala Glu Met Ser Tyr Lys Ala
                195                 200                 205

Leu Val Gly Glu Ile Lys Ile Glu His Gly Ser Glu Met Glu Lys Gln
210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
                260                 265                 270

Met Asp Phe Ser Thr Glu Ser Leu Gln Pro Ile Trp Ala Leu Ala Asp
                275                 280                 285

Lys Pro Glu Arg Arg Val Glu Leu Glu Asp Ala Phe Pro Glu Phe Met
290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
                325                 330                 335

Ala Ser Glu Asp Leu Ala Val Phe Asn Pro Ser Thr Ser Asn Gly Tyr
                340                 345                 350

Lys Met Val Gly Gln Phe Gly Gln Arg Asn His Ala Ser Val Ala Asp
                355                 360                 365

Gly His Ala Pro Ile Phe Lys Asp Leu Phe Asp Leu Gly Val Leu Lys
                370                 375                 380

Ala Pro Val Gly Trp Gln Arg Val Trp Asp Asp Ala Gly Ser Gly Lys
385                 390                 395                 400

Ser Lys Asp Tyr Ala Cys Trp Arg Ala Ile Pro Pro Gln Gly Tyr Arg
                405                 410                 415

Ala Leu Gly Asp Val Lys Phe Leu Ala Thr Ser Gly Tyr Asn Pro Pro
                420                 425                 430

Asn Leu Pro Asp Tyr Val Cys Val His Gln Ser Leu Cys Ala Asp Val
                435                 440                 445

Gln Thr Leu Gln Asn Arg Val Trp Trp Asp Lys Gly Thr Gly Ala Arg
                450                 455                 460

Lys Asp Val Ser Leu Trp Gln Pro Gly Ala Ala Gly Ala Val Ala Ser
465                 470                 475                 480
```

Ser Cys Phe Ala Gly Val Pro Asn Tyr Asn Asn Pro Pro Asn Ser Gly
                485                 490                 495

Asp Ile Glu Arg Leu Arg Gly Ser Ile Ala Cys Val Lys Thr Ser Ala
            500                 505                 510

Ile Ala Ser Met Gln Glu Met Lys Ser Met Leu Ser Gln His Gln Gly
        515                 520                 525

Met Glu Ala Met Met Ser Lys Leu
    530                 535

<210> SEQ ID NO 104
<211> LENGTH: 1614
<212> TYPE: DNA
<213> ORGANISM: Artificial Sequence
<220> FEATURE:
<223> OTHER INFORMATION: eAxmi205 #34F

<400> SEQUENCE: 104

| | | |
|---|---|---|
| atggcatccg cagcaaatgc aggtcagctt ggcaacctcc ccggcgttac ttctatgggc | 60 |
| atgggctatg acgtgaatgg tttgtacgcc agcccggaaa gcctgcttgg ccaacccttg | 120 |
| ttcgatttcg gcggcgagct ggacagcatc gaaatcgagg gccgcagcta cacctttccc | 180 |
| cgcagcatgc atgtacacac ctatttccat tccgacttca acaggatgt cagcaaggaa | 240 |
| atcgaagagt atcgggagaa aatgagccag acgtgggcg tgtccggccg ctacaagttg | 300 |
| ttcagcgctt cgctgagcgt ggatttcacc accacggacc agcaactgac cgagattacc | 360 |
| tacagctcca cccgcgaagc ccatgtgctg tggtacatca gcctgcctgg cgcggccacg | 420 |
| ctgcgttcga tgctgcgccg cgatttccgc gacgacctga caaccccaa tatgccggcc | 480 |
| atggagctgt tcaagcgcta tggtccctac tacatatcgg aagcggcggt gggcggccgg | 540 |
| ctggactaca gcgcggccag caagaccttg aagatggaca gcagccagtc gctgtccacc | 600 |
| accgccgaaa tgtcctacaa ggcgctggtg ggcgagatca gatcgagca tggctcggag | 660 |
| atggaaaagc aggtcaacag cttccgcagc aactccacca tccgtctcac cgccaccggc | 720 |
| ggcaagccgg gcatgaccga tcgcatactg cacggtccgg attcgcagca ggcgttctcg | 780 |
| caatgggcgg aatcgctgct cgactatgcg acgctgatgg acttttccac cgaaagcctg | 840 |
| caaccgatct gggcgctggc cgacaagccc gagcgccgcg tcgagcttga ggacgccttc | 900 |
| cccgaattca tgaagcagtc gcagcagtcc atccccaagg tggacaaggt gctgctgatg | 960 |
| gacgcgcggc cgcctatggt gaaggctggg gaggatagcg gctccggcgc gtcggaggat | 1020 |
| ctggctgtgt tcaatcccag cacctccaat ggctacaaga tggttggcca gttcggtcag | 1080 |
| cgcaaccatg ccagcgtggc ggatggccat gcgccgattt tcaaggatct gttcgatctg | 1140 |
| ggcgtgctga aggcgccggt gggttggcag cgggtgtggg acgacgccgg ctccggcaag | 1200 |
| tccaaggact acgcgtgctg gcgcgcgatt ccgccgcagg gctaccgcgc gctgggcgat | 1260 |
| gtgatgatgc tggccaccag cggctataac cgccgaatc tgccggacta tgtttgcgtg | 1320 |
| catcaaagcc tgtgcgcgga tgtgcagacg ctgcaaaacc gggtgtggtg ggacaagggc | 1380 |
| accggcgcgc gcaaggatgt cagcctgtgg caaccgggcg cggcctttgg cgcggtggcg | 1440 |
| tcctcttgct cgccggcgt gcctaattac aacaacccgc ccaattccgg cgacatcgag | 1500 |
| cgcttgcgcg gcagcatcgc atgcgtgaag accagcgcga tcgcgtccat gcaggaaatg | 1560 |
| aagtccatgc tcagccagca ccaaggcatg gaagcgatga tgtccaagct gtga | 1614 |

<210> SEQ ID NO 105

<211> LENGTH: 537
<212> TYPE: PRT
<213> ORGANISM: Artificial Sequence
<220> FEATURE:
<223> OTHER INFORMATION: eAxmi205 #34F Protein

<400> SEQUENCE: 105

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
    130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
        195                 200                 205

Leu Val Gly Glu Ile Lys Ile Glu His Gly Ser Glu Met Glu Lys Gln
    210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
        275                 280                 285

Lys Pro Glu Arg Arg Val Glu Leu Glu Asp Ala Phe Pro Glu Phe Met
    290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
                325                 330                 335

Ala Ser Glu Asp Leu Ala Val Phe Asn Pro Ser Thr Ser Asn Gly Tyr
            340                 345                 350

Lys Met Val Gly Gln Phe Gly Gln Arg Asn His Ala Ser Val Ala Asp
        355                 360                 365

Gly His Ala Pro Ile Phe Lys Asp Leu Phe Asp Leu Gly Val Leu Lys
    370                 375                 380
```

```
Ala Pro Val Gly Trp Gln Arg Val Trp Asp Asp Ala Gly Ser Gly Lys
385                 390                 395                 400

Ser Lys Asp Tyr Ala Cys Trp Arg Ala Ile Pro Pro Gln Gly Tyr Arg
            405                 410                 415

Ala Leu Gly Asp Val Met Met Leu Ala Thr Ser Gly Tyr Asn Pro Pro
        420                 425                 430

Asn Leu Pro Asp Tyr Val Cys Val His Gln Ser Leu Cys Ala Asp Val
    435                 440                 445

Gln Thr Leu Gln Asn Arg Val Trp Trp Asp Lys Gly Thr Gly Ala Arg
450                 455                 460

Lys Asp Val Ser Leu Trp Gln Pro Gly Ala Ala Phe Gly Ala Val Ala
465                 470                 475                 480

Ser Ser Cys Phe Ala Gly Val Pro Asn Tyr Asn Asn Pro Pro Asn Ser
            485                 490                 495

Gly Asp Ile Glu Arg Leu Arg Gly Ser Ile Ala Cys Val Lys Thr Ser
        500                 505                 510

Ala Ile Ala Ser Met Gln Glu Met Lys Ser Met Leu Ser Gln His Gln
    515                 520                 525

Gly Met Glu Ala Met Met Ser Lys Leu
530                 535
```

<210> SEQ ID NO 106
<211> LENGTH: 1614
<212> TYPE: DNA
<213> ORGANISM: Artificial Sequence
<220> FEATURE:
<223> OTHER INFORMATION: eAxmi205 #34D

<400> SEQUENCE: 106

```
atggcatccg cagcaaatgc aggtcagctt ggcaacctcc ccggcgttac ttctatgggc      60
atgggctatg acgtgaatgg tttgtacgcc agcccggaaa gcctgcttgg ccaacccttg     120
ttcgatttcg gcggcgagct ggacagcatc gaaatcgagg ccgcagcta cacctttccc      180
cgcagcatgc atgtacacac ctatttccat tccgacttca acaggatgt cagcaaggaa      240
atcgaagagt atcgggagaa aatgagccag cacgtgggcg tgtccggccg ctacaagttg     300
ttcagcgctt cgctgagcgt ggatttcacc accacggacc agcaactgac cgagattacc     360
tacagctcca cccgcgaagc ccatgtgctg tggtacatca gctgcctgg cgcggccacg      420
ctgcgttcga tgctgcgccg cgatttccgc gacgacctga caaccccaa tatgccggcc      480
atggagctgt tcaagcgcta tggtccctac tacatatcgg aagcggcggt gggcggccgg     540
ctggactaca gcgcggccag caagaccttg aagatggaca gcagccagtc gctgtccacc     600
accgccgaaa tgtcctacaa ggcgctggtg ggcgagatca gatcgagca tggctcggag      660
atggaaaagc aggtcaacag cttccgcagc aactccacca tccgtctcac cgccaccggc     720
ggcaagccgg gcatgaccga tcgcatactg acggtccgg attcgcagca ggcgttctcg      780
caatgggcgg aatcgctgct cgactatgcg acgctgatgg acttttccac cgaaagcctg     840
caaccgatct gggcgctggc cgacaagccc gagcgccgcg tcgagcttga ggacgccttc     900
cccgaattca tgaagcagtc gcagcagtcc atccccaagg tggacaaggt gctgctgatg     960
gacgcgcggc cgcctatggt gaaggctggg gaggatagcg gctccggcgc gtcggaggat    1020
ctggctgtgt tcaatcccag cacctccaat ggctacaaga tggttggcca gttcggtcag    1080
cgcaaccatg ccagcgtggc ggatggccat gcgccgattt tcaaggatct gttcgatctg    1140
```

-continued

```
ggcgtgctga aggcgccggt gggttggcag cgggtgtggg acgacgccgg ctccggcaag    1200
tccaaggact acgcgtgctg gcgcgcgatt ccgccgcagg ctaccgcgc gctgggcgat     1260 gtgatgatgc tggccaccag cggctataac ccgccgaatc tgccggacta tgtttgcgtg    1320
catcaaagcc tgtgcgcgga tgtgcagacg ctgcaaaacc gggtgtggtg ggacaagggc    1380
accggcgcgc gcaaggatgt cagcctgtgg caaccgggcg cggccgatgg cgcggtggcg    1440
tcctcttgct cgccggcgt gcctaattac aacaacccgc ccaattccgg cgacatcgag     1500
cgcttgcgcg gcagcatcgc atgcgtgaag accagcgcga tcgcgtccat gcaggaaatg    1560
aagtccatgc tcagccagca ccaaggcatg gaagcgatga tgtccaagct gtga          1614
```

<210> SEQ ID NO 107
<211> LENGTH: 537
<212> TYPE: PRT
<213> ORGANISM: Artificial Sequence
<220> FEATURE:
<223> OTHER INFORMATION: eAxmi205 #34D Protein

<400> SEQUENCE: 107

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
    130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
        195                 200                 205

Leu Val Gly Glu Ile Lys Ile Glu His Gly Ser Glu Met Glu Lys Gln
    210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
        275                 280                 285
```

Lys Pro Glu Arg Arg Val Glu Leu Glu Asp Ala Phe Pro Glu Phe Met
        290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
                325                 330                 335

Ala Ser Glu Asp Leu Ala Val Phe Asn Pro Ser Thr Ser Asn Gly Tyr
            340                 345                 350

Lys Met Val Gly Gln Phe Gly Gln Arg Asn His Ala Ser Val Ala Asp
        355                 360                 365

Gly His Ala Pro Ile Phe Lys Asp Leu Phe Asp Leu Gly Val Leu Lys
    370                 375                 380

Ala Pro Val Gly Trp Gln Arg Val Trp Asp Asp Ala Gly Ser Gly Lys
385                 390                 395                 400

Ser Lys Asp Tyr Ala Cys Trp Arg Ala Ile Pro Pro Gln Gly Tyr Arg
                405                 410                 415

Ala Leu Gly Asp Val Met Met Leu Ala Thr Ser Gly Tyr Asn Pro Pro
            420                 425                 430

Asn Leu Pro Asp Tyr Val Cys Val His Gln Ser Leu Cys Ala Asp Val
        435                 440                 445

Gln Thr Leu Gln Asn Arg Val Trp Trp Asp Lys Gly Thr Gly Ala Arg
    450                 455                 460

Lys Asp Val Ser Leu Trp Gln Pro Gly Ala Ala Asp Gly Ala Val Ala
465                 470                 475                 480

Ser Ser Cys Phe Ala Gly Val Pro Asn Tyr Asn Pro Pro Asn Ser
                485                 490                 495

Gly Asp Ile Glu Arg Leu Arg Gly Ser Ile Ala Cys Val Lys Thr Ser
            500                 505                 510

Ala Ile Ala Ser Met Gln Glu Met Lys Ser Met Leu Ser Gln His Gln
        515                 520                 525

Gly Met Glu Ala Met Met Ser Lys Leu
    530                 535

<210> SEQ ID NO 108
<211> LENGTH: 1614
<212> TYPE: DNA
<213> ORGANISM: Artificial Sequence
<220> FEATURE:
<223> OTHER INFORMATION: eAxmi205 #34R

<400> SEQUENCE: 108
atggcatccg cagcaaatgc aggtcagctt ggcaacctcc ccggcgttac ttctatgggc    60
atgggctatg acgtgaatgg tttgtacgcc agcccggaaa gcctgcttgg ccaaccctTg   120
ttcgatttcg gcggcgagct ggacagcatc gaaatcgagg ccgcagcta caccttTccc    180 cgcagcatgc atgtacacac ctatttccat tccgacttca acaggatgt cagcaaggaa    240 atcgaagagt atcgggagaa atgagccag cacgtgggcg tgtccggccg ctacaagttg    300
ttcagcgctt cgctgagcgt ggatttcacc accacggacc agcaactgac cgagattacc    360
tacagctcca cccgcgaagc ccatgtgctg tggtacatca gcctgcctgg cgcggccacg    420
ctgcgttcga tgctgcgccg cgatttccgc gacgacctga caacccccaa tatgccggcc    480
atggagctgt tcaagcgcta tggtccctac tacatatcgg aagcggcggt gggcggccgg    540
ctggactaca gcgcggccag caagaccttg aagatggaca gcagccagtc gctgtccacc    600

```
accgccgaaa tgtcctacaa ggcgctggtg ggcgagatca agatcgagca tggctcggag    660
atggaaaagc aggtcaacag cttccgcagc aactccacca tccgtctcac cgccaccggc    720
ggcaagccgg gcatgaccga tcgcatactg cacggtccgg attcgcagca ggcgttctcg    780
caatgggcgg aatcgctgct cgactatgcg acgctgatgg acttttccac cgaaagcctg    840
caaccgatct gggcgctggc cgacaagccc gagcgccgcg tcgagcttga ggacgccttc    900
cccgaattca tgaagcagtc gcagcagtcc atccccaagg tggacaaggt gctgctgatg    960
gacgcgcggc cgcctatggt gaaggctggg gaggatagcg gctccggcgc gtcggaggat   1020
ctggctgtgt tcaatcccag cacctccaat ggctacaaga tggttggcca gttcggtcag   1080
cgcaaccatg ccagcgtggc ggatggccat gcgccgattt tcaaggatct gttcgatctg   1140
ggcgtgctga aggcgccggt gggttggcag cgggtgtggg acgacgccgg ctccggcaag   1200
tccaaggact acgcgtgctg gcgcgcgatt ccgccgcagg gctaccgcgc gctgggcgat   1260
gtgatgatgc tggccaccag cggctataac ccgccgaatc tgccggacta tgtttgcgtg   1320
catcaaagcc tgtgcgcgga tgtgcagacg ctgcaaaacc gggtgtggtg ggacaagggc   1380
accggcgcgc gcaaggatgt cagcctgtgg caaccgggcg cggcccgtgg cgcggtggcg   1440
tcctcttgct tcgccggcgt gcctaattac aacaacccgc ccaattccgg cgacatcgag   1500
cgcttgcgcg gcagcatcgc atgcgtgaag accagcgcga tcgcgtccat gcaggaaatg   1560
aagtccatgc tcagccagca ccaaggcatg gaagcgatga tgtccaagct gtga          1614
```

<210> SEQ ID NO 109
<211> LENGTH: 537
<212> TYPE: PRT
<213> ORGANISM: Artificial Sequence
<220> FEATURE:
<223> OTHER INFORMATION: eAxmi205 #34R Protein

<400> SEQUENCE: 109

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
    130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
            180                 185                 190
```

Asp Ser Ser Gln Ser Leu Ser Thr Thr Ala Glu Met Ser Tyr Lys Ala
            195                 200                 205

Leu Val Gly Glu Ile Lys Ile Glu His Gly Ser Glu Met Glu Lys Gln
    210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
        275                 280                 285

Lys Pro Glu Arg Arg Val Glu Leu Glu Asp Ala Phe Pro Glu Phe Met
    290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
                325                 330                 335

Ala Ser Glu Asp Leu Ala Val Phe Asn Pro Ser Thr Ser Asn Gly Tyr
            340                 345                 350

Lys Met Val Gly Gln Phe Gly Gln Arg Asn His Ala Ser Val Ala Asp
        355                 360                 365

Gly His Ala Pro Ile Phe Lys Asp Leu Phe Asp Leu Gly Val Leu Lys
    370                 375                 380

Ala Pro Val Gly Trp Gln Arg Val Trp Asp Asp Ala Gly Ser Gly Lys
385                 390                 395                 400

Ser Lys Asp Tyr Ala Cys Trp Arg Ala Ile Pro Pro Gln Gly Tyr Arg
                405                 410                 415

Ala Leu Gly Asp Val Met Met Leu Ala Thr Ser Gly Tyr Asn Pro Pro
            420                 425                 430

Asn Leu Pro Asp Tyr Val Cys Val His Gln Ser Leu Cys Ala Asp Val
        435                 440                 445

Gln Thr Leu Gln Asn Arg Val Trp Trp Asp Lys Gly Thr Gly Ala Arg
    450                 455                 460

Lys Asp Val Ser Leu Trp Gln Pro Gly Ala Ala Arg Gly Ala Val Ala
465                 470                 475                 480

Ser Ser Cys Phe Ala Gly Val Pro Asn Tyr Asn Asn Pro Asn Ser
                485                 490                 495

Gly Asp Ile Glu Arg Leu Arg Gly Ser Ile Ala Cys Val Lys Thr Ser
            500                 505                 510

Ala Ile Ala Ser Met Gln Glu Met Lys Ser Met Leu Ser Gln His Gln
        515                 520                 525

Gly Met Glu Ala Met Met Ser Lys Leu
    530                 535

<210> SEQ ID NO 110
<211> LENGTH: 1614
<212> TYPE: DNA
<213> ORGANISM: Artificial Sequence
<220> FEATURE:
<223> OTHER INFORMATION: eAxmi205 #36D

<400> SEQUENCE: 110
atggcatccg cagcaaatgc aggtcagctt ggcaacctcc ccggcgttac ttctatgggc    60

```
atgggctatg acgtgaatgg tttgtacgcc agcccggaaa gcctgcttgg ccaacccttg    120
ttcgatttcg gcggcgagct ggacagcatc gaaatcgagg gccgcagcta cacctttccc    180
cgcagcatgc atgtacacac ctatttccat tccgacttca acaggatgt cagcaaggaa     240 atcgaagagt atcgggagaa aatgagccag cacgtgggcg tgtccggccg ctacaagttg    300
ttcagcgctt cgctgagcgt ggatttcacc accacggacc agcaactgac cgagattacc    360
tacagctcca cccgcgaagc ccatgtgctg tggtacatca gcctgcctgg cgcggccacg    420
ctgcgttcga tgctgcgccg cgatttccgc gacgacctga caaccccaa tatgccggcc     480 atggagctgt tcaagcgcta tggtccctac tacatatcgg aagcggcggt gggcggccgg    540
ctggactaca gcgcggccag caagaccttg aagatggaca gcagccagtc gctgtccacc    600
accgccgaaa tgtcctacaa ggcgctggtg ggcgagatca agatcgagca tggctcggag    660
atggaaaagc aggtcaacag cttccgcagc aactccacca tccgtctcac cgccaccggc    720
ggcaagccgg gcatgaccga tcgcatactg cacggtccgg attcgcagca ggcgttctcg    780
caatgggcgg aatcgctgct cgactatgcg acgctgatga cttttccac cgaaagcctg     840 caaccgatct gggcgctggc cgacaagccc gagcgccgcg tcgagcttga ggacgccttc    900
cccgaattca tgaagcagtc gcagcagtcc atccccaagg tggacaaggt gctgctgatg    960
gacgcgcggc cgcctatggt gaaggctggg gaggatagcg gctccggcgc gtcggaggat    1020
ctggctgtgt tcaatcccag cacctccaat ggctacaaga tggttggcca gttcggtcag    1080
cgcaaccatg ccagcgtggc ggatggccat gcgccgattt tcaaggatct gttcgatctg    1140
ggcgtgctga aggcgccggt gggttggcag cgggtgtggg acgacgccgg ctccggcaag    1200
tccaaggact acgcgtgctg gcgcgcgatt ccgccgcagg gctaccgcgc gctgggcgat    1260
gtgatgatgc tggccaccag cggctataac cgccgaatc tgccggacta tgtttgcgtg     1320
catcaaagcc tgtgcgcgga tgtgcagacg ctgcaaaacc gggtgtggtg gacaagggc     1380 accggcgcgc gcaaggatgt cagcctgtgg caaccgggcg cggccggcgc ggtggcgtcc    1440
tcttgcttcg ccggcgtgcc taattacaac aacccgccca attccggcga tgacatcgag    1500
cgcttgcgcg gcagcatcgc atgcgtgaag accagcgcga tcgcgtccat gcaggaaatg    1560
aagtccatgc tcagccagca ccaaggcatg gaagcgatga tgtccaagct gtga          1614
```

<210> SEQ ID NO 111  
<211> LENGTH: 537  
<212> TYPE: PRT  
<213> ORGANISM: Artificial Sequence  
<220> FEATURE:  
<223> OTHER INFORMATION: eAxmi205 #36D Protein

<400> SEQUENCE: 111

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95
```

-continued

```
Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
            115                 120                 125

Val Leu Trp Tyr Ile Ser Leu Pro Gly Ala Ala Thr Leu Arg Ser Met
130                 135                 140

Leu Arg Arg Asp Phe Arg Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
            195                 200                 205

Leu Val Gly Glu Ile Lys Ile Glu His Gly Ser Glu Met Glu Lys Gln
210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
            275                 280                 285

Lys Pro Glu Arg Arg Val Glu Leu Glu Asp Ala Phe Pro Glu Phe Met
290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
                325                 330                 335

Ala Ser Glu Asp Leu Ala Val Phe Asn Pro Ser Thr Ser Asn Gly Tyr
            340                 345                 350

Lys Met Val Gly Gln Phe Gly Gln Arg Asn His Ala Ser Val Ala Asp
            355                 360                 365

Gly His Ala Pro Ile Phe Lys Asp Leu Phe Asp Leu Gly Val Leu Lys
370                 375                 380

Ala Pro Val Gly Trp Gln Arg Val Trp Asp Asp Ala Gly Ser Gly Lys
385                 390                 395                 400

Ser Lys Asp Tyr Ala Cys Trp Arg Ala Ile Pro Pro Gln Gly Tyr Arg
                405                 410                 415

Ala Leu Gly Asp Val Met Met Leu Ala Thr Ser Gly Tyr Asn Pro Pro
            420                 425                 430

Asn Leu Pro Asp Tyr Val Cys Val His Gln Ser Leu Cys Ala Asp Val
            435                 440                 445

Gln Thr Leu Gln Asn Arg Val Trp Trp Asp Lys Gly Thr Gly Ala Arg
450                 455                 460

Lys Asp Val Ser Leu Trp Gln Pro Gly Ala Ala Gly Ala Val Ala Ser
465                 470                 475                 480

Ser Cys Phe Ala Gly Val Pro Asn Tyr Asn Pro Asn Ser Gly
                485                 490                 495

Asp Asp Ile Glu Arg Leu Arg Gly Ser Ile Ala Cys Val Lys Thr Ser
            500                 505                 510
```

Ala Ile Ala Ser Met Gln Glu Met Lys Ser Met Leu Ser Gln His Gln
    515                 520                 525

Gly Met Glu Ala Met Met Ser Lys Leu
    530                 535

<210> SEQ ID NO 112
<211> LENGTH: 1614
<212> TYPE: DNA
<213> ORGANISM: Artificial Sequence
<220> FEATURE:
<223> OTHER INFORMATION: eAxmi205 #36F

<400> SEQUENCE: 112

| | | | | | |
|---|---|---|---|---|---|
| atggcatccg | cagcaaatgc | aggtcagctt | ggcaacctcc | ccggcgttac | ttctatgggc | 60 |
| atgggctatg | acgtgaatgg | tttgtacgcc | agcccggaaa | gcctgcttgg | ccaacccttg | 120 |
| ttcgatttcg | gcggcgagct | ggacagcatc | gaaatcgagg | ccgcagcta | cacctttccc | 180 |
| cgcagcatgc | atgtacacac | ctatttccat | tccgacttca | acaggatgt | cagcaaggaa | 240 |
| atcgaagagt | atcgggagaa | aatgagccag | cacgtgggcg | tgtccggccg | ctacaagttg | 300 |
| ttcagcgctt | cgctgagcgt | ggatttcacc | accacggacc | agcaactgac | cgagattacc | 360 |
| tacagctcca | cccgcgaagc | ccatgtgctg | tggtacatca | gctgcctgg | cgcggccacg | 420 |
| ctgcgttcga | tgctgcgccg | cgatttccgc | gacgacctga | caaccccaa | tatgccggcc | 480 |
| atggagctgt | tcaagcgcta | tggtccctac | tacatatcgg | aagcggcggt | gggcggccgg | 540 |
| ctggactaca | gcgcggccag | caagaccttg | aagatggaca | gcagccagtc | gctgtccacc | 600 |
| accgccgaaa | tgtcctacaa | ggcgctggtg | gcgagatca | agatcgagca | tggctcggag | 660 |
| atggaaaagc | aggtcaacag | cttccgcagc | aactccacca | tccgtctcac | cgccaccggc | 720 |
| ggcaagccgg | gcatgaccga | tcgcatactg | cacggtccgg | attcgcagca | ggcgttctcg | 780 |
| caatgggcgg | aatcgctgct | cgactatgcg | acgctgatgg | acttttccac | cgaaagcctg | 840 |
| caaccgatct | gggcgctggc | cgacaagccc | gagcgccgcg | tcgagcttga | ggacgccttc | 900 |
| cccgaattca | tgaagcagtc | gcagcagtcc | atccccaagg | tggacaaggt | gctgctgatg | 960 |
| gacgcgcggc | cgcctatggt | gaaggctggg | gaggatagcg | gctccggcgc | gtcggaggat | 1020 |
| ctggctgtgt | tcaatcccag | cacctccaat | ggctacaaga | tggttggcca | gttcggtcag | 1080 |
| cgcaaccatg | ccagcgtggc | ggatggccat | gcgccgattt | tcaaggatct | gttcgatctg | 1140 |
| ggcgtgctga | aggcgccggt | gggttggcag | cgggtgtggg | acgacgccgg | ctccggcaag | 1200 |
| tccaaggact | acgcgtgctg | gcgcgcgatt | ccgccgcagg | gctaccgcgc | gctgggcgat | 1260 |
| gtgatgatgc | tggccaccag | cggctataac | ccgccgaatc | tgccggacta | tgtttgcgtg | 1320 |
| catcaaagcc | tgtgcgcgga | tgtgcagacg | ctgcaaaacc | gggtgtggtg | ggacaagggc | 1380 |
| accggcgcgc | gcaaggatgt | cagcctgtgg | caaccgggcg | cggccggcgc | ggtggcgtcc | 1440 |
| tcttgcttcg | ccggcgtgcc | taattacaac | aacccgccca | attccggctt | tgacatcgag | 1500 |
| cgcttgcgcg | gcagcatcgc | atgcgtgaag | accagcgcga | tcgcgtccat | gcaggaaatg | 1560 |
| aagtccatgc | tcagccagca | ccaaggcatg | gaagcgatga | tgtccaagct | gtga | 1614 |

<210> SEQ ID NO 113
<211> LENGTH: 537
<212> TYPE: PRT
<213> ORGANISM: Artificial Sequence
<220> FEATURE:
<223> OTHER INFORMATION: eAxmi205 #36F Protein

<400> SEQUENCE: 113

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
            35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65              70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
                100                 105                 110

Asp Gln Gln Leu Thr Glu Ile Thr Tyr Ser Ser Thr Arg Glu Ala His
                115                 120                 125

Val Leu Trp Tyr Ile Ser Leu Pro Gly Ala Ala Thr Leu Arg Ser Met
            130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
                180                 185                 190

Asp Ser Ser Gln Ser Leu Ser Thr Thr Ala Glu Met Ser Tyr Lys Ala
                195                 200                 205

Leu Val Gly Glu Ile Lys Ile Glu His Gly Ser Glu Met Glu Lys Gln
210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
                260                 265                 270

Met Asp Phe Ser Thr Glu Ser Leu Gln Pro Ile Trp Ala Leu Ala Asp
                275                 280                 285

Lys Pro Glu Arg Arg Val Glu Leu Glu Asp Ala Phe Pro Glu Phe Met
                290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
                325                 330                 335

Ala Ser Glu Asp Leu Ala Val Phe Asn Pro Ser Thr Ser Asn Gly Tyr
                340                 345                 350

Lys Met Val Gly Gln Phe Gly Gln Arg Asn His Ala Ser Val Ala Asp
                355                 360                 365

Gly His Ala Pro Ile Phe Lys Asp Leu Phe Asp Leu Gly Val Leu Lys
    370                 375                 380

Ala Pro Val Gly Trp Gln Arg Val Trp Asp Asp Ala Gly Ser Gly Lys
385                 390                 395                 400

Ser Lys Asp Tyr Ala Cys Trp Arg Ala Ile Pro Pro Gln Gly Tyr Arg
                405                 410                 415
```

```
Ala Leu Gly Asp Val Met Met Leu Ala Thr Ser Gly Tyr Asn Pro Pro
            420                 425                 430

Asn Leu Pro Asp Tyr Val Cys Val His Gln Ser Leu Cys Ala Asp Val
        435                 440                 445

Gln Thr Leu Gln Asn Arg Val Trp Trp Asp Lys Gly Thr Gly Ala Arg
450                 455                 460

Lys Asp Val Ser Leu Trp Gln Pro Gly Ala Gly Ala Val Ala Ser
465                 470                 475                 480

Ser Cys Phe Ala Gly Val Pro Asn Tyr Asn Asn Pro Pro Asn Ser Gly
                485                 490                 495

Phe Asp Ile Glu Arg Leu Arg Gly Ser Ile Ala Cys Val Lys Thr Ser
            500                 505                 510

Ala Ile Ala Ser Met Gln Glu Met Lys Ser Met Leu Ser Gln His Gln
        515                 520                 525

Gly Met Glu Ala Met Met Ser Lys Leu
530                 535
```

<210> SEQ ID NO 114
<211> LENGTH: 1614
<212> TYPE: DNA
<213> ORGANISM: Artificial Sequence
<220> FEATURE:
<223> OTHER INFORMATION: eAxmi205 #36R

<400> SEQUENCE: 114

```
atggcatccg cagcaaatgc aggtcagctt ggcaaccctc ccggcgttac ttctatgggc      60
atgggctatg acgtgaatgg tttgtacgcc agcccggaaa gcctgcttgg ccaacccttg     120
ttcgatttcg cggcgagctg gacagcatc gaaatcgagg ccgcagcta cactttccc       180
cgcagcatgc atgtacacac ctatttccat tccgacttca acaggatgt cagcaaggaa     240
atcgaagagt atcgggagaa atgagccag acgtgggcg tgtccggccg ctacaagttg      300
ttcagcgctt cgctgagcgt ggatttcacc accacggacc agcaactgac cgagattacc     360
tacagctcca cccgcgaagc ccatgtgctg tggtacatca gcctgcctgg cgcggccacg     420
ctgcgttcga tgctgcgccg cgatttccgc gacgacctga caacccccaa tatgccggcc     480
atggagctgt tcaagcgcta tggtccctac tacatatcgg aagcggcggt gggcggccgg     540
ctggactaca gcgcggccag caagaccttg aagatggaca gcagccagtc gctgtccacc     600
accgccgaaa tgtcctacaa ggcgctggtg ggcgagatca agatcgagca tggctcggag     660
atggaaaagc aggtcaacag cttccgcagc aactccacca tccgtctcac cgccaccggc     720
ggcaagccgg gcatgaccga tcgcatactg cacggtccgg attcgcagca ggcgttctcg     780
caatgggcgg aatcgctgct cgactatgcg acgctgatgg acttttccac cgaaagcctg     840
caaccgatct gggcgctggc cgacaagccc gagcgccgcg tcgagcttga ggacgccttc     900
cccgaattca tgaagcagtc gcagcagtcc atccccaagg tggacaaggt gctgctgatg     960
gacgcgcggc cgcctatggt gaaggctggg gaggatagcg ctccggcgc gtcggaggat    1020
ctggctgtgt tcaatcccag cacctccaat ggctacaaga tggttggcca gttcggtcag    1080
cgcaaccatg ccagcgtggc ggatggccat gcgccgattt tcaaggatct gttcgatctg    1140
ggcgtgctga aggcgccggt gggttggcag cgggtgtggg acgacgccgg ctccggcaag    1200
tccaaggact acgcgtgctg gcgcgcgatt ccgccgcagg gctaccgcgc gctgggcgat    1260
gtgatgatgc tggccaccag cggctataac ccgccgaatc tgccggacta tgtttgcgtg    1320
catcaaagcc tgtgcgcgga tgtgcagacg ctgcaaaacc gggtgtggtg ggacaagggc    1380
```

```
accggcgcgc gcaaggatgt cagcctgtgg caaccgggcg cggccggcgc ggtggcgtcc    1440
tcttgcttcg ccggcgtgcc taattacaac aacccgccca attccggccg tgacatcgag    1500
cgcttgcgcg gcagcatcgc atgcgtgaag accagcgcga tcgcgtccat gcaggaaatg    1560
aagtccatgc tcagccagca ccaaggcatg gaagcgatga tgtccaagct gtga           1614
```

<210> SEQ ID NO 115
<211> LENGTH: 537
<212> TYPE: PRT
<213> ORGANISM: Artificial Sequence
<220> FEATURE:
<223> OTHER INFORMATION: eAxmi205 #36R Protein

<400> SEQUENCE: 115

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
    130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
        195                 200                 205

Leu Val Gly Glu Ile Lys Ile Glu His Gly Ser Glu Met Glu Lys Gln
    210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
        275                 280                 285

Lys Pro Glu Arg Arg Val Glu Leu Glu Asp Ala Phe Pro Glu Phe Met
    290                 295                 300

Lys Gln Ser Gln Gln Ser Ile Pro Lys Val Asp Lys Val Leu Leu Met
305                 310                 315                 320
```

```
Asp Ala Arg Pro Pro Met Val Lys Ala Gly Glu Asp Ser Gly Ser Gly
            325                 330                 335

Ala Ser Glu Asp Leu Ala Val Phe Asn Pro Ser Thr Ser Asn Gly Tyr
        340                 345                 350

Lys Met Val Gly Gln Phe Gly Gln Arg Asn His Ala Ser Val Ala Asp
    355                 360                 365

Gly His Ala Pro Ile Phe Lys Asp Leu Phe Asp Leu Gly Val Leu Lys
370                 375                 380

Ala Pro Val Gly Trp Gln Arg Val Trp Asp Ala Gly Ser Gly Lys
385                 390                 395                 400

Ser Lys Asp Tyr Ala Cys Trp Arg Ala Ile Pro Pro Gln Gly Tyr Arg
        405                 410                 415

Ala Leu Gly Asp Val Met Met Leu Ala Thr Ser Gly Tyr Asn Pro Pro
    420                 425                 430

Asn Leu Pro Asp Tyr Val Cys Val His Gln Ser Leu Cys Ala Asp Val
435                 440                 445

Gln Thr Leu Gln Asn Arg Val Trp Trp Asp Lys Gly Thr Gly Ala Arg
    450                 455                 460

Lys Asp Val Ser Leu Trp Gln Pro Gly Ala Ala Gly Ala Val Ala Ser
465                 470                 475                 480

Ser Cys Phe Ala Gly Val Pro Asn Tyr Asn Asn Pro Asn Ser Gly
        485                 490                 495

Arg Asp Ile Glu Arg Leu Arg Gly Ser Ile Ala Cys Val Lys Thr Ser
                500                 505                 510

Ala Ile Ala Ser Met Gln Glu Met Lys Ser Met Leu Ser Gln His Gln
    515                 520                 525

Gly Met Glu Ala Met Met Ser Lys Leu
530                 535
```

<210> SEQ ID NO 116
<211> LENGTH: 1614
<212> TYPE: DNA
<213> ORGANISM: Artificial Sequence
<220> FEATURE:
<223> OTHER INFORMATION: eAxmi205 #37F

<400> SEQUENCE: 116

```
atggcatccg cagcaaatgc aggtcagctt ggcaacctcc ccggcgttac ttctatgggc    60
atgggctatg acgtgaatgg tttgtacgcc agcccggaaa gcctgcttgg ccaacccttg   120
ttcgatttcg gcggcgagct ggacagcatc gaaatcgagg ccgcagcta  cacctttccc   180
cgcagcatgc atgtacacac ctatttccat tccgacttca acaggatgt  cagcaaggaa   240
atcgaagagt atcgggagaa atgagccag cacgtgggcg tgtccggccg ctacaagttg    300
ttcagcgctt cgctgagcgt ggatttcacc accacggacc agcaactgac cgagattacc   360
tacagctcca cccgcgaagc ccatgtgctg tggtacatca gcctgcctgg cgcggccacg   420
ctgcgttcga tgctgcgccg cgatttccgc gacgacctga caaccccaa  tatgccggcc   480
atggagctgt tcaagcgcta tggtccctac tacatatcgg aagcggcggt gggcggccgg   540
ctggactaca gcgcggccag caagaccttg aagatggaca gcagccagtc gctgtccacc   600
accgccgaaa tgtcctacaa ggcgctggtg gcgagatca agatcgagca tggctcggag   660
atggaaaagc aggtcaacag cttccgcagc aactccacca tccgtctcac cgccaccggc   720
ggcaagccgg gcatgaccga tcgcatactg cacggtccgg attcgcagca ggcgttctcg   780
caatgggcgg aatcgctgct cgactatgcg acgctgatgg acttttccac cgaaagcctg   840
```

```
caaccgatct gggcgctggc cgacaagccc gagcgccgcg tcgagcttga ggacgccttc    900
cccgaattca tgaagcagtc gcagcagtcc atccccaagg tggacaaggt gctgctgatg    960
gacgcgcggc cgcctatggt gaaggctggg gaggatagcg gctccggcgc gtcggaggat   1020
ctggctgtgt tcaatcccag cacctccaat ggctacaaga tggttggcca gttcggtcag   1080
cgcaaccatg ccagcgtggc ggatggccat gcgccgattt tcaaggatct gttcgatctg   1140
ggcgtgctga aggcgccggt gggttggcag cgggtgtggg acgacgccgg ctccggcaag   1200
tccaaggact acgcgtgctg gcgcgcgatt ccgccgcagg gctaccgcgc gctgggcgat   1260
gtgatgatgc tggccaccag cggctataac ccgccgaatc tgccggacta tgtttgcgtg   1320
catcaaagcc tgtgcgcgga tgtgcagacg ctgcaaaacc gggtgtggtg ggacaagggc   1380
accggcgcgc gcaaggatgt cagcctgtgg caatttccgg gcgcggccgg cgcggtggcg   1440
tcctcttgct cgccggcgt gcctaattac aacaacccgc ccaattccgg cgacatcgag   1500
cgcttgcgcg gcagcatcgc atgcgtgaag accagcgcga tcgcgtccat gcaggaaatg   1560
aagtccatgc tcagccagca ccaaggcatg gaagcgatga tgtccaagct gtga         1614
```

<210> SEQ ID NO 117
<211> LENGTH: 537
<212> TYPE: PRT
<213> ORGANISM: Artificial Sequence
<220> FEATURE:
<223> OTHER INFORMATION: eAxmi205 #37F Protein

<400> SEQUENCE: 117

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
    130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
        195                 200                 205

Leu Val Gly Glu Ile Lys Ile Glu His Gly Ser Glu Met Glu Lys Gln
    210                 215                 220
```

| | | | | | | | | | | | | | | |
|---|---|---|---|---|---|---|---|---|---|---|---|---|---|---|
| Val | Asn | Ser | Phe | Arg | Ser | Asn | Ser | Thr | Ile | Arg | Leu | Thr | Ala | Thr | Gly |
| 225 | | | | | 230 | | | | | 235 | | | | | 240 |
| Gly | Lys | Pro | Gly | Met | Thr | Asp | Arg | Ile | Leu | His | Gly | Pro | Asp | Ser | Gln |
| | | | | 245 | | | | | 250 | | | | | 255 | |
| Gln | Ala | Phe | Ser | Gln | Trp | Ala | Glu | Ser | Leu | Leu | Asp | Tyr | Ala | Thr | Leu |
| | | | 260 | | | | | 265 | | | | | 270 | | |
| Met | Asp | Phe | Ser | Thr | Glu | Ser | Leu | Gln | Pro | Ile | Trp | Ala | Leu | Ala | Asp |
| | | | 275 | | | | | 280 | | | | | 285 | | |
| Lys | Pro | Glu | Arg | Arg | Val | Glu | Leu | Glu | Asp | Ala | Phe | Pro | Glu | Phe | Met |
| 290 | | | | | 295 | | | | | 300 | | | | | |
| Lys | Gln | Ser | Gln | Gln | Ser | Ile | Pro | Lys | Val | Asp | Lys | Val | Leu | Leu | Met |
| 305 | | | | | 310 | | | | | 315 | | | | | 320 |
| Asp | Ala | Arg | Pro | Pro | Met | Val | Lys | Ala | Gly | Glu | Asp | Ser | Gly | Ser | Gly |
| | | | | 325 | | | | | 330 | | | | | 335 | |
| Ala | Ser | Glu | Asp | Leu | Ala | Val | Phe | Asn | Pro | Ser | Thr | Ser | Asn | Gly | Tyr |
| | | | | 340 | | | | | 345 | | | | | 350 | |
| Lys | Met | Val | Gly | Gln | Phe | Gly | Gln | Arg | Asn | His | Ala | Ser | Val | Ala | Asp |
| | | | 355 | | | | | 360 | | | | | 365 | | |
| Gly | His | Ala | Pro | Ile | Phe | Lys | Asp | Leu | Phe | Asp | Leu | Gly | Val | Leu | Lys |
| | 370 | | | | | 375 | | | | | 380 | | | | |
| Ala | Pro | Val | Gly | Trp | Gln | Arg | Val | Trp | Asp | Asp | Ala | Gly | Ser | Gly | Lys |
| 385 | | | | | 390 | | | | | 395 | | | | | 400 |
| Ser | Lys | Asp | Tyr | Ala | Cys | Trp | Arg | Ala | Ile | Pro | Pro | Gln | Gly | Tyr | Arg |
| | | | | 405 | | | | | 410 | | | | | 415 | |
| Ala | Leu | Gly | Asp | Val | Met | Met | Leu | Ala | Thr | Ser | Gly | Tyr | Asn | Pro | Pro |
| | | | 420 | | | | | 425 | | | | | 430 | | |
| Asn | Leu | Pro | Asp | Tyr | Val | Cys | Val | His | Gln | Ser | Leu | Cys | Ala | Asp | Val |
| | | | 435 | | | | | 440 | | | | | 445 | | |
| Gln | Thr | Leu | Gln | Asn | Arg | Val | Trp | Trp | Asp | Lys | Gly | Thr | Gly | Ala | Arg |
| | 450 | | | | | 455 | | | | | 460 | | | | |
| Lys | Asp | Val | Ser | Leu | Trp | Gln | Phe | Pro | Gly | Ala | Ala | Gly | Ala | Val | Ala |
| 465 | | | | | 470 | | | | | 475 | | | | | 480 |
| Ser | Ser | Cys | Phe | Ala | Gly | Val | Pro | Asn | Tyr | Asn | Asn | Pro | Pro | Asn | Ser |
| | | | | 485 | | | | | 490 | | | | | 495 | |
| Gly | Asp | Ile | Glu | Arg | Leu | Arg | Gly | Ser | Ile | Ala | Cys | Val | Lys | Thr | Ser |
| | | | | 500 | | | | | 505 | | | | | 510 | |
| Ala | Ile | Ala | Ser | Met | Gln | Glu | Met | Lys | Ser | Met | Leu | Ser | Gln | His | Gln |
| | | | 515 | | | | | 520 | | | | | 525 | | |
| Gly | Met | Glu | Ala | Met | Met | Ser | Lys | Leu |
| | 530 | | | | | 535 | | |

<210> SEQ ID NO 118
<211> LENGTH: 1614
<212> TYPE: DNA
<213> ORGANISM: Artificial Sequence
<220> FEATURE:
<223> OTHER INFORMATION: eAxmi205 #37L

<400> SEQUENCE: 118

```
atggcatccg cagcaaatgc aggtcagctt ggcaacctcc ccggcgttac ttctatgggc      60
atgggctatg acgtgaatgg tttgtacgcc agcccggaaa gcctgcttgg ccaacccttg     120
ttcgatttcg gcggcgagct ggacagcatc gaaatcgagg ccgcagcta caccttttccc    180 cgcagcatgc atgtacacac ctatttccat tccgacttca acaggatgt cagcaaggaa     240 atcgaagagt atcggagaa aatgagccag cacgtgggcg tgtccggccg ctacaagttg     300
```

```
ttcagcgctt cgctgagcgt ggatttcacc accacggacc agcaactgac cgagattacc    360
tacagctcca cccgcgaagc ccatgtgctg tggtacatca gcctgcctgg cgcggccacg    420
ctgcgttcga tgctgcgccg cgatttccgc gacgacctga acaacccaa tatgccggcc     480
atggagctgt tcaagcgcta tggtccctac tacatatcgg aagcggcggt gggcggccgg    540
ctggactaca gcgcggccag caagaccttg aagatggaca gcagccagtc gctgtccacc    600
accgccgaaa tgtcctacaa ggcgctggtg ggcgagatca agatcgagca tggctcggag    660
atggaaaagc aggtcaacag cttccgcagc aactccacca tccgtctcac cgccaccggc    720
ggcaagccgg gcatgaccga tcgcatactg cacggtccgg attcgcagca ggcgttctcg    780
caatgggcgg aatcgctgct cgactatgcg acgctgatgg acttttccac cgaaagcctg    840
caaccgatct gggcgctggc cgacaagccc gagcgccgcg tcgagcttga ggacgccttc    900
cccgaattca tgaagcagtc gcagcagtcc atccccaagg tggacaaggt gctgctgatg    960
gacgcgcggc cgcctatggt gaaggctggg gaggatagcg gctccggcgc gtcggaggat    1020
ctggctgtgt tcaatcccag cacctccaat ggctacaaga tggttggcca gttcggtcag    1080
cgcaaccatg ccagcgtggc ggatggccat gcgccgattt tcaaggatct gttcgatctg    1140
ggcgtgctga aggcgccggt gggttggcag cgggtgtggg acgacgccgg ctccggcaag    1200
tccaaggact acgcgtgctg gcgcgcgatt ccgccgcagg gctaccgcgc gctgggcgat    1260
gtgatgatgc tggccaccag cggctataac ccgccgaatc tgccggacta tgtttgcgtg    1320
catcaaagcc tgtgcgcgga tgtgcagacg ctgcaaaacc gggtgtggtg ggacaagggc    1380
accggcgcgc gcaaggatgt cagcctgtgg caactgccgg gcgcggccgg cgcggtggcg    1440
tcctcttgct cgccggcgt gcctaattac aacaacccgc ccaattccgg cgacatcgag     1500
cgcttgcgcg gcagcatcgc atgcgtgaag accagcgcga tcgcgtccat gcaggaaatg    1560
aagtccatgc tcagccagca ccaaggcatg gaagcgatga tgtccaagct gtga          1614
```

<210> SEQ ID NO 119
<211> LENGTH: 537
<212> TYPE: PRT
<213> ORGANISM: Artificial Sequence
<220> FEATURE:
<223> OTHER INFORMATION: eAxmi205 #37L Protein

<400> SEQUENCE: 119

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125
```

```
Val Leu Trp Tyr Ile Ser Leu Pro Gly Ala Ala Thr Leu Arg Ser Met
    130                 135                 140

Leu Arg Arg Asp Phe Arg Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
                180                 185                 190

Asp Ser Ser Gln Ser Leu Ser Thr Thr Ala Glu Met Ser Tyr Lys Ala
                195                 200                 205

Leu Val Gly Glu Ile Lys Ile Glu His Gly Ser Glu Met Glu Lys Gln
    210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
                260                 265                 270

Met Asp Phe Ser Thr Glu Ser Leu Gln Pro Ile Trp Ala Leu Ala Asp
                275                 280                 285

Lys Pro Glu Arg Arg Val Glu Leu Glu Asp Ala Phe Pro Glu Phe Met
290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
                325                 330                 335

Ala Ser Glu Asp Leu Ala Val Phe Asn Pro Ser Thr Ser Asn Gly Tyr
                340                 345                 350

Lys Met Val Gly Gln Phe Gly Gln Arg Asn His Ala Ser Val Ala Asp
                355                 360                 365

Gly His Ala Pro Ile Phe Lys Asp Leu Phe Asp Leu Gly Val Leu Lys
    370                 375                 380

Ala Pro Val Gly Trp Gln Arg Val Trp Asp Asp Ala Gly Ser Gly Lys
385                 390                 395                 400

Ser Lys Asp Tyr Ala Cys Trp Arg Ala Ile Pro Pro Gln Gly Tyr Arg
                405                 410                 415

Ala Leu Gly Asp Val Met Met Leu Ala Thr Ser Gly Tyr Asn Pro Pro
                420                 425                 430

Asn Leu Pro Asp Tyr Val Cys Val His Gln Ser Leu Cys Ala Asp Val
                435                 440                 445

Gln Thr Leu Gln Asn Arg Val Trp Trp Asp Lys Gly Thr Gly Ala Arg
    450                 455                 460

Lys Asp Val Ser Leu Trp Gln Leu Pro Gly Ala Ala Gly Ala Val Ala
465                 470                 475                 480

Ser Ser Cys Phe Ala Gly Val Pro Asn Tyr Asn Asn Pro Pro Asn Ser
                485                 490                 495

Gly Asp Ile Glu Arg Leu Arg Gly Ser Ile Ala Cys Val Lys Thr Ser
                500                 505                 510

Ala Ile Ala Ser Met Gln Glu Met Lys Ser Met Leu Ser Gln His Gln
                515                 520                 525

Gly Met Glu Ala Met Met Ser Lys Leu
    530                 535
```

<210> SEQ ID NO 120
<211> LENGTH: 1614
<212> TYPE: DNA
<213> ORGANISM: Artificial Sequence
<220> FEATURE:
<223> OTHER INFORMATION: eAxmi205 #38F

<400> SEQUENCE: 120

```
atggcatccg cagcaaatgc aggtcagctt ggcaacctcc ccggcgttac ttctatgggc      60
atgggctatg acgtgaatgg tttgtacgcc agcccggaaa gcctgcttgg ccaacccttg     120
ttcgatttcg gcggcgagct ggacagcatc gaaatcgagg gccgcagcta caccttccc     180
cgcagcatgc atgtacacac ctatttccat tccgacttca acaggatgt cagcaaggaa     240
atcgaagagt atcgggagaa atgagccag cacgtgggcg tgtccggccg ctacaagttg     300
ttcagcgctt cgctgagcgt ggatttcacc accacggacc agcaactgac cgagattacc     360
tacagctcca cccgcgaagc ccatgtgctg tggtacatca gcctgcctgg cgcggccacg     420
ctgcgttcga tgctgcgccg cgatttccgc gacgacctga caaccccaa tatgccggcc     480
atggagctgt tcaagcgcta tggtccctac tacatatcgg aagcggcggt gggcggccgg     540
ctggactaca gcgcggccag caagaccttg aagatggaca gcagccagtc gctgtccacc     600
accgccgaaa tgtcctacaa ggcgctggtg ggcgagatca agatcgagca tggctcggag     660
atggaaaagc aggtcaacag cttccgcagc aactccacca tccgtctcac cgccaccggc     720
ggcaagccgg gcatgaccga tcgcatactg cacggtccgg attcgcagca ggcgttctcg     780
caatgggcgg aatcgctgct cgactatgcg acgctgatgg acttttccac cgaaaagcctg     840
caaccgatct gggcgctggc cgacaagccc gagcgccgcg tcgagcttga ggacgccttc     900
cccgaattca tgaagcagtc gcagcagtcc atccccaagg tggacaaggt gctgctgatg     960
gacgcgcggc cgcctatggt gaaggctggg gaggatagcg gctccggcgc gtcggaggat    1020
ctggctgtgt tcaatcccag cacctccaat ggctacaaga tggttggcca gttcggtcag    1080
cgcaaccatg ccagcgtggc ggatggccat gcgccgattt tcaaggatct gttcgatctg    1140
ggcgtgctga aggcgccggt gggttggcag cgggtgtggg acgacgccgg ctccggcaag    1200
tccaaggact acgcgtgctg gcgcgcgatt ccgccgcagg gctaccgcgc gctgggcgat    1260
gtgatgatgc tggccaccag cggctataac ccgccgaatc tgccggacta tgtttgcgtg    1320
catcaaagcc tgtgcgcgga tgtgcagacg ctgcaaaacc gggtgtggtg ggacaagggc    1380
accggcgcgc gcaaggatgt cagcctgtgg caaccgggcg cggccggcgc ggtggcgttt    1440
tcctcttgct cgccggcgt gcctaattac aacaacccgc ccaattccgg cgacatcgag    1500
cgcttgcgcg gcagcatcgc atgcgtgaag accagcgcga tcgcgtccat gcaggaaatg    1560
aagtccatgc tcagccagca ccaaggcatg gaagcgatga tgtccaagct gtga          1614
```

<210> SEQ ID NO 121
<211> LENGTH: 537
<212> TYPE: PRT
<213> ORGANISM: Artificial Sequence
<220> FEATURE:
<223> OTHER INFORMATION: eAxmi205 #38F Protein

<400> SEQUENCE: 121

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30
```

-continued

Glu Ser Leu Leu Gly Gln Pro Leu Phe Asp Phe Gly Glu Leu Asp
         35                  40                  45

Ser Ile Glu Ile Glu Gly Arg Ser Tyr Thr Phe Pro Arg Ser Met His
 50                  55                  60

Val His Thr Tyr Phe His Ser Asp Phe Lys Gln Asp Val Ser Lys Glu
 65                  70                  75                  80

Ile Glu Glu Tyr Arg Glu Lys Met Ser Gln His Val Gly Val Ser Gly
                 85                  90                  95

Arg Tyr Lys Leu Phe Ser Ala Ser Leu Ser Val Asp Phe Thr Thr Thr
             100                 105                 110

Asp Gln Gln Leu Thr Glu Ile Thr Tyr Ser Ser Thr Arg Glu Ala His
             115                 120                 125

Val Leu Trp Tyr Ile Ser Leu Pro Gly Ala Ala Thr Leu Arg Ser Met
130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                 165                 170                 175

Val Gly Arg Leu Asp Tyr Ser Ala Ala Ser Lys Thr Leu Lys Met
             180                 185                 190

Asp Ser Ser Gln Ser Leu Ser Thr Thr Ala Glu Met Ser Tyr Lys Ala
             195                 200                 205

Leu Val Gly Glu Ile Lys Ile Glu His Gly Ser Glu Met Glu Lys Gln
             210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                 245                 250                 255

Gln Ala Phe Ser Gln Trp Ala Glu Ser Leu Leu Asp Tyr Ala Thr Leu
             260                 265                 270

Met Asp Phe Ser Thr Glu Ser Leu Gln Pro Ile Trp Ala Leu Ala Asp
             275                 280                 285

Lys Pro Glu Arg Arg Val Glu Leu Glu Asp Ala Phe Pro Glu Phe Met
290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
                 325                 330                 335

Ala Ser Glu Asp Leu Ala Val Phe Asn Pro Ser Thr Ser Asn Gly Tyr
             340                 345                 350

Lys Met Val Gly Gln Phe Gly Gln Arg Asn His Ala Ser Val Ala Asp
             355                 360                 365

Gly His Ala Pro Ile Phe Lys Asp Leu Phe Asp Leu Gly Val Leu Lys
370                 375                 380

Ala Pro Val Gly Trp Gln Arg Val Trp Asp Asp Ala Gly Ser Gly Lys
385                 390                 395                 400

Ser Lys Asp Tyr Ala Cys Trp Arg Ala Ile Pro Pro Gln Gly Tyr Arg
                 405                 410                 415

Ala Leu Gly Asp Val Met Met Leu Ala Thr Ser Gly Tyr Asn Pro Pro
             420                 425                 430

Asn Leu Pro Asp Tyr Val Cys Val His Gln Ser Leu Cys Ala Asp Val
             435                 440                 445

Gln Thr Leu Gln Asn Arg Val Trp Trp Asp Lys Gly Thr Gly Ala Arg

```
                450               455               460
Lys Asp Val Ser Leu Trp Gln Pro Gly Ala Ala Gly Ala Val Ala Phe
465                 470                 475                 480

Ser Ser Cys Phe Ala Gly Val Pro Asn Tyr Asn Asn Pro Pro Asn Ser
                485                 490                 495

Gly Asp Ile Glu Arg Leu Arg Gly Ser Ile Ala Cys Val Lys Thr Ser
            500                 505                 510

Ala Ile Ala Ser Met Gln Glu Met Lys Ser Met Leu Ser Gln His Gln
        515                 520                 525

Gly Met Glu Ala Met Met Ser Lys Leu
    530                 535

<210> SEQ ID NO 122
<211> LENGTH: 1614
<212> TYPE: DNA
<213> ORGANISM: Artificial Sequence
<220> FEATURE:
<223> OTHER INFORMATION: eAxmi205 #38L

<400> SEQUENCE: 122
atggcatccg cagcaaatgc aggtcagctt ggcaacctcc ccggcgttac ttctatgggc     60
atgggctatg acgtgaatgg tttgtacgcc agcccggaaa gcctgcttgg ccaacccttg    120
ttcgatttcg gcggcgagct ggacagcatc gaaatcgagg ccgcagcta cacctttccc     180 cgcagcatgc atgtacacac ctatttccat tccgacttca acaggatgt cagcaaggaa     240 atcgaagagt atcgggagaa aatgagccag acgtgggcg tgtccggccg ctacaagttg     300
ttcagcgctt cgctgagcgt ggatttcacc accacggacc agcaactgac cgagattacc    360
tacagctcca cccgcgaagc ccatgtgctg tggtacatca gcctgcctgg cgcggccacg    420
ctgcgttcga tgctgcgccg cgatttccgc gacgacctga caaccccaa tatgccggcc     480 atggagctgt tcaagcgcta tggtccctac tacatatcgg aagcggcggt gggcggccgg    540
ctggactaca gcgcggccag caagaccttg aagatggaca gcagccagtc gctgtccacc    600
accgccgaaa tgtcctacaa ggcgctggtg ggcgagatca agatcgagca tggctcggag    660
atggaaaagc aggtcaacag cttccgcagc aactccacca tccgtctcac cgccaccggc    720
ggcaagccgg gcatgaccga tcgcatactg cacggtccgg attcgcagca ggcgttctcg    780
caatgggcgg aatcgctgct cgactatgcg acgctgatgg acttttccac cgaaaagcctg   840 caaccgatct gggcgctggc cgacaagccc gagcgccgcg tcgagcttga ggacgccttc    900
cccgaattca tgaagcagtc gcagcagtcc atccccaagg tggacaaggt gctgctgatg    960
gacgcgcggc cgcctatggt gaaggctggg gaggatagcg gctccggcgc gtcggaggat   1020
ctggctgtgt tcaatcccag cacctccaat ggctacaaga tggttggcca gttcggtcag   1080
cgcaaccatg ccagcgtggc ggatggccat gcgccgattt tcaaggatct gttcgatctg   1140
ggcgtgctga aggcgccggt gggttggcag cgggtgtggg acgacgccgg ctccggcaag   1200
tccaaggact acgcgtgctg gcgcgcgatt ccgccgcagg gctaccgcgc gctgggcgat   1260
gtgatgatgc tggccaccag cggctataac ccgccgaatc tgccggacta tgtttgcgtg   1320
catcaaagcc tgtgcgcgga tgtgcagacg ctgcaaaacc gggtgtggtg ggacaagggc   1380
accggcgcgc gcaaggatgt cagcctgtgg caaccgggcg cggccggcgc ggtggcgctg   1440
tcctcttgct tcgccggcgt gcctaattac aacaacccgc ccaattccgg cgacatcgag   1500
cgcttgcgcg gcagcatcgc atgcgtgaag accagcgcga tcgcgtccat gcaggaaatg   1560
```
aagtccatgc tcagccagca ccaaggcatg gaagcgatga tgtccaagct gtga        1614

<210> SEQ ID NO 123
<211> LENGTH: 537
<212> TYPE: PRT
<213> ORGANISM: Artificial Sequence
<220> FEATURE:
<223> OTHER INFORMATION: eAxmi205 #38L Protein

<400> SEQUENCE: 123

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
    130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
        195                 200                 205

Leu Val Gly Glu Ile Lys Ile Glu His Gly Ser Glu Met Glu Lys Gln
    210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
        275                 280                 285

Lys Pro Glu Arg Arg Val Glu Leu Glu Asp Ala Phe Pro Glu Phe Met
    290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Asp Ser Gly Ser Gly
                325                 330                 335

Ala Ser Glu Asp Leu Ala Val Phe Asn Pro Ser Thr Ser Asn Gly Tyr
            340                 345                 350

Lys Met Val Gly Gln Phe Gly Gln Arg Asn His Ala Ser Val Ala Asp
```

|       |       |       |       | 355   |       |       |       |       | 360   |       |       |       |       | 365   |
|-------|-------|-------|-------|-------|-------|-------|-------|-------|-------|-------|-------|-------|-------|-------|

Gly His Ala Pro Ile Phe Lys Asp Leu Phe Asp Leu Gly Val Leu Lys
   370                            375                      380

Ala Pro Val Gly Trp Gln Arg Val Trp Asp Asp Ala Gly Ser Gly Lys
385                      390                     395                     400

Ser Lys Asp Tyr Ala Cys Trp Arg Ala Ile Pro Pro Gln Gly Tyr Arg
                405                     410                    415

Ala Leu Gly Asp Val Met Met Leu Ala Thr Ser Gly Tyr Asn Pro Pro
           420                     425                    430

Asn Leu Pro Asp Tyr Val Cys Val His Gln Ser Leu Cys Ala Asp Val
        435                     440                    445

Gln Thr Leu Gln Asn Arg Val Trp Trp Asp Lys Gly Thr Gly Ala Arg
     450                      455                    460

Lys Asp Val Ser Leu Trp Gln Pro Gly Ala Ala Gly Ala Val Ala Leu
465                      470                     475                     480

Ser Ser Cys Phe Ala Gly Val Pro Asn Tyr Asn Asn Pro Pro Asn Ser
                485                     490                    495

Gly Asp Ile Glu Arg Leu Arg Gly Ser Ile Ala Cys Val Lys Thr Ser
           500                     505                    510

Ala Ile Ala Ser Met Gln Glu Met Lys Ser Met Leu Ser Gln His Gln
        515                     520                    525

Gly Met Glu Ala Met Met Ser Lys Leu
   530                          535

<210> SEQ ID NO 124
<211> LENGTH: 1614
<212> TYPE: DNA
<213> ORGANISM: Artificial Sequence
<220> FEATURE:
<223> OTHER INFORMATION: eAxmi205 #39F

<400> SEQUENCE: 124

```
atggcatccg cagcaaatgc aggtcagctt ggcaacctcc ccggcgttac ttctatgggc      60
atgggctatg acgtgaatgg tttgtacgcc agcccggaaa gcctgcttgg ccaacccttg     120
ttcgatttcg gcggcgagct ggacagcatc gaaatcgagg ccgcagcta cacctttccc     180
cgcagcatgc atgtacacac ctatttccat tccgacttca acaggatgt cagcaaggaa     240
atcgaagagt atcgggagaa aatgagccag cacgtgggcg tgtccggccg ctacaagttg     300
ttcagcgctt cgctgagcgt ggatttcacc accacggacc agcaactgac cgagattacc     360
tacagctcca cccgcgaagc ccatgtgctg tggtacatca gctgcctgg cgcggccacg     420
ctgcgttcga tgctgcgccg cgatttccgc gacgacctga caacccccaa tatgccggcc     480
atggagctgt tcaagcgcta tggtccctac tacatatcgg aagcggcggt gggcggccgg     540
ctggactaca gcgcggccag caagaccttg aagatggaca gcagccagtc gctgtccacc     600
accgccgaaa tgtcctacaa ggcgctggtg ggcgagatca gatcgagca tggctcggag     660
atggaaaagc aggtcaacag cttccgcagc aactccacca tccgtctcac cgccaccggc     720
ggcaagccgg gcatgaccga tcgcatactg cacggtccgg attcgcagca ggcgttctcg     780
caatgggcgg aatcgctgct cgactatgcg acgctgatgg acttttccac cgaaagcctg     840
caaccgatct gggcgctggc cgacaagccc gagcgccgcg tcgagcttga ggacgccttc     900
cccgaattca tgaagcagtc gcagcagtcc atccccaagg tggacaaggt gctgctgatg     960
gacgcgcggc cgcctatggt gaaggctggg gaggatagcg gctccggcgc gtcggaggat    1020
```

-continued

```
ctggctgtgt tcaatcccag cacctccaat ggctacaaga tggttggcca gttcggtcag   1080
cgcaaccatg ccagcgtggc ggatggccat gcgccgattt tcaaggatct gttcgatctg   1140
ggcgtgctga aggcgccggt gggttggcag cgggtgtggg acgacgccgg ctccggcaag   1200
tccaaggact acgcgtgctg gcgcgcgatt ccgccgcagg gctaccgcgc gctgggcgat   1260
gtgatgatgc tggccaccag cggctataac ccgccgaatc tgccggacta tgtttgcgtg   1320
catcaaagcc tgtgcgcgga tgtgcagacg ctgcaaaacc gggtgtggtg ggacaagggc   1380
accggcgcgc gcaaggatgt cagcctgtgg caaccgggcg cggccggcgc ggtggcgtcc   1440
tcttgcttcg ccggcgtgcc taattacttt aacaacccgc ccaattccgg cgacatcgag   1500
cgcttgcgcg gcagcatcgc atgcgtgaag accagccgcg atcgcgtcca tgcaggaaatg   1560 aagtccatgc tcagccagca ccaaggcatg gaagcgatga tgtccaagct gtga          1614
```

<210> SEQ ID NO 125
<211> LENGTH: 537
<212> TYPE: PRT
<213> ORGANISM: Artificial Sequence
<220> FEATURE:
<223> OTHER INFORMATION: eAxmi205 #39F Protein

<400> SEQUENCE: 125

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
                20                  25                  30

Glu Ser Leu Leu Gly Gln Pro Leu Phe Asp Phe Gly Gly Glu Leu Asp
            35                  40                  45

Ser Ile Glu Ile Glu Gly Arg Ser Tyr Thr Phe Pro Arg Ser Met His
        50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
    130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
        195                 200                 205

Leu Val Gly Glu Ile Lys Ile Glu His Gly Ser Glu Met Glu Lys Gln
    210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
```

```
                    260                 265                 270
Met Asp Phe Ser Thr Glu Ser Leu Gln Pro Ile Trp Ala Leu Ala Asp
                275                 280                 285
Lys Pro Glu Arg Arg Val Glu Leu Glu Asp Ala Phe Pro Glu Phe Met
            290                 295                 300
Lys Gln Ser Gln Gln Ser Ile Pro Lys Val Asp Lys Val Leu Leu Met
305                 310                 315                 320
Asp Ala Arg Pro Pro Met Val Lys Ala Gly Glu Asp Ser Gly Ser Gly
                325                 330                 335
Ala Ser Glu Asp Leu Ala Val Phe Asn Pro Ser Thr Ser Asn Gly Tyr
            340                 345                 350
Lys Met Val Gly Gln Phe Gly Gln Arg Asn His Ala Ser Val Ala Asp
        355                 360                 365
Gly His Ala Pro Ile Phe Lys Asp Leu Phe Asp Leu Gly Val Leu Lys
    370                 375                 380
Ala Pro Val Gly Trp Gln Arg Val Trp Asp Asp Ala Gly Ser Gly Lys
385                 390                 395                 400
Ser Lys Asp Tyr Ala Cys Trp Arg Ala Ile Pro Pro Gln Gly Tyr Arg
                405                 410                 415
Ala Leu Gly Asp Val Met Met Leu Ala Thr Ser Gly Tyr Asn Pro Pro
            420                 425                 430
Asn Leu Pro Asp Tyr Val Cys Val His Gln Ser Leu Cys Ala Asp Val
        435                 440                 445
Gln Thr Leu Gln Asn Arg Val Trp Trp Asp Lys Gly Thr Gly Ala Arg
    450                 455                 460
Lys Asp Val Ser Leu Trp Gln Pro Gly Ala Ala Gly Ala Val Ala Ser
465                 470                 475                 480
Ser Cys Phe Ala Gly Val Pro Asn Tyr Phe Asn Pro Pro Asn Ser
                485                 490                 495
Gly Asp Ile Glu Arg Leu Arg Gly Ser Ile Ala Cys Val Lys Thr Ser
            500                 505                 510
Ala Ile Ala Ser Met Gln Glu Met Lys Ser Met Leu Ser Gln His Gln
        515                 520                 525
Gly Met Glu Ala Met Met Ser Lys Leu
    530                 535

<210> SEQ ID NO 126
<211> LENGTH: 1614
<212> TYPE: DNA
<213> ORGANISM: Artificial Sequence
<220> FEATURE:
<223> OTHER INFORMATION: eAxmi205 #39L

<400> SEQUENCE: 126
atggcatccg cagcaaatgc aggtcagctt ggcaacctcc ccggcgttac ttctatgggc      60
atgggctatg acgtgaatgg tttgtacgcc agcccggaaa gcctgcttgg ccaacccttg     120
ttcgatttcg gcggcgagct ggacagcatc gaaatcgagg ccgcagcta cacctttccc      180 cgcagcatgc atgtacacac ctatttccat tccgacttca acaggatgt cagcaaggaa      240 atcgaagagt atcgggagaa aatgagccag cacgtgggcg tgtccggccg ctacaagttg     300
ttcagcgctt cgctgagcgt ggatttcacc accacggacc agcaactgac cgagattacc     360
tacagctcca cccgcgaagc ccatgtgctg tggtacatca gctgcctgg cgcggccacg      420 ctgcgttcga tgctgcgccg cgatttccgc gacgacctga caaccccaa tatgccggcc      480
```

```
atggagctgt tcaagcgcta tggtccctac tacatatcgg aagcggcggt gggcggccgg      540
ctggactaca gcgcggccag caagaccttg aagatggaca gcagccagtc gctgtccacc      600
accgccgaaa tgtcctacaa ggcgctggtg ggcgagatca agatcgagca tggctcggag      660
atggaaaagc aggtcaacag cttccgcagc aactccacca tccgtctcac cgccaccggc      720
ggcaagccgg gcatgaccga tcgcatactg cacggtccgg attcgcagca ggcgttctcg      780
caatgggcgg aatcgctgct cgactatgcg acgctgatgg acttttccac cgaaagcctg      840
caaccgatct gggcgctggc cgacaagccc gagcgccgcg tcgagcttga ggacgccttc      900
cccgaattca tgaagcagtc gcagcagtcc atccccaagg tggacaaggt gctgctgatg      960
gacgcgcggc cgcctatggt gaaggctggg gaggatagcg gctccggcgc gtcggaggat     1020
ctggctgtgt tcaatcccag cacctccaat ggctacaaga tggttggcca gttcggtcag     1080
cgcaaccatg ccagcgtggc ggatggccat gcgccgattt tcaaggatct gttcgatctg     1140
ggcgtgctga aggcgccggt gggttggcag cgggtgtggg acgacgccgg ctccggcaag     1200
tccaaggact acgcgtgctg gcgcgcgatt ccgccgcagg gctaccgcgc gctgggcgat     1260
gtgatgatgc tggccaccag cggctataac ccgccgaatc tgccggacta tgtttgcgtg     1320
catcaaagcc tgtgcgcgga tgtgcagacg ctgcaaaacc gggtgtggtg ggacaagggc     1380
accggcgcgc gcaaggatgt cagcctgtgg caaccgggcg cggccggcgc ggtggcgtcc     1440
tcttgcttcg ccggcgtgcc taattacctg aacaacccgc ccaattccgg cgacatcgag     1500
cgcttgcgcg gcagcatcgc atgcgtgaag accagcgcga tcgcgtccat gcaggaaatg     1560
aagtccatgc tcagccagca ccaaggcatg gaagcgatga tgtccaagct gtga           1614
```

<210> SEQ ID NO 127
<211> LENGTH: 537
<212> TYPE: PRT
<213> ORGANISM: Artificial Sequence
<220> FEATURE:
<223> OTHER INFORMATION: eAxmi205 #39L Protein

<400> SEQUENCE: 127

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
    130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
```

```
                165                 170                 175
Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
            195                 200                 205

Leu Val Gly Glu Ile Lys Ile Glu His Gly Ser Glu Met Glu Lys Gln
            210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
            245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
            275                 280                 285

Lys Pro Glu Arg Arg Val Glu Leu Glu Asp Ala Phe Pro Glu Phe Met
            290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
            325                 330                 335

Ala Ser Glu Asp Leu Ala Val Phe Asn Pro Ser Thr Ser Asn Gly Tyr
            340                 345                 350

Lys Met Val Gly Gln Phe Gly Gln Arg Asn His Ala Ser Val Ala Asp
            355                 360                 365

Gly His Ala Pro Ile Phe Lys Asp Leu Phe Asp Leu Gly Val Leu Lys
            370                 375                 380

Ala Pro Val Gly Trp Gln Arg Val Trp Asp Asp Ala Gly Ser Gly Lys
385                 390                 395                 400

Ser Lys Asp Tyr Ala Cys Trp Arg Ala Ile Pro Pro Gln Gly Tyr Arg
            405                 410                 415

Ala Leu Gly Asp Val Met Met Leu Ala Thr Ser Gly Tyr Asn Pro Pro
            420                 425                 430

Asn Leu Pro Asp Tyr Val Cys Val His Gln Ser Leu Cys Ala Asp Val
            435                 440                 445

Gln Thr Leu Gln Asn Arg Val Trp Trp Asp Lys Gly Thr Gly Ala Arg
            450                 455                 460

Lys Asp Val Ser Leu Trp Gln Pro Gly Ala Ala Gly Ala Val Ala Ser
465                 470                 475                 480

Ser Cys Phe Ala Gly Val Pro Asn Tyr Leu Asn Asn Pro Pro Asn Ser
            485                 490                 495

Gly Asp Ile Glu Arg Leu Arg Gly Ser Ile Ala Cys Val Lys Thr Ser
            500                 505                 510

Ala Ile Ala Ser Met Gln Glu Met Lys Ser Met Leu Ser Gln His Gln
            515                 520                 525

Gly Met Glu Ala Met Met Ser Lys Leu
530                 535
```

ENGINEERED PESTICIDAL PROTEINS AND METHODS OF CONTROLLING PLANT PESTS

CROSS-REFERENCE

This application is a § 371 of PCT/US2018/053687, filed, Oct. 1, 2018, and published Apr. 11, 2019 as WO2019/070554, which claims priority from U.S. Provisional Application No. 62/566,692, filed Oct. 2, 2017, both of which are incorporated herein by reference in their entirety.

FIELD OF THE INVENTION

This invention relates to engineered pesticidal proteins and the nucleic acid molecules that encode them, as well as compositions and methods for controlling plant pests.

STATEMENT REGARDING ELECTRONIC SUBMISSION OF A SEQUENCE LISTING

A Sequence Listing in ASCII text format, submitted under 37 C.F.R. § 1.821, entitled "81453_US_REG_ORG_P_1_ST25", 425 KB in size, generated on Sep. 28, 2018 and filed via EFS-Web is provided in lieu of a paper copy. This Sequence Listing is hereby incorporated by reference into the specification for its disclosure.

BACKGROUND

Insect pests are a major cause of crop losses. In the US alone, billions of dollars are lost every year due to infestation by various genera of insects. In addition to losses in field crops, insect pests are also a burden to vegetable and fruit growers, to producers of ornamental flowers, and they are a nuisance to gardeners and homeowners.

Species of corn rootworm are considered to be the most destructive corn pests. In the United States, the three important species are *Diabrotica virgifera virgifera*, the western corn rootworm (WCRW), *D. longicornis barberi*, the northern corn rootworm (NCRW and *D. undecimpunctata howardi*, the southern corn rootworm (SCRW). Only western and northern corn rootworms are considered primary pests of corn in the US Corn Belt. Additionally, an important corn rootworm pest in the Southern US is the Mexican corn rootworm, *Diabrotica virgifera zeae* (MCRW). Corn rootworm larvae cause the most substantial plant damage by feeding almost exclusively on corn roots. This injury has been shown to increase plant lodging, to reduce grain yield and vegetative yield as well as alter the nutrient content of the grain. Larval feeding also causes indirect effects on corn by opening avenues through the roots for bacterial and fungal infections which lead to root and stalk rot diseases. Adult corn rootworms are active in cornfields in late summer where they feed on ears, silks and pollen, thus interfering with normal pollination.

Corn rootworms are mainly controlled by intensive applications of chemical pesticides, which are active through inhibition of insect growth, prevention of insect feeding or reproduction, or cause death. Good corn rootworm control can thus be reached, but these chemicals can sometimes also affect other, beneficial organisms. Another problem resulting from the wide use of chemical pesticides is the appearance of resistant insect varieties. Yet another problem is due to the fact that corn rootworm larvae feed underground thus making it difficult to apply rescue treatments of insecticides. Therefore, most insecticide applications are made prophylactically at the time of planting. This practice results in a large environmental burden. This has been partially alleviated by various farm management practices, but there is an increasing need for alternative pest control mechanisms.

Biological pest control agents, such as *Bacillus thuringiensis* (Bt) strains expressing pesticidal toxins like delta-endotoxins (also called crystal toxins or Cry proteins), have been applied to crop plants with satisfactory results against insect pests. The delta-endotoxins are proteins held within a crystalline matrix that are known to possess insecticidal activity when ingested by certain insects. Several native Cry proteins from *Bacillus thuringiensis*, or engineered Cry proteins, have been expressed in transgenic crop plants and exploited commercially to control certain lepidopteran and coleopteran insect pests. For example, starting in 2003, transgenic corn hybrids that control corn rootworm by expressing a Cry3Bb1 (e.g., in corn event MON88017), Cry34Ab1/Cry35Ab1 (e.g., in corn event DAS-59122) or modified Cry3A (mCry3A; e.g., in corn event MIR604) or Cry3Ab (eCry3.1Ab; e.g., in corn event MIR604) protein have been available commercially in the US.

Although the usage of transgenic plants expressing Cry proteins has been shown to be extremely effective, insect pests that now have resistance against the Cry proteins expressed in certain transgenic plants are known. Therefore, there remains a need to identity new and effective pest control agents that provide an economic benefit to farmers and that are environmentally acceptable. Particularly needed are proteins that are toxic to *Diabrotica* species, a major pest of corn, that have a different mode of action than existing insect control products as a way to mitigate the development of resistance. Furthermore, delivery of insect control agents through products that minimize the burden on the environment, as through transgenic plants, are desirable.

SUMMARY OF THE INVENTION

The invention provides nucleic acids, polypeptides, compositions and methods for conferring pesticidal activity (e.g., insecticidal activity) to bacteria, plants, plant cells, tissues and seeds. In particular, the invention provides novel engineered pesticidal proteins (e.g., engineered insecticidal proteins), optionally with altered or enhanced pesticidal (e.g., insecticidal) activity and/or processing (i.e., cleavage) by mammalian digestive proteases as compared with the parent molecule (i.e., an Axmi205 protein that does not comprise a modification according to the present invention).

In embodiments, the engineered proteins of the invention are toxic to economically important insect pests (e.g., by inhibiting the ability of the insect pest to survive, grow and/or reproduce), particularly insect pests that infest plants. For example, in embodiments, the insecticidal proteins of the invention can be used to control one or more economically important coleopteran pests including without limitation Bean Leaf Beetle (*Cerotoma trifurcata*), Colorado Potato Beetle (*Leptinotarsa decemlineata*), Boll Weevil (*Anthonomus grandis*) and/or a corn rootworm pest (e.g., *Diabrotica* spp.), for example, Western Corn Rootworm (WCRW; *Diabrotica virgifera virgifera*), Northern Corn Rootworm (NCRW; *D. barberi*), Southern Corn Rootworm (*D. undecimpunctata howardi*), Mexican Corn Rootworm (MCRW; *D. virgifera zeae*), and the like. In embodiments, the insecticidal protein has activity against a WCRW pest that is resistant to a mCry3A protein (e.g., in corn event MIR604), a eCry3.1Ab protein (e.g., in corn event 5307), a Cry3Bb1 protein (e.g., in corn event MON88017), a Cry34/

35Ab1 binary protein (e.g., in corn event DAS-59122) and/or a RNAi trait, such as DvSnf7 dsRNA (e.g., in corn event MON87411). Accordingly, as one aspect, the invention provides a modified Axmi205 toxin, wherein said modified Axmi205 toxin has insecticidal activity against a plant pest (e.g., an insect pest, such as a coleopteran pest) and comprises a modification (e.g., deletion, substitution and/or insertion) of one or more amino acids incorporated in the amino acid sequence of SEQ ID NO: 1 or an amino acid sequence that is substantially identical to the amino acid sequence of the polypeptide of SEQ ID NO: 1, and wherein the modification results in enhanced digestion of the modified Axmi205 toxin by a mammalian digestive protease (e.g., pepsin) as compared with an Axmi205 toxin that is identical except that it does not comprise the modification.

In other aspects, the modified Axmi205 toxin is toxic to a coleopteran insect pest, for example, a corn rootworm (e.g., a *Diabrotica* species), Bean leaf beetle (*Cerotoma trifurcata*), Colorado Potato Beetle (*Leptinotarsa decemlineata*) and/or Boll Weevil (*Anthonomus grandis*).

As a further aspect, the invention provides a modified Axmi205 toxin that comprises, consists essentially of, or consists of the polypeptide of SEQ ID NO: 1, which has been modified by the modification (e.g., deletion, substitution and/or insertion) of one or more amino acids resulting in enhanced digestion by a mammalian digestive protease (e.g., pepsin).

In further aspects, digestion of the modified Axmi205 toxin is enhanced (faster and/or more complete) by a mammalian digestive protease (e.g., pepsin) such that there is a lesser amount of fragments above 4 kDa remaining as compared with an Axmi205 toxin that does not comprise the modification (e.g., deletion, substitution and/or insertion), when tested under the same conditions (e.g., enzyme concentration, protein concentration, pH, temperature and/or time). For example, as described in Example 5, digestion with pepsin can be carried out at approximately 37° C. and approximately pH 1.2, optionally with an enzyme concentration of approximately 10 Units (U) pepsin per microgram of protein. In embodiments, no fragments of the modified Axmi205 toxin above 4 kDa are present (e.g., detectable) after 10 minutes of digestion with the mammalian digestive protease (e.g., pepsin).

As a further aspect, the modification (deletion, substitution and/or insertion of one or more amino acids) is in a portion of the polypeptide of SEQ ID NO: 1 from amino acid 402 to amino acid 497 or the corresponding portion of another Axmi205 toxin.

In some aspects, the invention provides a modified Axmi205 toxin comprising:
a) one or more amino acids with an aliphatic hydrophobic side chain are deleted, substituted and/or inserted;
b) one or more amino acids with an aromatic hydrophobic side chain are deleted, substituted and/or inserted;
c) one or more amino acids with a polar neutral side chain are deleted, substituted and/or inserted;
d) one or more amino acids with an acidic side chain are deleted, substituted and/or inserted;
e) one or more amino acids with a basic side chain are deleted, substituted and/or inserted; or
f) any combination of (a) to (e).

In further exemplary aspects, the modifications incorporated in the modified Axmi205 toxin produces a new protease (e.g., pepsin) cleavage site. Optionally, according to this aspect, one or more amino acids with an aliphatic hydrophobic side chain and/or an aromatic hydrophobic side chain are substituted and/or inserted.

In another aspect, the modification incorporated in the modified Axmi205 toxin eliminates one or more cysteine residues in the Axmi205 toxin by substitution with another amino acid.

According to still further aspects, the invention provides a modified Axmi205 toxin comprising:
a) an amino acid substitution at amino acid K402 in the polypeptide of SEQ ID NO:1 or the corresponding lysine residue in another Axmi205 toxin;
b) amino acid substitutions at amino acids K402 and Y404 in the polypeptide of SEQ ID NO:1 or the corresponding lysine and tyrosine residues in another Axmi205 toxin;
c) an amino acid substitution at amino acid C482 in the polypeptide of SEQ ID NO:1 or the corresponding cysteine residue in another Axmi205 toxin;
d) an amino acid substitution at amino acid C507 in the polypeptide of SEQ ID NO:1 or the corresponding cysteine residue in another Axmi205 toxin;
e) amino acid substitutions at amino acids M422 and M423 in the polypeptide of SEQ ID NO:1 or the corresponding methionine residues in another Axmi205 toxin;
f) an amino acid insertion between amino acids A475 and G476 in the polypeptide of SEQ ID NO:1 or the corresponding alanine and glycine residues in another Axmi205 toxin;
g) an amino acid insertion between amino acids G496 and D497 in the polypeptide of SEQ ID NO:1 or the corresponding glycine and aspartic acid residues in another Axmi205 toxin;
h) an amino acid insertion between amino acids Q471 and P472 in the polypeptide of SEQ ID NO:1 or the corresponding glycine and aspartic acid residues in another Axmi205 toxin;
i) an amino acid insertion between amino acids A479 and S480 in the polypeptide of SEQ ID NO:1 or the corresponding glycine and aspartic acid residues in another Axmi205 toxin;
j) an amino acid insertion between amino acids Y489 and N490 in the polypeptide of SEQ ID NO:1 or the corresponding glycine and aspartic acid residues in another Axmi205 toxin;
k) a single amino acid insertion within the region bounded by amino acid positions 469 and 483 of SEQ ID NO: 1; or
l) a single amino acid insertion within the region bounded by amino acid positions 483 and 501 of SEQ ID NO:1.

In yet another aspect, the invention provides a modified Axmi205 toxin comprising:
a) a substitution of an amino acid with an aliphatic hydrophobic side chain, an amino acid with an aromatic hydrophobic side chain, an amino acid with a polar neutral side chain, an amino acid with an acidic side chain, or an amino acid with a basic side chain at amino acid K402 in the polypeptide of SEQ ID NO:1 or the corresponding lysine in another Axmi205 toxin;
b) amino acid substitutions of (i) an amino acid with an aliphatic hydrophobic side chain, an amino acid with an aromatic hydrophobic side chain, an amino acid with a polar neutral side chain, an amino acid with an acidic side chain, or an amino acid with a basic side chain at amino acid K402 in the polypeptide of SEQ ID NO:1 or the corresponding lysine residue in another Axmi205 toxin; and (ii) an amino acid with an aliphatic hydrophobic side chain, an amino acid with an aromatic hydrophobic side chain, an amino acid with a polar neutral side chain, an amino acid with an acidic side chain, or an amino acid with a basic side chain at amino acid Y404 in the polypeptide of SEQ ID NO:1 or the corresponding tyrosine residue in another Axmi205 toxin;

c) a substitution of an amino acid with an aliphatic hydrophobic side chain, an amino acid with an aromatic hydrophobic side chain, an amino acid with a polar neutral side chain, an amino acid with an acidic side chain, or an amino acid with a basic side chain at amino acid C482 in the polypeptide of SEQ ID NO:1 or the corresponding cysteine residue in another Axmi205 toxin;

d) a substitution of an amino acid with an aliphatic hydrophobic side chain, an amino acid with an aromatic hydrophobic side chain, an amino acid with a polar neutral side chain, an amino acid with an acidic side chain, or an amino acid with a basic side chain at amino acid C507 in the polypeptide of SEQ ID NO:1 or the corresponding cysteine residue in another Axmi205 toxin;

e) amino acid substitutions of (i) an amino acid with an aliphatic hydrophobic side chain, an amino acid with an aromatic hydrophobic side chain, an amino acid with a polar neutral side chain, an amino acid with an acidic side chain, or an amino acid with a basic side chain at amino acid M422 in the polypeptide of SEQ ID NO:1 or the corresponding methionine residue in another Axmi205 toxin; and (ii) an amino acid with an aliphatic hydrophobic side chain, an amino acid with an aromatic hydrophobic side chain, an amino acid with a polar neutral side chain, an amino acid with an acidic side chain, or an amino acid with a basic side chain at amino acid M423 in the polypeptide of SEQ ID NO:1 or the corresponding methionine residue in another Axmi205 toxin;

f) an insertion of an amino acid with an aliphatic hydrophobic side chain, an amino acid with an aromatic hydrophobic side chain, an amino acid with a polar neutral side chain, an amino acid with an acidic side chain, or an amino acid with a basic side chain between amino acids A475 and G476 in the polypeptide of SEQ ID NO:1 or the corresponding alanine and glycine residues in another Axmi205 toxin;

g) an insertion of an amino acid with an aliphatic hydrophobic side chain, an amino acid with an aromatic hydrophobic side chain, an amino acid with a polar neutral side chain, an amino acid with an acidic side chain, or an amino acid with a basic side chain between amino acids G496 and D497 in the polypeptide of SEQ ID NO:1 or the corresponding glycine and aspartic acid residues in another Axmi205 toxin;

h) an insertion of an amino acid with an aliphatic hydrophobic side chain, an amino acid with an aromatic hydrophobic side chain, an amino acid with a polar neutral side chain, an amino acid with an acidic side chain, or an amino acid with a basic side chain between amino acids Q471 and P472 in the polypeptide of SEQ ID NO:1 or the corresponding alanine and glycine residues in another Axmi205 toxin;

i) an insertion of an amino acid with an aliphatic hydrophobic side chain, an amino acid with an aromatic hydrophobic side chain, an amino acid with a polar neutral side chain, an amino acid with an acidic side chain, or an amino acid with a basic side chain between amino acids A479 and S480 in the polypeptide of SEQ ID NO:1 or the corresponding alanine and glycine residues in another Axmi205 toxin; or j) an insertion of an amino acid with an aliphatic hydrophobic side chain, an amino acid with an aromatic hydrophobic side chain, an amino acid with a polar neutral side chain, an amino acid with an acidic side chain, or an amino acid with a basic side chain between amino acids Y489 and N490 in the polypeptide of SEQ ID NO:1 or the corresponding alanine and glycine residues in another Axmi205 toxin.

In further illustrative aspects, the invention provides a modified Axmi205 toxin comprising:

a) an amino acid substitution of K402F, K402N or K402D in the polypeptide of SEQ ID NO:1 or the corresponding lysine in another Axmi205 toxin;

b) amino acid substitutions of (i) K402L and Y404F, or (ii) K402D and Y404L in the polypeptide of SEQ ID NO:1 or the corresponding lysine and tyrosine residues in another Axmi205 toxin;

c) an amino acid substitution of C482S, C482D or C482F in the polypeptide of SEQ ID NO:1 or the corresponding cysteine residue in another Axmi205 toxin;

d) an amino acid substitution of C507S, C507L, C507A, C507F, C507D or C507R in the polypeptide of SEQ ID NO:1 or the corresponding cysteine residue in another Axmi205 toxin;

e) amino acid substitutions of (i) M422S and M423L, (ii) M422T and M423F, (iii) M422S and M423E, (iv) M422D and M423E, (v) M422K and M423R, or (vi) M422K and M423F or the corresponding methionine residues in another Axmi205 toxin;

f) an insertion of a leucine, phenylalanine, aspartic acid or arginine between amino acids A475 and G476 in the polypeptide of SEQ ID NO:1 or the corresponding alanine and glycine residues in another Axmi205 toxin;

g) an insertion of a leucine, phenylalanine, aspartic acid or arginine between amino acids G496 and D497 in the polypeptide of SEQ ID NO:1 or the corresponding glycine and aspartic acid residues in another Axmi205 toxin;

h) an insertion of a leucine, phenylalanine, aspartic acid or arginine between amino acids Q471 and P472 in the polypeptide of SEQ ID NO:1 or the corresponding glycine and aspartic acid residues in another Axmi205 toxin;

i) an insertion of a leucine, phenylalanine, aspartic acid or arginine between amino acids A479 and S480 in the polypeptide of SEQ ID NO:1 or the corresponding glycine and aspartic acid residues in another Axmi205 toxin; or j) an insertion of a leucine, phenylalanine, aspartic acid or arginine between amino acids Y489 and N490 in the polypeptide of SEQ ID NO:1 or the corresponding glycine and aspartic acid residues in another Axmi205 toxin.

Still further, in representative aspects, the invention provides a modified Axmi205 toxin comprising, consisting essentially of, or consisting of the amino acid sequence of: SEQ ID NO: 11, SEQ ID NO: 13, SEQ ID NO: 17, SEQ ID NO: 43, SEQ ID NO: 47, SEQ ID NO: 57, SEQ ID NO: 69, SEQ ID NO: 73, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, or SEQ ID NO: 127.

As further aspects, the invention provides polynucleotides comprising a nucleotide sequence encoding a modified Axmi205 toxin of the invention, optionally codon optimized for expression in a plant. Also provided are expression cassettes and vectors comprising the polynucleotides of the invention.

According to some aspects, the invention provides a polynucleotide comprising a nucleotide sequence that comprises, consists essentially of, or consists of:
a) a nucleotide sequence of SEQ ID NO: 70, SEQ ID NO: 12, SEQ ID NO: 14, SEQ ID NO: 18, SEQ ID NO: 44, SEQ ID NO: 48, SEQ ID NO: 58, SEQ ID NO: 74, SEQ ID NO: 75, SEQ ID NO: 76, SEQ ID NO: 77, SEQ ID NO: 78, SEQ ID NO: 80, SEQ ID NO: 82, SEQ ID NO: 84, SEQ ID NO: 86, SEQ ID NO: 89, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, or SEQ ID NO: 126;
b) a nucleotide sequence that is substantially identical to the nucleotide sequence of (a);
c) a nucleotide sequence that anneals under stringent hybridization conditions to the nucleotide sequence of (a) or (b); or
d) a nucleotide sequence that differs from the nucleotide sequence of (a), (b) or (c) due to the degeneracy of the genetic code.

Optionally, according to this aspect, the polynucleotide comprises, consists essentially of, or consists of the nucleotide sequence of SEQ ID NO: 70, SEQ ID NO: 12, SEQ ID NO: 14, SEQ ID NO: 18, SEQ ID NO: 44, SEQ ID NO: 48, SEQ ID NO: 58, SEQ ID NO: 74, SEQ ID NO: 75, SEQ ID NO: 76, SEQ ID NO: 77, SEQ ID NO: 78, SEQ ID NO: 80, SEQ ID NO: 82, SEQ ID NO: 84, SEQ ID NO: 86, SEQ ID NO: 89, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, or SEQ ID NO: 126.

As a further aspect, the invention provides a transgenic cell (e.g., a transgenic plant cell such as a dicot cell or monocot cell, or a transgenic bacterial cell), transgenic plant part, transgenic plant culture, and transgenic plant seed that comprises a nucleotide sequence, expression cassette, vector and/or insecticidal protein of the invention.

As still a further aspect, the invention encompasses transgenic plants comprising a plant cell, plant part, nucleotide sequence, expression cassette, vector and/or insecticidal protein of the invention.

As a further aspect are seeds that produce the transgenic plants of the invention and seeds produced by the transgenic plants of the invention.

Also provided are harvested products derived from the transgenic plants of the invention, wherein the harvested product optionally comprises a nucleotide sequence, expression cassette, vector and/or insecticidal protein of the invention. Further provided are processed products derived from the harvested products of the invention, wherein the harvested product optionally comprises a nucleotide sequence, expression cassette, vector and/or insecticidal protein of the invention. In embodiments, the harvested product or processed product comprises an insecticidal protein of the invention and has increased resistance to an insect pest (e.g., a coleopteran insect pest, such as WCRW)).

As still a further aspect, the invention provides an insecticidal composition comprising an insecticidal protein of the invention and an agriculturally acceptable carrier.

Still further, the invention provides as an additional aspect a method of producing a transgenic plant with increased resistance to an insect pest (e.g., a coleopteran insect pest, such as WCRW)). In embodiments, the method comprises introducing into a plant a polynucleotide, expression cassette, or vector of the invention, wherein the insecticidal protein is expressed in the plant, thereby producing a transgenic plant with increased resistance to an insect pest. Optionally, the introducing step comprises: (i) transforming a plant cell with the polynucleotide, expression cassette or vector and regenerating a transgenic plant; or (ii) crossing a first plant comprising the polynucleotide, expression cassette or vector with a second plant. In embodiments, the method further comprises producing a seed from the transgenic plant. In embodiments, the method further comprises obtaining a progeny plant from the transgenic plant, wherein the progeny plant comprises the polynucleotide, the expression cassette or the vector, expresses the insecticidal protein and has increased resistance to an insect pest.

As yet another aspect, the invention provides a method of producing a transgenic plant with increased resistance to an insect pest (e.g., a coleopteran insect pest, such as WCRW)), the method comprising: (a) planting a seed comprising a polynucleotide, expression cassette or vector of the invention; and (b) growing a transgenic plant from the seed, wherein the transgenic plant comprises the polynucleotide, expression cassette or vector and produces the insecticidal protein and has increased resistance to an insect pest. In embodiments, the method further comprises: (c) harvesting a seed from the transgenic plant of (b), wherein the harvested seed comprises the polynucleotide, expression cassette, vector and/or the insecticidal protein. Optionally, the seed has increased resistance against an insect pest (e.g., a coleopteran insect pest, such as WCRW)).

Still further, as another aspect, the invention provides a method of producing a seed. In embodiments, the method comprises: (a) providing a transgenic plant that comprises a polynucleotide, expression cassette or vector of the invention; and (b) harvesting a seed from the transgenic plant of (a), wherein the harvested seed comprises the polynucleotide, expression cassette or vector and/or an insecticidal protein of the invention. Optionally, the seed has increased resistance against an insect pest (e.g., a coleopteran insect pest, such as WCRW).

The invention further contemplates a method of producing a hybrid plant seed. In representative embodiments, the method comprises: (a) crossing a first inbred plant, which is a transgenic plant comprising a polynucleotide, expression cassette or vector of the invention with a different inbred plant, which may or may not comprise a polynucleotide, expression cassette or vector of the invention; and (b) allowing a hybrid seed to form. In embodiments, the hybrid seed comprises a polynucleotide, expression cassette or vector and/or an insecticidal protein of the invention. Optionally, the seed has increased resistance against an insect pest (e.g., a coleopteran insect pest, such as WCRW)).

As another aspect, the invention provides a method of controlling an insect pest (e.g., a coleopteran insect pest, such as corn rootworm), the method comprising delivering to the insect pest or an environment thereof a composition comprising an effective amount of an insecticidal protein or insecticidal composition of the invention. In embodiments, the method is a method of controlling a coleopteran insect pest (e.g., a corn rootworm, such as WCRW) that is resistant to a mCry3A protein (e.g., in maize event MIR604), a eCry3.1Ab protein (e.g., in maize event 5307), a Cry3Bb1 protein (e.g., in corn event MON88017), a Cry34/35Ab1 binary protein (e.g., in corn event DAS-59122) and/or a RNAi trait, such as DvSnf7 dsRNA (e.g., in corn event MON87411).

The invention is also drawn to methods of using the polynucleotides of the invention, for example, in DNA constructs or expression cassettes or vectors for transformation and expression in organisms, including plants and microorganisms, such as bacteria. The nucleotide or amino acid sequences may be native or synthetic sequences that have been designed for expression in an organism such as a plant or bacteria. The invention is further drawn to methods of making the insecticidal proteins of the invention and to methods of using the polynucleotide sequences and insecticidal proteins, for example in microorganisms to control insects or in transgenic plants to confer protection from insect damage.

Another aspect of the invention includes insecticidal compositions and formulations comprising the insecticidal proteins of the invention, and methods of using the compositions or formulations to control insect populations, for example by applying the compositions or formulations to insect-infested areas, or to prophylactically treat insect-susceptible areas or plants to confer protection against the insect pests. Optionally, the compositions or formulations of the invention may, in addition to the insecticidal protein of the invention, comprise other pesticidal agents such as chemical pesticides, other pesticidal proteins, or dsRNA, e.g., in order to augment or enhance the insect-controlling capability of the composition or formulation and/or for insect resistance management.

The compositions and methods of the invention are useful for controlling insect pests that attack plants, particularly crop plants. The compositions of the invention are also useful for detecting the presence of an insecticidal protein or a nucleic acid encoding the same in commercial products or transgenic organisms.

The invention also provides for uses of the insecticidal proteins, nucleic acids, transgenic plants, plant parts, seed and insecticidal compositions of the invention, for example, to control an insect pest, such as a coleopteran pest (e.g., WCRW).

In embodiments, the invention provides a method of using a polynucleotide, expression cassette, vector or host cell of the invention to produce an insecticidal composition for controlling an insect pest (e.g., a coleopteran insect pest, such as WCRW)).

In embodiments, the invention provides a method of using a polynucleotide, expression cassette or vector of the invention to produce a transgenic seed, where the transgenic seed grows a transgenic plant with increased resistance to an insect pest.

As another aspect, the invention also contemplates the use of a transgenic plant of the invention to produce a transgenic seed, which is optionally a hybrid seed.

In embodiments, the invention provides a method of using an insecticidal protein, polynucleotide, expression cassette, vector, transgenic plant or insecticidal composition of the invention to prevent the development of resistance in a population of a target coleopteran insect pest to a mCry3A protein (e.g., in maize event MIR604), an eCry3.1Ab protein (e.g., in maize event 5307), a Cry3Bb1 protein (e.g., in corn event MON88017), a Cry34/35Ab1 binary protein (e.g., in corn event DAS-59122) and/or a RNAi trait, such as DvSnf7 dsRNA (e.g., in corn event MON87411).

These and other features, aspects, and advantages of the invention will become better understood with reference to the following detailed description and claims.

BRIEF DESCRIPTION OF THE DRAWINGS

FIG. 1—Axmi205 sequence showing $2^{nd}$ domain underlined, predicted pepsin cleavage sites shaded in gray and Cysteine residues in C-terminal domain in bold-face type.

BRIEF DESCRIPTION OF THE SEQUENCES

Figure 2:
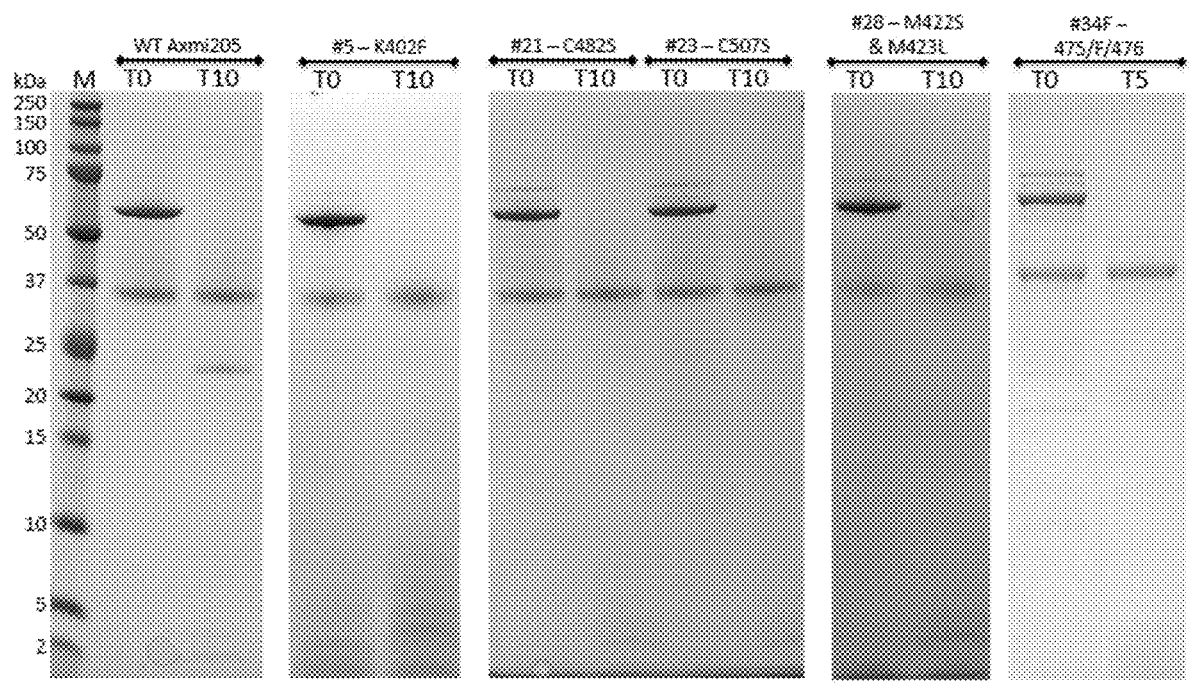
FIG. 2—Results of SGF assay at times T0 and T10 for wild-type Axmi205 and eAxmi205 mutants #5 (K402F), #21 (C482S), #23 (C507S), #28 (M4222S & M423L) and #34 (475-Phe-476).

SEQ ID NO: 1 is the amino acid sequence of the native Axmi205 protein.

SEQ ID NO: 2 is the cDNA sequence of the native Axmi205 protein.

SEQ ID NO: 3 is the amino acid sequence of the eAxmi205 #1 mutant protein (K328Y).

SEQ ID NO: 4 is a nucleotide sequence encoding the eAxmi205 #1 mutant protein of SEQ ID NO: 3.

SEQ ID NO: 5 is the amino acid sequence of the eAxmi205 #2 mutant protein (K328L).

SEQ ID NO: 6 is a nucleotide sequence encoding the eAxmi205 #2 mutant protein of SEQ ID NO: 5.

SEQ ID NO: 7 is the amino acid sequence of the eAxmi205 #3 mutant protein (K328F).

SEQ ID NO: 8 is a nucleotide sequence encoding the eAxmi205 #3 mutant protein of SEQ ID NO: 7.

SEQ ID NO: 9 is the amino acid sequence of the eAxmi205 #4 mutant protein (Y404F).

SEQ ID NO: 10 is a nucleotide sequence encoding the eAxmi205 #4 mutant protein of SEQ ID NO: 9.

SEQ ID NO: 11 is the amino acid sequence of the eAxmi205 #5 mutant protein (K402F).

SEQ ID NO: 12 is a nucleotide sequence encoding the eAxmi205 #5 mutant protein of SEQ ID NO: 11.

SEQ ID NO: 13 is the amino acid sequence of the eAxmi205 #6 mutant protein (K402N).

SEQ ID NO: 14 is a nucleotide sequence encoding the eAxmi205 #6 mutant protein of SEQ ID NO: 13.

SEQ ID NO: 15 is the amino acid sequence of the eAxmi205 #7 mutant protein (K402L).

SEQ ID NO: 16 is a nucleotide sequence encoding the eAxmi205 #7 mutant protein of SEQ ID NO: 15.

SEQ ID NO: 17 is the amino acid sequence of the eAxmi205 #8 mutant protein (Y404F+K402L).

SEQ ID NO: 18 is a nucleotide sequence encoding the eAxmi205 #8 mutant protein of SEQ ID NO: 17.

SEQ ID NO: 19 is the amino acid sequence of the eAxmi205 #9 mutant protein (R416L).

SEQ ID NO: 20 is a nucleotide sequence encoding the eAxmi205 #9 mutant protein of SEQ ID NO: 19.

SEQ ID NO: 21 is the amino acid sequence of the eAxmi205 #10 mutant protein (P386L).

SEQ ID NO: 22 is a nucleotide sequence encoding the eAxmi205 #10 mutant protein of SEQ ID NO: 21.

SEQ ID NO: 23 is the amino acid sequence of the eAxmi205 #11 mutant protein (R391L).

SEQ ID NO: 24 is a nucleotide sequence encoding the eAxmi205 #11 mutant protein of SEQ ID NO: 23.

SEQ ID NO: 25 is the amino acid sequence of the eAxmi205 #12 mutant protein (R391I).

SEQ ID NO: 26 is a nucleotide sequence encoding the eAxmi205 #12 mutant protein of SEQ ID NO: 25.

SEQ ID NO: 27 is the amino acid sequence of the eAxmi205 #13 mutant protein (C406S).

SEQ ID NO: 28 is a nucleotide sequence encoding the eAxmi205 #13 mutant protein of SEQ ID NO: 27.

SEQ ID NO: 29 is the amino acid sequence of the eAxmi205 #14 mutant protein (C406L).

SEQ ID NO: 30 is a nucleotide sequence encoding the eAxmi205 #14 mutant protein of SEQ ID NO: 29.

SEQ ID NO: 31 is the amino acid sequence of the eAxmi205 #15 mutant protein (P411L).

SEQ ID NO: 32 is a nucleotide sequence encoding the eAxmi205 #15 mutant protein of SEQ ID NO: 31.

SEQ ID NO: 33 is the amino acid sequence of the eAxmi205 #16 mutant protein (C439S).

SEQ ID NO: 34 is a nucleotide sequence encoding the eAxmi205 #16 mutant protein of SEQ ID NO: 33.

SEQ ID NO: 35 is the amino acid sequence of the eAxmi205 #17 mutant protein (C439L).

SEQ ID NO: 36 is a nucleotide sequence encoding the eAxmi205 #17 mutant protein of SEQ ID NO: 35.

SEQ ID NO: 37 is the amino acid sequence of the eAxmi205 #18 mutant protein (C445S).

SEQ ID NO: 38 is a nucleotide sequence encoding the eAxmi205 #18 mutant protein of SEQ ID NO: 37.

SEQ ID NO: 39 is the amino acid sequence of the eAxmi205 #19 mutant protein (R454F).

SEQ ID NO: 40 is a nucleotide sequence encoding the eAxmi205 #19 mutant protein of SEQ ID NO: 39.

SEQ ID NO: 41 is the amino acid sequence of the eAxmi205 #20 mutant protein (R464L).

SEQ ID NO: 42 is a nucleotide sequence encoding the eAxmi205 #20 mutant protein of SEQ ID NO: 41.

SEQ ID NO: 43 is the amino acid sequence of the eAxmi205 #21 mutant protein (C482S).

SEQ ID NO: 44 is a nucleotide sequence encoding the eAxmi205 #21 mutant protein of SEQ ID NO: 43.

SEQ ID NO: 45 is the amino acid sequence of the eAxmi205 #22 mutant protein (C482L).

SEQ ID NO: 46 is a nucleotide sequence encoding the eAxmi205 #22 mutant protein of SEQ ID NO: 45.

SEQ ID NO: 47 is the amino acid sequence of the eAxmi205 #23 mutant protein (C507S).

SEQ ID NO: 48 is a nucleotide sequence encoding the eAxmi205 #23 mutant protein of SEQ ID NO: 47.

SEQ ID NO: 49 is the amino acid sequence of the eAxmi205 #24 mutant protein (C406S+C439S+C445S+C482S+C507S).

SEQ ID NO: 50 is a nucleotide sequence encoding the eAxmi205 #24 mutant protein of SEQ ID NO: 49.

SEQ ID NO: 51 is the amino acid sequence of the eAxmi205 #25 mutant protein (F378L).

SEQ ID NO: 52 is a nucleotide sequence encoding the eAxmi205 #25 mutant protein of SEQ ID NO: 51.

SEQ ID NO: 53 is the amino acid sequence of the eAxmi205 #26 mutant protein (S495L).

SEQ ID NO: 54 is a nucleotide sequence encoding the eAxmi205 #26 mutant protein of SEQ ID NO: 53.

SEQ ID NO: 55 is the amino acid sequence of the eAxmi205 #27 mutant protein (G496L).

SEQ ID NO: 56 is a nucleotide sequence encoding the eAxmi205 #27 mutant protein of SEQ ID NO: 55.

SEQ ID NO: 57 is the amino acid sequence of the eAxmi205 #28 mutant protein (M422S+M423L).

SEQ ID NO: 58 is a nucleotide sequence encoding the eAxmi205 #28 mutant protein of SEQ ID NO: 57.

SEQ ID NO: 59 is the amino acid sequence of the eAxmi205 #29 mutant protein (V467S+S468L).

SEQ ID NO: 60 is a nucleotide sequence encoding the eAxmi205 #29 mutant protein of SEQ ID NO: 59.

SEQ ID NO: 61 is the amino acid sequence of the eAxmi205 #30 mutant protein (V467S+S468L+W470G).

SEQ ID NO: 62 is a nucleotide sequence encoding the eAxmi205 #30 mutant protein of SEQ ID NO: 61.

SEQ ID NO: 63 is the amino acid sequence of the eAxmi205 #31 mutant protein (396-Leu-397).

SEQ ID NO: 64 is a nucleotide sequence encoding the eAxmi205 #31 mutant protein of SEQ ID NO: 63.

SEQ ID NO: 65 is the amino acid sequence of the eAxmi205 #32 mutant protein (330-Leu-331).

SEQ ID NO: 66 is a nucleotide sequence encoding the eAxmi205 #32 mutant protein of SEQ ID NO: 65.

SEQ ID NO: 67 is the amino acid sequence of the eAxmi205 #33 mutant protein (456-Leu-457).

SEQ ID NO: 68 is a nucleotide sequence encoding the eAxmi205 #33 mutant protein of SEQ ID NO: 67.

SEQ ID NO: 69 is the amino acid sequence of the eAxmi205 #34 mutant protein (475-Leu-476).

SEQ ID NO: 70 is a nucleotide sequence encoding the eAxmi205 #34 mutant protein of SEQ ID NO: 69.

SEQ ID NO: 71 is the amino acid sequence of the eAxmi205 #35 mutant protein (367-Leu-368).

SEQ ID NO: 72 is a nucleotide sequence encoding the eAxmi205 #35 mutant protein of SEQ ID NO: 71.

SEQ ID NO: 73 is the amino acid sequence of the eAxmi205 #36 mutant protein (496-Leu-497).

SEQ ID NO: 74 is a nucleotide sequence encoding the eAxmi205 #36 mutant protein of SEQ ID NO: 73.

SEQ ID NO: 75 is a maize optimized nucleotide sequence encoding the eAxmi205 #23 mutant protein of

SEQ ID NO: 47.

SEQ ID NO: 76 is a maize optimized nucleotide sequence encoding the eAxmi205 #28 mutant protein of

SEQ ID NO: 57.

SEQ ID NO: 77 is a maize optimized nucleotide sequence encoding the eAxmi205 #34 mutant protein of

SEQ ID NO: 69.

SEQ ID NO: 78 is a nucleotide sequence encoding the eAxmi205 #5D mutant protein of SEQ ID NO: 79.

SEQ ID NO: 79 is the amino acid sequence of the eAxmi205 #5D mutant protein (K402D).

SEQ ID NO: 80 is a nucleotide sequence encoding the eAxmi205 #21F mutant protein of SEQ ID NO: 81.

SEQ ID NO: 81 is the amino acid sequence of the eAxmi205 #21F mutant protein (C482F).

SEQ ID NO: 82 is a nucleotide sequence encoding the eAxmi205 #21D mutant protein of SEQ ID NO: 83.

SEQ ID NO: 83 is the amino acid sequence of the eAxmi205 #21D mutant protein (C482D).

SEQ ID NO: 84 is a nucleotide sequence encoding the eAxmi205 #23L mutant protein of SEQ ID NO: 85.

SEQ ID NO: 85 is the amino acid sequence of the eAxmi205 #23L mutant protein (C507L).

SEQ ID NO: 86 is a nucleotide sequence encoding the eAxmi205 #23A mutant protein of SEQ ID NO: 87.

SEQ ID NO: 87 is the amino acid sequence of the eAxmi205 #23A mutant protein (C507A).

SEQ ID NO: 88 is a nucleotide sequence encoding the eAxmi205 #23F mutant protein of SEQ ID NO: 89.

SEQ ID NO: 89 is the amino acid sequence of the eAxmi205 #23F mutant protein (C507F).

SEQ ID NO: 90 is a nucleotide sequence encoding the eAxmi205 #23D mutant protein of SEQ ID NO: 91.

SEQ ID NO: 91 is the amino acid sequence of the eAxmi205 #23D mutant protein (C507D).

SEQ ID NO: 92 is a nucleotide sequence encoding the eAxmi205 #23R mutant protein of SEQ ID NO: 93.

SEQ ID NO: 93 is the amino acid sequence of the eAxmi205 #23R mutant protein (C507R).

SEQ ID NO: 94 is a nucleotide sequence encoding the eAxmi205 #28TF mutant protein of SEQ ID NO: 95.

SEQ ID NO: 95 is the amino acid sequence of the eAxmi205 #28TF mutant protein (M422T+M423F).

SEQ ID NO: 96 is a nucleotide sequence encoding the eAxmi205 #28DE mutant protein of SEQ ID NO: 97.

SEQ ID NO: 97 is the amino acid sequence of the eAxmi205 #28DE mutant protein (M422D+M423E).

SEQ ID NO: 98 is a nucleotide sequence encoding the eAxmi205 #28KR mutant protein of SEQ ID NO: 99.

SEQ ID NO: 99 is the amino acid sequence of the eAxmi205 #28KR mutant protein (M422K+M423R).

SEQ ID NO: 100 is a nucleotide sequence encoding the eAxmi205 #28SE mutant protein of SEQ ID NO: 101.

SEQ ID NO: 101 is the amino acid sequence of the eAxmi205 #28SE mutant protein (M422S+M423E).

SEQ ID NO: 102 is a nucleotide sequence encoding the eAxmi205 #28KF mutant protein of SEQ ID NO: 103.

SEQ ID NO: 103 is the amino acid sequence of the eAxmi205 #28KF mutant protein (M422K+M423F).

SEQ ID NO: 104 is a nucleotide sequence encoding the eAxmi205 #34F mutant protein of SEQ ID NO: 105.

SEQ ID NO: 105 is the amino acid sequence of the eAxmi205 #34F mutant protein (475-Phe-476).

SEQ ID NO: 106 is a nucleotide sequence encoding the eAxmi205 #34D mutant protein of SEQ ID NO: 107.

SEQ ID NO: 107 is the amino acid sequence of the eAxmi205 #34D mutant protein (475-Asp-476).

SEQ ID NO: 108 is a nucleotide sequence encoding the eAxmi205 #34R mutant protein of SEQ ID NO: 109.

SEQ ID NO: 109 is the amino acid sequence of the eAxmi205 #34R mutant protein (475-Arg-476).

SEQ ID NO: 110 is a nucleotide sequence encoding the eAxmi205 #36D mutant protein of SEQ ID NO: 111.

SEQ ID NO: 111 is the amino acid sequence of the eAxmi205 #36D mutant protein (496-Asp-497).

SEQ ID NO: 112 is a nucleotide sequence encoding the eAxmi205 #36F mutant protein of SEQ ID NO: 113.

SEQ ID NO: 113 is the amino acid sequence of the eAxmi205 #36F mutant protein (496-Phe-497).

SEQ ID NO: 114 is a nucleotide sequence encoding the eAxmi205 #36R mutant protein of SEQ ID NO: 115.

SEQ ID NO: 115 is the amino acid sequence of the eAxmi205 #36R mutant protein (496-Arg-497).

SEQ ID NO: 116 is a nucleotide sequence encoding the eAxmi205 #37F mutant protein of SEQ ID NO: 117.

SEQ ID NO: 117 is the amino acid sequence of the eAxmi205 #37F mutant protein (471-Phe-472).

SEQ ID NO: 118 is a nucleotide sequence encoding the eAxmi205 #37L mutant protein of SEQ ID NO: 119.

SEQ ID NO: 119 is the amino acid sequence of the eAxmi205 #37L mutant protein (471-Leu-472).

SEQ ID NO: 120 is a nucleotide sequence encoding the eAxmi205 #38F mutant protein of SEQ ID NO: 121.

SEQ ID NO: 121 is the amino acid sequence of the eAxmi205 #38F mutant protein (479-Phe-480).

SEQ ID NO: 122 is a nucleotide sequence encoding the eAxmi205 #38L mutant protein of SEQ ID NO: 123.

SEQ ID NO: 123 is the amino acid sequence of the eAxmi205 #38L mutant protein (479-Leu-480).

SEQ ID NO: 124 is a nucleotide sequence encoding the eAxmi205 #39F mutant protein of SEQ ID NO: 125.

SEQ ID NO: 125 is the amino acid sequence of the eAxmi205 #39F mutant protein (489-Phe-490).

SEQ ID NO: 126 is a nucleotide sequence encoding the eAxmi205 #39L mutant protein of SEQ ID NO: 127.

SEQ ID NO: 127 is the amino acid sequence of the eAxmi205 #39L mutant protein (489-Leu-490).

DETAILED DESCRIPTION

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Nucleotide sequences provided herein are presented in the 5' to 3' direction, from left to right and are presented using the standard code for representing nucleotide bases as set forth in 37 CFR §§ 1.821-1.825 and the World Intellectual Property Organization (WIPO) Standard ST.25, for example: adenine (A), cytosine (C), thymine (T), and guanine (G).

Amino acids are likewise indicated using the WIPO Standard ST.25, for example: alanine (Ala; A), arginine (Arg; R), asparagine (Asn; N), aspartic acid (Asp; D), cysteine (Cys; C), glutamine (Gln; Q), glutamic acid (Glu; E), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

Definitions

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like, is meant to encompass variations of ±20%, ±10%, ±5%, ±1%, ±0.5%, or even ±0.1% of the specified amount. As used herein, phrases such as "between about X and Y" mean "between about X and about Y" and phrases such as "from about X to Y" mean "from about X to about Y."

As used herein, phrases such as "between about X and Y", "between about X and about Y", "from X to Y" and "from about X to about Y" (and similar phrases) should be interpreted to include X and Y, unless the context indicates otherwise.

By "activity" of an insecticidal protein of the invention is meant that the insecticidal protein functions as an orally active insect control agent, has a toxic effect, for example, by inhibiting the ability of the insect pest to survive, grow, and/or reproduce (e.g., causing morbidity and/or mortality) and/or is able to disrupt and/or deter insect feeding, which may or may not cause death of the insect. Thus, when an insecticidal protein of the invention is delivered to the insect, the result is typically morbidity and/or mortality of the insect and/or the insect reduces or stops feeding upon the source that makes the insecticidal protein available to the insect.

A "coding sequence" is a nucleic acid sequence that is transcribed into RNA such as mRNA, rRNA, tRNA, snRNA, sense RNA or antisense RNA. In embodiments, the RNA is then translated to produce a protein.

As used herein, a "codon optimized" nucleotide sequence means a nucleotide sequence of a recombinant, transgenic, or synthetic polynucleotide wherein the codons are chosen to reflect the particular codon bias that a host cell or organism may have. This is typically done in such a way so as to preserve the amino acid sequence of the polypeptide encoded by the codon optimized nucleotide sequence. In certain embodiments, a nucleotide sequence is codon optimized for the cell (e.g., an animal, plant, fungal or bacterial cell) in which the construct is to be expressed. For example, a construct to be expressed in a plant cell can have all or parts of its sequence codon optimized for expression in a plant. See, for example, U.S. Pat. No. 6,121,014. In embodiments, the polynucleotides of the invention are codon-optimized for expression in a plant cell (e.g., a dicot cell or a monocot cell) or bacterial cell.

To "control" an insect pest means to inhibit, through a toxic effect, the ability of the insect pest to survive, grow, feed and/or reproduce and/or to limit insect-related damage or loss in a crop plant caused by the insect pest and/or to protect the yield potential of a crop caused by the pest when grown in the presence of an insect pest. To "control" an insect pest may or may not mean killing the insect, although in embodiments of the invention, "control" of the insect means killing the insect.

The term "comprise", "comprises" or "comprising," when used in this specification, indicates the presence of the stated features, integers, steps, operations, elements, or components, but does not preclude the presence or addition of one or more other features, integers, steps, operations, elements, components, and/or groups thereof.

As used herein, the transitional phrase "consisting essentially of" (and grammatical variants) means that the scope of a claim is to be interpreted to encompass the specified materials or steps recited in the claim "and those that do not materially alter the basic and novel characteristic(s)" of the claimed invention. Thus, the term "consisting essentially of" when used in a claim of this invention is not intended to be interpreted to be equivalent to "comprising."

In the context of the invention, "corresponding to" or "corresponds to" means that when the amino acid sequences of modified or homolog proteins are aligned with each other, the amino acids that "correspond to" certain enumerated positions in the modified or homolog protein are those that align with these positions in a reference protein, but are not necessarily in the same exact numerical positions relative to the particular reference amino acid sequence of the invention. For example, if SEQ ID NO: 1 (native Axmi205) is the reference sequence and is aligned with SEQ ID NO: 73

(Axmi205-36 mutant), the sequence of amino acid residues 498 to 537 of SEQ ID NO: 73 (immediately following the leucine insertion in mutant Axmi205-36) "corresponds to" amino acid residues 497 to 536 of SEQ ID NO: 1 (native Axmi205).

As used herein, the term "Cry protein" means an insecticidal protein of a *Bacillus thuringiensis* crystal delta-endotoxin type. The term "Cry protein" can refer to the protoxin form or any insecticidally active fragment or toxin thereof including partially processed and the mature toxin form (e.g., without the N-terminal peptidyl fragment and/or the C-terminal protoxin tail).

As used herein, to "deliver" or "delivering" (and grammatical variations) a composition or insecticidal protein means that the composition or insecticidal protein comes in contact with an insect, which facilitates the oral ingestion of the composition or insecticidal protein, resulting in a toxic effect and control of the insect. The composition or insecticidal protein can be delivered in many recognized ways, including but not limited to, by transgenic plant expression, a formulated protein composition(s), a sprayable protein composition(s), a bait matrix, or any other art-recognized protein delivery system.

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely important in the structure, stability and/or function of a protein. Identified by their high degree of conservation in aligned sequences of a family of protein homologues, they can be used as identifiers to determine if any polypeptide in question belongs to a previously identified polypeptide group.

"Effective insect-controlling amount" means that concentration of an insecticidal protein that inhibits, through a toxic effect, the ability of an insect to survive, grow, feed and/or reproduce and/or that limits insect-related damage or loss in a crop plant. An "effective insect-controlling amount" may or may not mean killing the insect, although in embodiments it indicates killing the insect.

"Expression cassette" as used herein means a nucleic acid molecule capable of directing expression of at least one polynucleotide of interest, such as a polynucleotide that encodes an insecticidal protein of the invention, in an appropriate host cell, comprising a promoter operably linked to the polynucleotide of interest which is operably linked to a termination signal. An "expression cassette" also typically comprises additional polynucleotides to facilitate proper translation of the polynucleotide of interest. The expression cassette may also comprise other polynucleotides not related to the expression of a polynucleotide of interest but which are present due to convenient restriction sites for removal of the cassette from an expression vector. In embodiments, at least one of the components in the expression cassette may be heterologous (i.e., foreign) with respect to at least one of the other components (e.g., a heterologous promoter operatively associated with a polynucleotide of interest). The expression cassette may also be one that is naturally occurring but has been obtained in a recombinant form useful for heterologous expression. Typically, however, the expression cassette is heterologous with respect to the host, i.e., the expression cassette (or even the polynucleotide of interest) does not occur naturally in the host cell and has been introduced into the host cell or an ancestor cell thereof by a transformation process or a breeding process. The expression of the polynucleotide(s) of interest in the expression cassette is generally under the control of a promoter. In the case of a multicellular organism, such as a plant, the promoter can also be specific or preferential to a particular tissue, or organ, or stage of development (as described in more detail herein). An expression cassette, or fragment thereof, can also be referred to as "inserted polynucleotide" or "insertion polynucleotide" when transformed into a plant.

A "gene" is defined herein as a hereditary unit comprising one or more polynucleotides that occupies a specific location on a chromosome or plasmid and that contains the genetic instruction for a particular characteristic or trait in an organism.

As used herein, a "gut protease" or "digestive protease" refers to a protease naturally found in the digestive tract of an animal (e.g., an insect or a mammal, such as a human). In embodiments, the "gut protease" or "digestive protease" is from a mammalian (e.g., human). The protease is usually involved in the digestion of ingested proteins. Examples of gut proteases include trypsin, which typically cleaves peptides on the C-terminal side of lysine (K) or arginine (R) residues, and chymotrypsin, which typically cleaves peptides on the C-terminal side of phenylalanine (F), tryptophan (W) or tyrosine (Y). Pepsin typically cleaves between two hydrophobic residues.

As used herein, the term "heterologous" means foreign, exogenous, non-native and/or non-naturally occurring. In embodiments, a "heterologous" polynucleotide or polypeptide is a polynucleotide or polypeptide that is not naturally associated with a host cell into which it is introduced, including non-naturally occurring multiple copies of a naturally occurring nucleotide sequence or polypeptide. In embodiments, a nucleotide sequence is heterologous to another sequence with which it is operatively associated, e.g., a promoter may be heterologous (i.e., foreign) to an operatively associated coding sequence.

As used here, "homologous" means native. For example, a homologous nucleotide sequence or amino acid sequence is a nucleotide sequence or amino acid sequence naturally associated with a host cell into which it is introduced, a homologous promoter sequence is the promoter sequence that is naturally associated with a coding sequence, and the like.

The terms "increase," "increasing," "increased," "enhance," "enhanced," "enhancing," and "enhancement" (and grammatical variations thereof) and similar terms, as used herein, describe an elevation and/or improvement in the specified parameter. Thus, in embodiments, the terms "increase," "increasing," "increased," "enhance," "enhanced," "enhancing," and "enhancement" (and grammatical variations thereof), and similar terms can indicate an elevation of at least about 5%, 10%, 15%, 20%, 25%, 30%, 35%, 40%, 45%, 50%, 55%, 60%, 65%, 70%, 75%, 80%, 85%, 90%, 95%, 100%, 125%, 150%, 200%, 300%, 400%, 500% or more as compared to a suitable control.

The terms "increase," "increasing," "increased," "enhance," "enhanced," "enhancing," and "enhancement" (and grammatical variations thereof) and similar terms, as used herein with respect to the digestion (e.g., cleavage) of a modified Axmi205 protein of the invention by a digestive protease refers to an elevation or improvement in the speed and/or extent of the digestion of the modified Axmi205 toxin. This increase in digestion can be with reference to the level of digestion observed with a suitable control (e.g., the Axmi205 protein of SEQ ID NO: 1 and/or an Axmi205 toxin that is identical to the modified Axmi205 protein of the invention with the exception that it lacks the modifications of the present invention) when tested under the same conditions. For example, as described in Example 5, digestion with pepsin can be carried out at approximately 37° C. and approximately pH 1.2, optionally, with an enzyme concentration of approximately 10 Units (U) pepsin per microgram of protein. Thus, in embodiments, the terms "increase," "increasing," "increased," "enhance," "enhanced," "enhancing," and "enhancement" (and grammatical variations thereof), indicate that protease digestion of the modified Axmi205 toxin is elevated and/or faster by at least about 5%, 10%, 15%, 20%, 25%, 30%, 35%, 40%, 45%, 50%, 55%, 60%, 65%, 70%, 75%, 80%, 85%, 90%, 95%, 100%, 125%, 150%, 200%, 300%, 400%, 500% or more and/or is more complete (e.g., a lesser amount of undigested or partially digested fragments remain, optionally at a specified time point, e.g., after about 0.5, 1, 2, 3, 4, 5, 6, 7, 8, 9, 10, 15, 20, 25, 30, 35, 40, 45, 50, 55 or 60 minutes of digestion) as compared with the suitable control. In embodiments, no detectable fragments (e.g., immunoreactive fragments) of the modified Axmi205 toxin of the invention remain above approximately 4 kDa after about 0.5, 1, 2, 3, 4, 5, 6, 7, 8, 9, 10, 15, 20, 25, 30, 35, 40, 45, 50, 55 or 60 minutes digestion with the digestive protease (e.g., pepsin), optionally under conditions as defined herein (e.g., approximately 37° C. and approximately pH 1.2, optionally at an enzyme concentration of 10 Units (U)/μg protein). Methods of detecting undigested or partially digested fragments of the modified Axmi205 toxin can be done using any suitable method (e.g., SDS-PAGE), and immunoreactive fragments can be detected with a suitable antibody (e.g., directed against the Axmi205 toxin of SEQ ID NO: 1), for example, as described in the working Examples.

The terms "increase," "increasing," "increased," "enhance," "enhanced," "enhancing," and "enhancement" (and grammatical variations thereof) and similar terms, as used herein with respect to the level of control of a plant pest describe an elevation in the control of the plant pest, e.g., by contacting a plant with a polypeptide of the invention (such as, for example, by transgenic expression or by topical application methods). This increase in control can be in reference to the level of control of the plant pest in the absence of the polypeptide of the invention (e.g., a plant that is not transgenically expressing the polypeptide or is not topically treated with the polypeptide). Thus, in embodiments, the terms "increase," "increasing," "increased," "enhance," "enhanced," "enhancing," and "enhancement" (and grammatical variations thereof), and similar terms can indicate an elevation of at least about 5%, 10%, 15%, 20%, 25%, 30%, 35%, 40%, 45%, 50%, 55%, 60%, 65%, 70%, 75%, 80%, 85%, 90%, 95%, 100%, 125%, 150%, 200%, 300%, 400%, 500% or more as compared to a suitable control (e.g., a plant, plant part, plant cell that is not contacted with a polypeptide of the invention).

"Insecticidal" as used herein is defined as a toxic biological activity capable of controlling an insect pest, optionally but preferably by killing them.

A nucleic acid sequence is "isocoding" with a reference nucleic acid sequence when the nucleic acid sequence encodes a polypeptide having the same amino acid sequence as the polypeptide encoded by the reference nucleic acid sequence.

In representative embodiments, the nucleic acids molecules, polynucleotides or proteins of the invention are "isolated." An "isolated" nucleic acid molecule, polynucleotide or protein, and the like, is a nucleic acid molecule, polynucleotide or protein, and the like that no longer exists in its natural environment. An isolated nucleic acid molecule, polynucleotide or protein of the invention may exist in a purified form or may exist in a recombinant host such as in a transgenic bacteria or a transgenic plant. In embodiments, an isolated nucleic acid molecule, nucleotide sequence or polypeptide exists in a purified form that is at least partially separated from at least some of the other components of the naturally occurring organism or virus, for example, the cell or viral structural components or other polypeptides or nucleic acids commonly found associated with the polynucleotide. In other embodiments, an "isolated" nucleic acid molecule, nucleotide sequence or polypeptide may exist in a non-native environment such as, for example, a recombinant host cell. Thus, for example, with respect to nucleotide sequences, the term "isolated" can mean that the nucleotide sequence is separated from the chromosome and/or cell in which it naturally occurs. A polynucleotide is also isolated if it is separated from the chromosome and/or cell in which it naturally occurs in and is then inserted into a genetic context, a chromosome and/or a cell in which it does not naturally occur (e.g., a different host cell, different regulatory sequences, and/or different position in the genome than as found in nature). Accordingly, recombinant nucleic acid molecules, nucleotide sequences and their encoded polypeptides are "isolated" in that, by the hand of man, they exist apart from their native environment and therefore are not products of nature, however, in some embodiments, they can be introduced into and exist in a recombinant host cell. In representative embodiments, the isolated nucleic acid molecule, the isolated nucleotide sequence and/or the isolated polypeptide is at least about 1%, 5%, 10%, 20%, 30%, 40%, 50%, 60%, 70%, 80%, 90%, 95%, or more pure.

The term "motif" or "consensus sequence" or "signature" refers to a short conserved region in the sequence of evolutionarily related proteins. Motifs are frequently highly conserved parts of domains, but may also include only part of the domain, or be located outside of conserved domain (if all of the amino acids of the motif fall outside of a defined domain).

A "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type mRNA" is an mRNA that is naturally occurring in or endogenous to the organism.

The terms "nucleic acid," "nucleic acid molecule," "nucleotide sequence," "oligonucleotide" and "polynucleotide" are used interchangeably herein, unless the context indicates otherwise, and refer to a heteropolymer of nucleotides. These terms include without limitation DNA and RNA molecules, including cDNA, genomic DNA, synthetic (e.g., chemically synthesized) DNA and RNA, plasmid DNA, mRNA, anti-sense RNA, and RNA/DNA hybrids, any of which can be linear or branched, single stranded or double stranded, or a combination thereof. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. In embodiments, the "nucleic acid," "nucleic acid molecule,", "nucleotide sequence,", "oligonucleotide" or "polynucleotide" refer to DNA.

By "operably linked" or "operably associated" as used herein, it is meant that the indicated elements are functionally related to each other, and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence, means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, sequences can be present between a promoter and a nucleotide sequence, and the promoter can still be considered "operably linked" to or "operatively associated" with the nucleotide sequence.

A "plant" as used herein, refers to any plant at any stage of development.

Any plant (or groupings of plants, for example, into a genus or higher order classification) can be employed in practicing the present invention including angiosperms or gymnosperms, monocots or dicots.

Exemplary plants include, but are not limited to corn (*Zea mays*), canola (*Brassica napus, Brassica rapa* ssp.), alfalfa (*Medicago saliva*), rice (*Oryza* saliva, including without limitation Indica and/or *Japonica* varieties), rape (*Brassica napus*), rye (*Secale cereale*), sorghum (*Sorghum bicolor, Sorghum vulgare*), sunflower (*Helianthus annus*), wheat (*Triticum aestivum*), soybean (*Glycine max*), tobacco (*Nicotiana tobacum*), potato (*Solanum tuberosum*), peanut (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), apple (*Malus pumila*), blackberry (*Rubus*), strawberry (*Fragaria*), walnut (*Juglans regia*), grape (*Vitis vinifera*), apricot (*Prunus armeniaca*), cherry (*Prunus*), peach (*Prunus persica*), plum (*Prunus domestica*), pear (*Pyrus communis*), watermelon (*Citrullus vulgaris*), duckweed (*Lemna* spp.), oats (*Avena sativa*), barley (*Hordium vulgare*), vegetables, ornamentals, conifers, and turfgrasses (e.g., for ornamental, recreational or forage purposes), and biomass grasses (e.g., switchgrass and miscanthus).

Vegetables include without limitation Solanaceous species (e.g., tomatoes; *Lycopersicon esculentum*), lettuce (e.g., *Lactuca sativa*), carrots (*Caucus carota*), cauliflower (*Brassica oleracea*), celery (*Apium graveolens*), eggplant (*Solanum melongena*), asparagus (*Asparagus officinalis*), ochra (*Abelmoschus esculentus*), green beans (*Phaseolus vulgaris*), lima beans (*Phaseolus limensis*), peas (*Lathyrus* spp.), members of the genus *Cucurbita* such as hubbard squash (*C. hubbard*), butternut squash (*C. moschata*), zucchini (*C. pepo*), crookneck squash (*C. crookneck*), *C. argyrosperma, C. argyrosperma* ssp *sororia, C. digitata, C. ecuadorensis, C. foetidissima, C. lundelliana*, and *C. martinezii*, and members of the genus *Cucumis* such as cucumber (*Cucumis sativus*), cantaloupe (*C. cantalupensis*), and musk melon (*C. melo*).

Ornamentals include without limitation azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherima*), and chrysanthemum.

Conifers, which may be employed in practicing the present invention, include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

Turfgrass include but are not limited to zoysiagrasses, bentgrasses, fescue grasses, bluegrasses, St. Augustinegrasses, bermudagrasses, bufallograsses, ryegrasses, and orchardgrasses.

Also included are plants that serve primarily as laboratory models, e.g., *Arabidopsis*.

A "plant cell" is a structural and physiological unit of a plant, comprising a protoplast and a cell wall. The plant cell may be in the form of an isolated single cell or a cultured cell, or as a part of a higher organized unit such as, for example, plant tissue, a plant organ, or a whole plant. In embodiments, the plant cell is non-propagating and/or cannot regenerate a whole plant.

A "plant cell culture" means a culture of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

As used herein, the term "plant part" includes but is not limited to embryos, pollen, ovules, seeds, leaves, flowers, branches, fruit, stalks, roots, root tips, anthers, and/or plant cells including plant cells that are intact in plants and/or parts of plants, plant protoplasts, plant tissues, plant cell tissue cultures, plant calli, plant clumps, and the like.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural or functional units. The use of this term in conjunction with, or in the absence of, any specific type of plant tissue as listed above or otherwise embraced by this definition is not intended to be exclusive of any other type of plant tissue.

A "polynucleotide of interest" refers to any polynucleotide which, when transferred to an organism, e.g., a plant, confers upon the organism a desired characteristic such as insect resistance, disease resistance, herbicide tolerance, antibiotic resistance, improved nutritional value, improved performance in an industrial process, production of a commercially valuable enzyme or metabolite, an altered reproductive capability, and the like.

A "portion" or "fragment" of a polypeptide of the invention will be understood to mean an amino acid sequence of reduced length relative to a reference amino acid sequence of a polypeptide of the invention.

Such a portion or fragment according to the invention may be, where appropriate, included in a larger polypeptide of which it is a constituent (e.g., a tagged or fusion protein). In embodiments, the "portion" or "fragment" substantially retains insecticidal activity (e.g., at least 40%, 50%, 60%, 70%, 80%, 85%, 90%, 95% or even 100% of the activity of the full-length protein, or has even greater insecticidal activity than the full-length protein).

The terms "protein," "peptide" and "polypeptide" are used interchangeably herein.

The term "promoter" as used herein refers to a polynucleotide, typically upstream (5') of a coding polynucleotide, which controls the expression of the coding polynucleotide by providing the recognition for RNA polymerase and other transcriptional machinery.

A "protoplast" as used herein, refers to an isolated plant cell without a cell wall or with only parts of the cell wall.

As used herein, the term "recombinant" refers to a form of nucleic acid (e.g., DNA or RNA) or protein or an organism that would not normally be found in nature and as such was created by human intervention. As used herein, a "recombinant nucleic acid molecule" (and similar terms) is a nucleic acid molecule comprising a combination of polynucleotides that would not naturally occur together and is the result of human intervention, e.g., a nucleic acid molecule that is comprised of a combination of at least two polynucleotides heterologous to each other, or a nucleic acid molecule that is artificially synthesized and comprises a polynucleotide that deviates from the polynucleotide that would normally exist in nature, or a nucleic acid molecule that comprises a transgene artificially incorporated into a host cell's genomic DNA and the associated flanking DNA of the host cell's genome. An example of a recombinant nucleic acid molecule is a DNA molecule resulting from the insertion of a transgene into a plant's genomic DNA, which may ultimately result in the expression of a recombinant RNA or protein molecule in that organism. In embodiments, a "recombinant" protein is a protein that does not normally exist in nature or is present in a non-naturally occurring context, and is expressed from a recombinant nucleic acid molecule. As used herein, a "recombinant plant" is a plant that would not normally exist in nature, is the result of human intervention, and contains a recombinant polynucleotide (e.g., a transgene or heterologous nucleic acid molecule incorporated into its genome). As a result of such genomic alteration, the recombinant plant is distinctly different from the related wild-type plant.

The terms "reduce," "reduced," "reducing," "reduction," "diminish," and "suppress" (and grammatical variations thereof) and similar terms, as used herein, refer to a decrease in the relevant parameter. In embodiments, the terms "reduce," "reduced," "reducing," "reduction," "diminish," and "suppress" (and grammatical variations thereof) and similar terms mean a decrease of at least about 5%, 10%, 15%, 20%, 25%, 30%, 35%, 40%, 45%, 50%, 55%, 60%, 65%, 70%, 75%, 80%, 85%, 90%, 95% or more as compared with a suitable control.

The terms "reduce," "reduced," "reducing," "reduction," "diminish," and "suppress" (and grammatical variations thereof) and similar terms, as used herein with reference to control of a plant pest indicate a decrease in the survival, growth and/or reproduction of a plant pest, e.g., by contacting a plant with a polypeptide of the invention (such as, for example, by transgenic expression or by topical application methods). This decrease in survival, growth and/or reproduction can be in reference to the level observed in the absence of the polypeptide of the invention (e.g., a plant that is not transgenically expressing the polypeptide or is not topically treated with the polypeptide). Thus, in embodiments, the terms "reduce," "reduced," "reducing," "reduction," "diminish," and "suppress" (and grammatical variations thereof) and similar terms mean a decrease of at least about 5%, 10%, 15%, 20%, 25%, 30%, 35%, 40%, 45%, 50%, 55%, 60%, 65%, 70%, 75%, 80%, 85%, 90%, 95% or more as compared with a plant that is not contacted with a polypeptide of the invention (e.g., a plant that is not transgenically expressing the polypeptide or is not topically treated with the polypeptide). In representative embodiments, the reduction results in no or essentially no (i.e., an insignificant amount, e.g., less than about 10%, less than about 5% or even less than about 1%) detectable survival, growth and/or reproduction of the plant pest.

A "regulatory element" refers to a nucleotide sequence involved in controlling the expression of a polynucleotide. Examples of regulatory elements include promoters, termination signals, and nucleotide sequences that facilitate proper translation of a polynucleotide.

As used herein, "selectable marker" means a nucleotide sequence that when expressed imparts a distinct phenotype to the plant, plant part and/or plant cell expressing the marker and thus allows such transformed plants, plant parts and/or plant cells to be distinguished from those that do not have the marker. Such a nucleotide sequence may encode either a selectable or screenable marker, depending on whether the marker confers a trait that can be selected for by chemical means, such as by using a selective agent (e.g., an antibiotic, herbicide, or the like), or on whether the marker is simply a trait that one can identify through observation or testing, such as by screening (e.g., the R-locus trait).

As used herein, "specific activity" refers to the amount of protein required to have an insecticidal effect. Therefore, when a first protein has a higher specific activity than a second protein means that it takes a lesser amount of the first protein compared the second protein to have an insecticidal effect on the same percentage of insects.

The phrase "substantially identical," in the context of two nucleic acids or two amino acid sequences, refers to two or more sequences or subsequences that have at least about 50% nucleotide or amino acid residue identity when compared and aligned for maximum correspondence as measured using a sequence comparison algorithm or by visual inspection. In certain embodiments, substantially identical sequences have at least about 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more nucleotide or amino acid residue identity. In certain embodiments, substantial identity exists over a region of the sequences that is at least about 50 amino acid residues, 100 amino acid residues, 150 amino acid residues, 200 amino acid residues, 250 amino acid residues, 300 amino acid residues, 350 amino acid residues, 400 amino acid residues, 450 amino acid residues, 500 amino acid residues, 525 amino acid residues, 526, amino acid residues 527 amino acid residues, 528 amino acid residues, 529 amino acid residues, 530 amino acid residues, 531 amino acid residues, 532 amino acid residues, 533 amino acid residues, 534 amino acid residues, 535 amino acid residues, 536 amino acid residues or more with respect to the protein sequence or the nucleotide sequence encoding the same. In further embodiments, the sequences are substantially identical when they are identical over the entire length of the coding regions.

"Identity" or "percent identity" refers to the degree of identity between two nucleic acid or amino acid sequences. For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2: 482 (1981), by the homology alignment algorithm of Needleman & Wunsch, J. Mol. Biol. 48: 443 (1970), by the search for similarity method of Pearson & Lipman, Proc. Nat'l. Acad. Sci. USA 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally).

One example of an algorithm that is suitable for determining percent sequence identity and sequence similarity is the BLAST algorithm, which is described in Altschul et al., J. Mol. Biol. 215: 403-410 (1990). Software for performing BLAST analyses is publicly available through the National Center for Biotechnology Information (on the world wide web at ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., J. Mol. Biol. 215: 403-410 (1990)). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see, Henikoff & Henikoff, Proc. Natl. Acad. Sci. USA 89: 10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

Another widely used and accepted computer program for performing sequence alignments is CLUSTALW v1.6 (Thompson, et al. Nuc. Acids Res., 22: 4673-4680, 1994). The number of matching bases or amino acids is divided by the total number of bases or amino acids, and multiplied by 100 to obtain a percent identity. For example, if two 580 base pair sequences had 145 matched bases, they would be 25 percent identical. If the two compared sequences are of different lengths, the number of matches is divided by the shorter of the two lengths. For example, if there were 100 matched amino acids between a 200 and a 400 amino acid proteins, they are 50 percent identical with respect to the shorter sequence. If the shorter sequence is less than 150 bases or 50 amino acids in length, the number of matches are divided by 150 (for nucleic acid bases) or 50 (for amino acids), and multiplied by 100 to obtain a percent identity.

Two nucleotide sequences can also be considered to be substantially identical when the two sequences hybridize to each other under stringent conditions. In representative embodiments, two nucleotide sequences considered to be substantially identical hybridize to each other under highly stringent conditions.

The terms "stringent conditions" or "stringent hybridization conditions" include reference to conditions under which a nucleic acid will selectively hybridize to a target sequence to a detectably greater degree than other sequences (e.g., at least 2-fold over a non-target sequence), and optionally may substantially exclude binding to non-target sequences. Stringent conditions are sequence-dependent and will vary under different circumstances. By controlling the stringency of the hybridization and/or washing conditions, target sequences can be identified that can be up to 100% complementary to the reference nucleotide sequence. Alternatively, conditions of moderate or even low stringency can be used to allow some mismatching in sequences so that lower degrees of sequence similarity are detected. For example, those skilled in the art will appreciate that to function as a primer or probe, a nucleic acid sequence only needs to be sufficiently complementary to the target sequence to substantially bind thereto so as to form a stable double-stranded structure under the conditions employed. Thus, primers or probes can be used under conditions of high, moderate or even low stringency. Likewise, conditions of low or moderate stringency can be advantageous to detect homolog, ortholog and/or paralog sequences having lower degrees of sequence identity than would be identified under highly stringent conditions.

The terms "complementary" or "complementarity" (and similar terms), as used herein, refer to the natural binding of polynucleotides under permissive salt and temperature conditions by base-pairing. For example, the sequence "A-G-T" binds to the complementary sequence "T-C-A." Complementarity between two single-stranded molecules may be partial, in which only some of the nucleotides bind, or it may be complete when total complementarity exists between the single stranded molecules. The degree of complementarity between nucleic acid strands has significant effects on the efficiency and strength of hybridization between the molecules. As used herein, the term "substantially complementary" (and similar terms) means that two nucleic acid sequences are at least about 50%, 60%, 70%, 75%, 80%, 85%, 90%, 95%, 96%, 97%, 98%, 99% or more complementary. Alternatively, the term "substantially complementary" (and similar terms) can mean that two nucleic acid sequences can hybridize together under high stringency conditions (as described herein).

As used herein, "specifically" or "selectively" hybridizing (and similar terms) refers to the binding, duplexing, or hybridizing of a molecule to a particular nucleic acid target sequence under stringent conditions when that sequence is present in a complex mixture (e.g., total cellular DNA or RNA) to the substantial exclusion of non-target nucleic acids, or even with no detectable binding, duplexing or hybridizing to non-target sequences. Specifically or selectively hybridizing sequences typically are at least about 40% complementary and are optionally substantially complementary or even completely complementary (i.e., 100% identical).

For DNA-DNA hybrids, the $T_m$ can be approximated from the equation of Meinkoth and Wahl, Anal. Biochem., 138: 267-84 (1984): $T_m$=81.5° C.+16.6 (log M)+0.41 (% GC)– 0.61 (% formamide)–500/L; where M is the molarity of monovalent cations, % GC is the percentage of guanosine and cytosine nucleotides in the DNA, % formamide is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired degree of identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, highly stringent conditions can utilize a hybridization and/or wash at the thermal melting point ($T_m$) or 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). If the desired degree of mismatching results in a $T_m$ of less than 45° C. (aqueous solution) or 32° C. (formamide solution), optionally the SSC concentration can be increased so that a higher temperature can be used. An extensive guide to the hybridization of nucleic acids is found in Tijssen, Laboratory Techniques in Biochemistry and Molecular Biology-Hybridization with Nucleic Acid Probes, part I, chapter 2, "Overview of principles of hybridization and the strategy of nucleic acid probe assays," Elsevier, New York (1993); Current Protocols in Molecular Biology, chapter 2, Ausubel, et al., eds, Greene Publishing and Wiley-Interscience, New York (1995); and Green & Sambrook, In: Molecular Cloning, A Laboratory Manual, 4th Edition, Cold Spring Harbor Press, Cold Spring Harbor, N.Y. (2012).

Typically, stringent conditions are those in which the salt concentration is less than about 1.5 M Na ion, typically about 0.01 to 1.0 M Na ion concentration (or other salts) at about pH 7.0 to pH 8.3 and the temperature is at least about 30° C. for short probes (e.g., 10 to 50 nucleotides) and at least about 60° C. for longer probes (e.g., greater than 50 nucleotides). Stringent conditions may also be achieved with the addition of destabilizing agents such as formamide or Denhardt's (5 g Ficoll, 5 g polyvinylpyrrolidone, 5 g bovine serum albumin in 500 ml of water). Exemplary low stringency conditions include hybridization with a buffer solution of 30% to 35% formamide, 1 M NaCl, 1% SDS (sodium dodecyl sulfate) at 37° C. and a wash in 1× to 2×SSC (20×SSC=3.0 M NaCl/0.3 M trisodium citrate) at 50° C. to 55° C. Exemplary moderate stringency conditions include hybridization in 40% to 45% formamide, 1 M NaCl, 1% SDS at 37° C. and a wash in 0.5× to 1×SSC at 55° C. to 60° C. Exemplary high stringency conditions include hybridization in 50% formamide, 1 M NaCl, 1% SDS at 37° C. and a wash in 0.1×SSC at 60° C. to 65° C. A further non-limiting example of high stringency conditions include hybridization in 4×SSC, 5×Denhardt's, 0.1 mg/ml boiled salmon sperm DNA, and 25 mM Na phosphate at 65° C. and a wash in 0.1×SSC, 0.1% SDS at 65° C. Another illustration of high stringency hybridization conditions includes hybridization in 7% SDS, 0.5 M $NaPO_4$, 1 mM EDTA at 50° C. with washing in 2×SSC, 0.1% SDS at 50° C., alternatively with washing in 1×SSC, 0.1% SDS at 50° C., alternatively with washing in 0.5×SSC, 0.1% SDS at 50° C., or alternatively with washing in 0.1×SSC, 0.1% SDS at 50° C., or even with washing in 0.1×SSC, 0.1% SDS at 65° C. Those skilled in the art will appreciate that specificity is typically a function of post-hybridization washes, the relevant factors being the ionic strength and temperature of the final wash solution.

Nucleic acids that do not hybridize to each other under stringent conditions are still substantially identical if the proteins that they encode are substantially identical (e.g., due to the degeneracy of the genetic code).

A further indication that two nucleic acids or proteins are substantially identical is that the protein encoded by the first nucleic acid is immunologically cross reactive with the protein encoded by the second nucleic acid. Thus, a protein is typically substantially identical to a second protein, for example, where the two proteins differ only by conservative substitutions.

As used herein, if a modified polypeptide or fragment (and the like) "substantially retains" insecticidal activity, it is meant that the modified polypeptide or fragment retains at least about 40%, 50%, 60%, 70%, 80%, 85%, 90%, 95% or even 100% of the insecticidal activity of the reference protein against one or more target insects, or has even greater insecticidal activity.

"Synthetic" refers to a nucleotide sequence comprising bases or a structural feature(s) that is not present in the natural sequence. For example, an artificial sequence encoding a protein of the invention that resembles more closely the G+C content and the normal codon distribution of dicot or monocot plant genes is said to be synthetic.

As used herein, a protein that is "toxic" to an insect pest is an orally-active insect control agent that kills the insect pest, causes a reduction in growth and/or reproduction of the insect pest and/or is able to disrupt or deter insect feeding, which may or may not cause death of the insect. When a protein of the invention is delivered to an insect or an insect comes into contact with the protein, the result is typically death of the insect, the insect's growth and/or reproduction is slowed and/or the insect reduces or stops feeding upon the source that makes the toxic protein available to the insect.

The terms "toxin fragment" and "toxin portion" are used interchangeably herein to refer to a fragment or portion of a longer (e.g., full-length) insecticidal protein of the invention, where the "toxin fragment" or "toxin portion" retains insecticidal activity. In embodiments, the "toxin fragment" or "toxin portion" of an insecticidal protein of the invention is truncated at the N-terminus and/or C-terminus. In embodiments, the "toxin fragment" or "toxin portion" is truncated at the N-terminus, and optionally comprises at least about 405, 410, 425, 450, 475, 500, 510, 520, 525, 530, 531, 532, 533, 534, 535, 536, 537 or 538 contiguous amino acids of an insecticidal protein specifically described herein or an amino acid sequence that is substantially identical thereto. Thus, in embodiments, a "toxin fragment" or "toxin portion" of an insecticidal protein is truncated at the N-terminus, for example, an N-terminal truncation of one amino acid or more than one amino acid, e.g., up to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more amino acids, for example, an N-terminal truncation of the Axmi205 toxin of SEQ ID NO: 1 incorporating one or more modifications according to the present invention. In embodiments, a "toxin fragment" or "toxin portion" of an insecticidal protein is truncated at the C-terminus, for example, a C-terminal truncation of one amino acid or more than one amino acid, e.g., up to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more amino acids. In embodiments, the "toxin fragment" or "toxin portion" comprises the MAC/PF (Membrane Attack Complex/Perforin protein superfamily) domain found in the N-terminal region of the native Axmi205 protein of SEQ ID NO: 1 (within the region defined by about amino acids 101 to 300 of SEQ ID NO: 1; see GenBank Accession No. AML23188.1) or the corresponding region of other Axmi205 toxins and/or the Beta-Prism domain in the C-terminal half of the Axmi205 toxin (e.g., within about amino acids 300 to 526 SEQ ID NO: 1 or the corresponding region of other Axmi205 toxins).

"Transformation" is a process for introducing a heterologous nucleic acid into a host cell or organism. In particular embodiments, "transformation" means the stable integration of a DNA molecule into the genome of an organism of interest (e.g., a plant cell).

The terms "transformed" and "transgenic" as used herein refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. "Transformed" or "transgenic" cells, tissues, or plants are understood to encompass not only the end product of a transformation process, but also progeny thereof comprising the heterologous nucleic acid molecule. A "non-transformed" or "non-transgenic" host refers to a wild-type organism, e.g., a bacterium or plant, which does not contain the heterologous nucleic acid molecule.

The term "vector" refers to a composition for transferring, delivering or introducing a nucleic acid (or nucleic acids) into a cell. A vector comprises a nucleic acid molecule comprising the nucleotide sequence(s) to be transferred, delivered or introduced.

Pesticidal Proteins.

The present invention provides novel pesticidal (e.g., insecticidal) proteins comprising a modified Axmi205 toxin that has enhanced digestion (e.g., cleavage) by a digestive protease (e.g., pepsin) as compared with an Axmi205 toxin that does not comprise the modification (e.g., the Axmi205 protein of SEQ ID NO: 1 and/or an Axmi205 toxin that is identical to the modified Axmi205 protein of the invention with the exception that it lacks the modifications of the present invention). Modifications within the scope of the present invention include without limitations deletions, substitutions and/or insertions.

The native Axmi205 toxin of SEQ ID NO: 1 has previously been described in U.S. Pat. No. 8,575,425 B2 and Sampson et al. (Discovery of a novel insecticidal protein from *Chromobacterium piscinae* with activity against Western Corn Rootworm, *Diabrotica virgifera virgifera, J. Invertebrate Pathology* 142: 34-43 (2016)). See also GenBank Accession No. AML23188.1. U.S. Pat. No. 8,575,425 B2 also describes a number of Axmi205 point mutations and truncations that retain activity against WCRW (see, Examples 7 and 8 of U.S. Pat. No. 8,575,425 B2). Such mutants include the following mutations in the Axmi205 protein sequence of SEQ ID NO: 1 of the present application (SEQ ID NO: 2 of U.S. Pat. No. 8,575,425 B2): S307A, D315A, V317A, S349A, G351A, K353A, V355A, D395A, G399A, W407A, G419A, P355A, P435A, S443A, K465A, V467A, F483A, P487A, S495A, D497A, E499A, K509A and I513A. Also disclosed are Axmi205 proteins having C-terminal truncations of 10 or 20 amino acids from the C-terminus of the Axmi205 of SEQ ID NO: 1 of the present application (SEQ ID NO: 2 of U.S. Pat. No. 8,575,425 B2).

As used herein, an "Axmi205 toxin" to be modified according to the present invention (e.g., to enhance digestion by a digestive protease such as pepsin) comprises, consists essentially of, or consists of the amino acid sequence of SEQ ID NO: 1 or an amino acid sequence that is substantially identical to SEQ ID NO: 1. Generally, the Axmi205 toxin to be modified according to the present invention has an undesirable digestion profile by a mammalian digestive protease (e.g., pepsin), e.g., undigested or partially digested fragments of the Axmi205 toxin above about 4 kDa remain after about 15, 20, 25, 30, 35, 40, 45, 50, 55, 60 or more minutes of digestion with the digestive protease, optionally under conditions of approximately 37° C. and approximately pH 1.2, and as a further option with a protease concentration of 10 U per microgram protein. Thus, the modifications disclosed herein can be incorporated into the Axmi205 toxin so as to enhance/improve the digestion by a digestive protease (e.g., protease).

The Axmi205 toxin of SEQ ID NO: 1 was isolated from *Chromobacterium piscinae*. In embodiments, as used herein, an "Axmi205 toxin" to be modified according to the present invention is from the genus *Chromobacterium*, optionally *C. piscinae* (either isolated directly from the organism, or partly or completely synthesized to replicate a naturally occurring *Chromobacterium*, optionally *C. piscinae*, protein). United States patent publication US2014/0223599 (Athenix) describes Axmi279 (SEQ ID NO: 2 of that patent publication), which was also isolated from *C. piscinae*, has 97.9% amino acid identity with Axmi205, and is active in controlling WCRW. US2014/0223599 also describes two Axmi279 variants from which the C-terminal amino acid and the N-terminal 18 or 20 amino acids are truncated (SEQ ID NO:

3 and SEQ ID NO: 4, respectively, of US2014/0223599). The Axmi279 protein and variants thereof described in US2014/0223599 are also encompassed by the Axmi205 toxins according to the present invention.

WO2013/016617 (Athenix) also describes a number of variants of the Axmi205 protein of SEQ ID NO: 1 of the present application: S468L, V467L, V467T, R464N, Q517R and E86T having activity against WCRW. Furthermore, US 2014/0274885 A1 (Pioneer Hi-Bred) also describes a large number of Axmi205 variants having insecticidal activity against WCRW.

Thus, in embodiments, as used herein an "Axmi205 toxin" to be modified according to the present invention comprises, consists essentially of, or consists of a variant Axmi205 protein, for example, the Axmi205 toxins described in U.S. Pat. No. 8,575,425 B2 (Athenix), WO2013/016617 (Athenix) or in US 2014/0274885 A1 (Pioneer Hi-Bred)).

Accordingly, the term "Axmi205 toxin" as used herein encompasses SEQ ID NO: 1 as well as the Axmi205 variants disclosed in U.S. Pat. No. 8,575,425 B2, WO2013/016617 and/or US 2014/0274885 A1, and/or Axmi279 and variants thereof disclosed in US2014/0223599.

In embodiments, the modified Axmi205 toxin comprises a deletion (including a truncation), substitution and/or insertion of one or more amino acids as compared with the Axmi205 toxin of SEQ ID NO: 1 or a substantially identical protein, wherein the deletion, substitution and/or insertion results in enhanced digestion of the modified Axmi205 toxin by pepsin and/or other mammalian digestive proteases (e.g., human digestive proteases) such as trypsin and/or chymotrypsin as compared with an Axmi205 toxin that does not comprise the deletion, substitution and/or insertion (e.g., SEQ ID NO: 1 and/or an Axmi205 toxin that is identical to the modified Axmi205 protein of the invention with the exception that it lacks the modifications of the present invention).

In embodiments, the modified Axmi205 toxins of the invention substantially retain the insecticidal activity of the parent molecule (e.g., SEQ ID NO:1) against one or more target pests, e.g., a coleopteran pest such as WCRW.

In embodiments, the insecticidal proteins of the invention can provide new modes of action against one or more target insect pests. For example, an insecticidal protein of the invention can have insecticidal activity against an insect pest or colony that is generally resistant to the insecticidal activity of another insect control agent, e.g., an insecticidal protein or an insecticidal dsRNA. To illustrate, the insecticidal protein of the invention may have insecticidal activity against a corn rootworm (e.g., WCRW) pest or colony that is resistant to a mCry3A protein (e.g., in corn event MIR604), an eCry3.1Ab protein (e.g., in corn event 5307), a Cry3Bb1 protein (e.g., in corn event MON88017), a Cry34/35Ab1 binary protein (e.g., in corn event DAS-59122) and/or a RNAi trait, such as DvSnf7 dsRNA (e.g., in corn event MON87411).

In embodiments, the modified Axmi205 proteins of the invention have enhanced digestion by a mammalian digestive protease (e.g., pepsin) as compared with a suitable control (e.g., SEQ ID NO: 1 and/or the parental molecule not containing a modification of the invention) when tested under the same conditions (e.g., enzyme concentration, protein concentration, pH, temperature and/or time). Methods for assessing protein digestion by pepsin and other digestive proteases are well-known in the art, for example, the Simulated Gastric Fluid (SGF) assay described in Examples 3 and 5. For example, digestion with pepsin can be carried out at approximately 37° C. and approximately pH 1.2, optionally with an enzyme concentration of approximately 10 Units (U) pepsin per microgram of protein.

In representative embodiments, no detectable fragments (e.g., immunoreactive fragments) of the modified Axmi205 toxin of the invention remain above approximately 4 kDa after about 0.5, 1, 2, 3, 4, 5, 6, 7, 8, 9, 10, 15, 20, 25, 30, 35, 40, 45, 50, 55 or 60 minutes of digestion with the digestive protease (e.g., pepsin), optionally under the conditions described in the preceding paragraph. Methods of detecting undigested or partially digested fragments of the modified Axmi205 protein are known in the art (e.g., SDS-PAGE), and immunoreactive fragments can be detected with a suitable antibody (e.g., directed against the Axmi205 toxin of SEQ ID NO: 1), for example, as described in the working Examples.

In embodiments, the modified Axmi205 toxin comprises the MAC/PF (Membrane Attack Complex/Perforin protein superfamily) domain found in the N-terminal region of the native Axmi205 protein of SEQ ID NO: 1 (within the region defined by about amino acids 101 to 300 of SEQ ID NO: 1; see GenBank: AML23188.1) and/or the Beta-Prism domain in the C-terminal half of the Axmi205 toxin (e.g., within about amino acids 300 to 526 SEQ ID NO: 1 or the corresponding region of other Axmi205 toxins).

The modification(s) of the invention can be made in any portion(s) of the parental Axmi205 toxin that results in an enhanced digestion by a mammalian digestive protease (e.g., pepsin), optionally with substantial retention of the insecticidal activity of the parental Axmi205 toxin. In embodiments, the Axmi205 toxin is modified by deletion, substitution and/or insertion of one or more amino acids in a portion of the Axmi205 toxin of SEQ ID NO: 1 from about amino acid 400 or 402 to about amino acid 497, 500, or 536, or the corresponding portion of another Axmi205 toxin. In embodiments, the deletion, substitution and/or insertion of one or more amino acids is in a portion of the Axmi205 toxin of SEQ ID NO: 1 from about amino acid 402 to about amino acid 497, or the corresponding portion of another Axmi205 toxin.

In representative embodiments, the modification can comprise substitution and/or insertion of one or more of any naturally-occurring and/or non-naturally occurring amino acid. In embodiments, the modification comprises an insertion and/or substitution of one or more of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and/or valine. In embodiments, the insertion and/or substitution is not an alanine.

In embodiments, the Axmi205 toxin is modified by substitution and/or insertion of (a) one or more amino acids with an aliphatic hydrophobic side chain (e.g., alanine, isoleucine, methionine and/or valine; in embodiments, the amino acid is not an alanine); (b) one or more amino acids with an aromatic hydrophobic side chain (e.g., phenylalanine, tryptophan and/or tyrosine); (c) one or more amino acids with a polar neutral side chain (e.g., asparagine, cysteine, glutamine, serine and/or threonine); (d) one or more amino acids with an acidic side chain (e.g., aspartic acid and/or glutamic acid); one or more amino acids with a basic side chain (e.g., arginine, histidine and/or lysine); (e) one or more glycine residues; (f) one or more proline residues; or (g) any combination of (a) to (f).

In representative embodiments, the deletion, substitution and/or insertion of one or more amino acids creates a new cleavage site for a mammalian digestive protease (e.g., pepsin) that did not exist in the parent Axmi205 toxin, for example, a non-naturally occurring pepsin cleavage site incorporated into the Axmi205 toxin of SEQ ID NO: 1. To illustrate, as is known in the art, pepsin preferentially cleaves between two hydrophobic amino acids (e.g., alanine, isoleucine, valine, phenylalanine, tryptophan and/or tyrosine). Thus, in embodiments, the modification comprises the insertion or substitution of a hydrophobic amino acid (with an aliphatic and/or aromatic side chain) adjacent to an existing hydrophobic amino acid to create a new pepsin cleavage site. In embodiments, the modification comprises insertion or substitution of two amino acids to create two adjacent hydrophobic amino acids. In embodiments, one amino acid is substituted and one amino acid inserted to create two adjacent hydrophobic amino acids. In representative embodiments, one or more amino acids with an aliphatic hydrophobic side chain and/or an aromatic hydrophobic side chain are substituted and/or inserted. In further representative embodiments, a deletion of one or more (e.g., 2, 3, 4 or 5) amino acids brings two hydrophobic amino acids into adjacent positions so as to create a protease cleavage site.

Without being bound by any theory of the invention, in embodiments, the modification to the Axmi205 toxin opens up the secondary and/or tertiary structure of the protein thereby providing better access to digestive proteases. In embodiments, the modification to the Axmi205 toxin comprises a deletion or substitution of one or more cysteine residues (e.g., 1, 2, 3, 4, or 5 cysteine residues) by another amino acid residue, optionally to reduce potential disulfide bond formation (e.g., by reducing the total number of cysteine residues in the protein).

In embodiments, the modified Axmi205 toxin comprises: (a) an amino acid substitution at amino acid K402 in the polypeptide of SEQ ID NO:1 or the corresponding lysine residue in another Axmi205 toxin; (b) amino acid substitutions at amino acids K402 and Y404 in the polypeptide of SEQ ID NO:1 or the corresponding lysine and tyrosine residues in another Axmi205 toxin; (c) an amino acid substitution at amino acid C482 in the polypeptide of SEQ ID NO:1 or the corresponding cysteine residue in another Axmi205 toxin; (d) an amino acid substitution at amino acid C507 in the polypeptide of SEQ ID NO:1 or the corresponding cysteine residue in another Axmi205 toxin; (e) amino acid substitutions at amino acids M422 and M423 in the polypeptide of SEQ ID NO:1 or the corresponding methionine residues in another Axmi205 toxin; (f) an amino acid insertion between amino acids A475 and G476 in the polypeptide of SEQ ID NO:1 or the corresponding alanine and glycine residues in another Axmi205 toxin; (g) an amino acid insertion between amino acids G496 and D497 in the polypeptide of SEQ ID NO:1 or the corresponding glycine and aspartic acid residues in another Axmi205 toxin; (h) an amino acid insertion between amino acids Q471 and P472 in the polypeptide of SEQ ID NO:1 or the corresponding glycine and aspartic acid residues in another Axmi205 toxin; (i) an amino acid insertion between amino acids A479 and S480 in the polypeptide of SEQ ID NO:1 or the corresponding glycine and aspartic acid residues in another Axmi205 toxin; (j) an amino acid insertion between amino acids Y489 and N490 in the polypeptide of SEQ ID NO:1 or the corresponding glycine and aspartic acid residues in another Axmi205 toxin; or (k) any combination of (a) to (j) above.

In embodiments, the modified Axmi205 toxin comprises: a substitution of an amino acid with an aliphatic hydrophobic side chain, an amino acid with an aromatic hydrophobic side chain, an amino acid with a polar neutral side chain, an amino acid with an acidic side chain, or an amino acid with a basic side chain at amino acid K402 in the polypeptide of SEQ ID NO:1 or the corresponding lysine in another Axmi205 toxin;

a) amino acid substitutions of (i) an amino acid with an aliphatic hydrophobic side chain, an amino acid with an aromatic hydrophobic side chain, an amino acid with a polar neutral side chain, an amino acid with an acidic side chain, an amino acid with a basic side chain, a glycine or a proline at amino acid K402 in the polypeptide of SEQ ID NO:1 or the corresponding lysine residue in another Axmi205 toxin; and (ii) an amino acid with an aliphatic hydrophobic side chain, an amino acid with an aromatic hydrophobic side chain, an amino acid with a polar neutral side chain, an amino acid with an acidic side chain, an amino acid with a basic side chain, a glycine or a proline at amino acid Y404 in the polypeptide of SEQ ID NO:1 or the corresponding tyrosine residue in another Axmi205 toxin;

b) a substitution of an amino acid with an aliphatic hydrophobic side chain, an amino acid with an aromatic hydrophobic side chain, an amino acid with a polar neutral side chain, an amino acid with an acidic side chain, an amino acid with a basic side chain, a glycine or a proline at amino acid C482 in the polypeptide of SEQ ID NO:1 or the corresponding cysteine residue in another Axmi205 toxin;

c) a substitution of an amino acid with an aliphatic hydrophobic side chain, an amino acid with an aromatic hydrophobic side chain, an amino acid with a polar neutral side chain, an amino acid with an acidic side chain, an amino acid with a basic side chain, a glycine or a proline at amino acid C507 in the polypeptide of SEQ ID NO:1 or the corresponding cysteine residue in another Axmi205 toxin;

d) amino acid substitutions of (i) an amino acid with an aliphatic hydrophobic side chain, an amino acid with an aromatic hydrophobic side chain, an amino acid with a polar neutral side chain, an amino acid with an acidic side chain, an amino acid with a basic side chain, a glycine or a proline at amino acid M422 in the polypeptide of SEQ ID NO:1 or the corresponding methionine residue in another Axmi205 toxin; and (ii) an amino acid with an aliphatic hydrophobic side chain, an amino acid with an aromatic hydrophobic side chain, an amino acid with a polar neutral side chain, an amino acid with an acidic side chain, an amino acid with a basic side chain, a glycine or a proline at amino acid M423 in the polypeptide of SEQ ID NO:1 or the corresponding methionine residue in another Axmi205 toxin;

e) an insertion of an amino acid with an aliphatic hydrophobic side chain, an amino acid with an aromatic hydrophobic side chain, an amino acid with a polar neutral side chain, an amino acid with an acidic side chain, an amino acid with a basic side chain, a glycine or a proline between amino acids A475 and G476 in the polypeptide of SEQ ID NO:1 or the corresponding alanine and glycine residues in another Axmi205 toxin;

f) an insertion of an amino acid with an aliphatic hydrophobic side chain, an amino acid with an aromatic hydrophobic side chain, an amino acid with a polar neutral side chain, an amino acid with an acidic side chain, an amino acid with a basic side chain, a glycine or a proline between amino acids G496 and D497 in the polypeptide of SEQ ID NO:1 or the corresponding glycine and aspartic acid residues in another Axmi205 toxin;
g) an insertion of an amino acid with an aliphatic hydrophobic side chain, an amino acid with an aromatic hydrophobic side chain, an amino acid with a polar neutral side chain, an amino acid with an acidic side chain, or an amino acid with a basic side chain between amino acids Q471 and P472 in the polypeptide of SEQ ID NO:1 or the corresponding alanine and glycine residues in another Axmi205 toxin;
h) an insertion of an amino acid with an aliphatic hydrophobic side chain, an amino acid with an aromatic hydrophobic side chain, an amino acid with a polar neutral side chain, an amino acid with an acidic side chain, or an amino acid with a basic side chain between amino acids A479 and S480 in the polypeptide of SEQ ID NO:1 or the corresponding alanine and glycine residues in another Axmi205 toxin;
i) an insertion of an amino acid with an aliphatic hydrophobic side chain, an amino acid with an aromatic hydrophobic side chain, an amino acid with a polar neutral side chain, an amino acid with an acidic side chain, or an amino acid with a basic side chain between amino acids Y489 and N490 in the polypeptide of SEQ ID NO:1 or the corresponding alanine and glycine residues in another Axmi205 toxin; or
j) any combination of (a) to (i).

Amino acids with an aliphatic hydrophobic side chain, an aromatic hydrophobic side chain, a polar neutral side chain, an acidic side chain, or a basic side chain are as described elsewhere herein.

In exemplary embodiments, the modified Axmi205 toxin comprises:
a) an amino acid substitution of K402F, K402N or K402D in the polypeptide of SEQ ID NO:1 or the corresponding lysine in another Axmi205 toxin;
b) amino acid substitutions of (i) K402L and Y404F, or (ii) K402D and Y404L in the polypeptide of SEQ ID NO:1 or the corresponding lysine and tyrosine residues in another Axmi205 toxin;
c) an amino acid substitution of C482S, C482D or C482F in the polypeptide of SEQ ID NO:1 or the corresponding cysteine residue in another Axmi205 toxin;
d) an amino acid substitution of C507S, C507L, C507A, C507F, C507D or C507R in the polypeptide of SEQ ID NO:1 or the corresponding cysteine residue in another Axmi205 toxin;
e) amino acid substitutions of (i) M422S and M423L, (ii) M422T and M423F, (iii) M422K and M423F, (iv) M422D and M423E, (v) M422K and M423R, or (vi) M422S and M423E, or the corresponding methionine residues in another Axmi205 toxin;
f) an insertion of a leucine, phenylalanine, aspartic acid or arginine between amino acids A475 and G476 in the polypeptide of SEQ ID NO:1 or the corresponding alanine and glycine residues in another Axmi205 toxin;
g) an insertion of a leucine, phenylalanine, aspartic acid or arginine between amino acids G496 and D497 in the polypeptide of SEQ ID NO:1 or the corresponding glycine and aspartic acid residues in another Axmi205 toxin;
h) an insertion of a leucine, phenylalanine, aspartic acid or arginine between amino acids Q471 and P472 in the polypeptide of SEQ ID NO:1 or the corresponding glycine and aspartic acid residues in another Axmi205 toxin;
i) an insertion of a leucine, phenylalanine, aspartic acid or arginine between amino acids A479 and S480 in the polypeptide of SEQ ID NO:1 or the corresponding glycine and aspartic acid residues in another Axmi205 toxin;
j) an insertion of a leucine, phenylalanine, aspartic acid or arginine between amino acids Y489 and N490 in the polypeptide of SEQ ID NO:1 or the corresponding glycine and aspartic acid residues in another Axmi205 toxin; or
k) any combination of (a) to (j).

In particular embodiments, a insecticidal protein of the invention comprises, consists essentially of, or consists of (a) the amino acid sequence of any one of SEQ ID NO: 11, SEQ ID NO: 13, SEQ ID NO: 17, SEQ ID NO: 43, SEQ ID NO: 47, SEQ ID NO: 57, SEQ ID NO: 69, or SEQ ID NO: 73, or a toxin fragment thereof; or (b) an amino acid sequence that is substantially identical to the amino acid sequence of (a).

Those skilled in the art will appreciate that the insecticidal proteins of the invention can further comprise other functional domains and/or peptide tags, for example a peptide tag on the N-terminus and/or C-terminus. To illustrate, it may be useful to express the insecticidal protein with a peptide tag that can be recognized by a commercially available antibody (e.g., a FLAG motif) or with a peptide tag that facilitates purification (e.g., by addition of a poly-His tag) and/or detection. Alternatively, an epitope can be introduced into the protein to facilitate the generation of antibodies that specifically recognize the modified protein to distinguish the modified protein from the unmodified chimera and/or a parent protein(s). For example, one or more amino acids can be substituted into an antigenic loop to create a new epitope. In other embodiments, the protein can be modified to enhance its stability, for example, by fusing a maltose binding protein (MBP) or glutathione-S-transferase to the polypeptide. As another alternative, the insecticidal protein can be a fusion protein comprising a reporter molecule. Further, subcellular targeting peptides can be incorporated into the protein, such as a KDEL sequence tag that targets to the endoplasmic reticulum.

As discussed above, the invention encompasses polypeptides having amino acid sequences that are substantially identical to those specifically disclosed herein, and toxin fragments thereof. It will be understood that the insecticidal proteins specifically disclosed herein will typically tolerate modifications in the amino acid sequence and substantially retain biological activity (e.g., insecticidal activity). Such modifications include insertions, deletions (including truncations at either terminus), and substitutions of one or more amino acids, including up to about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 100, about 105, about 110, about 115, about 120, about 125, about 130, about 135, about 140, about 145, about 150, about 155, or more amino acid substitutions, deletions and/or insertions.

In embodiments, the polypeptide of the invention comprises a modification as disclosed in WO2013/016617 (Athenix) and/or US 2014/0274885 A1 (Pioneer Hi-Bred).

To identify substantially identical polypeptides to the insecticidal proteins specifically disclosed herein, amino acid substitutions may be based on any characteristic known in the art, including the relative similarity or differences of the amino acid side-chain substituents, for example, their hydrophobicity, hydrophilicity, charge, size, and the like.

For example, in identifying amino acid sequences encoding insecticidal polypeptides other than those specifically disclosed herein, the hydropathic index of amino acids may be considered. The importance of the hydropathic amino acid index in conferring interactive biologic function on a protein is generally understood in the art (see, Kyte and Doolittle, (1982) J. Mol. Biol. 157:105; incorporated herein by reference in its entirety). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle, Id.), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

Accordingly, the hydropathic index of the amino acid (or amino acid sequence) may be considered when modifying the polypeptides specifically disclosed herein.

It is also understood in the art that the substitution of amino acids can be made on the basis of hydrophilicity. U.S. Pat. No. 4,554,101 states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (.+−0.3.0); aspartate (+3.0.+−0.1); glutamate (+3.0.+−0.1); serine (+0.3); asparagine (+0.2); glutamine (+0.2); glycine (0); threonine (−0.4); proline (−0.5+I); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

Thus, the hydrophilicity of the amino acid (or amino acid sequence) may be considered when identifying additional insecticidal polypeptides beyond those specifically disclosed herein.

The insecticidal proteins of the invention, including modifications and toxin fragments of the polypeptides specifically disclosed herein, can be made by any suitable method known in the art, generally by modifying the coding nucleic acid sequences. Methods of manipulating and modifying nucleic acids to achieve a desired modification are well-known in the art. In addition, gene editing techniques can also be used produce an insecticidal protein of the invention or to make further modifications thereto.

As another approach, the polypeptide to be modified can be expressed in a host cell that exhibits a high rate of base mis-incorporation during DNA replication, such as XL-1 Red (Stratagene, La Jolla, Calif.). After propagation in such strains, one can isolate the DNA (for example, by preparing plasmid DNA or by PCR amplification and cloning of the resulting PCR fragment into a vector), culture the protein mutations in a non-mutagenic strain, and identify mutated genes with insecticidal activity, for example, by performing an assay to test for insecticidal activity. In exemplary methods, the protein is mixed and used in feeding assays. See, for example, Marrone et al. (1985) J. of Economic Entomology 78:290-293. Such assays can include contacting plants with one or more pests and determining the plant's ability to survive or cause the death of the pests. Examples of mutations that result in increased toxicity are found in Schnepf et al. (1998) Microbiol. Mol. Biol. Rev. 62:775-806.

In embodiments, the insecticidal protein (including substantially similar polypeptides and toxin fragments) of the invention is isolated. In embodiments, the insecticidal protein (including substantially similar polypeptides and toxin fragments) of the invention is a recombinant protein.

Variants of the insecticidal proteins of the invention can be generated by any method known in the art including genome editing technologies. For example, after a heterologous polynucleotide sequence encoding in insecticidal protein encompassed by the invention is introduced into a plant the introduced polynucleotide is stably integrated into the genome of the now transgenic plant. Thus, according to the invention, the encoded insecticidal protein can be further modified in situ by targeted DNA editing using various genome editing techniques such as zinc finger nucleases (ZNFs), transcription activator-like effector nucleases (TALENS), meganucleases and Clustered Regularly Interspaced Short Palindromic Repeats (CRISPR) (U.S. Pat. No. 8,697, 359; Ran et al.). The CRISPR system can be used to introduce specific nucleotide modifications at the target sequence. Originally discovered in bacteria, where several different CRISPR cascades function as innate immune systems and natural defense mechanisms, the engineered CRISPR-Cas9 system can be programmed to target specific stretches of genetic code and to make cuts at precise locations. Over the past few years, those capabilities have been harnessed and used as genome editing tools, enabling researchers to permanently modify genes in plant cells.

The insecticidal proteins of the invention have activity against one or more insect pests. In embodiments, the insecticidal proteins of the invention have activity against a coleopteran, lepidopteran, dipteran, hemipteran, orthopteran and/or thysanopteran insect pest. In embodiments, the insecticidal protein is active against a coleopteran pest.

Insects in the order Coleoptera include but are not limited to any coleopteran insect now known or later identified including those in suborders Archostemata, Myxophaga, Adephaga and Polyphaga, and any combination thereof.

In one aspect of this embodiment, the insecticidal proteins of the invention are active against *Diabrotica* spp. *Diabrotica* is a genus of beetles of the order Coleoptera commonly referred to as "corn rootworms" or "cucumber beetles." Exemplary *Diabrotica* species include without limitation *Diabrotica* barber/(northern corn rootworm), *D. virgifera virgifera* (western corn rootworm), *D. undecimpunctata howardii* (southern corn rootworm), *D. balteata* (banded cucumber beetle), *D. undecimpunctata undecimpunctata* (western spotted cucumber beetle), *D. significata* (3-spotted leaf beetle), *D. speciosa* (chrysanthemum beetle), *D. virgifera zeae* (Mexican corn rootworm), *D. beniensis, D. cristata, D. curviplustalata, D. dissimilis, D. elegantula, D. emorsitans, D. graminea, D. hispanloe, D. lemniscata, D. linsleyi, D. milleri, D. nummularis, D. occlusal, D. porrecea, D. scutellata, D. tibialis, D. trifasciata* and *D. viridula*; and any combination thereof.

Other nonlimiting examples of Coleopteran insect pests according to the present invention include *Leptinotarsa* spp. such as *L. decemlineata* (Colorado potato beetle); *Chrysomela* spp. such as *C. scripta* (cottonwood leaf beetle); *Hypothenemus* spp. such as *H. hampei* (coffee berry borer); *Sitophilus* spp. such as *S. zeamais* (maize weevil); *Epitrix* spp. such as *E. hiripennis* (tobacco flea beetle) and *E. cucumeris* (potato flea beetle); *Phyllotreta* spp. such as *P.*

*cruciferae* (crucifer flea beetle) and *P. pusilla* (western black flea beetle); *Anthonomus* spp. such as *A. grandis* (boll weevil) and *A. eugenii* (pepper weevil); *Hemicrepidus* spp. such as *H. memnonius* (wireworms); *Melanotus* spp. such as *M. communis* (wireworm); *Ceutorhychus* spp. such as *C. assimilis* (cabbage seedpod weevil); *Phyllotreta* spp. such as *P. cruciferae* (crucifer flea beetle); *Aeolus* spp. such as *A. mellilus* (wireworm); *Aeolus* spp. such as *A. mancus* (wheat wireworm); *Horistonotus* spp. such as *H. uhlerii* (sand wireworm); *Sphenophorus* spp. such as *S. maidis* (maize billbug), *S. zeae* (timothy billbug), *S. parvulus* (bluegrass billbug), and *S. callosus* (southern corn billbug); *Phyllophaga* spp. (White grubs); *Chaetocnema* spp. such as *C. pulicaria* (corn flea beetle); *Popillia* spp. such as *P. japonica* (Japanese beetle); *Epilachna* spp. such as *E. varivestis* (Mexican bean beetle); *Cerotoma* spp. such as *C. trifurcate* (Bean leaf beetle); *Epicauta* spp. such as *E. pestifera* and *E. lemniscata* (Blister beetles); and any combination of the foregoing.

In embodiments, the insecticidal protein has activity against one or more of the following non-limiting examples of a lepidopteran pest: *Ostrinia* spp. such as *O. nubilalis* (European corn borer) and/or *O. furnacalis* (Asian corn borer); *Plutella* spp. such as *P. xylostella* (diamondback moth); *Spodoptera* spp. such as *S. frugiperda* (fall armyworm), *S. littoralis* (Egyptian cotton leafworm), *S. ornithogalli* (yellowstriped armyworm), *S. praefica* (western yellowstriped armyworm), *S. eridania* (southern armyworm) and/or *S. exigua* (beet armyworm); *Agrotis* spp. such as *A. ipsilon* (black cutworm), *A. segetum* (common cutworm), *A. gladiaria* (claybacked cutworm), and/or *A. orthogonia* (pale western cutworm); *Striacosta* spp. such as *S. albicosta* (western bean cutworm); *Helicoverpa* spp. such as *H. zea* (corn earworm), *H. punctigera* (native budworm), and/or *H. armigera* (cotton bollworm); *Heliothis* spp. such as *H. virescens* (tobacco budworm); *Diatraea* spp. such as *D. grandiosella* (southwestern corn borer) and/or *D. saccharalis* (sugarcane borer); *Trichoplusia* spp. such as *T. ni* (cabbage looper); *Sesamia* spp. such as *S. nonagroides* (Mediterranean corn borer) and/or *S. calamistis* (pink stem borer); *Pectinophora* spp. such as *P. gossypiella* (pink bollworm); *Cochylis* spp. such as *C. hospes* (banded sunflower moth); *Manduca* spp. such as *M. sexta* (tobacco hornworm) and/or *M. quinquemaculata* (tomato hornworm); *Elasmopalpus* spp. such as *E. lignosellus* (lesser cornstalk borer); *Pseudoplusia* spp. such as *P. includens* (soybean looper); *Anticarsia* spp. such as *A. gemmatalis* (velvetbean caterpillar); *Plathypena* spp. such as *P. scabra* (green cloverworm); *Pieris* spp. such as *P. brassicae* (cabbage butterfly), *Papaipema* spp. such as *P. nebris* (stalk borer); *Pseudaletia* spp. such as *P. umpuncta* (common armyworm); *Peridroma* spp. such as *P. saucia* (variegated cutworm); *Keiferia* spp. such as *K. lycopersicella* (tomato pinworm); *Artogeia* spp. such as *A. rapae* (imported cabbageworm); *Phthorimaea* spp. such as *P. operculella* (potato tuberworm); *Chrysodeixis* spp. such as *C. includes* (soybean looper); *Feltia* spp. such as *F. ducens* (dingy cutworm); *Chilo* spp. such as *C. suppressalis* (striped stem borer), *Cnaphalocrocis* spp. such as *C. medinalis* (rice leaffolder), or any combination of the foregoing.

Insects in the order Hemiptera include *Lygus* spp. stink bugs (including *Nezara* spp., *Halyomorpha* spp, *Brochymena* spp., and *Euschistus* spp.), aphids (including *Aphis* spp. and *Nasonovia* spp.), and other piercing and sucking insects.

Insects in the order Diptera include but are not limited to any dipteran insect now known or later identified including but not limited to *Liriomyza* spp. such as *L. trifolii* (leafminer) and *L. sativae* (vegetable leafminer); *Scrobipalpula* spp. such as *S. absoluta* (tomato leafminer); *Delia* spp. such as *D. platura* (seedcorn maggot), *D. brassicae* (cabbage maggot) and *D. radicum* (cabbage root fly); *Psilia* spp. such as *P. rosae* (carrot rust fly); *Tetanops* spp. such as *T. myopaeformis* (sugarbeet root maggot); and any combination of the foregoing.

Insects in the order Orthoptera include but are not limited to any orthopteran insect now known or later identified including but not limited to *Melanoplus* spp. such as *M. differentialis* (Differential grasshopper), *M. femurrubrum* (Redlegged grasshopper), *M. bivittatus* (Twostriped grasshopper); and any combination thereof.

Insects in the order Thysanoptera include but are not limited to any thysanopteran insect now known or later identified including but not limited to *Frankliniella* spp. such as *F. occidentalis* (western flower thrips) and *F. fusca* (tobacco thrips); and *Thrips* spp. such as *T. tabaci* (onion thrips), *T. palmi* (melon thrips); and any combination of the foregoing.

In embodiments, the insecticidal proteins of the invention are active against nematodes. The term "nematode" as used herein encompasses any organism that is now known or later identified that is classified in the animal kingdom, phylum Nematoda, including without limitation nematodes within class Adenophorea (including for example, orders Enoplida, Isolaimida, Mononchida, Dorylaimida, Trichocephalida, Mermithida, Muspiceida, Araeolaimida, Chromadorida, Desmoscolecida, Desmodorida and Monhysterida) and/or class Secernentea (including, for example, orders Rhabdita, Strongylida, Ascaridida, Spirurida, Camallanida, Diplogasterida, Tylenchida and Aphelenchida).

Nematodes include but are not limited to parasitic nematodes such as root-knot nematodes, cyst nematodes and/or lesion nematodes. Exemplary genera of nematodes according to the present invention include but are not limited to, *Meloidogyne* (root-knot nematodes), *Heterodera* (cyst nematodes), *Globodera* (cyst nematodes), *Radopholus* (burrowing nematodes), *Rotylenchulus* (reniform nematodes), *Pratylenchus* (lesion nematodes), *Aphelenchoides* (foliar nematodes), *Helicotylenchus* (spiral nematodes), *Hoplolaimus* (lance nematodes), *Paratrichodorus* (stubby-root nematodes), *Longidorus, Nacobbus* (false root-knot nematodes), *Subanguina, Belonlaimus* (sting nematodes), *Criconemella, Criconemoides* (ring nematodes), *Ditylenchus, Dolichodorus, Hemicriconemoides, Hemicycliophora, Hirschmaniella, Hypsoperine, Macroposthonia, Melinius, Punctodera, Quinisulcius, Scutellonema, Xiphinema* (dagger nematodes), *Tylenchorhynchus* (stunt nematodes), *Tylenchulus, Bursaphelenchus* (round worms), and any combination thereof.

Exemplary plant parasitic nematodes according to the present invention include, but are not limited to, *Belonolaimus gracilis, Belonolaimus longicaudatus, Bursaphelenchus xylophilus* (pine wood nematode), *Criconemoides ornata, Ditylenchus destructor* (potato rot nematode), *Ditylenchus dipsaci* (stem and bulb nematode), *Globodera pallida* (potato cyst nematode), *Globodera rostochiensis* (golden nematode), *Heterodera glycines* (soybean cyst nematode), *Heterodera schachtii* (sugar beet cyst nematode); *Heterodera zeae* (corn cyst nematode), *Heterodera avenae* (cereal cyst nematode), *Heterodera carotae, Heterodera trifolii, Hoplolaimus columbus, Hoplolaimus galeatus, Hoplolaimus magnistylus, Longidorus breviannulatus, Meloidogyne arenaria, Meloidogyne chitwoodi, Meloidogyne hapla, Meloidogyne incognita, Meloidogyne javanica, Mesocriconema xenoplax, Nacobbus aberrans,*

*Naccobus dorsalis, Paratrichodorus christiei, Paratrichodorus minor, Pratylenchus brachyurus, Pratylenchus crenatus, Pratylenchus hexincisus, Pratylenchus neglectus, Pratylenchus penetrans, Pratylenchus projectus, Pratylenchus scribneri, Pratylenchus tenuicaudatus, Pratylenchus thornei, Pratylenchus zeae, Punctodera chaccoensis, Quinisulcius acutus, Radopholus similis, Rotylenchulus reniformis, Tylenchorhynchus dubius, Tylenchulus semipenetrans* (citrus nematode), *Siphinema americanum, X. mediterraneum*, and any combination of the foregoing.

The invention also encompasses antibodies that specifically bind to the insecticidal proteins of the invention. The antibody can optionally be a monoclonal antibody or a polyclonal antisera. In embodiments, the antibody is selective for the modified Axmi205 protein and does not bind to the unmodified Axmi205 toxin, e.g., the native Axmi205 protein of SEQ ID NO: 1, and can be used to distinguish the modified protein from the unmodified Axmi205 protein. Such antibodies may be produced using standard immunological techniques for production of polyclonal antisera and, if desired, immortalizing the antibody-producing cells of the immunized host for sources of monoclonal antibody production. Techniques for producing antibodies to any substance of interest are well known, e.g., as described in Harlow and Lane (1988. Antibodies a laboratory manual. pp. 726. Cold Spring Harbor Laboratory) and as in Goding (Monoclonal Antibodies: Principles & practice. 1986. Academic Press, Inc., Orlando, Fla.). The present invention also encompasses an insecticidal protein that cross-reacts with an antibody, particularly a monoclonal antibody, raised against one or more of the insecticidal proteins of the present invention.

The antibodies according to the invention are useful, e.g., in immunoassays for determining the amount or presence of an insecticidal protein of the invention or an antigenically related polypeptide, e.g., in a biological sample. Such assays are also useful in quality-controlled production of compositions containing one or more of the insecticidal proteins of the invention or an antigenically related polypeptide. In addition, the antibodies can be used to assess the efficacy of recombinant production of one or more of the insecticidal proteins of the invention or an antigenically related polypeptide, as well as for screening expression libraries for the presence of a nucleotide sequence encoding one or more of the proteins of the invention or an antigenically related polypeptide. Antibodies further find use as affinity ligands for purifying or isolating any one or more of the proteins of the invention or an antigenically related polypeptide. In embodiments, the antibody does not recognize (i.e., specifically bind to) native Axmi205 and/or the parental Axmi205 toxin that does not contain the modifications of the invention, and can be used to distinguish and/or separate an insecticidal protein of the invention from native Axmi205.

Nucleic Acids, Expression Cassettes, and Vectors.

As a further aspect, the invention provides nucleic acids encoding the polypeptides of the invention, including modified polypeptides and toxin fragments as described herein.

According to some embodiments, the invention provides a nucleic acid molecule comprising a nucleotide sequence that comprises, consists essentially of, or consists of: (a) a nucleotide sequence encoding the amino acid sequence of SEQ ID NO: 11, SEQ ID NO: 13, SEQ ID NO: 17, SEQ ID NO: 43, SEQ ID NO: 47, SEQ ID NO: 57, SEQ ID NO: 69, SEQ ID NO: 73, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127 ora toxin fragment thereof; (b) a nucleotide sequence encoding an amino acid sequence that is substantially identical to the amino acid sequence of (a); (c) a nucleotide sequence that anneals under stringent hybridization conditions to the nucleotide sequence of (a) or (b); or (d) a nucleotide sequence that differs from the nucleotide sequences of (a), (b) or (c) due to the degeneracy of the genetic code.

In embodiments, the nucleic acid molecule comprises a nucleotide sequence that comprises, consists essentially of, or consists of: (a) a nucleotide sequence of SEQ ID NO: 12, SEQ ID NO: 14, SEQ ID NO: 18, SEQ ID NO: 44, SEQ ID NO: 48, SEQ ID NO: 58, SEQ ID NO: 70, SEQ ID NO: 74, SEQ ID NO: 75, SEQ ID NO: 76, SEQ ID NO: 77, SEQ ID NO: 78, SEQ ID NO: 80, SEQ ID NO: 82, SEQ ID NO: 84, SEQ ID NO: 86, SEQ ID NO: 89, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, or SEQ ID NO: 126 or a toxin-encoding fragment thereof; (b) a nucleotide sequence that is substantially identical to the nucleotide sequence of (a); (c) a nucleotide sequence that anneals under stringent hybridization conditions to the nucleotide sequence of (a) or (b); or (d) a nucleotide sequence that differs from the nucleotide sequences of (a), (b) or (c) due to the degeneracy of the genetic code. Optionally, the nucleotide sequence comprises, consists essentially of, or consists of the nucleotide sequence of SEQ ID NO: 12, SEQ ID NO: 14, SEQ ID NO: 18, SEQ ID NO: 44, SEQ ID NO: 48, SEQ ID NO: 58, SEQ ID NO: 70, SEQ ID NO: 74, SEQ ID NO: 75, SEQ ID NO: 76, SEQ ID NO: 77, SEQ ID NO: 78, SEQ ID NO: 80, SEQ ID NO: 82, SEQ ID NO: 84, SEQ ID NO: 86, SEQ ID NO: 89, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, or SEQ ID NO: 126.

In embodiments, the nucleotide sequence is a partially or completely synthetic sequence, e.g., that has codons optimized for expression in a host organism, e.g., in a bacterium host or a plant host (for example, a transgenic monocot plant host or a transgenic dicot plant host). Non-limiting examples nucleotide sequences that are codon-optimized for expression in a maize plant include SEQ ID NO: 75, SEQ ID NO: 76, and SEQ ID NO: 77.

In representative embodiments, for expression in transgenic plants, the nucleotide sequences of the invention are modified and/or optimized. For example, although in many cases genes from microbial organisms can be expressed in plants at high levels without modification, low expression in transgenic plants may result from microbial nucleotide sequences having codons that are not preferred in plants. It is known in the art that living organisms have specific preferences for codon usage, and the codons of the nucleotide sequences described in this invention can be changed to conform with plant preferences, while maintaining the amino acids encoded thereby. Furthermore, it is known in the art that high expression in plants, for example corn plants, can be achieved from coding sequences that have at least about 35% GC content, or at least about 45%, or at least about 50%, or at least about 60%. Microbial nucleotide sequences that have low GC contents may express poorly in plants. Although certain nucleotide sequences can be adequately expressed in both monocotyledonous and dicotyledonous plant species, sequences can be modified to account for the specific codon preferences and GC content preferences of monocotyledons or dicotyledons as these preferences have been shown to differ (Murray et al. Nucl. Acids Res. 17:477-498 (1989)). In addition, in embodiments, the nucleotide sequence is modified to remove illegitimate splice sites that may cause message truncation. Such modifications to the nucleotide sequences can be made using well known techniques of site directed mutagenesis, PCR, and synthetic gene construction using the methods described, for example, in U.S. Pat. Nos. 5,625,136; 5,500,365 and 6,013,523.

In some embodiments, the invention provides synthetic coding sequences or polynucleotide made according to the procedure disclosed in U.S. Pat. No. 5,625,136. In this procedure, maize preferred codons, i.e., the single codon that most frequently encodes that amino acid in maize, are used. The maize preferred codon for a particular amino acid can be derived, for example, from known gene sequences from maize. For example, maize codon usage for 28 genes from maize plants is found in Murray et al., Nucleic Acids Research 17:477-498 (1989). It is recognized that codons optimized for expression in one plant species will also function in other plant species but possibly not at the same level as the plant species for which the codons were optimized. In this manner, the nucleotide sequences can be optimized for expression in any plant. It is recognized that all or any part of a nucleotide sequence may be optimized or synthetic. That is, a polynucleotide may comprise a nucleotide sequence that is part native sequence and part codon optimized sequence.

In representative embodiments, a polynucleotide of the invention is an isolated polynucleotide. In embodiments, a polynucleotide of the invention is a recombinant polynucleotide.

In embodiments, the invention further provides a nucleic acid molecule comprising a polynucleotide of the operably associated with a promoter (e.g., a heterologous promoter). Promoters can include, for example, constitutive, inducible, temporally regulated, developmentally regulated, chemically regulated, tissue-preferred and/or tissue-specific promoters. In particular aspects, a promoter useful with the invention is a promoter capable of initiating transcription of a nucleotide sequence in a plant cell, e.g., in a cell of a monocot (e.g., maize or rice) or dicot (e.g., soybean, cotton) plant.

In embodiments, a heterologous promoter is a plant-expressible promoter (e.g., monocot expressible or dicot expressible). For example, without limitation, the plant-expressible promoter can be selected from the following promoters: ubiquitin, cestrum yellow virus, corn TrpA, OsMADS 6, maize H3 histone, bacteriophage T3 gene 9 5' UTR, corn sucrose synthetase 1, corn alcohol dehydrogenase 1, corn light harvesting complex, corn heat shock protein, maize mtl, pea small subunit RuBP carboxylase, rice actin, rice cyclophilin, Ti plasmid mannopine synthase, Ti plasmid nopaline synthase, petunia chalcone isomerase, bean glycine rich protein 1, potato patatin, lectin, CaMV 35S and S-E9 small subunit RuBP carboxylase promoter.

Although many promoters from dicotyledons have been shown to be operational in monocotyledons and vice versa, in embodiments, dicotyledonous promoters are selected for expression in dicotyledons, and monocotyledonous promoters for expression in monocotyledons. However, there is no restriction to the provenance of selected promoters; it is sufficient that they are operational in driving the expression of the nucleotide sequences in the desired cell.

The choice of promoter can vary depending on the temporal and spatial requirements for expression, and also depending on the host cell to be transformed. Thus, for example, expression of the nucleotide sequences of the invention can be in any plant and/or plant part, (e.g., in leaves, in stalks or stems, in ears, in inflorescences (e.g., spikes, panicles, cobs, etc.), in roots, seeds and/or seedlings, and the like). For example, where expression in a specific tissue or organ is desired, a tissue-specific or tissue-preferred promoter can be used (e.g., a root specific/preferred promoter). In contrast, where expression in response to a stimulus is desired a promoter inducible by stimuli or chemicals can be used. Where continuous expression at a relatively constant level is desired throughout the cells of a plant a constitutive promoter can be chosen.

Promoters useful with the invention include, but are not limited to, those that drive expression of a nucleotide sequence constitutively, those that drive expression when induced, and those that drive expression in a tissue- or developmentally-specific manner. These various types of promoters are known in the art.

Suitable constitutive promoters include, for example, CaMV 35S promoter (Odell et al., Nature 313:810-812, 1985); *Arabidopsis* At6669 promoter (see PCT Publication No. W004081173A2); maize Ubi 1 (Christensen et al., Plant Mol. Biol. 18:675-689, 1992); rice actin (McElroy et al., Plant Cell 2:163-171, 1990); pEMU (Last et al., Theor. Appl. Genet. 81:581-588, 1991); CaMV 19S (Nilsson et al., Physiol. Plant 100:456-462, 1997); GOS2 (de Pater et al., Plant J November; 2(6):837-44, 1992); ubiquitin (Christensen et al., Plant Mol. Biol. 18: 675-689, 1992); Rice cyclophilin (Bucholz et al., Plant Mol Biol. 25(5):837-43, 1994); Maize H3 histone (Lepetit et al., Mol. Gen. Genet. 231: 276-285, 1992); Actin 2 (An et al., Plant J. 10(1); 107-121, 1996), constitutive root tip CT2 promoter (SEQ ID NO:1535; see also PCT application No. IL/2005/000627) and Synthetic Super MAS (Ni et al., The Plant Journal 7: 661-76, 1995). Other constitutive promoters include those in U.S. Pat. Nos. 5,659,026, 5,608,149; 5,608,144; 5,604,121; 5,569,597: 5,466,785; 5,399,680; 5,268,463; and 5,608,142.

Tissue-specific or tissue-preferential promoters useful for the expression of the polypeptides of the invention in plants, optionally maize, include those that direct expression in root, pith, leaf or pollen. Suitable tissue-specific promoters include, but not limited to, leaf-specific promoters (such as described, for example, by Yamamoto et al., Plant J. 12:255-265, 1997; Kwon et al., Plant Physiol. 105:357-67, 1994; Yamamoto et al., Plant Cell Physiol. 35:773-778, 1994; Gotor et al., Plant J. 3:509-18, 1993; Orozco et al., Plant Mol. Biol. 23:1129-1138, 1993; and Matsuoka et al., Proc. Natl. Acad. Sci. USA 90:9586-9590, 1993), seed-preferred promoters (e.g., from seed specific genes; Simon, et al., Plant Mol. Biol. 5. 191, 1985; Scofield, et al., J. Biol. Chem. 262: 12202, 1987; Baszczynski, et al., Plant Mol. Biol. 14: 633, 1990), Brazil Nut albumin (Pearson et al., Plant Mol. Biol. 18: 235-245, 1992), legumin (Ellis, et al. Plant Mol. Biol. 10: 203-214, 1988), Glutelin (Takaiwa, et al., Mol. Gen. Genet. 208: 15-22, 1986; Takaiwa, et al., FEBS Letts. 221: 43-47, 1987), Zein (Matzke et al., Plant Mol Biol, 143).323-32 1990), napA (Stalberg, et al., Planta 199: 515-519, 1996), Wheat SPA (Albanietal, Plant Cell, 9: 171-184, 1997), sunflower oleosin (Cummins, et al., Plant Mol. Biol. 19: 873-876, 1992)], endosperm specific promoters (e.g., wheat LMW and HMW, glutenin-1 (Mol Gen Genet 216: 81-90, 1989; NAR 17:461-2), wheat a, b and g gliadins (EMB03:1409-15, 1984), Barley ltrl promoter, barley B1, C, D hordein (Theor Appl Gen 98:1253-62, 1999; Plant J 4:343-55, 1993; Mol Gen Genet 250:750-60, 1996), Barley DOF (Mena et al., The Plant Journal, 116(1): 53-62, 1998), Biz2 (EP99106056.7), Synthetic promoter (Vicente-Carbajosa et al., Plant J. 13: 629-640, 1998), rice prolamin NRP33, rice-globulin Glb-1 (Wu et al., Plant Cell Physiology 39(8) 885-889, 1998), rice alpha-globulin REB/OHP-1 (Nakase et al. Plant Mol. Biol. 33: 513-S22, 1997), rice ADP-glucose PP (Trans Res 6:157-68, 1997), maize ESR gene family (Plant J 12:235-46, 1997), sorgum gamma-kafirin (Plant Mol. Biol 32:1029-35, 1996)], embryo specific promoters (e.g., rice OSH1; Sato et al., Proc. Nati. Acad. Sci. USA, 93: 8117-8122), KNOX (Postma-Haarsma of al, Plant Mol. Biol. 39:257-71, 1999), rice oleosin (Wu et at, J. Biochem., 123:386, 1998)] flower-specific promoters, for example, AtPRP4, chalene synthase (chsA) (Van der Meer, et al., Plant Mol. Biol. 15, 95-109, 1990), LAT52 (Twell et al., Mol. Gen Genet. 217:240-245; 1989), *apetala*-3, and promoters specific for plant reproductive tissues (e.g., OsMADS promoters; U.S. Patent Publication 2007/0006344).

Examples of promoters suitable for preferential expression in green tissue include many that regulate genes involved in photosynthesis and many of these have been cloned from both monocotyledons and dicotyledons. One such promoter is the maize PEPC promoter from the phosphoenol carboxylase gene (Hudspeth & Grula, Plant Molec. Biol. 12:579-589 (1989)). Another promoter for root specific expression is that described by de Framond (FEBS 290:103-106 (1991) or U.S. Pat. No. 5,466,785). Another promoter useful in the invention is the stem specific promoter described in U.S. Pat. No. 5,625,136, which naturally drives expression of a maize trpA gene.

In addition, promoters functional in plastids can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

In some embodiments of the invention, inducible promoters can be used. Thus, for example, chemical-regulated promoters can be used to modulate the expression of a gene in a plant through the application of an exogenous chemical regulator. Regulation of the expression of nucleotide sequences of the invention via promoters that are chemically regulated enables the polypeptides of the invention to be synthesized only when the crop plants are treated with the inducing chemicals. Depending upon the objective, the promoter may be a chemical-inducible promoter, where application of a chemical induces gene expression, or a chemical-repressible promoter, where application of the chemical represses gene expression. Examples of such technology for chemical induction of gene expression is detailed in published application EP 0 332 104 and U.S. Pat. No. 5,614,395.

Chemical inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1 a promoter, which is activated by salicylic acid (e.g., the PR1a system), steroid steroid-responsive promoters (see, e.g., the glucocorticoid-inducible promoter in Schena et al. (1991) Proc. Natl. Acad. Sci. USA 88, 10421-10425 and McNellis et al. (1998) Plant J. 14, 247-257) and tetracycline-inducible and tetracycline-repressible promoters (see, e.g., Gatz et al. (1991) Mol. Gen. Genet. 227, 229-237, and U.S. Pat. Nos. 5,814,618 and 5,789,156, Lac repressor system promoters, copper-inducible system promoters, salicylate-inducible system promoters (e.g., the PR1a system), glucocorticoid-inducible promoters (Aoyama et al. (1997) Plant J. 11:605-612), and ecdysone-inducible system promoters.

Other non-limiting examples of inducible promoters include ABA- and turgor-inducible promoters, the auxin-binding protein gene promoter (Schwob et al. (1993) Plant J. 4:423-432), the UDP glucose flavonoid glycosyl-transferase promoter (Ralston et al. (1988) Genetics 119:185-197), the MPI proteinase inhibitor promoter (Cordero et al. (1994) Plant J. 6:141-150), and the glyceraldehyde-3-phosphate dehydrogenase promoter (Kohler et al. (1995) Plant Mol. Biol. 29:1293-1298; Martinez et al. (1989) J. Mol. Biol. 208:551-565; and Quigley et al. (1989) J. Mol. Evol. 29:412-421). Also included are the benzene sulphonamide-inducible (U.S. Pat. No. 5,364,780) and alcohol-inducible (Int'l Patent Application Publication Nos. WO 97/06269 and WO 97/06268) systems and glutathione S-transferase promoters. Likewise, one can use any of the inducible promoters described in Gatz (1996) Current Opinion Biotechnol. 7:168-172 and Gatz (1997) Annu. Rev. Plant Physiol. Plant Mol. Biol. 48:89-108. Other chemically inducible promoters useful for directing the expression of the nucleotide sequences of this invention in plants are disclosed in U.S. Pat. No. 5,614,395. Chemical induction of gene expression is also detailed in EP 0 332 104 (to Ciba-Geigy) and U.S. Pat. No. 5,614,395.

Another category of promoters useful in the invention are wound inducible promoters. Numerous promoters have been described that are expressed at wound sites and also at the sites of phytopathogen infection. Ideally, such a promoter should only be active locally at the sites of insect invasion, and in this way the insecticidal proteins only accumulate in cells that need to synthesize the insecticidal proteins to kill the invading insect pest. Examples of promoters of this kind include those described by Stanford et al. Mol. Gen. Genet. 215:200-208 (1989), Xu et al. Plant Molec. Biol. 22:573-588 (1993), Logemann et al. Plant Cell 1:151-158 (1989), Rohrmeier & Lehle, Plant Molec. Biol. 22:783-792 (1993), Firek et al. Plant Molec. Biol. 22:129-142 (1993), and Warner et al. Plant J. 3:191-201 (1993).

In embodiments a nucleic acid of the invention can comprise, consist essentially of, or consist of an expression cassette, or can be comprised within an expression cassette.

An expression cassette comprising a polynucleotide of interest may be chimeric, meaning that at least one of its components is heterologous with respect to at least one other of its other components. An expression cassette may also be one that is naturally occurring but has been obtained in a recombinant form useful for heterologous expression. Typically, the expression cassette is heterologous with respect to the host, i.e., the particular nucleic acid sequence of the expression cassette does not occur naturally in the host cell and must have been introduced into the host cell or an ancestor of the host cell by a transformation event.

In addition to the promoters operatively associated with the nucleotide sequences of the invention, an expression cassette of this invention can also include other regulatory elements. Regulatory elements include, but are not limited to, enhancers, introns, translation leader sequences, termination signals, and polyadenylation signal sequences.

Examples of suitable transcription terminator signals are available and known in the art (e.g., tml from CaMV, E9 from rbcS). Any available terminator known to function in plants can be used in the context of this invention.

Numerous other sequences can be incorporated into expression cassettes described in this invention. These include sequences that have been shown to enhance expression such as intron sequences (e.g., from Adhl and bronzel) and viral leader sequences (e.g., from TMV, MCMV and AMV).

For more efficient initiation of translation, sequences adjacent to the initiating methionine may be modified. For example, they can be modified by the inclusion of sequences known to be effective in plants. Joshi has suggested an appropriate consensus for plants (NAR 15:6643-6653 (1987)) and Clonetech suggests a further consensus translation initiator (1993/1994 catalog, page 210). These consensuses are suitable for use with the nucleotide sequences of this invention. The sequences are incorporated into constructions comprising the nucleotide sequences, up to and including the ATG (while leaving the second amino acid unmodified), or alternatively up to and including the GTC subsequent to the ATG (with the possibility of modifying the second amino acid of the transgene).

In embodiments, it may be desired to target expression of the polypeptides of the present invention to a specific cellular location in the plant cell. In some cases, localization in the cytosol may be desirable, whereas in other cases, localization in some subcellular organelle may be preferred. Any mechanism for targeting gene products, e.g., in plants, can be used to practice this invention, and such mechanisms are known to exist in plants and the sequences controlling the functioning of these mechanisms have been characterized in some detail. Sequences have been characterized which cause the targeting of gene products to other cell compartments. For example, amino terminal sequences can be responsible for targeting a protein of interest to a cell compartment, such as, a vacuole, mitochondrion, peroxisome, protein bodies, endoplasmic reticulum, chloroplast, starch granule, amyloplast, apoplast or cell wall of a plant cell (e.g. Unger et. al. Plant Molec. Biol. 13: 411-418 (1989); Rogers et. al. (1985) Proc. Natl. Acad. Sci. USA 82: 6512-651; U.S. Pat. No. 7,102,057; WO 2005/096704. Optionally, the signal sequence may be an N-terminal signal sequence from waxy, an N-terminal signal sequence from gamma-zein, a starch binding domain, a C-terminal starch binding domain, a chloroplast targeting sequence, which imports the mature protein to the chloroplast (Comai et. al. (1988) J. Biol. Chem. 263: 15104-15109; van den Broeck, et. al. (1985) Nature 313: 358-363; U.S. Pat. No. 5,639,949) or a secretion signal sequence from aleurone cells (Koehler & Ho, Plant Cell 2: 769-783 (1990)). Additionally, amino terminal sequences in conjunction with carboxyl terminal sequences are responsible for vacuolar targeting of gene products and can be used with the present invention (Shinshi et. al. (1990) Plant Molec. Biol. 14: 357-368). In one embodiment, the signal sequence selected includes the known cleavage site, and the fusion constructed takes into account any amino acids after the cleavage site(s), which are required for cleavage. In some cases this requirement may be fulfilled by the addition of a small number of amino acids between the cleavage site and the transgene ATG or, alternatively, replacement of some amino acids within the transgene sequence. These construction techniques are well known in the art and are equally applicable to any cellular compartment.

It will be recognized that the above-described mechanisms for cellular targeting can be utilized not only in conjunction with their cognate promoters, but also in conjunction with heterologous promoters so as to effect a specific cell-targeting goal under the transcriptional regulation of a promoter that has an expression pattern different to that of the promoter from which the targeting signal derives.

An expression cassette of the invention also can include a nucleotide sequence for a selectable marker, which can be used to select a transformed plant, plant part and/or plant cell. Many examples of suitable selectable markers are known in the art and can be used in the expression cassettes described herein.

Examples of selectable markers include, but are not limited to, a nucleotide sequence encoding neo or nptII, which confers resistance to kanamycin, G418, and the like (Potrykus et al. (1985) Mol. Gen. Genet. 199:183-188); a nucleotide sequence encoding bar, which confers resistance to phosphinothricin; a nucleotide sequence encoding an altered 5-enolpyruvylshikimate-3-phosphate (EPSP) synthase, which confers resistance to glyphosate (Hinchee et al. (1988) Biotech. 6:915-922); a nucleotide sequence encoding a nitrilase such as bxn from *Klebsiella ozaenae* that confers resistance to bromoxynil (Stalker et al. (1988) Science 242:419-423); a nucleotide sequence encoding an altered acetolactate synthase (ALS) that confers resistance to imidazolinone, sulfonylurea or other ALS-inhibiting chemicals (EP Patent Application No. 154204); a nucleotide sequence encoding a methotrexate-resistant dihydrofolate reductase (DHFR) (Thillet et al. (1988) J. Biol. Chem. 263:12500-12508); a nucleotide sequence encoding a dalapon dehalogenase that confers resistance to dalapon; a nucleotide sequence encoding a mannose-6-phosphate isomerase (also referred to as phosphomannose isomerase (PMI)) that confers an ability to metabolize mannose (U.S. Pat. Nos. 5,767,378 and 5,994,629); a nucleotide sequence encoding an altered anthranilate synthase that confers resistance to 5-methyl tryptophan; or a nucleotide sequence encoding hph that confers resistance to hygromycin. One of skill in the art is capable of choosing a suitable selectable marker for use in an expression cassette of this invention.

Additional selectable markers include, but are not limited to, a nucleotide sequence encoding (3-glucuronidase or uidA (GUS) that encodes an enzyme for which various chromogenic substrates are known; an R-locus nucleotide sequence that encodes a product that regulates the production of anthocyanin pigments (red color) in plant tissues (Dellaporta et al., "Molecular cloning of the maize R-nj allele by transposon-tagging with Ac" 263-282 In: Chromosome Structure and Function: Impact of New Concepts, 18th Stadler Genetics Symposium (Gustafson & Appels eds., Plenum Press 1988)); a nucleotide sequence encoding β-lactamase, an enzyme for which various chromogenic substrates are known (e.g., PADAC, a chromogenic cephalosporin) (Sutcliffe (1978) Proc. Natl. Acad. Sci. USA 75:3737-3741); a nucleotide sequence encoding xylE that encodes a catechol dioxygenase (Zukowsky et al. (1983) Proc. Natl. Acad. Sci. USA 80:1101-1105); a nucleotide sequence encoding tyrosinase, an enzyme capable of oxidizing tyrosine to DOPA and dopaquinone, which in turn condenses to form melanin (Katz et al. (1983) J. Gen. Microbiol. 129:2703-2714); a nucleotide sequence encoding β-galactosidase, an enzyme for which there are chromogenic substrates; a nucleotide sequence encoding luciferase (lux) that allows for bioluminescence detection (Ow et al. (1986) Science 234:856-859); a nucleotide sequence encoding aequorin which may be employed in calcium-sensitive bioluminescence detection (Prasher et al. (1985) Biochem. Biophys. Res. Comm. 126:1259-1268); or a nucleotide sequence encoding green fluorescent protein (Niedz et al. (1995) Plant Cell Reports 14:403-406). One of skill in the art can choose a suitable selectable marker for use in an expression cassette of this invention.

In some embodiments, an expression cassette of the invention also can include polynucleotides that encode other desired traits in addition to the insecticidal proteins of the invention. Examples of such other polynucleotides include that those encode a polypeptide or a dsRNA for the other desired trait(s) of interest. Such expression cassettes comprising the "stacked" traits may be used, e.g., to create plants, plant parts or plant cells having a desired phenotype with the stacked traits (i.e., molecular stacking). Such stacked combinations in plants can also be created by other methods including, but not limited to, cross breeding plants by any conventional methodology (i.e., a breeding stack). If stacked by genetically transforming the plants, the nucleotide sequences of interest can be combined at any time and in any order. For example, a transgenic plant comprising one or more desired traits can be used as the target to introduce further traits by subsequent transformation. The additional nucleotide sequences can be introduced simultaneously in a co-transformation protocol with a nucleotide sequence, nucleic acid molecule, nucleic acid construct, or composition of this invention, provided by any combination of expression cassettes. For example, if two nucleotide sequences will be introduced, they can be incorporated in separate cassettes (trans) or can be incorporated on the same cassette (cis). Expression of polynucleotides can be driven by the same promoter or by different promoters. It is further recognized that polynucleotides can be stacked at a desired genomic location using a site-specific recombination system. See, e.g., Int'l Patent Application Publication Nos. WO 99/25821; WO 99/25854; WO 99/25840; WO 99/25855 and WO 99/25853.

In representative embodiments, the expression cassette can also include an additional coding sequence for one or more polypeptides or double stranded RNA molecules (dsRNA) of interest for an agronomic trait (e.g., an agronomic trait that is primarily of benefit to a seed company, grower or grain processor). A polypeptide of interest can be any polypeptide encoded by a nucleotide sequence of interest. Non-limiting examples of polypeptides of interest that are suitable for production in plants include those resulting in agronomically important traits such as herbicide resistance (also sometimes referred to as "herbicide tolerance"), virus resistance, bacterial pathogen resistance, insect resistance, nematode resistance, or fungal resistance. See, e.g., U.S. Pat. Nos. 5,569,823; 5,304,730; 5,495,071; 6,329,504; and 6,337,431. In embodiments, the polypeptide of interest can be one that increases plant vigor or yield (including traits that allow a plant to grow at different temperatures, soil conditions and levels of sunlight and precipitation), or one that allows identification of a plant exhibiting a trait of interest (e.g., a selectable marker, seed coat color, etc.). Various polypeptides of interest, as well as methods for introducing these polypeptides into a plant, are described, for example, in U.S. Pat. Nos. 4,761,373; 4,769,061; 4,810, 648; 4,940,835; 4,975,374; 5,013,659; 5,162,602; 5,276, 268; 5,304,730; 5,495,071; 5,554,798; 5,561,236; 5,569, 823; 5,767,366; 5,879,903, 5,928,937; 6,084,155; 6,329,504 and 6,337,431; as well as US Patent Publication No. 2001/ 0016956. See also, on the World Wide Web at lifesci.sussex.ac.uk/home/NeilCrickmore/Bt/.

Polynucleotides conferring resistance/tolerance to an herbicide that inhibits the growing point or meristem, such as an imidazalinone or a sulfonylurea can also be suitable in some embodiments of the invention. Exemplary polynucleotides in this category code for mutant ALS and AHAS enzymes as described, e.g., in U.S. Pat. Nos. 5,767,366 and 5,928,937. U.S. Pat. Nos. 4,761,373 and 5,013,659 are directed to plants resistant to various imidazalinone or sulfonamide herbicides. U.S. Pat. No. 4,975,374 relates to plant cells and plants containing a nucleic acid encoding a mutant glutamine synthetase (GS) resistant to inhibition by herbicides that are known to inhibit GS, e.g., phosphinothricin and methionine sulfoximine. U.S. Pat. No. 5,162,602 discloses plants resistant to inhibition by cyclohexanedione and aryloxyphenoxypropanoic acid herbicides. The resistance is conferred by an altered acetyl coenzyme A carboxylase (ACCase).

Polypeptides encoded by nucleotides sequences conferring resistance to glyphosate are also suitable for the invention. See, e.g., U.S. Pat. Nos. 4,940,835 and 4,769,061. U.S. Pat. No. 5,554,798 discloses transgenic glyphosate resistant maize plants, which resistance is conferred by an altered 5-enolpyruvyl-3-phosphoshikimate (EPSP) synthase gene.

Polynucleotides coding for resistance to phosphono compounds such as glufosinate ammonium or phosphinothricin, and pyridinoxy or phenoxy propionic acids and cyclohexones are also suitable. See, European Patent Application No. 0 242 246. See also, U.S. Pat. Nos. 5,879,903, 5,276,268 and 5,561,236.

Other suitable polynucleotides include those coding for resistance to herbicides that inhibit photosynthesis, such as a triazine and a benzonitrile (nitrilase). See, U.S. Pat. No. 4,810,648. Additional suitable polynucleotides coding for herbicide resistance include those coding for resistance to 2,2-dichloropropionic acid, sethoxydim, haloxyfop, imidazolinone herbicides, sulfonylurea herbicides, triazolopyrimidine herbicides, s-triazine herbicides and bromoxynil. Also suitable are polynucleotides conferring resistance to a protox enzyme, or that provide enhanced resistance to plant diseases; enhanced tolerance of adverse environmental conditions (abiotic stresses) including but not limited to drought, excessive cold, excessive heat, or excessive soil salinity or extreme acidity or alkalinity; and alterations in plant architecture or development, including changes in developmental timing. See, e.g., U.S. Patent Publication No. 2001/0016956 and U.S. Pat. No. 6,084,155.

Additional suitable polynucleotides include those coding for pesticidal (e.g., insecticidal) polypeptides. These polypeptides may be produced in amounts sufficient to control, for example, insect pests (i.e., insect controlling amounts). In embodiments, the polypeptide is a lepidopteran-active, coleopteran-active, hemipteran-active and/or dipteran-active polypeptide, or any combination thereof. It is recognized that the amount of production of a pesticidal polypeptide in a plant to control insects or other pests may vary depending upon the cultivar, type of pest, environmental factors and the like. Polynucleotides useful for additional insect or other pest resistance include, for example, those that encode toxins identified in *Bacillus* organisms. Polynucleotides comprising nucleotide sequences encoding *Bacillus thuringiensis* (Bt) Cry proteins from several subspecies have been cloned and recombinant clones have been found to be toxic to lepidopteran, dipteran and coleopteran insect larvae. Examples of such Bt insecticidal proteins include the Cry proteins such as Cry1Aa, Cry1Ab, Cry1Ac, Cry1B, Cry1C, Cry1D, Cry1Ea, Cry1Fa, Cry3A, Cry9A, Cry9B, Cry9C, the binary toxin Cry34/35, and modified Cry proteins including Cry3Bb1, mCry3A, eCry3.1A., and the like, as well as vegetative insecticidal proteins such as Vip1, Vip2, Vip3, and the like, and any combination of the foregoing Bt insecticidal proteins. A full list of Bt-derived proteins can be found on the worldwide web at the *Bacillus thuringiensis* Toxin Nomenclature Database maintained by the University of Sussex (see also, Crickmore et al. (1998) Microbiol. Mol. Biol. Rev. 62:807-813).

In embodiments, an additional polypeptide is an insecticidal polypeptide derived from a non-Bt source, including without limitation, an alpha-amylase, a peroxidase, a cholesterol oxidase, a patatin, a protease, a protease inhibitor, a urease, an alpha-amylase inhibitor, a pore-forming protein, a chitinase, a lectin, an engineered antibody or antibody fragment, a *Bacillus cereus* insecticidal protein, a *Xenorhabdus* spp. (such as *X. nematophila* or *X. bovienii*) insecticidal protein, a *Photorhabdus* spp. (such as *P. luminescens* or *P. asymobiotica*) insecticidal protein, a *Brevibacillus* spp. (such as *B. laterosporous*) insecticidal protein, a *Lysinibacillus* spp. (such as *L. sphearicus*) insecticidal protein, a *Chromobacterium* spp. (such as *C. subtsugae* or *C. piscinae*) insecticidal protein, a *Yersinia* spp. (such as *Y. entomophaga*) insecticidal protein, a *Paenibacillus* spp. (such as *P. propylaea*) insecticidal protein, a *Clostridium* spp. (such as *C. bifermentans*) insecticidal protein, a *Pseudomonas* spp. (such as *P. fluorescens*) and a lignin.

Also included are insecticidal traits based on RNA interference (RNAi). Double stranded RNA (dsRNA) molecules useful with the invention include, but are not limited to those that suppress target pest (e.g., insect) genes. In embodiments, the dsRNA targets a gene in a lepidopteran, coleopteran, hemipteran or dipteran insect pest, or any combination of the foregoing. As used herein the words "gene suppression", when taken together, are intended to refer to any of the well-known methods for reducing the levels of protein produced as a result of gene transcription to mRNA and subsequent translation of the mRNA. Gene suppression is also intended to mean the reduction of protein expression from a gene or a coding sequence including posttranscriptional gene suppression and transcriptional suppression.

Posttranscriptional gene suppression is mediated by the homology between all or a part of a mRNA transcribed from a gene or coding sequence targeted for suppression and the corresponding double stranded RNA used for suppression, and refers to the substantial and measurable reduction of the amount of available mRNA available in the cell for binding by ribosomes. The transcribed RNA can be in the sense orientation to effect what is called co-suppression, in the anti-sense orientation to effect what is called anti-sense suppression, or in both orientations producing a dsRNA to effect what is called RNA interference (RNAi). Transcriptional suppression is mediated by the presence in the cell of a dsRNA, a gene suppression agent, exhibiting substantial sequence identity to a promoter DNA sequence or the complement thereof to effect what is referred to as promoter trans suppression. Gene suppression may be effective against a native plant gene associated with a trait, e.g., to provide plants with reduced levels of a protein encoded by the native gene or with enhanced or reduced levels of an affected metabolite. Gene suppression can also be effective against target genes in plant pests that may ingest or contact plant material containing gene suppression agents, specifically designed to inhibit or suppress the expression of one or more homologous or complementary sequences in the cells of the pest. Such genes targeted for suppression can encode an essential protein, the predicted function of which is selected from the group consisting of muscle formation, juvenile hormone formation, juvenile hormone regulation, ion regulation and transport, digestive enzyme synthesis, maintenance of cell membrane potential, amino acid biosynthesis, amino acid degradation, sperm formation, pheromone synthesis, pheromone sensing, antennae formation, wing formation, leg formation, development and differentiation, egg formation, larval maturation, digestive enzyme formation, haemolymph synthesis, haemolymph maintenance, neurotransmission, cell division, energy metabolism, respiration, and apoptosis.

In embodiments, the dsRNA includes, without limitation, a dsRNA targeting a vacuolar ATP synthase, a beta-tubulin, a 26S proteosome subunit p28 protein, a EF1α 48D, a troponin I, a tetraspanin, a gamma-coatomer, a beta-coatomer, and/or a juvenile hormone epoxide hydrolase. In embodiments, the polynucleotide encodes a DvSnf7 dsRNA (e.g., in corn event MON87411).

In some embodiments, the insecticidal protein of the invention and the additional insect control agent are directed against the same target insect.

Polypeptides that are suitable for production in plants further include those that improve or otherwise facilitate the conversion of harvested plants or plant parts into a commercially useful product, including, for example, increased or altered carbohydrate content or distribution, improved fermentation properties, increased oil content, increased protein content, improved digestibility, and increased nutraceutical content, e.g., increased phytosterol content, increased tocopherol content, increased stanol content or increased vitamin content. Polypeptides of interest also include, for example, those resulting in or contributing to a reduced content of an unwanted component in a harvested crop, e.g., phytic acid, or sugar degrading enzymes. By "resulting in" or "contributing to" is intended that the polypeptide of interest can directly or indirectly contribute to the existence of a trait of interest (e.g., increasing cellulose degradation by the use of a heterologous cellulase enzyme).

In some embodiments, the polypeptide contributes to improved digestibility for food or feed. Xylanases are hemicellulolytic enzymes that improve the breakdown of plant cell walls, which leads to better utilization of the plant nutrients by an animal. This leads to improved growth rate and feed conversion. Also, the viscosity of the feeds containing xylan can be reduced. Heterologous production of xylanases in plant cells also can facilitate lignocellulosic conversion to fermentable sugars in industrial processing.

Numerous xylanases from fungal and bacterial microorganisms have been identified and characterized (see, e.g., U.S. Pat. No. 5,437,992; Coughlin et al. (1993) "Proceedings of the Second TRICEL Symposium on *Trichoderma reesei* Cellulases and Other Hydrolases" Espoo; Souminen and Reinikainen, eds. (1993) Foundation for Biotechnical and Industrial Fermentation Research 8:125-135; U.S. Patent Publication No. 2005/0208178; and PCT Publication No. WO 03/16654). In particular, three specific xylanases (XYL-I, XYL-II, and XYL-III) have been identified in *T. reesei* (Tenkanen et al. (1992) Enzyme Microb. Technol. 14:566; Torronen et al. (1992) Bio/Technology 10:1461; and Xu et al. (1998) Appl. Microbiol. Biotechnol. 49:718).

In other embodiments, a polypeptide useful for the invention can be a polysaccharide degrading enzyme. Plants of this invention producing such an enzyme may be useful for generating, for example, fermentation feedstocks for bioprocessing. In some embodiments, enzymes useful for a fermentation process include alpha amylases, proteases, pullulanases, isoamylases, cellulases, hemicellulases, xylanases, cyclodextrin glycotransferases, lipases, phytases, laccases, oxidases, esterases, cutinases, granular starch hydrolyzing enzyme and other glucoamylases.

Polysaccharide-degrading enzymes include: starch degrading enzymes such as alpha-amylases (EC 3.2.1.1), glucuronidases (E.C. 3.2.1.131); exo-1,4-alpha-D glucanases such as amyloglucosidases and glucoamylase (EC 3.2.1.3), beta-amylases (EC 3.2.1.2), alpha-glucosidases (EC 3.2.1.20), and other exo-amylases; starch debranching enzymes, such as a) isoamylase (EC 3.2.1.68), pullulanase (EC 3.2.1.41), and the like; b) cellulases such as exo-1,4-3-cellobiohydrolase (EC 3.2.1.91), exo-1,3-beta-D-glucanase (EC 3.2.1.39), beta-glucosidase (EC 3.2.1.21); c) L-arabinases, such as endo-1,5-alpha-L-arabinase (EC 3.2.1.99), alpha-arabinosidases (EC 3.2.1.55) and the like; d) galactanases such as endo-1,4-beta-D-galactanase (EC 3.2.1.89), endo-1,3-beta-D-galactanase (EC 3.2.1.90), alpha-galactosidase (EC 3.2.1.22), beta-galactosidase (EC 3.2.1.23) and the like; e) mannanases, such as endo-1,4-beta-D-mannanase (EC 3.2.1.78), beta-mannosidase (EC 3.2.1.25), alpha-mannosidase (EC 3.2.1.24) and the like; 0 xylanases, such as endo-1,4-beta-xylanase (EC 3.2.1.8), beta-D-xylosidase (EC 3.2.1.37), 1,3-beta-D-xylanase, and the like; and g) other enzymes such as alpha-L-fucosidase (EC 3.2.1.51), alpha-L-rhamnosidase (EC 3.2.1.40), levanase (EC 3.2.1.65), inulanase (EC 3.2.1.7), and the like. In one embodiment, the alpha-amylase is the synthetic alpha-amylase, Amy797E, described is U.S. Pat. No. 8,093,453.

Further enzymes which may be used with the invention include proteases, such as fungal and bacterial proteases. Fungal proteases include, but are not limited to, those obtained from *Aspergillus*, *Trichoderma*, *Mucor* and *Rhizopus*, such as *A. niger*, *A. awamori*, *A. oryzae* and *M. miehei*. In some embodiments, the polypeptides of this invention can be cellobiohydrolase (CBH) enzymes (EC 3.2.1.91). In one embodiment, the cellobiohydrolase enzyme can be CBH1 or CBH2.

Other enzymes useful with the invention include, but are not limited to, hemicellulases, such as mannases and arabinofuranosidases (EC 3.2.1.55); ligninases; lipases (e.g., E.C. 3.1.1.3), glucose oxidases, pectinases, xylanases, transglucosidases, alpha 1,6 glucosidases (e.g., E.C. 3.2.1.20); esterases such as ferulic acid esterase (EC 3.1.1.73) and acetyl xylan esterases (EC 3.1.1.72); and cutinases (e.g., E.C. 3.1.1.74).

In embodiments, the nucleic acids of the invention can further comprise, consist essentially of, or consist of a vector.

In embodiments, the polynucleotides and expression cassettes of the invention are comprised within a vector. Vectors for use in transformation of plants and other organisms are well known in the art. Non-limiting examples of general classes of vectors include a plasmid, phage vector, phagemid vector, cosmid vector, fosmid, bacteriophage, artificial chromosome, or a viral vector. In embodiments, the vector is plant vector, e.g., for use in transformation of plants. In embodiments, the vector is a bacterial vector, e.g., for use in transformation of bacteria. Suitable vectors for plants, bacteria and other organisms are known in the art.

Transgenic Plants, Plant Parts, Plant Cells, Seed.

The invention also encompasses a transgenic non-human host cell comprising a polynucleotide, a nucleic acid molecule, an expression cassette, a vector, or a polypeptide of the invention. The transgenic non-human host cell can include, but is not limited to, a plant cell (including a monocot cell and/or a dicot cell), a yeast cell, a bacterial cell or an insect cell. Accordingly, in some embodiments, the invention provides a bacterial cell selected from the genera *Bacillus*, *Brevibacillus*, *Clostridium*, *Xenorhabdus*, *Photorhabdus*, *Pasteuria*, *Escherichia*, *Pseudomonas*, *Erwinia*, *Serratia*, *Klebsiella*, *Salmonella*, *Pasteurella*, *Xanthomonas*, *Streptomyces*, *Rhizobium*, *Rhodopseudomonas*, *Methylophilius*, *Agrobacterium*, *Acetobacter*, *Lactobacillus*, *Arthrobacter*, *Azotobacter*, *Leuconostoc*, or *Alcaligenes*. Thus, for example, as biological insect control agents, the insecticidal proteins of the invention can be produced by expression of a polynucleotide encoding the same in a bacterial cell. For example, in some embodiments, a *Bacillus thuringiensis* cell comprising a polynucleotide encoding an insecticidal protein of the invention is provided.

In embodiments, the transgenic plant cell is a dicot plant cell or a monocot plant cell. In additional embodiments, the dicot plant cell is a soybean cell, sunflower cell, tomato cell, cole crop cell, cotton cell, sugar beet cell or a tobacco cell. In further embodiments, the monocot cell is a barley cell, maize cell, oat cell, rice cell, sorghum cell, sugar cane cell or wheat cell. In embodiments, the invention provides a plurality of dicot cells or monocot cells comprising a polynucleotide expressing an insecticidal protein of the invention. In embodiments, the plurality of cells are juxtaposed to form an apoplast and are grown in natural sunlight. In embodiments, the transgenic plant cell is non-propagating and/or cannot regenerate a whole plant.

In embodiments of the invention, an insecticidal protein of the invention is expressed in a higher organism, for example, a plant. In this case, transgenic plants expressing effective amounts of the insecticidal protein protect themselves from plant pests such as insect pests. When an insect starts feeding on such a transgenic plant, it ingests the expressed insecticidal protein. This can deter the insect from further biting into the plant tissue or may even harm or kill the insect. In embodiments, a polynucleotide of the invention is inserted into an expression cassette, which is then stably integrated in the genome of the plant. In other embodiments, the polynucleotide is included in a non-pathogenic self-replicating virus.

In some embodiments of the invention, a transgenic plant cell comprising a nucleic acid molecule or polypeptide of the invention is a cell of a plant part, a plant organ or a plant culture (each as described herein) including, but not limited to, a root, a leaf, a seed, a flower, a fruit, a pollen cell, organ or plant culture, and the like, or a callus cell or culture.

A transgenic plant or plant cell in accordance with the invention may be a monocot or dicot plant or plant cell and includes, but is not limited to, corn (maize), soybean, rice, wheat, barley, rye, oat, sorghum, millet, sunflower, safflower, sugar beet, cotton, sugarcane, oilseed rape, alfalfa, tobacco, peanut, vegetable (including, sweet potato, bean, pea, chicory, lettuce, cabbage, cauliflower, broccoli, turnip, carrot, eggplant, cucumber, radish, spinach, potato, tomato, asparagus, onion, garlic, melon, pepper, celery, squash, pumpkin, zucchini, and the like), fruit (including, apple, pear, quince, plum, cherry, peach, nectarine, apricot, strawberry, grape, raspberry, blackberry, pineapple, avocado, papaya, mango, banana, and the like), a specialty plant or plant cell (such as *Arabidopsis*), or a woody plant or plant cell (such as coniferous and/or deciduous trees). In embodiments, a plant or plant cell of the of the invention is a crop plant or plant cell such as maize, sorghum, wheat, sunflower, tomato, a crucifer, pepper, potato, cotton, rice, soybean, sugar beet, sugarcane, tobacco, barley, oilseed rape plant or plant cell, and the like.

The invention further provides a part of a transgenic plant of the invention. Optionally, the plant part comprises an insecticidal protein of the invention and/or a nucleic acid encoding the same.

The invention further provides a seed of a transgenic plant of the invention or a seed that produces the transgenic plant of the invention. Optionally, the seed comprises an insecticidal protein of the invention and/or a nucleic acid encoding the same.

Additional embodiments of the invention include harvested products produced from the transgenic plants, plant parts or seed of the invention, as well as a processed product produced from a harvested product. A harvested product can be a whole plant or any plant part, as described herein. Thus, in some embodiments, non-limiting examples of a harvested product include a seed, a fruit, a flower or part thereof (e.g., an anther, a stigma, and the like), a leaf, a stem, and the like. In other embodiments, a processed product includes, but is not limited to, a flour, meal, oil, starch, cereal, and the like produced from a harvested seed or other plant part of the invention. Optionally, the harvested product or the processed product comprises an insecticidal protein of the invention and/or a nucleic acid encoding the same.

In other embodiments, the invention provides an extract from a transgenic plant, plant part or of the invention, optionally wherein the extract comprises an insecticidal protein of the invention and/or a nucleic acid encoding the same. Extracts from plants or plant parts can be made according to procedures well known in the art (See, de la Torre et al., Food, Agric. Environ. 2(1):84-89 (2004); Guidet, Nucleic Acids Res. 22(9): 1772-1773 (1994); Lipton et al., Food Agric. Immun. 12:153-164 (2000)).

The insecticidal protein of the invention can function in the plant part, plant cell, plant organ, seed, harvested product, processed product or extract, and the like, as an insect control agent. In other words, the insecticidal protein can continue to perform the insecticidal function it had in the transgenic plant. The nucleic acid can function to express the insecticidal protein. As an alternative to encoding the insecticidal protein of the invention, the nucleic acid can function to identify a transgenic plant part, plant cell, plant organ, seed, harvested product, processed product or extract of the invention.

In embodiments, a transgenic plant, plant part, plant cell, plant organ, or seed of the invention is hemizygous for a polynucleotide or expression cassette of the invention. In embodiments, a transgenic plant, plant part, plant cell, plant organ, or seed of the invention is homozygous for a polynucleotide or expression cassette of the invention.

In embodiments, a transgenic plant, plant part, plant cell, plant organ, seed, harvested product, processed product or extract has increased resistance to one or more insect pests (e.g., a coleopteran pest, such as a corn rootworm, for example, WCRW) as compared with a suitable control that does not comprise a nucleic acid encoding an insecticidal protein of the invention.

Plant Transformation.

Procedures for transforming plants are well known and routine in the art and are described throughout the literature. Non-limiting examples of methods for transformation of plants include transformation via bacterial-mediated nucleic acid delivery (e.g., via *Agrobacterium*), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) or biological mechanism that results in the introduction of nucleic acid into the plant cell, including any combination thereof. General guides to various plant transformation methods known in the art include Miki et al. ("Procedures for Introducing Foreign DNA into Plants" in Methods in Plant Molecular Biology and Biotechnology, Glick, B. R. and Thompson, J. E., Eds. (CRC Press, Inc., Boca Raton, 1993), pages 67-88) and Rakowoczy-Trojanowska (Cell. Mol. Biol. Lett. 7:849-858 (2002)).

For *Agrobacterium*-mediated transformation, binary vectors or vectors carrying at least one T-DNA border sequence are generally suitable, whereas for direct gene transfer (e.g., particle bombardment and the like) any vector is suitable and linear DNA containing only the construction of interest can be used. In the case of direct gene transfer, transformation with a single DNA species or co-transformation can be used (Schocher et al., Biotechnology 4:1093-1096 (1986)). For both direct gene transfer and *Agrobacterium*-mediated transfer, transformation is usually (but not necessarily) undertaken with a selectable marker that may be a positive selection (e.g., Phosphomannose Isomerase), provide resistance to an antibiotic (e.g., kanamycin, hygromycin or methotrexate) or a herbicide (e.g., glyphosate or glufosinate). However, the choice of selectable marker is not critical to the invention.

*Agrobacterium*-mediated transformation is a commonly used method for transforming plants because of its high efficiency of transformation and because of its broad utility with many different species. *Agrobacterium*-mediated transformation typically involves transfer of the binary vector carrying the foreign DNA of interest to an appropriate *Agrobacterium* strain that may depend on the complement of vir genes carried by the host *Agrobacterium* strain either on a co-resident Ti plasmid or chromosomally (Uknes et al. (1993) Plant Cell 5:159-169). The transfer of the recombinant binary vector to *Agrobacterium* can be accomplished by a triparental mating procedure using *Escherichia coli* carrying the recombinant binary vector, a helper *E. coli* strain that carries a plasmid that is able to mobilize the recombinant binary vector to the target *Agrobacterium* strain. Alternatively, the recombinant binary vector can be transferred to *Agrobacterium* by nucleic acid transformation (Höfgen & Willmitzer (1988) Nucleic Acids Res. 16:9877).

Dicots as well as monocots may be transformed using *Agrobacterium*. Methods for *Agrobacterium*-mediated transformation of rice include well known methods for rice transformation, such as those described in any of the following: European patent application EP 1198985 A1, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acids or the construct to be expressed is preferably cloned into a vector, which is suitable for transforming *Agrobacterium tumefaciens*, for example pBin19 (Bevan et al., Nucl. Acids Res. 12 (1984) 8711). *Agrobacteria* transformed by such a vector can then be used in known manner for the transformation of plants, such as plants used as a model, like *Arabidopsis* or crop plants such as, by way of example, tobacco plants, for example by immersing bruised leaves or chopped leaves in an Agrobacterial solution and then culturing them in suitable media. The transformation of plants by means of *Agrobacterium tumefaciens* is described, for example, by Hagen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

Transformation of a plant by recombinant *Agrobacterium* usually involves co-cultivation of the *Agrobacterium* with explants from the plant and follows methods well known in the art. Transformed tissue is regenerated on selection medium carrying an antibiotic or herbicide resistance marker between the binary plasmid T-DNA borders.

As discussed previously, another method for transforming plants, plant parts and plant cells involves propelling inert or biologically active particles at plant tissues and cells. See, e.g., U.S. Pat. Nos. 4,945,050; 5,036,006 and 5,100,792. Generally, this method involves propelling inert or biologically active particles at the plant cells under conditions effective to penetrate the outer surface of the cell and afford incorporation within the interior thereof. When inert particles are utilized, the vector can be introduced into the cell by coating the particles with the vector containing the nucleic acid of interest. Alternatively, a cell or cells can be surrounded by the vector so that the vector is carried into the cell by the wake of the particle. Biologically active particles (e.g., a dried yeast cell, a dried bacterium or a bacteriophage, each containing one or more nucleic acids sought to be introduced) also can be propelled into plant tissue.

In other embodiments, a polynucleotide of the invention can be directly transformed into the plastid genome. A major advantage of plastid transformation is that plastids are generally capable of expressing bacterial genes without substantial modification, and plastids are capable of expressing multiple open reading frames under control of a single promoter. Plastid transformation technology is extensively described in U.S. Pat. Nos. 5,451,513, 5,545,817, and 5,545,818, in PCT application no. WO 95/16783, and in McBride et al. (1994) Proc. Nati. Acad. Sci. USA 91, 7301-7305. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin or streptomycin can be utilized as selectable markers for transformation (Svab, Z., Hajdukiewicz, P., and Maliga, P. (1990) Proc. Natl. Acad. Sci. USA 87, 8526-8530; Staub, J. M., and Maliga, P. (1992) Plant Cell 4, 39-45). The presence of cloning sites between these markers allows creation of a plastid targeting vector for introduction of foreign genes (Staub, J. M., and Maliga, P. (1993) EMBO J. 12, 601-606). Substantial increases in transformation frequency can be obtained by replacement of the recessive rRNA or r-protein antibiotic resistance genes with a dominant selectable marker, the bacterial aadA gene encoding the spectinomycin-cletoxifying enzyme aminoglycoside-3'-adenyltransferase (Svab, Z., and Maliga, P. (1993) Proc. Natl. Acad. Sci. USA 90, 913-917). Previously, this marker had been used successfully for high-frequency transformation of the plastid genome of the green alga *Chlamydomonas reinhardtii* (Goldschmidt-Clermont, M. (1991) Nucl. Acids Res. 19:4083-4089). Other selectable markers useful for plastid transformation are known in the art and encompassed within the scope of the invention. Typically, approximately 15-20 cell division cycles following transformation are required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein. In one embodiment, a polynucleotide of the invention can be inserted into a plastid-targeting vector and transformed into the plastid genome of a desired plant host. Thus, plants homoplastic for plastid genomes containing a nucleotide sequence of the invention can be obtained, which are capable of high expression of the polynucleotide.

Methods of selecting for transformed, transgenic plants, plant cells or plant tissue culture are routine in the art and can be employed in the methods of the invention provided herein. For example, a recombinant vector of the invention also can include an expression cassette comprising a nucleotide sequence for a selectable marker, which can be used to select a transformed plant, plant part or plant cell.

Further, as is well known in the art, intact transgenic plants can be regenerated from transformed plant cells, plant tissue culture or cultured protoplasts using any of a variety of known techniques. Plant regeneration from plant cells, plant tissue culture or cultured protoplasts is described, for example, in Evans et al. (Handbook of Plant Cell Cultures, Vol. 1, MacMilan Publishing Co. New York (1983)); and Vasil I. R. (ed.) (Cell Culture and Somatic Cell Genetics of Plants, Acad. Press, Orlando, Vol. I (1984), and Vol. II (1986)).

Additionally, the genetic properties engineered into the transgenic seeds and plants, plant parts, or plant cells of the invention described above can be passed on by sexual reproduction or vegetative growth and therefore can be maintained and propagated in progeny plants. Generally, maintenance and propagation make use of known agricultural methods developed to fit specific purposes such as harvesting, sowing or tilling.

A polynucleotide therefore can be introduced into the plant, plant part or plant cell in any number of ways that are well known in the art, as described above. Therefore, no particular method for introducing one or more polynucleotides into a plant is relied upon, rather any method that allows the one or more polynucleotides to be stably integrated into the genome of the plant can be used. Where more than one polynucleotides is to be introduced, the respective polynucleotides can be assembled as part of a single nucleic acid molecule, or as separate nucleic acid molecules, and can be located on the same or different nucleic acid molecules. Accordingly, the polynucleotides can be introduced into the cell of interest in a single transformation event, in separate transformation events, or, for example, in plants, as part of a breeding protocol.

Once a desired polynucleotide has been transformed into a particular plant species, it may be propagated in that species or moved into other varieties of the same species, particularly including commercial varieties, using traditional breeding techniques. Furthermore, an Axmi205 transgene can be modified in situ to incorporate the modifications of the present invention using genome editing techniques.

Pesticidal Compositions.

In embodiments, the invention provides an insecticidal composition comprising an insecticidal protein of the invention in an agriculturally acceptable carrier. As used herein an "agriculturally-acceptable carrier" can include natural or synthetic, organic or inorganic material which is combined with the active protein to facilitate its application to or in the plant, or part thereof. Examples of agriculturally acceptable carriers include, without limitation, powders, dusts, pellets, granules, sprays, emulsions, colloids, and solutions. Agriculturally-acceptable carriers further include, but are not limited to, inert components, dispersants, surfactants, adjuvants, tackifiers, stickers, binders, or combinations thereof, that can be used in agricultural formulations. Such compositions can be applied in any manner that brings the pesticidal proteins or other pest control agents in contact with the pests. Accordingly, the compositions can be applied to the surfaces of plants or plant parts, including seeds, leaves, flowers, stems, tubers, roots, and the like. In other embodiments, a plant producing an insecticidal protein of the invention in planta is an agriculturally-acceptable carrier of the expressed insecticidal protein. In embodiments, the compositions and agriculturally-acceptable carriers of the invention exclude transgenic plants.

In further embodiments, the insecticidal composition comprises a bacterial cell or a transgenic bacterial cell of the invention, wherein the bacterial cell or transgenic bacterial cell produces an insecticidal protein of the invention. Such an insecticidal composition can be prepared by desiccation, lyophilization, homogenization, extraction, filtration, centrifugation, sedimentation, or concentration of a culture of *Bacillus thuringiensis* (Bt), including a transgenic Bt culture. In embodiments, a composition of the invention may comprise at least about 1%, at least about 5%, at least about 10%, at least about 20%, at least about 25%, at least about 30%, at least about 35%, at least about 40%, at least about 50%, at least about 60%, at least about 70%, at least about 80%, at least about 90%, at least about 95%, at least about 97%, or at least 99% by weight a polypeptide of the invention. In additional embodiments, the composition comprises from about 1% to about 99% by weight of the insecticidal protein of the invention.

The insecticidal proteins of the invention can be used in combination with other pest control agents (e.g., insect control agents) to increase the target pest (e.g., insect) spectrum and/or for the prevention or management of insect resistance. Furthermore, the use of the insecticidal proteins of the invention in combination with an insecticidal agent which has a different mode of action and/or targets a different receptor in the insect gut has particular utility for the prevention and/or management of insect resistance. In embodiments, the insecticidal protein of the invention is used in combination with another insect control agent that targets the same insect pest.

Therefore, in some embodiments, the invention provides a composition that controls one or more plant pests (e.g., an insect pest such as a lepidopteran insect pest, a coleopteran insect pest, a hemipteran insect pest and/or a dipteran insect pest), wherein the composition comprises a first pest control agent, which is an insecticidal protein of the invention and at least a second pest control agent (e.g., an insect control agent) that is different from the first pest control agent. In other embodiments, the composition is a formulation for topical application to a plant. In still other embodiments, the composition is a transgenic plant. In further embodiments, the composition is a combination of a formulation topically applied to a transgenic plant. In some embodiments, the formulation comprises the first pest control agent, which is an insecticidal protein of the invention when the transgenic plant comprises the second pest control agent. In other embodiments, the formulation comprises the second pest control agent when the transgenic plant comprises the first pest control agent, which is an insecticidal protein of the invention.

In some embodiments, the second pest control agent can be one or more of a chemical pesticide, such as an insecticide, a Bt insecticidal protein, and/or a non-Bt pesticidal agent including without limitation a *Xenorhabdus* insecticidal protein, a *Photorhabdus* insecticidal protein, a *Brevibacillus laterosporus* insecticidal protein, a *Bacillus sphaericus* insecticidal protein, a protease inhibitor (both serine and cysteine types), a lectin, an alpha-amylase, a peroxidase, a cholesterol oxidase, or a double stranded RNA (dsRNA) molecule.

In other embodiments, the second pest control agent is one or more chemical pesticides, which is optionally a seed coating. Non-limiting examples of chemical pesticides include pyrethroids, carbamates, neonicotinoids, neuronal sodium channel blockers, insecticidal macrocyclic lactones, gamma-aminobutyric acid (GABA) antagonists, insecticidal ureas and juvenile hormone mimics. In other embodiments, the chemical pesticide is one or more of abamectin, acephate, acetamiprid, amidoflumet (S-1955), avermectin, azadirachtin, azinphos-methyl, bifenthrin, binfenazate, buprofezin, carbofuran, chlorfenapyr, chlorfluazuron, chlorpyrifos, chlorpyrifos-methyl, chromafenozide, clothianidin, cyfluthrin, beta-cyfluthrin, cyhalothrin, lambda-cyhalothrin, cypermethrin, cyromazine, deltamethrin, diafenthiuron, diazinon, diflubenzuron, dimethoate, diofenolan, emamectin, endosulfan, esfenvalerate, ethiprole, fenothicarb, fenoxycarb, fenpropathrin, fenproximate, fenvalerate, fipronil, flonicamid, flucythrinate, tau-fluvalinate, flufenerim (UR-50701), flufenoxuron, fonophos, halofenozide, hexaflumuron, imidacloprid, indoxacarb, isofenphos, lufenuron, malathion, metaldehyde, methamidophos, methidathion, methomyl, methoprene, methoxychlor, monocrotophos, methoxyfenozide, nithiazin, novaluron, noviflumuron (XDE-007), oxamyl, parathion, parathion-methyl, permethrin, phorate, phosalone, phosmet, phosphamidon, pirimicarb, profenofos, pymetrozine, pyridalyl, pyriproxyfen, rotenone, spinosad, spiromesifin (BSN 2060), sulprofos, tebufenozide, teflubenzuron, tefluthrin, terbufos, tetrachlorvinphos, thiacloprid, thiamethoxam, thiodicarb, thiosultapsodium, tralomethrin, trichlorfon and triflumuron, aldicarb, oxamyl, fenamiphos, amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad. In still other embodiments, the chemical pesticide is selected from one or more of cypermethrin, cyhalothrin, cyfluthrin and beta-cyfluthrin, esfenvalerate, fenvalerate, tralomethrin, fenothicarb, methomyl, oxamyl, thiodicarb, clothianidin, imidacloprid, thiacloprid, indoxacarb, spinosad, abamectin, avermectin, emamectin, endosulfan, ethiprole, fipronil, flufenoxuron, triflumuron, diofenolan, pyriproxyfen, pymetrozine and amitraz.

In additional embodiments, the second pest control agent can be one or more of any number of Bt insecticidal proteins including but not limited to a Cry protein, a vegetative insecticidal protein (VIP) and insecticidal chimeras of any of the preceding insecticidal proteins. In other embodiments, the second pest control agent is a Cry protein selected from:

Cry1Aa, Cry1Ab, Cry1Ac, Cry1Ad, Cry1Ae, Cry1Af, Cry1Ag, Cry1Ah, Cry1Ai, Cry1Aj, Cry1Ba, Cry1Bb, Cry1Bc, Cry1Bd, Cry1Be, Cry1Bf, Cry1Bg, Cry1Bh, Cry1Bi, Cry1Ca, Cry1Cb, Cry1Da, Cry1Db, Cry1Dc, Cry1Dd, Cry1Ea, Cry1Eb, Cry1Fa, Cry1Fb, Cry1Ga, Cry1Gb, Cry1Gc, Cry1Ha, Cry1Hb, Cry1Hc, Cry1Ia, Cry1Ib, Cry1Ic, Cry1Id, Cry1Ie, Cry1If, Cry1Ig, Cry1Ja, Cry1b, Cry1Jc, Cry1Jd, Cry1Ka, Cry1La, Cry1Ma, Cry1Na, Cry1Nb, Cry2Aa, Cry2Ab, Cry2Ac, Cry2Ad, Cry2Ae, Cry2Af, Cry2Ag, Cry2Ah, Cry2Ai, Cry2Aj, Cry2Ak, Cry2Al, Cry2Ba, Cry3Aa, Cry3Ba, Cry3Bb, Cry3Ca, Cry4Aa, Cry4Ba, Cry4Ca, Cry4Cb, Cry4Cc, Cry5Aa, Cry5Ab, Cry5Ac, Cry5Ad, Cry5Ba, Cry5Ca, Cry5 Da, Cry5Ea, Cry6Aa, Cry6Ba, Cry7Aa, Cry7Ab, Cry7Ac, Cry7Ba, Cry7Bb, Cry7Ca, Cry7Cb, Cry7 Da, Cry7Ea, Cry7Fa, Cry7Fb, Cry7Ga, Cry7Gb, Cry7Gc, Cry7Gd, Cry7Ha, Cry7Ia, Cry7Ja, Cry7Ka, Cry7Kb, Cry7La, Cry8Aa, Cry8Ab, Cry8Ac, Cry8Ad, Cry8Ba, Cry8Bb, Cry8Bc, Cry8Ca, Cry8 Da, Cry8Db, Cry8Ea, Cry8Fa, Cry8Ga, Cry8Ha, Cry8Ia, Cry8Ib, Cry8Ja, Cry8Ka, Cry8Kb, Cry8La, Cry8Ma, Cry8Na, Cry8 Pa, Cry8Qa, Cry8Ra, Cry8Sa, Cry8Ta, Cry9Aa, Cry9Ba, Cry9Bb, Cry9Ca, Cry9 Da, Cry9Db, Cry9Dc, Cry9Ea, Cry9Eb, Cry9Ec, Cry9Ed, Cry9Ee, Cry9Fa, Cry9Ga, Cry10Aa, Cry11Aa, Cry11Ba, Cry11Bb, Cry12Aa, Cry13Aa, Cry14Aa, Cry14Ab, Cry15Aa, Cry16Aa, Cry17Aa, Cry18Aa, Cry18Ba, Cry18Ca, Cry19Aa, Cry19Ba, Cry19Ca, Cry20Aa, Cry20Ba, Cry21Aa, Cry21Ba, Cry21Ca, Cry21 Da, Cry21Ea, Cry21Fa, Cry21Ga, Cry21Ha, Cry22Aa, Cry22Ab, Cry22Ba, Cry22Bb, Cry23Aa, Cry24Aa, Cry24Ba, Cry24Ca, Cry25Aa, Cry26Aa, Cry27Aa, Cry28Aa, Cry29Aa, Cry29Ba, Cry30Aa, Cry30Ba, Cry30Ca, Cry30 Da, Cry30Db, Cry30Ea, Cry30Fa, Cry30Ga, Cry31Aa, Cry31Ab, Cry31Ac, Cry31Ad, Cry32Aa, Cry32Ab, Cry32Ba, Cry32Ca, Cry32Cb, Cry32 Da, Cry32Ea, Cry32Eb, Cry32Fa, Cry32Ga, Cry32Ha, Cry32Hb, Cry32Ia, Cry32Ja, Cry32Ka, Cry32La, Cry32Ma, Cry32 Mb, Cry32Na, Cry32Oa, Cry32 Pa, Cry32Qa, Cry32Ra, Cry32Sa, Cry32Ta, Cry32Ua, Cry33Aa, Cry34Aa, Cry34Ab, Cry34Ac, Cry34Ba, Cry35Aa, Cry35Ab, Cry35Ac, Cry35Ba, Cry36Aa, Cry37Aa, Cry38Aa, Cry39Aa, Cry40Aa, Cry40Ba, Cry40Ca, Cry40 Da, Cry41Aa, Cry41Ab, Cry41Ba, Cry42Aa, Cry43Aa, Cry43Ba, Cry43Ca, Cry43Cb, Cry43Cc, Cry44Aa, Cry45Aa, Cry46Aa, Cry46Ab, Cry47Aa, Cry48Aa, Cry48Ab, Cry49Aa, Cry49Ab, Cry50Aa, Cry50Ba, Cry51Aa, Cry52Aa, Cry52Ba, Cry53Aa, Cry53Ab, Cry54Aa, Cry54Ab, Cry54Ba, Cry55Aa, Cry56Aa, Cry57Aa, Cry57Ab, Cry58Aa, Cry59Aa, Cry59Ba, Cry60Aa, Cry60Ba, Cry61Aa, Cry62Aa, Cry63Aa, Cry64Aa, Cry65Aa, Cry66Aa, Cry67Aa, Cry68Aa, Cry69Aa, Cry69Ab, Cry70Aa, Cry70Ba, Cry70Bb, Cry71Aa, Cry72Aa, Cry73Aa, or any combination of the foregoing. In embodiments, the Cry protein is a mCry3A protein (e.g., in corn event MIR604), a eCry3.1Ab protein (e.g., in corn event 5307), a Cry3Bb1 protein (e.g., in corn event MON88017) and/or a Cry34/35Ab1 binary protein (e.g., in corn event DAS-59122).

In further embodiments, the second pest control agent is one or more Vip3 vegetative insecticidal proteins selected from Vip3Aa1, Vip3Aa2, Vip3Aa3, Vip3Aa4, Vip3Aa5, Vip3Aa6, Vip3Aa7, Vip3Aa8, Vip3Aa9, Vip3Aa10, Vip3Aa11, Vip3Aa12, Vip3Aa13, Vip3Aa14, Vip3Aa15, Vip3Aa16, Vip3Aa17, Vip3Aa18, Vip3Aa19, Vip3Aa20, Vip3Aa21, Vip3Aa22, Vip3Aa2, Vip3Aa24, Vip3Aa25, Vip3Aa26, Vip3Aa27, Vip3Aa28, Vip3Aa29, Vip3Aa30, Vip3Aa31, Vip3Aa32, Vip3Aa33, Vip3Aa34, Vip3Aa35, Vip3Aa36, Vip3Aa37, Vip3Aa38, Vip3Aa39, Vip3Aa40, Vip3Aa41, Vip3Aa42, Vip3Aa43, Vip3Aa44, Vip3Ab1, Vip3Ab2, Vip3Ac1, Vip3Ad1, Vip3Ad2, Vip3Ae1, Vip3Af1, Vip3Af2, Vip3Af3, Vip3Ag1, Vip3Ag2, Vip3Ag3, HM117633, Vip3Ag4, Vip3Ag5, Vip3Ah1, Vip3Ba1, Vip3Ba2, Vip3Bb1, Vip3Bb2, Vip3Bb3, or any combination of the foregoing. In embodiments, the Vip3 protein is Vip3Aa (U.S. Pat. No. 6,137,033), for example, as represented by corn event MIR162 (U.S. Pat. Nos. 8,232,456; 8,455,720; and 8,618,272).

In embodiments, the second pest control agent may be derived from sources other than *B. thuringiensis*. For example, the second pest control agent can be an alpha-amylase, a peroxidase, a cholesterol oxidase, a patatin, a protease, a protease inhibitor, a urease, an alpha-amylase inhibitor, a pore-forming protein, a chitinase, a lectin, an engineered antibody or antibody fragment, a *Bacillus cereus* insecticidal protein, a *Xenorhabdus* spp. (such as *X. nematophila* or *X. bovienii*) insecticidal protein, a *Photorhabdus* spp. (such as *P. luminescens* or *P. asymobiotica*) insecticidal protein, a *Brevibacillus* spp. (such as *B. laterosporous*) insecticidal protein, a *Lysinibacillus* spp. (such as *L. sphearicus*) insecticidal protein, a *Chromobacterium* spp. (such as *C. subtsugae* or *C. piscinae*) insecticidal protein, a *Yersinia* spp. (such as *Y. entomophaga*) insecticidal protein, a *Paenibacillus* spp. (such as *P. propylaea*) insecticidal protein, a *Clostridium* spp. (such as *C. bifermentans*) insecticidal protein, a *Pseudomonas* spp. (such as *P. fluorescens*) and a lignin. In other embodiments, the second agent may be at least one insecticidal protein derived from an insecticidal toxin complex (Tc) from *Photorhabdus, Xenorhabus, Serratia*, or *Yersinia*. In other embodiments. The insecticidal protein may be an ADP-ribosyltransferase derived from an insecticidal bacteria, such as *Photorhabdus* ssp. In other embodiments, the insecticidal protein may be a non-Bt VIP protein, such as VIP1 and/or VIP2 from *B. cereus*. In still other embodiments, the insecticidal protein may be a binary toxin derived from an insecticidal bacteria, such as ISP1A and ISP2A from *B. laterosporous* or BinA and BinB from *L. sphaericus*. In still other embodiments, the insecticidal protein may be engineered or may be a hybrid or chimera of any of the preceding insecticidal proteins.

In some embodiments, the second pesticidal agent can be non-proteinaceous, for example, an interfering RNA molecule such as a dsRNA, which can be expressed transgenically or applied as part of a composition (e.g., using topical methods). An interfering RNA typically comprises at least a RNA fragment against a target gene, a spacer sequence, and a second RNA fragment which is complementary to the first, so that a double-stranded RNA structure can be formed. RNA interference (RNAi) occurs when an organism recognizes double-stranded RNA (dsRNA) molecules and hydrolyzes them. The resulting hydrolysis products are small RNA fragments of about 19-24 nucleotides in length, called small interfering RNAs (siRNAs). The siRNAs then diffuse or are carried throughout the organism, including across cellular membranes, where they hybridize to mRNAs (or other RNAs) and cause hydrolysis of the RNA. Interfering RNAs are recognized by the RNA interference silencing complex (RISC) into which an effector strand (or "guide strand") of the RNA is loaded. This guide strand acts as a template for the recognition and destruction of the duplex sequences. This process is repeated each time the siRNA hybridizes to its complementary-RNA target, effectively preventing those mRNAs from being translated, and thus "silencing" the expression of specific genes from which the mRNAs were transcribed. Interfering RNAs are known in the art to be useful for insect control (see, for example, publication WO2013/192256, incorporated by reference herein). An interfering RNA designed for use in insect control produces a non-naturally occurring double-stranded RNA, which takes advantage of the native RNAi pathways in the insect to trigger down-regulation of target genes that may lead to the cessation of feeding and/or growth and may result in the death of the insect pest. The interfering RNA molecule may confer insect resistance against the same target pest as the protein of the invention, or may target a different pest. The targeted insect plant pest may feed by chewing, sucking, or piercing. Interfering RNAs are known in the art to be useful for insect control. In embodiments, the dsRNA useful for insect control is described in U.S. Provisional Application No. 62/371,259, 62/371,261, or 62/371,262, filed on Aug. 5, 2016. In embodiments, the dsRNA useful for insect control is described in U.S. Pat. Nos. 7,812,219; 9,238,822; 9,340,797; 8,946,510; or US patent publication US2014/0275208. In embodiments, the dsRNA useful for insect control is described in U.S. patent application Ser. No. 12/868,994; 14/207,313; or 14/207,318. In embodiments, the dsRNA targets a gene encoding a vacuolar ATP synthase, a beta-tubulin, a 26S proteosome subunit p28 protein, a EF1α 48D, a troponin I, a tetraspanin, a gamma-coatomer, a beta-coatomer, and/or a juvenile hormone epoxide hydrolase. In embodiments, the dsRNA is a DvSnf7 dsRNA (e.g., in corn event MON87411).

In embodiments, the interfering RNA confers resistance against a non-insect plant pest, such as a nematode pest or a virus pest.

In still further embodiments, the first insect control agent, which is an insecticidal protein of the invention and the second pest control agent are co-expressed in a transgenic plant. This co-expression of more than one pesticidal principle in the same transgenic plant can be achieved by genetically engineering a plant to contain and express the nucleic acid sequences encoding the insect control agents. For example, the co-expression of more than one pesticidal agent in the same transgenic plant can be achieved by making a single recombinant vector comprising coding sequences of more than one pesticidal agent in a "molecular stack" and genetically engineering a plant to contain and express all the pesticidal agents in the transgenic plant. Such molecular stacks may be also be made by using mini-chromosomes as described, for example in U.S. Pat. No. 7,235,716. Alternatively, a plant, Parent 1, can be genetically engineered for the expression of the insecticidal protein of the invention. A second plant, Parent 2, can be genetically engineered for the expression of a second pest control agent. By crossing Parent 1 with Parent 2, progeny plants are obtained which express both insect control agents from Parents 1 and 2 (i.e., a breeding stack).

In other embodiments, the invention provides a stacked transgenic plant resistant to plant pest infestation comprising a nucleic acid (e.g., DNA) sequence encoding a dsRNA for suppression of an essential gene in a target pest and a nucleic acid e.g., (DNA) sequence encoding an insecticidal protein of the invention exhibiting insecticidal activity against the target pest. It has been reported that dsRNAs are ineffective against certain lepidopteran pests (Rajagopol et al. 2002. J. Biol. Chem. 277:468-494), likely due to the high pH of the midgut which destabilizes the dsRNA. Therefore, in some embodiments where the target pest is a lepidopteran pest, an insecticidal protein of the invention may act to transiently reduce the midgut pH which serves to stabilize the co-ingested dsRNA rendering the dsRNA effective in silencing the target genes.

Transgenic plants or seed comprising and/or expressing an insecticidal protein of the invention can also be treated with an insecticide or insecticidal seed coating as described in U.S. Pat. Nos. 5,849,320 and 5,876,739. In embodiments, where both the insecticide or insecticidal seed coating and the transgenic plant or seed of the invention are active against the same target insect, for example a coleopteran pest (e.g., a corn rootworm, for example, WCRW), the combination is useful (i) in a method for further enhancing activity of the composition of the invention against the target insect, and/or (ii) in a method for preventing development of resistance to the composition of the invention by providing yet another mechanism of action against the target insect. Thus, in embodiments, the invention provides a method of enhancing control of a coleopteran insect population comprising providing a transgenic plant or seed of the invention and applying to the plant or the seed an insecticide or insecticidal seed coating to a transgenic plant or seed of the invention.

Even where the insecticide or insecticidal seed coating is active against a different insect, the insecticide or insecticidal seed coating is useful to expand the range of insect control, for example by adding an insecticide or insecticidal seed coating that has activity against lepidopteran insects to a transgenic seed of the invention, which, in some embodiments, has activity against coleopteran insects, the coated transgenic seed produced controls both lepidopteran and coleopteran insect pests.

Methods of Making and Using the Insecticidal Proteins, Nucleic Acids, and Transgenic Plants.

The invention also encompasses methods of producing an insect-resistant (e.g., a coleopteran insect-resistant) transgenic plant. In representative embodiments, the method comprises: introducing into a plant a polynucleotide, expression cassette or vector of the invention comprising a nucleotide sequence that encodes an insecticidal protein of the invention (including toxin fragments and modified forms that are substantially identical to the polypeptides specifically disclosed herein), wherein the nucleotide sequence is expressed in the plant to produce the insecticidal protein of the invention, thereby conferring to the plant resistance to the insect pest, and producing an insect-resistant transgenic plant (e.g., as compared with a suitable control plant, such as a plant that does not comprise the polynucleotide, expression cassette or vector of the invention and/or does not express a polypeptide of the invention).

In embodiments, the method of introducing the polynucleotide, expression cassette or vector of the invention into the plant comprises first transforming a plant cell with the polynucleotide, expression cassette or vector and regenerating a transgenic plant therefrom, where the transgenic plant comprises the polynucleotide, expression cassette or vector and expresses the insecticidal protein of the invention.

Alternatively, or additionally, the introducing step can comprise crossing a first plant comprising the polynucleotide, expression cassette or vector with a second plant (e.g., a different plant from the first plant, for example, a plant that does not comprise the polynucleotide, expression cassette or vector) and, optionally, producing a progeny plant that comprises the polynucleotide, expression cassette or vector and expresses an insecticidal protein of the invention, thereby resulting in increased resistance to at least one insect pest. Thus, a transgenic plant of the invention encompasses a plant that is the direct result of a transformation event and the progeny thereof (of any generation) that comprise the polynucleotide, expression cassette or vector and optionally expresses the insecticidal protein resulting in increased resistance to at least one insect pest.

As a further option, genome editing techniques can be used to modify in situ a transgene encoding a native Axmi205 protein (SEQ ID NO: 1) or a variant Axmi205 (for example, the Axmi205 variants described in WO2013/016617 to Athenix; and US 2014/0274885 A1 to Pioneer Hi-Bred) to incorporate the mutations of the invention. To illustrate, in a plant comprising a heterologous polynucleotide sequence encoding a native Axmi205 protein or a variant thereof, the coding sequence of the native or variant Axmi205 can be further modified in situ by targeted DNA editing using various genome editing techniques such as zinc finger nucleases (ZNFs), transcription activator-like effector nucleases (TALENS), meganucleases and Clustered Regularly Interspaced Short Palindromic Repeats (CRISPR) (U.S. Pat. No. 8,697,359; Ran et al.). The CRISPR system can be used to introduce specific nucleotide modifications at the target sequence. Originally discovered in bacteria, where several different CRISPR cascades function as innate immune systems and natural defense mechanisms, the engineered CRISPR-Cas9 system can be programmed to target specific stretches of genetic code and to make cuts at precise locations. Over the past few years, those capabilities have been harnessed and used as genome editing tools, enabling researchers to permanently modify genes in plant cells.

Thus, the invention encompasses methods for generating a polynucleotide encoding a modified Axmi205 protein of the invention wherein said method comprises modifying a plant genome comprising a polynucleotide encoding a native Axmi205 protein (e.g., SEQ ID NO: 1) or an Axmi205 variant using a gene editing technique such as CRISPR to incorporate one or more mutations according to the present invention. In embodiments, the method involves targeting of Cas9 to the specific genomic locus, in this case a native Axmi205 protein-encoding polynucleotide or a polynucleotide encoding an Axmi205 variant, via a 20nt guide sequence of the single-guide RNA. An online CRISPRO Design Tool can identify suitable target sites (on the world wide web at tools.genome-engineering.org; Ran et al., Genome engineering using the CRISPR-Cas9 system. Nature Protocols I; 2281-2308 (2013)). Target plants for the mutagenesis/genome editing methods according to the invention are any monocot or dicot plant (each as described further herein) into which a polynucleotide encoding a native Axmi205 protein or Axmi205 mutant protein has been introduced.

Optionally, the methods of producing a transgenic plant with increased resistance to an insect pest (e.g., a coleopteran insect pest, such as WCRW) further comprises obtaining a progeny plant for one or more generations, wherein the progeny plant comprises the polynucleotide, the nucleic acid molecule or the vector and has increased resistance to a coleopteran insect pest.

The invention further provides a method of identifying a transgenic plant of the invention, the method comprising detecting the presence of a polynucleotide, expression cassette, vector or insecticidal protein of the invention in a plant (or a plant cell, plant part, and the like derived therefrom), and thereby identifying the plant as a transgenic plant of the invention based on the presence of the polynucleotide, expression cassette, vector or insecticidal protein of the invention.

The invention further provides a method of producing a transgenic plant with increased resistance to at least one insect pest (e.g., a least one coleopteran pest), the method comprising: planting a seed comprising a polynucleotide, expression cassette or vector of the invention, and growing a transgenic plant from the seed, where the transgenic plant comprises the polynucleotide, expression cassette or vector and produces the insecticidal protein.

In embodiments, transgenic plants produced by the methods of the invention comprise a polynucleotide, expression cassette or vector of the invention. In embodiments, a transgenic plant produced by the methods of the invention comprise an insecticidal protein of the invention and, optionally have increased resistance to at least one insect pest.

The methods of producing a transgenic plant described herein optionally comprise a further step of harvesting a seed from the transgenic plant, where the seed comprises the polynucleotide, expression cassette or vector and produces the insecticidal protein. Optionally, the seed produces a further transgenic plant that comprises the polynucleotide, expression cassette or vector and produces the insecticidal protein, and thereby has increased resistance to at least one insect pest.

The invention further provides plant parts, plant cells, plant organs, plant cultures, seed, plant extracts, harvested products and processed products of the transgenic plants produced by the methods of the invention.

As a further aspect, the invention also provides a method of producing seed, the method comprising: providing a transgenic plant that comprises a polynucleotide, expression cassette or vector of the invention, and harvesting a seed from the transgenic plant, wherein the seed comprises the polynucleotide, expression cassette, vector and produces the insecticidal protein. Optionally, the seed produces a further transgenic plant that comprises the polynucleotide, expression cassette or vector and produces the insecticidal protein, and thereby has increased resistance to at least one insect pest. In representative embodiments, the step of providing the transgenic plant comprises planting a seed that produces the transgenic plant.

The invention further provides a method of producing a hybrid plant seed, the method comprising: crossing a first inbred plant, which is a transgenic plant comprising a polynucleotide, expression cassette or vector of the invention, and optionally expressing an insecticidal protein of the invention with a different inbred plant (e.g., an inbred plant that does not comprise a polynucleotide, expression cassette or vector of the invention) and allowing hybrid seed to form. Optionally, the method further comprises harvesting a hybrid seed. In embodiments, the hybrid seed comprises the polynucleotide, expression cassette or vector of the invention, and in embodiments may further comprise an insecticidal protein of the invention and have increased resistance to an insect pest. In embodiments, the hybrid seed produces a transgenic plant that comprises the polynucleotide, expression cassette or vector of the invention, expresses the insecticidal protein of the invention, and has increased resistance to at least one insect pest.

In some embodiments, a transgenic plant of the invention controls at least one coleopteran insect pest (as described herein). In embodiments, the transgenic plant controls a corn rootworm insect pest or colony (e.g., a WCRW insect pest or colony) that is resistant to a mCry3A protein (e.g., in corn event MIR604), a eCry3.1Ab protein (e.g., in corn event 5307), a Cry3Bb1 protein (e.g., in corn event MON88017), a Cry34/35Ab1 binary protein (e.g., in corn event DAS-59122) and/or a RNAi trait, such as DvSnf7 dsRNA (e.g., in corn event MON87411).

In further embodiments, a method of controlling at least one insect pest (e.g., at least one coleopteran insect pest, such as a corn rootworm, for example, WCRW) comprises providing an insecticidal protein of the invention. In embodiments, the method comprises delivering (e.g., orally delivering) to the insect pest or an environment thereof an effective amount of an insecticidal protein of the invention. Generally, to be effective, the polypeptide is orally ingested by the insect. However, the insecticidal protein can be delivered to the insect in many recognized ways. The ways to deliver a protein orally to an insect include, but are not limited to, providing the protein (1) in a transgenic plant, wherein the insect eats (ingests) one or more parts of the transgenic plant, thereby ingesting the polypeptide that is expressed in the transgenic plant; (2) in a formulated protein composition(s) that can be applied to or incorporated into, for example, insect growth media; (3) in a protein composition(s) that can be applied to the surface, for example, sprayed, onto the surface of a plant part, which is then ingested by the insect as the insect eats one or more of the sprayed plant parts; (4) a bait matrix; or (5) any other art-recognized protein delivery system. Thus, any method of oral delivery to an insect can be used to deliver the toxic proteins of the invention. In some particular embodiments, the insecticidal protein of the invention is delivered orally to an insect, for example, where the insect ingests one or more parts of a transgenic plant of the invention.

In other embodiments, the insecticidal protein of the invention is delivered orally to an insect, wherein the insect ingests one or more parts of a plant sprayed with a composition comprising the insecticidal protein of the invention. Delivering the composition of the invention to a plant surface can be done using any method known to those of skill in the art for applying compounds, compositions, formulations and the like to plant surfaces. Some non-limiting examples of delivering to or contacting a plant or part thereof include spraying, dusting, sprinkling, scattering, misting, atomizing, broadcasting, soaking, soil injection, soil incorporation, drenching (e.g., root, soil treatment), dipping, pouring, coating, leaf or stem infiltration, side dressing or seed treatment, and the like, and combinations thereof. These and other procedures for contacting a plant or part thereof with a compound(s), composition(s) or formulation(s) are well-known to those of skill in the art.

In further embodiments, the invention provides a method of controlling a coleopteran insect pest that is resistant to a mCry3A protein (e.g., in corn event MIR604), a eCry3.1Ab protein (e.g., in corn event 5307), a Cry3Bb1 protein (e.g., in corn event MON88017), a Cry34/35Ab1 binary protein (e.g., in corn event DAS-59122) and/or a RNAi trait, such as DvSnf7 dsRNA (e.g., in corn event MON87411), the method comprising delivering to the coleopteran insect or an environment thereof an effective amount of an insecticidal protein or composition of the invention. In representative embodiments, the resistant insect pest is a resistant corn rootworm (e.g., WCRW) insect pest or colony.

In other embodiments, the invention provides a method of reducing or preventing the development of resistance in a population of a target coleopteran insect pest to a mCry3A protein (e.g., in corn event MIR604), a eCry3.1Ab protein (e.g., in corn event 5307), a Cry3Bb1 protein (e.g., in corn event MON88017), a Cry34/35Ab1 binary protein (e.g., in corn event DAS-59122) and/or a RNAi trait, such as DvSnf7 dsRNA (e.g., in corn event MON87411) expressed in a transgenic plant, the method comprising delivering to the target coleopteran insect population a transgenic plant comprising a polynucleotide comprising a nucleotide sequence encoding a mCry3A protein, a nucleotide sequence encoding a eCry3.1Ab protein, a nucleotide sequence encoding a Cry3Bb1 protein, a nucleotide sequence(s) encoding a Cry34/35Ab1 binary protein and/or a nucleotide sequence encoding a RNAi trait; and a polynucleotide, expression cassette or vector of the invention expressing an insecticidal protein of the invention. In some embodiments, the target coleopteran insect pest is a corn rootworm (e.g., WCRW). According to foregoing embodiments, the transgenic plant can comprise a breeding stack of two or more of the insecticidal traits, a molecular stack of two or more of the insecticidal traits, or a combination of both.

In some embodiments, the invention encompasses a method of providing a farmer with a means of controlling an insect pest (e.g., a coleopteran pest, such as a corn rootworm, for example, WCRW), the method comprising supplying or selling to the farmer plant material such as a seed, the plant material comprising a polynucleotide, expression cassette, vector capable of expressing an insecticidal protein of the invention. In embodiments, the plant material comprises the insecticidal protein of the invention and, optionally, has increased resistance to at least one insect pest. In embodiments, the plant material is a seed, and a plant grown from the seed comprises the polynucleotide, expression cassette or vector of the invention, expresses an insecticidal protein of the invention, and has increased resistance to the at least one insect pest.

In addition to providing compositions, the invention provides methods of producing an insecticidal protein toxic to a coleopteran pest. Such a method comprises, culturing a transgenic non-human host cell that comprises a polynucleotide, expression cassette or vector of the invention that expresses an insecticidal protein of the invention under conditions in which the host cell produces the insecticidal protein that is toxic to the coleopteran pest. In some embodiments, the transgenic non-human host cell is a plant cell. In some other embodiments, the plant cell is a maize cell. In other embodiments, the conditions under which the plant cell or maize cell are grown include natural sunlight. In other embodiments, the transgenic non-human host cell is a bacterial cell. In still other embodiments, the transgenic non-human host cell is a yeast cell.

In embodiments, the methods of the invention provide control of at least one coleopteran, lepidopteran, dipteran, hemipteran, orthopteran and/or thysanopteran insect pest (each as described in more detail herein). In embodiments, the insecticidal protein is active against a coleopteran pest, including without limitation: *Diabrotica* spp. (for example, *Diabrotica barberi* (northern corn rootworm); *D. virgifera virgifera* (western corn rootworm); *D. undecimpunctata howardii* (southern corn rootworm); *D. balteata* (banded cucumber beetle); *D. undecimpunctata undecimpunctata* (western spotted cucumber beetle); *D. significata* (3-spotted leaf beetle); *D. speciosa* (chrysanthemum beetle); *D. virgifera zeae* (Mexican corn rootworm); *D. beniensis; D. cristata, D. curviplustalata; D. dissimilis; D. elegantula; D. emorsitans; D. graminea; D. hispanloe; D. lemniscata; D. linsleyi; D. milleri; D. nummularis; D. occlusal; D. porrecea; D. scutellata; D. tibialis; D. trifasciata* and *D. viridula*; and any combination thereof), *Leptinotarsa* spp. (for example, *L. decemlineata*; Colorado potato beetle); *Chrysomela* spp. (for example, *C. scripta*; cottonwood leaf beetle); *Hypothenemus* spp. (for example, *H. hampei*; coffee berry borer); *Sitophilus* spp. (for example, *S. zeamais*; maize weevil); *Epitrix* spp. (for example, *E. hirtipennis* [tobacco flea beetle] and *E. cucumeris* [potato flea beetle]); *Phyllotreta* spp. (for example, *P. cruciferae* [crucifer flea beetle] and *P. pusilla* [western black flea beetle]; *Anthonomus* spp. (for example, *A. grandis* [boll weevil]) and *A. eugenii* [pepper weevil]); *Hemicrepidus* spp. (for example, *H. memnonius*; wireworms); *Melanotus* spp. (for example, *M. communis*; wireworm); *Ceutorhychus* spp. (for example, *C. assimilis*; cabbage seedpod weevil); *Phyllotreta* spp. (for example, *P. cruciferae*; crucifer flea beetle); *Aeolus* spp. (for example, *A. mellillus*; wireworm); *Aeolus* spp. (for example, *A. mancus*; wheat wireworm); *Horistonotus* spp. (for example, *H. uhlerii*; sand wireworm); *Sphenophorus* spp. (for example, *S. maidis* [maize billbug], *S. zeae* [timothy billbug], *S. parvulus* [bluegrass billbug], and *S. callosus* [southern corn billbug]); *Phyllophaga* spp. (for example, white grubs); *Chaetocnema* spp. (for example, *C. pulicaria*; corn flea beetle); *Popillia* spp. (for example, *P. japonica*; Japanese beetle); *Epilachna* spp. (for example, *E. varivestis*; Mexican bean beetle); *Cerotoma* spp. (for example, *C. trifurcate*; Bean leaf beetle); *Epicauta* spp. (for example, *E. pestifera* and *E. lemniscata*; Blister beetles); and any combination of the foregoing.

In embodiments, the methods of the invention provide control of a corn rootworm (e.g., WCRW) insect pest or colony that is resistant to a mCry3A protein (e.g., in corn event MIR604), a eCry3.1Ab protein (e.g., in corn event 5307), a Cry3Bb1 protein (e.g., in corn event MON88017), a Cry34/35Ab1 binary protein (e.g., in corn event DAS-59122) and/or a RNAi trait, such as DvSnf7 dsRNA (e.g., maize event MON87411).

The invention also provides for uses of the insecticidal proteins, nucleic acids, transgenic plants, plant parts, seed and insecticidal compositions of the invention, for example, to control an insect pest, such as a coleopteran pest (as described herein).

In embodiments, the invention provides a method of using a polynucleotide, expression cassette, vector or host cell of the invention to produce an insecticidal composition for controlling an insect pest (e.g., a coleopteran insect pest).

In embodiments, the invention provides a method of using a polynucleotide, expression cassette or vector of the invention to produce a transgenic seed, where the transgenic seed grows a transgenic plant with increased resistance to an insect pest.

As another aspect, the invention also contemplates the use of a transgenic plant of the invention to produce a transgenic seed, which is optionally a hybrid seed.

In embodiments, the invention provides a method of using an insecticidal protein, polynucleotide, expression cassette, vector, transgenic plant or insecticidal composition of the invention to prevent the development of resistance in a population of a target coleopteran insect pest to a mCry3A protein (e.g., in corn event MIR604), a eCry3.1Ab protein (e.g., in corn event 5307), a Cry3Bb1 protein (e.g., in corn event MON88017), a Cry34/35Ab1 binary protein (e.g., in corn event DAS-59122) and/or a RNAi trait such as DvSnf7 dsRNA (e.g., maize event MON87411).

The invention will now be described with reference to the following examples. It will be appreciated by those skilled in the art that these examples do not limit the scope of the claims to the invention, but are rather intended to be exemplary of certain embodiments. Other embodiments of the invention may be practiced without departing from the spirit and the scope of the invention, the scope of which is defined by the disclosure and the appended claims.

Example 1

Mutant Selection

Axmi205 is an insecticidal protein, isolated from *Chromobacterium piscinae* and previously described in U.S. Pat. No. 8,575,425 B2 and Sampson et al. (Discovery of a novel insecticidal protein from *Chromobacterium piscinae*, with activity against Western Corn Rootworm, *Diabrotica virgifera virgifera*, J. Invertebrate Pathology 142: 34-43 (2016)). See also GenBank Accession No. AML23188.1. The amino acid and cDNA sequences of native Axmi205 are provided as SEQ ID NO: 1 and SEQ ID NO: 2, respectively.

Previous experiments had determined that the native amino acid sequence of Axmi205 (SEQ ID NO: 1) showed delayed digestion in a standard Simulated Gastric Fluid (SGF) assay, with an undigested 23 kDa band still present at the 30 minutes time period, rendering this toxin less desirable from a regulatory standpoint. The SGF assay is used to approximate the digestion of the protein in the mammalian gut, and is a standard component of the evaluation of any new insecticidal protein for regulatory approval.

Mass spectrometry analysis identified the 23 kDa band as consisting of the entire second domain of the protein, corresponding approximately to residues 303-526 of the native Axmi205 protein (SEQ ID NO: 1). Sites of likely pepsin cleavage in the native Axmi205 protein were predicted using published guidelines for pepsin cleavage at pH<1.3 (Keil, B. *Specificity of proteolysis*. Springer-Verlag Berlin-Heidelberg-New York, pp. 335. (1992)). Stretches of the native Axmi205 protein without predicted pepsin cleavage sites were identified, and residues within these regions were selected for mutational analysis to increase proteolytic cleavage of the protein (e.g., by pepsin) while maintaining insecticidal activity. For example, in some mutants, one or more hydrophobic amino acids were substituted or inserted into the native Axmi205 protein sequence. In other cases, cysteine residues were replaced to reduce the possibility of disulfide bond formation, possibly opening up the tertiary protein structure to facilitate enzyme access. See FIG. 1.

Example 2

Production of Native Axmi205 and Engineered Axmi205 Variants

Expression vector pEBDuet28A containing the native Axmi205 cDNA sequence (SEQ ID NO: 2) with a Tobacco Etch Virus (TEV) protease removable N-terminal 10×His tag was used as the starting molecule for all engineered Axmi205 (eAxmi205) mutant production. A DNA fragment containing the Axmi205 mutations was synthesized and subsequently cloned into the EcoRI-SalI sites of the Axmi205 source vector.

Vectors expressing the eAxmi205 variants were transformed into *E. coli* BL21*(DE3) (INVITROGEN™) for protein production. Briefly, 100 mL cultures of Terrific Broth media were grown at 37° C. until mid-log phase ($OD_{600}$=0.6-1.0), upon which protein expression was induced using 0.1 mM IPTG (Isopropyl β-D-1-thiogalactopyranoside) and subsequently transferred to 18° C. overnight. Cells were harvested by centrifugation and lysed using mechanical lysis. Bacterial lysates were clarified and passed over His GRAVITRAP™ (GE Healthcare) nickel columns to isolate the protein of interest. Unbound proteins were removed via washing, and the eAxmi205 variants were then eluted using imidazole. Protein-containing fractions were pooled and dialyzed against 1×PBS overnight at 4° C. The protein concentration was determined, and the protein was aliquoted and snap frozen in liquid nitrogen for long term storage at −80° C.

Example 3

Simulated Gastric Fluid T10 Protocol

As a preliminary screen, purified eAxmi205 mutants were tested for digestability after 10 minutes (T10) of exposure to simulated gastric fluid (SGF). Briefly, test proteins were normalized to a common concentration (typically ~1 mg/mL) to allow for a single stock of SGF to be produced at the proper ratio of pepsin to test protein (approximately 1111 U pepsin/mL, in G-Con solution {2 mg/mL NaCl, pH 1.2}). The digestion reaction was initiated by adding 30 μL of test protein to 270 μL SGF at 37° C. At 10 minutes (T10), 100 μL of the test protein-SGF reaction mixture was removed and the reaction terminated by adding the test mixture aliquot to 100 μL of preheated (95° C.) Stop Solution comprised of 65% Tricine Loading Buffer (Bio-Rad 2× Tricine Load Buffer w/10% β-mercaptoethanol) and 35% 500 mM NaHCO$_3$ pH 11.0. A time zero (T0) data point was produced by adding 10 μL of test protein to 100 μL of preheated (95° C.) Stop Solution and 95 uL of SGF. All samples were heated at 95° C. for 5 minutes, and then stored on ice until SDS-PAGE analysis.

For SDS-PAGE, 30 μL of each reaction was loaded on a 10-20% Tris-tricine peptide gel (Bio-Rad) prior to standard protein gel electrophoresis. After electrophoresis for 20 minutes, the Tris-tricine gel was immediately fixed with a 40% methanol:10% acetic acid mixture. The gel was then stained with GELCODE™ Blue protein stain (ThermoFisher Scientific) for 1 hour at room temperature. After 1 hour, the gel was de-stained with distilled water overnight.

On SDS-PAGE, the native Axmi205 retains a band at approximately 23 kDa at T10. Mutants were identified in which no undigested fragments were observed that were larger than approximately 3-4 kDa at T10, indicating that these eAxmi205 mutants are likely to exhibit more complete digestion by pepsin as compared with the native Axmi205 protein, and were selected for further evaluation of insecticidal bioactivity and a more complete SGF digestion profile.

Example 4 eAxmi205 Bioactivity Against Western Corn Rootworm eAxmi205 mutants that showed loss of the ~23 kDa band at 10 minutes in the preliminary SGF testing (Example 2) were then evaluated for bioactivity against Western Corn Rootworm (WCRW; *Diabrotica virgifera virgifera*) larvae in an artificial diet bioassay.

Samples of purified protein for each mutant were normalized to 0.4 mg/mL (200 μg/mL final) and combined with an equal volume of heated artificial insect diet (Bioserv, Inc., Frenchtown N.J.) in 1.5 mL centrifuge tubes and then applied to small petri-dishes. After the diet-sample mixture cooled and solidified, 12 WCRW newly hatched larvae were added to each dish, and the dish was subsequently sealed. Petri dishes were kept at ambient conditions with regard to temperature, lighting and relative humidity. Protein storage buffer (i.e., PBS) was used as a negative control, and native Axmi205 used as the positive control. Mortality was assessed on day 3 or 4 and again on day 6.

eAxmi205 mutants showing bioactivity to WCRW were subjected to a more complete evaluation for digestion in SGF.

Example 5

SGF Time Course Assay

A full time course of SGF digestion was conducted on mutants that both passed the initial SGF T10 test (Example 2) and retained bioactivity to WCRW (Example 3).

In summary, solid pepsin (~3 mg, ~3640 U/mg solid) was dissolved in 1 mL G-Con solution (2 mg/mL NaCl, pH 1.2) to create a concentrated stock of pepsin. The pepsin stock was diluted to the appropriate concentration in G-Con solution to make 10 U pepsin/μg protein (determined by the initial test protein stock concentration), to produce the final SGF solution for use in the assay. The digestion reaction was initiated (T0) by adding 70 μL of the test protein stock to 630 μL of the SGF solution at 37° C. The reaction was stopped by removing 100 μL of the reaction mixture at 1, 2, 5, 10, 30 and 60 minutes (i.e., T1, T2, T5, T10, T30 and T60) and mixing with 100 μL Stop Solution (65% Tricine Loading buffer with 5% β-mercaptoethanol, 35% 500 mM NaHCO$_3$ pH 11.0) preheated to 95° C. Controls include a T0 control (10 μL test protein+100 μL Stop Solution+90 μL SGF), a SGF control (90 μL SGF+10 μL buffer+100 μL Stop Solution at T0 and T60), and a test protein control (90 μL G-Con solution+10 μL test protein+100 μL Stop Solution at T0 and T60). After adding the reaction mixture aliquot to the Stop Solution, all samples were heated at 95° C. for 5 minutes, and then stored on ice until SDS-PAGE analysis.

For SDS-PAGE, 30 μL of each reaction was loaded on a 10-20% Tris-tricine peptide gel (Bio-Rad) prior to standard protein gel electrophoresis. After 20 minutes of electrophoresis, the Tris-tricine gel was immediately fixed with a 40% methanol:10% acetic acid mixture. The gel was then stained with GELCODE™ Blue protein stain (ThermoFisher Scientific) for 1 hour at room temperature. After 1 hour, the gel was de-stained with distilled water overnight.

Standard Western analysis was also done with a polyclonal rabbit anti-Axmi205 antibody to identify immunoreactive bands.

Example 6

Synthesis, Expression and Purification of eAxmi205 Mutants

Thirty-six eAxmi205 mutants that were synthesized and purified are listed in Table 1. Mutants numbered 1 to 30 are substitution mutants, and mutants numbered 31 to 36 are insertion mutants. The amino acid positions of the eAxmi205 mutations indicated in the following tables and discussion are all with reference to the native Axmi205 protein sequence of SEQ ID NO: 1.

TABLE 1

| eAxmi205 Mutations | | | |
|---|---|---|---|
| # | eAxmi205 Mutant | SEQ ID Amino Acid | SEQ ID Coding Sequence |
| 1 | K328Y | 3 | 4 |
| 2 | K328L | 5 | 6 |

TABLE 1-continued eAxmi205 Mutations

| # | eAxmi205 Mutant | SEQ ID Amino Acid | SEQ ID Coding Sequence |
|---|---|---|---|
| 3 | K328F | 7 | 8 |
| 4 | Y404F | 9 | 10 |
| 5 | K402F | 11 | 12 |
| 6 | K402N | 13 | 14 |
| 7 | K402L | 15 | 16 |
| 8 | Y404F + K402L | 17 | 18 |
| 9 | R416L | 19 | 20 |
| 10 | P386L | 21 | 22 |
| 11 | R391L | 23 | 24 |
| 12 | R391I | 25 | 26 |
| 13 | C406S | 27 | 28 |
| 14 | C406L | 29 | 30 |
| 15 | P411L | 31 | 32 |
| 16 | C439S | 33 | 34 |
| 17 | C439L | 35 | 36 |
| 18 | C445S | 37 | 38 |
| 19 | R454F | 39 | 40 |
| 20 | R464L | 41 | 42 |
| 21 | C482S | 43 | 44 |
| 22 | C482L | 45 | 46 |
| 23 | C507S | 47 | 48 |
| 24 | C406S + C439S + C445S + C482S + C507S | 49 | 50 |
| 25 | F378L | 51 | 52 |
| 26 | S495L | 53 | 54 |
| 27 | G496L | 55 | 56 |
| 28 | M422S + M423L | 57 | 58 |
| 29 | V467S + S468L | 59 | 60 |
| 30 | V467S + S468L + W470G | 61 | 62 |
| 31 | 396-Leu-397 | 63 | 64 |
| 32 | 330-Leu-331 | 65 | 66 |
| 33 | 456-Leu-457 | 67 | 68 |
| 34 | 475-Leu-476 | 69 | 70 |
| 35 | 367-Leu-368 | 71 | 72 |
| 36 | 496-Leu-497 | 73 | 74 |

Each of the eAxmi205 proteins was expressed and purified as described in Example 2, although some proteins expressed at lower levels. In these experiments, eAxmi205 mutants #10 and #24 could not be purified in sufficient quantities for further analysis; the other thirty-four eAxmi205 mutant proteins were successfully purified and were further evaluated in a preliminary SGF digestion analysis.

Example 7

Preliminary Evaluation of eAxmi205 Mutants for SGF Digestion

The native eAxmi205 protein shows incomplete digestion in a standard SGF assay, with a persistent band at approximately 23 kDa. The 34 eAxmi205 mutant proteins that were expressed and purified in Example 6 were subjected to a single 10 minute time point (T10) evaluation for SGF digestability following the protocol described in Example 3. Mutants that showed no band at 23 kDa or lower at 10 minutes were deemed to have "passed" this preliminary T10 assessment (data not shown) and were evaluated for bioactivity.

The following eAxmi205 mutants were deemed to "pass" the T10 SGF digestion assessment: #5, #6, #21, #23, #28, #32, #33, #34, #35 and #36.

Several eAxmi205 variants (#8, #29 and #30) were scored as "Fail/Pass" because while they showed much better digestion than native Axmi205, a faint band appeared to be present at 10 minutes. Because this was a preliminary screen, these Axmi205 variants were kept for further evaluation.

The other eAxmi205 mutants "failed" the preliminary T10 SGF digestion because one or more bands were present at 23 kDa or lower at 10 minutes, and were not evaluated further.

Example 8

Control of Western Corn Rootworm by eAxmi205 Mutant Proteins

The eAxmi205 variants from Example 7 (#5, #6, #8, #21, #23, #28, #29, #30, #32, #33, #34, #35 and #36) that had acceptable SGF digestion at 10 minutes were evaluated for activity in controlling WCRW in an artificial diet bioassay following the protocol described in Example 4.

In the artificial diet bioassay, mortality was assessed at day 3 or 4 and on day 6. Native Axmi205 ("Axmi205 wt") was used as a positive control, and buffer alone as a negative control. The data are shown in Tables 2 to 4.

TABLE 2

| | WCR Mortality | | | | | |
|---|---|---|---|---|---|---|
| | Day 4 | | | Day 6 | | |
| Treatment | Total | Dead | Mort % | Total | Dead | Mort % |
| Axmi205 wt @ 0.4 mg/mL (200 μg/mL FINAL) | 12 | 7 | 58% | 12 | 11 | 92% |
| Axmi205 mutant #5 @ 0.4 mg/mL (200 μg/mL FINAL) | 12 | 3 | 25% | 12 | 7 | 58% |
| Axmi205 mutant #6 @ 0.4 mg/mL (200 μg/mL FINAL) | 12 | 8 | 67% | 12 | 9 | 75% |
| Axmi205 mutant #23 @ 0.4 mg/mL (200 μg/mL FINAL) | 12 | 8 | 67% | 12 | 11 | 92% |
| Axmi205 mutant #28 @ 0.4 mg/mL (200 μg/mL FINAL) | 12 | 9 | 75% | 12 | 12 | 100% |
| Axmi205 mutant #32 @ 0.4 mg/mL (200 μg/mL FINAL) | 12 | 1 | 8% | 12 | 1 | 8% |
| Axmi205 mutant #35 @ 0.4 mg/mL (200 μg/mL FINAL) | 12 | 2 | 17% | 12 | 3 | 25% |
| buffer (1x PBS) | 12 | 0 | 0% | 12 | 0 | 0% |

TABLE 3

| | WCR Mortality | | | | | |
| --- | --- | --- | --- | --- | --- | --- |
| | Day 4 | | | Day 6 | | |
| Treatment | Total | Dead | Mort % | Total | Dead | Mort % |
| Axmi205 wt @ 0.4 mg/mL (200 µg/mL FINAL) | 12 | 8 | 67% | 12 | 10 | 83% |
| Axmi205 mutant #8 @ 0.4 mg/mL (200 µg/mL FINAL) | 12 | 10 | 83% | 12 | 12 | 100% |
| Axmi205 mutant #29 @ 0.4 mg/mL (200 µg/mL FINAL) | 12 | 1 | 8% | 12 | 1 | 8% |
| Axmi205 mutant #33 @ 0.4 mg/mL (200 µg/mL FINAL) | 12 | 0 | 0% | 12 | 0 | 0% |
| Axmi205 mutant #34 @ 0.4 mg/mL (200 µg/mL FINAL) | 12 | 10 | 83% | 12 | 12 | 100% |
| Axmi205 mutant #36 @ 0.4 mg/mL (200 µg/mL FINAL) | 12 | 9 | 75% | 12 | 12 | 100% |
| buffer (1x PBS) | 12 | 3 | 25% | 12 | 4 | 33% |

TABLE 4

| | WCR Mortality | | | | | |
| --- | --- | --- | --- | --- | --- | --- |
| | Day 3 | | | Day 6 | | |
| Treatment | Total | Dead | Mort % | Total | Dead | Mort % |
| Axmi205 wt @ 0.4 mg/mL (200 µg/mL FINAL) | 12 | 6 | 50% | 12 | 8 | 67% |
| Axmi205 mutant #21 @ 0.4 mg/mL (200 µg/mL FINAL) | 12 | 5 | 42% | 12 | 9 | 75% |
| Axmi205 mutant #23 @ 0.4 mg/mL (200 µg/mL FINAL) | 12 | 5 | 42% | 12 | 9 | 75% |
| buffer (1x PBS) | 12 | 0 | 0% | 12 | 0 | 0% |

Example 9

Time Course Study of SGF Digestion of eAxmi205 Mutants eAxmi205 mutants #5, #6, #21, #23, #28, #34 and #36 were subjected to a more detailed time course evaluation for digestion by SGF. Each mutant was assessed for SGF digestion after 0, 1, 2, 5, 10, 30 and 60 minutes (i.e., T0, T1, T2, T5, T10, T30 and T60) as described in Example 5 by both SDS-PAGE and Western blot analysis using a polyclonal rabbit antibody against native Axmi205. The results are summarized below.

eAxmi205 #5:

On SDS-PAGE, the band corresponding to full-length Axmi205-5 at time zero (T0) was no longer visible after incubation in SGF for one minute. After 1 minute, 56 kDa, 23 kDa, 4 kDa and 3 kDa fragments appeared. A very faint 53 kDa band is seen at 5 minutes, and disappeared by 10 minutes. The 23 kDa fragment is not seen in the T30 sample. 3 and 4 kDa fragments were still visible after 60 minutes incubation in SGF.

Western blot analysis confirmed the results of SDS-PAGE. Full-length Axmi205-5 was no longer visible at 1 minute. The 56 kDa band is no longer visible in the T10 sample, and the 23 kDa fragment was no longer visible in the T30 sample. No other immunoreactive fragments were detected.

eAxmi205 #6:

The band corresponding to full-length Axmi205-6 at time zero (T0) was no longer visible after incubation in SGF for 1 minute. At the T1 time point, 56 kDa, 23 kDa, 4 kDa and 3 kDa fragments appeared. A very faint 53 kDa band is seen at T5, and disappears by T10. A very faint 23 kDa band is observed at T10, and disappears in the T30 sample. 3 and 4 kDa fragments were still visible after 60 minutes incubation in SGF.

Western blot analysis confirmed the results of SDS-PAGE. Full-length Axmi205-6 was no longer visible at 1 minute. The 56 kDa band is no longer visible in the T10 sample, and a very faint 23 kDa fragment was visible in the T30 sample. No other immunoreactive fragments were detected.

eAxmi205 #21:

On SDS-PAGE, the band corresponding to full-length Axmi205-21 at time zero (T0) was no longer visible after incubation in SGF for one minute. After 1 minute of incubation, 56 kDa, 23 kDa, 4 kDa and 3 kDa fragments appeared. 56 kDa and 23 kDa fragments were no longer visible after 5 and 10 minutes of incubation in SGF, respectively. 4 kDa and 3 kDa fragments diminished in intensity over time, however, were still visible after 60 minutes incubation in SGF.

Western blot analysis confirmed the results of SDS-PAGE. Full-length Axmi205-21 was no longer visible after incubation in SGF for one minute. Very faint bands corresponding to 56 kDa and 23 kDa fragments were visible after 5 minutes of incubation in SGF, which disappeared after 10 min. No other immunoreactive fragments were detected.

eAxmi205 #23:

On SDS-PAGE, the band corresponding to full-length Axmi205-23 at time zero (T0) was no longer visible after incubation in SGF for one minute. After 1 minute of incubation, 56 kDa, 23 kDa, 4 kDa and 3 kDa fragments appeared. Both 56 kDa and 23 kDa fragments were no longer visible after 5 minutes of incubation in SGF. 4 kDa and 3 kDa fragments diminished in intensity over time, however, they were still visible after 60 minutes incubation in SGF.

Western blot analysis confirmed the results of SDS-PAGE. Full-length Axmi205-23 was no longer visible after incubation in SGF for one minute. 56 kDa and 23 kDa fragments were not visible after 5 and 2 minutes of incubation in SGF, respectively. No other immunoreactive fragments were detected.

eAxmi205 #28:

On SDS-PAGE, the band corresponding to full-length Axmi205-28 at time zero (T0) was no longer visible after incubation in SGF for one minute. At 1 minute, 56 kDa, 23 kDa, 4 kDa and 3 kDa fragments appeared. Both 53 and 23 kDa fragment bands were not observed at 5 minutes. 3 and 4 kDa fragments were still visible after 60 minutes incubation in SGF.

Western blot analysis confirmed the results of SDS-PAGE. Full-length Axmi205-28 was no longer visible at one minute. The 56 kDa fragment was no longer visible at 5 minutes. A very faint 23 kDa band was still visible at 2 minutes, but not observed at 5 minutes. No other immunoreactive fragments were detected.
eAxmi205 #34:

On SDS-PAGE, the band corresponding to full-length Axmi205-34 at time zero (T0) was no longer visible after incubation in SGF for one minute. At one minute, 4 kDa and 3 kDa fragments appeared and were still visible after 60 minutes incubation in SGF. No other significant Coomassie stained bands were observed on the gel.

Western blot analysis confirmed the results of SDS-PAGE. Full-length Axmi205-34 was no longer visible after one minute of SGF digestion. No other immunoreactive fragments were detected.

Example 10

Summary of Results from Examples 6 to 9

Figure 3:
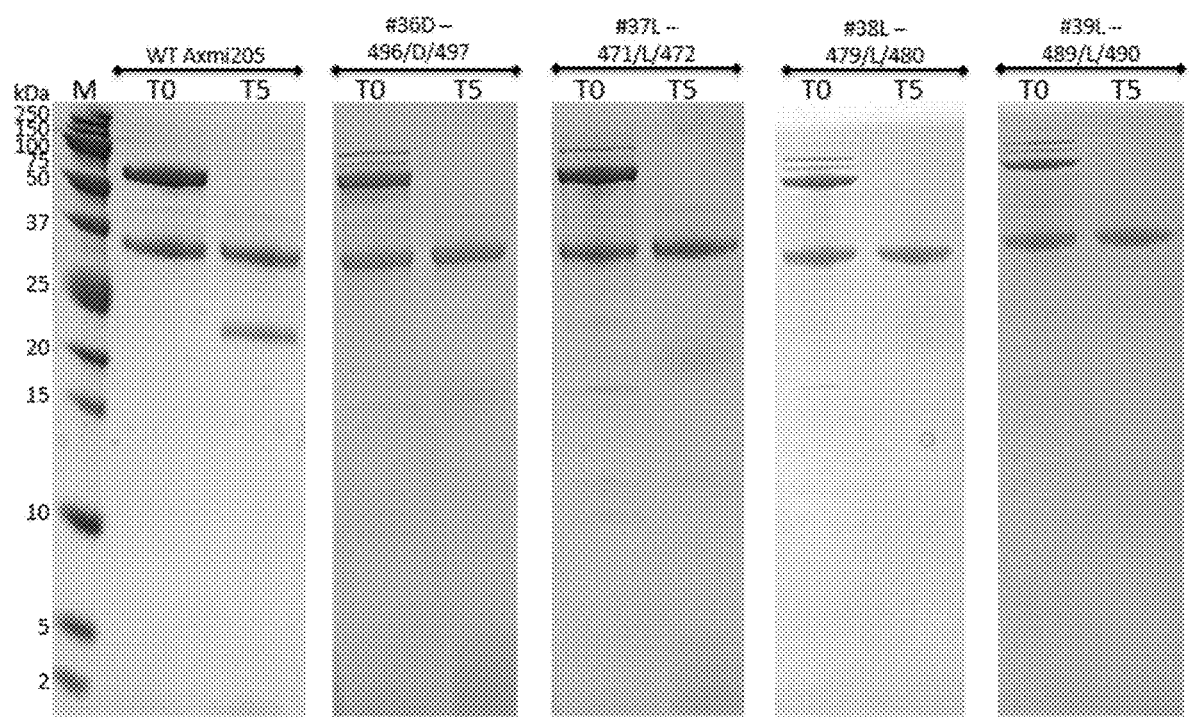
FIG. 3—Results of SGF assay at times T0 and T5 for wild-type Axmi205 and eAxmi205 mutants #36D (496-Asp-497), #37L (471-Leu-472), #38L (479-Leu-480) and #39L (489-Leu-490).
Figure 4:
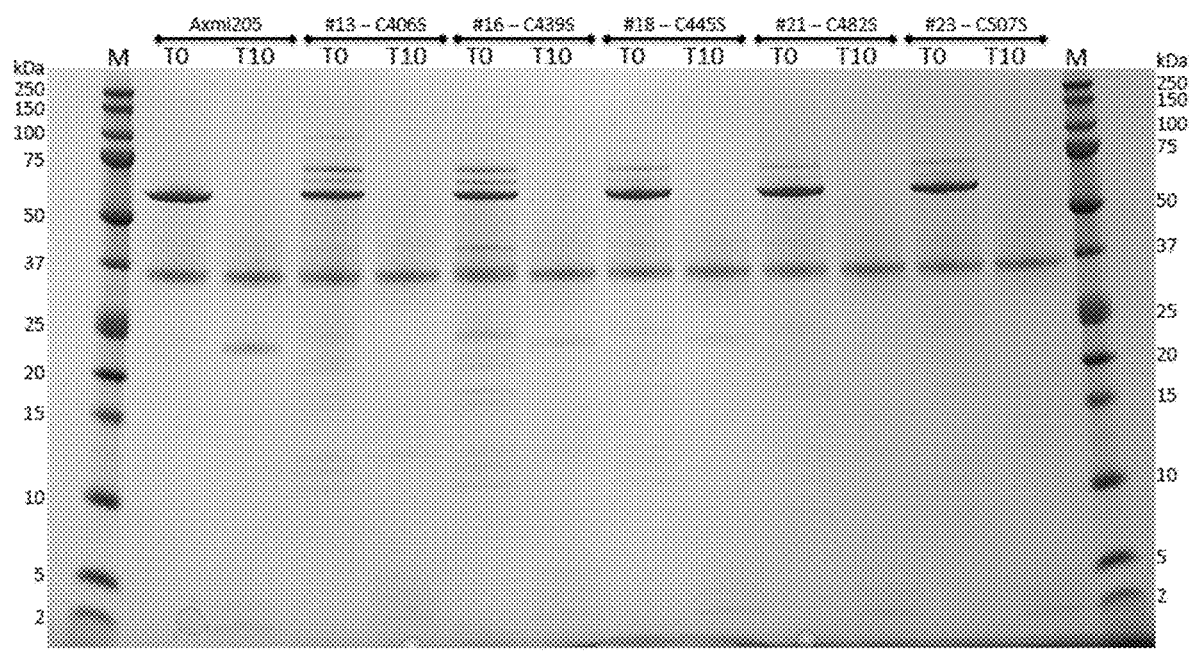
FIG. 4—Results of SGF assay at times T0 and T10 for wild-type Axmi205 and eAxmi205 mutants #13 (C406S), #16 (C482S), #18 (C445S), #21 (C482S) and #23 (C439S).
Figure 5:
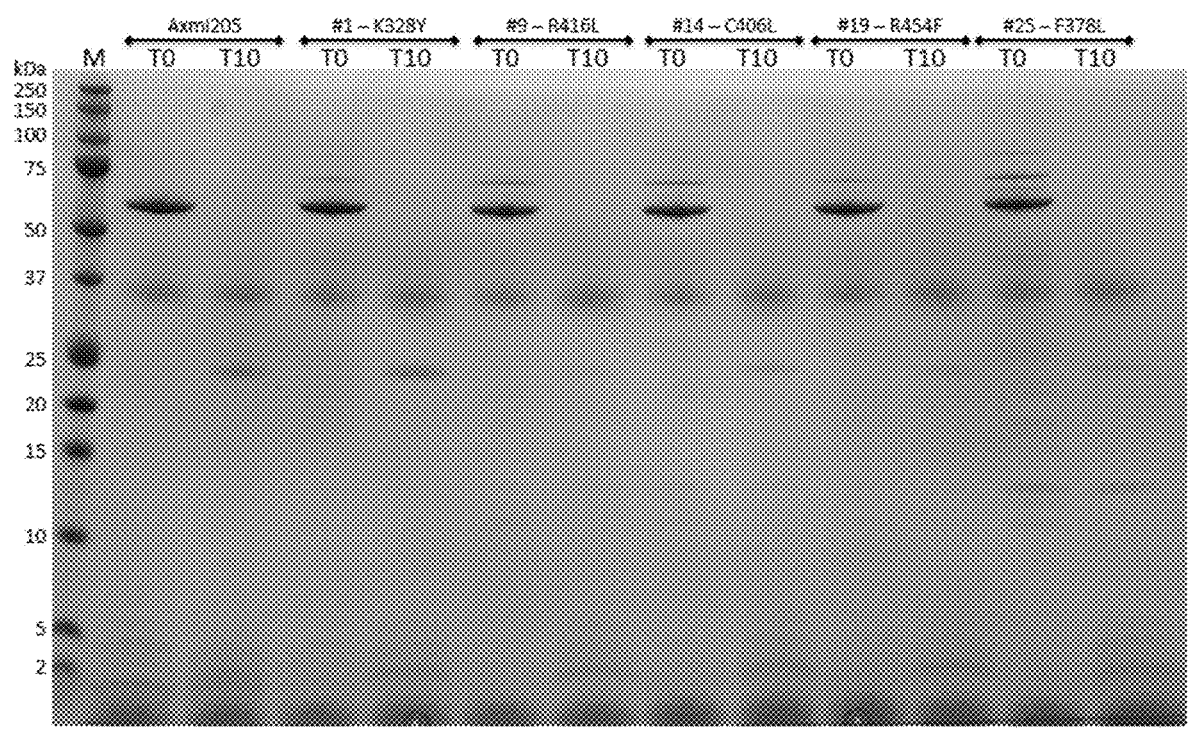
FIG. 5—Results of SGF assay at times T0 and T10 for wild-type Axmi205 and eAxmi205 mutants #1 (K328Y), #9 (R416L), #14 (C406L), #19 (R454F) and #25 (F378L).
Figure 6:
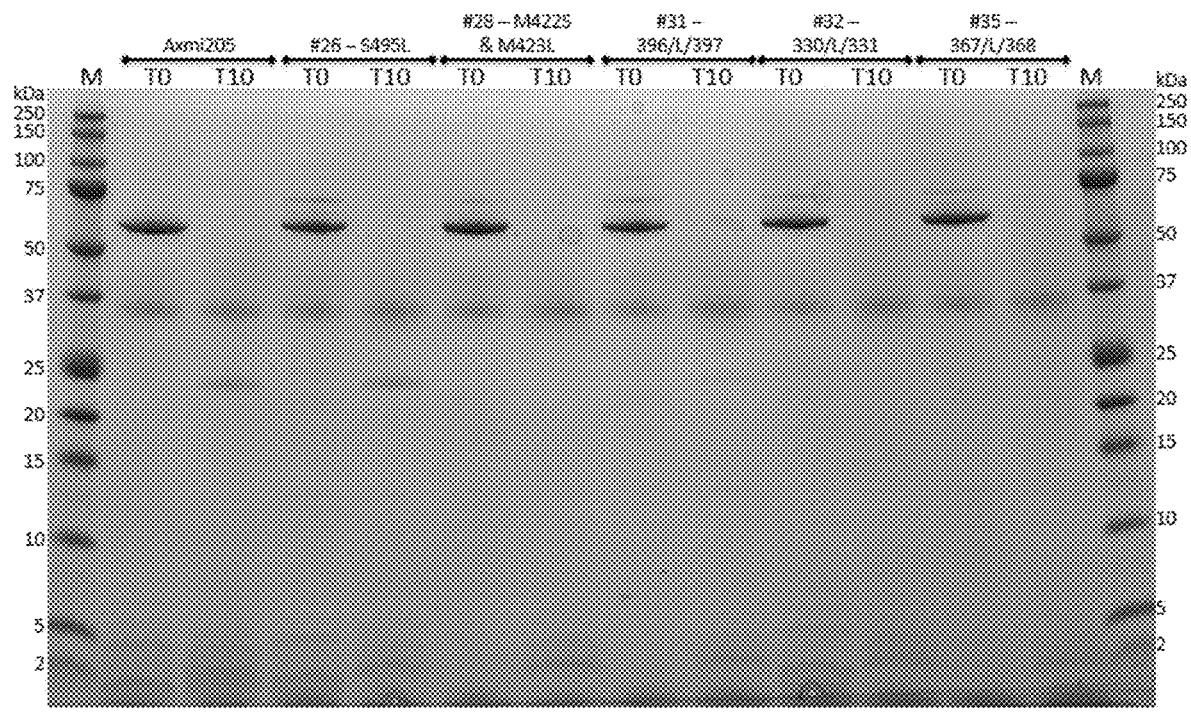
FIG. 6—Results of SGF assay at times T0 and T10 for wild-type Axmi205 and eAxmi205 mutants #26 (S495L), #28 (M4222S & M423L), #31 (396-Leu-397), #32 (330-Leu-331), and #35 (367-Leu-368).
Figure 7:
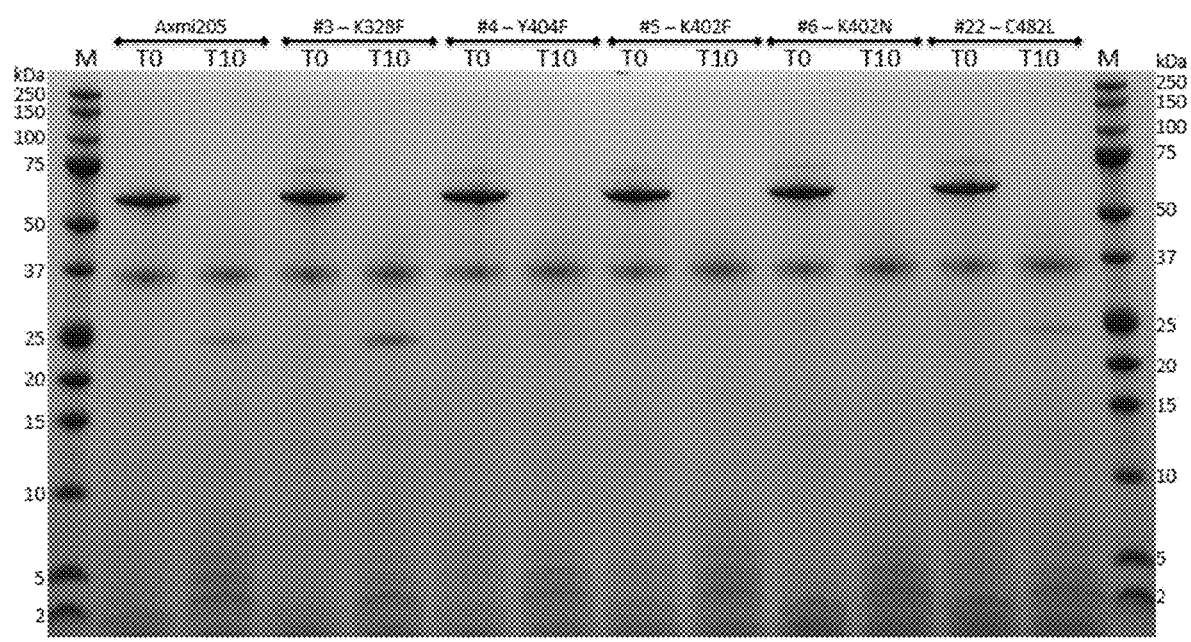
FIG. 7—Results of SGF assay at times T0 and T10 for wild-type Axmi205 and eAxmi205 mutants #3 (K328F), #4 (Y404F), #5 (K402F), #6 (K402N) and #22 (C482L).
Figure 8:
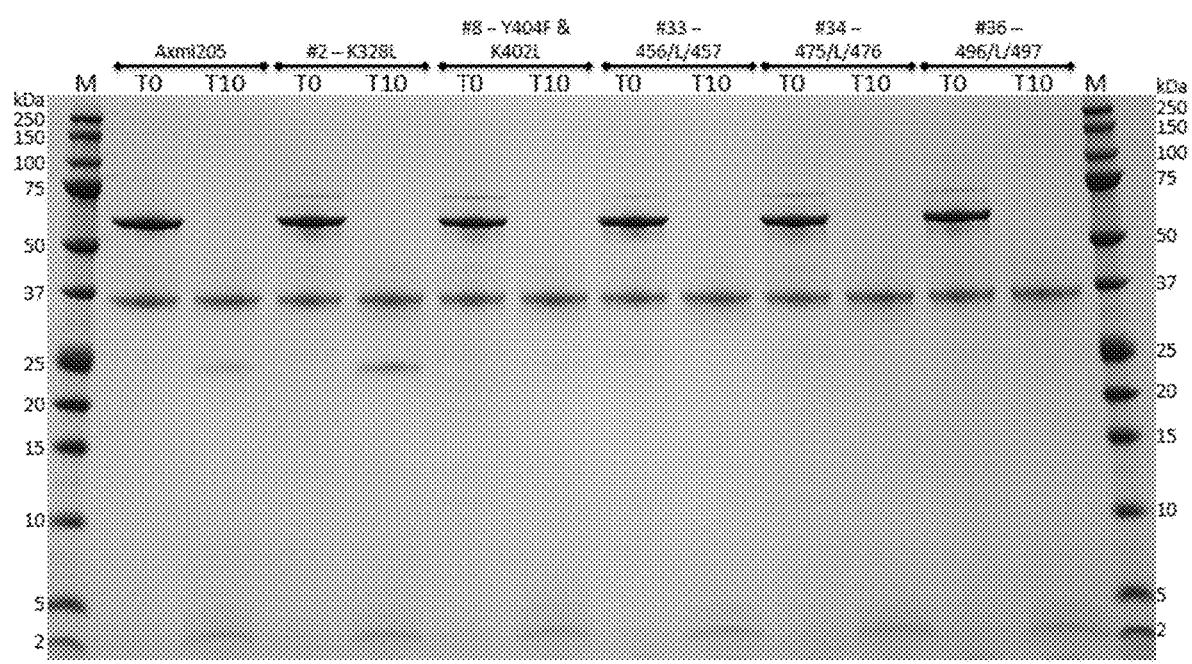
FIG. 8—Results of SGF assay at times T0 and T10 for wild-type Axmi205 and eAxmi205 mutants #2 (K328L), #8 (Y404F & K402L), #33 (456-Leu-457), #34 (475-Leu-476) and #36 (496-Leu-497).
Figure 9:
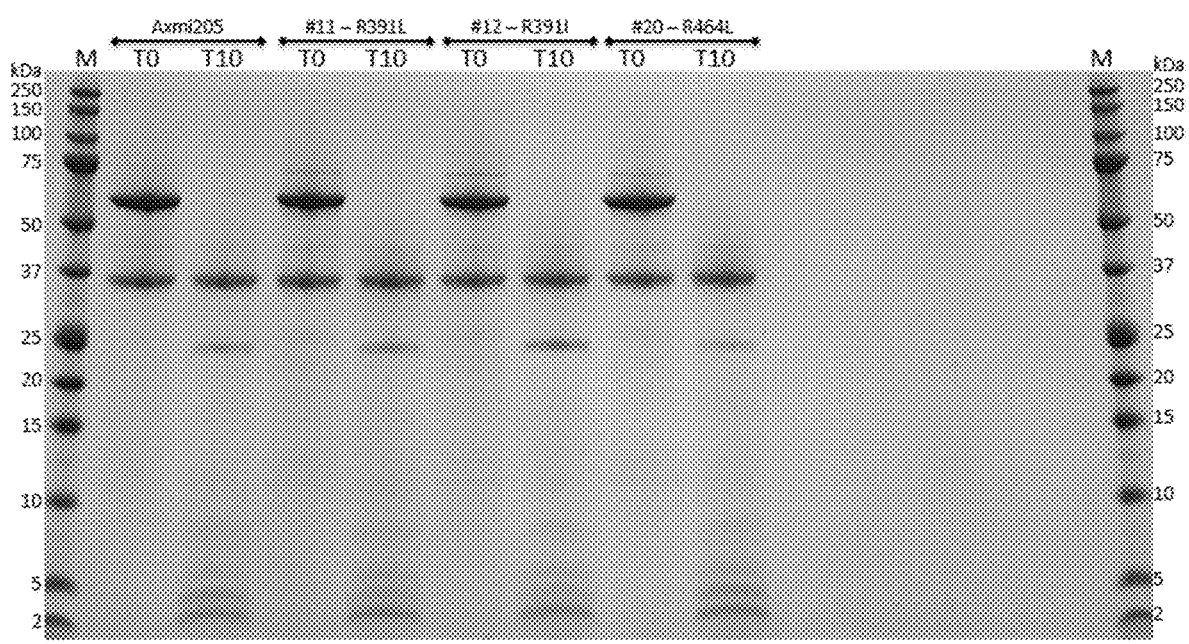
FIG. 9—Results of SGF assay at times T0 and T10 for wild-type Axmi205 and eAxmi205 mutants #11 (R391L), #12 (R391I) and #20 (R464L).
Figure 10:
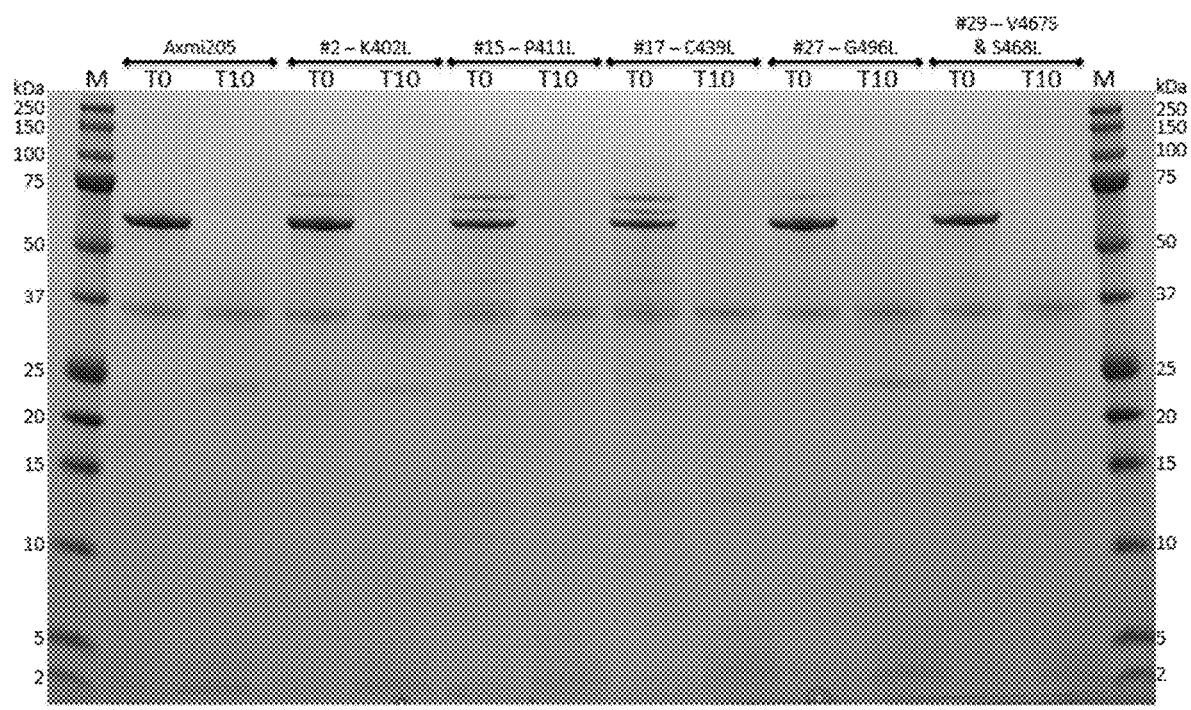
FIG. 10—Results of SGF assay at times T0 and T10 for wild-type Axmi205 and eAxmi205 mutants #2 (K402L), #15 (P411L), #17 (C439L), #27 (G496L) and #29 (V467S & S468L).

Table 5 below provides a summary of the results discussed Examples 6 to 9 above. FIGS. 2-10 show SGF assay results.

TABLE 5

| # | eAxmi205 Mutant | Protein Expression | Purified? | SGF T10 | WCRW Activity? | SGF Time Course |
|---|---|---|---|---|---|---|
| 1 | K328Y | ++++ | Yes | Fail | | |
| 2 | K328L | ++++ | Yes | Fail | | |
| 3 | K328F | ++++ | Yes | Fail | | |
| 4 | Y404F | ++++ | Yes | Fail | | |
| 5 | K402F | ++++ | Yes | Pass | Yes | Yes |
| 6 | K402N | ++++ | Yes | Pass | Yes | Yes |
| 7 | K402L | +++ | Yes | Fail | | |
| 8 | Y404F + K402L | +++ | Yes | Fail/Pass | Yes | Not Tested |
| 9 | R416L | +++ | Yes | Fail | | |
| 10 | P386L | + | No | N/A | | |
| 11 | R391L | ++++ | Yes | Fail | | |
| 12 | R391I | ++++ | Yes | Fail | | |
| 13 | C406S | ++++ | Yes | Fail | | |
| 14 | C406L | +++ | Yes | Fail | | |
| 15 | P411L | ++ | Yes | Fail | | |
| 16 | C439S | + | Yes | Fail | | |
| 17 | C439L | ++ | Yes | Fail | | |
| 18 | C445S | ++++ | Yes | Fail | | |
| 19 | R454F | ++++ | Yes | Fail | | |
| 20 | R464L | ++++ | Yes | Fail | | |
| 21 | C482S | ++++ | Yes | Pass | Yes | Yes |
| 22 | C482L | ++++ | Yes | Fail | | |
| 23 | C507S | ++++ | Yes | Pass | Yes | Yes |
| 24 | C406S + C439S + C445S + C482S + C507S | + | No | N/A | | |
| 25 | F378L | +++ | Yes | Fail | | |
| 26 | S495L | +++ | Yes | Fail | | |
| 27 | G496L | ++++ | Yes | Fail | | |
| 28 | M422S + M423L | ++++ | Yes | Pass | Yes | Yes |
| 29 | V467S + S468L | ++++ | Yes | Fail/Pass | NO | |
| 30 | V467S + S468L + W470G | +++ | Yes | Fail/Pass | | |
| 31 | 396-Leu-397 | +++ | Yes | Fail | | |
| 32 | 330-Leu-331 | +++ | Yes | Pass | NO | |
| 33 | 456-Leu-457 | ++++ | Yes | Pass | NO | |
| 34 | 475-Leu-476 | ++++ | Yes | Pass | Yes | Yes |
| 35 | 367-Leu-368 | +++ | Yes | Pass | NO | |
| 36 | 496-Leu-497 | ++++ | Yes | Pass | Yes | Yes | minutes incubation in SGF. No other significant Coomassie stained bands were observed on the gel.

Western blot analysis confirmed the results of SDS-PAGE. Full-length Axmi205-34 was no longer visible after one minute of SGF digestion. No other immunoreactive fragments were detected.
eAxmi205 #36:

On SDS-PAGE, the band corresponding to full-length Axmi205-36 (~59 kDa) at time zero (T0) was no longer visible after incubation in SGF for one minute (T1). At one minute, a smaller fragment (~56 kDa) appeared, but was no longer observed at T2. Fragments at 4 kDa and 3 kDa appeared at T1, and were still visible after 60 minutes Example 11

Dose-Response for WCRW Control Activity

A dose-response study for control of WCRW in an artificial diet bioassay was carried out for native Axmi205 ("Axmi205 WT") and eAxmi205 mutants #23, #28, and #34 using essentially the protocol described in Example 4. Mortality was assessed at days 1, 4 and 6.

The study was done in two replicates of 15 insects for each treatment. The results are shown in Table 6:

TABLE 6

| Treatment | WCRW Mortality | | | | | | |
|---|---|---|---|---|---|---|---|
| | | Day 1 | | Day 4 | | Day 6 | |
| | Total | Dead | Mort % | Dead | Mort % | Dead | Mort % |
| Replicate 1 | | | | | | | |
| Axmi205 WT @ 0.6 mg/mL (300 μg/mL FINAL) | 15 | 0 | 0% | 11 | 73% | 15 | 100% |
| Axmi205 WT @ 0.4 mg/mL (200 μg/mL FINAL) | 15 | 0 | 0% | 13 | 87% | 15 | 100% |
| Axmi205 WT @ 0.2 mg/mL (100 μg/mL FINAL) | 15 | 0 | 0% | 12 | 80% | 14 | 93% |
| Axmi205 WT @ 0.1 mg/mL (50 μg/mL FINAL) | 15 | 0 | 0% | 6 | 40% | 14 | 93% |
| Axmi205 WT @ 0.05 mg/mL (25 μg/mL FINAL) | 15 | 0 | 0% | 3 | 20% | 8 | 53% |
| Axmi205 WT Buffer (Neg) | 15 | 0 | 0% | 3 | 20% | 4 | 27% |
| Axmi205 Mutant #23 @ 0.6 mg/mL (300 μg/mL FINAL) | 15 | 0 | 0% | 12 | 80% | 15 | 100% |
| Axmi205 Mutant #23 @ 0.4 mg/mL (200 μg/mL FINAL) | 15 | 0 | 0% | 12 | 80% | 15 | 100% |
| Axmi205 Mutant #23 @ 0.2 mg/mL (100 μg/mL FINAL) | 15 | 0 | 0% | 10 | 67% | 13 | 87% |
| Axmi205 Mutant #23 @ 0.1 mg/mL (50 μg/mL FINAL) | 15 | 0 | 0% | 5 | 33% | 10 | 67% |
| Axmi205 Mutant #23 @ 0.05 mg/mL (25 μg/mL FINAL) | 15 | 0 | 0% | 3 | 20% | 8 | 53% |
| Axmi205 Mutant #23 Buffer (Neg) | 15 | 0 | 0% | 1 | 6% | 3 | 20% |
| Axmi205 Mutant #28 @ 0.6 mg/mL (300 μg/mL FINAL) | 15 | 0 | 0% | 15 | 100% | 15 | 100% |
| Axmi205 Mutant #28 @ 0.4 mg/mL (200 μg/mL FINAL) | 15 | 1 | 7% | 14 | 93% | 15 | 100% |
| Axmi205 Mutant #28 @ 0.2 mg/mL (100 μg/mL FINAL) | 15 | 0 | 0% | 9 | 60% | 14 | 93% |
| Axmi205 Mutant #28 @ 0.1 mg/mL (50 μg/mL FINAL) | 15 | 0 | 0% | 8 | 53% | 14 | 93% |
| Axmi205 Mutant #28 @ 0.05 mg/mL (25 μg/mL FINAL) | 15 | 0 | 0% | 10 | 67% | 15 | 100% |
| Axmi205 Mutant #28 Buffer (Neg) | 15 | 0 | 0% | 1 | 6% | 5 | 33% |
| Axmi205 Mutant #34 @ 0.6 mg/mL (300 μg/mL FINAL) | 15 | 0 | 0% | 14 | 93% | 15 | 100% |
| Axmi205 Mutant #34 @ 0.4 mg/mL (200 μg/mL FINAL) | 15 | 0 | 0% | 11 | 73% | 14 | 92% |
| Axmi205 Mutant #34 @ 0.2 mg/mL (100 μg/mL FINAL) | 15 | 0 | 0% | 14 | 93% | 15 | 100% |
| Axmi205 Mutant #34 @ 0.1 mg/mL (50 μg/mL FINAL) | 15 | 0 | 0% | 12 | 80% | 13 | 87% |
| Axmi205 Mutant #34 @ 0.05 mg/mL (25 μg/mL FINAL) | 15 | 0 | 0% | 8 | 53% | 9 | 60% |
| Axmi205 Mutant #34 Buffer (Neg) | 15 | 0 | 0% | 0 | 0 | 2 | 17% |
| Replicate 2 | | | | | | | |
| Axmi205 WT @ 0.6 mg/mL (300 μg/mL FINAL) | 15 | 0 | 0% | 13 | 87% | 15 | 100% |
| Axmi205 WT @ 0.4 mg/mL (200 μg/mL FINAL) | 15 | 0 | 0% | 11 | 73% | 15 | 100% |
| Axmi205 WT @ 0.2 mg/mL (100 μg/mL FINAL) | 15 | 0 | 0% | 12 | 80% | 14 | 93% |
| Axmi205 WT @ 0.1 mg/mL (50 μg/mL FINAL) | 15 | 0 | 0% | 7 | 47% | 13 | 87% |
| Axmi205 WT @ 0.05 mg/mL (25 μg/mL FINAL) | 15 | 0 | 0% | 6 | 40% | 14 | 93% |
| Axmi205 WT Buffer (Neg) | 15 | 0 | 0% | 3 | 20% | 10 | 67% |
| Axmi205 Mutant #23 @ 0.6 mg/mL (300 μg/mL FINAL) | 15 | 0 | 0% | 15 | 100% | 15 | 100% |
| Axmi205 Mutant #23 @ 0.4 mg/mL (200 μg/mL FINAL) | 15 | 0 | 0% | 11 | 73% | 14 | 92% |
| Axmi205 Mutant #23 @ 0.2 mg/mL (100 μg/mL FINAL) | 15 | 0 | 0% | 12 | 80% | 15 | 100% |
| Axmi205 Mutant #23 @0.1 mg/mL (50 μg/mL FINAL) | 15 | 0 | 0% | 3 | 20% | 13 | 87% |
| Axmi205 Mutant #23 @ 0.05 mg/mL (25 μg/mL FINAL) | 15 | 0 | 0% | 3 | 20% | 8 | 53% |
| Axmi205 Mutant #23 Buffer (Neg) | 15 | 0 | 0% | 1 | 7% | 2 | 17% |
| Axmi205 Mutant #28 @ 0.6 mg/mL (300 μg/mL FINAL) | 15 | 0 | 0% | 13 | 87% | 14 | 93% |
| Axmi205 Mutant #28 @ 0.4 mg/mL (200 μg/mL FINAL) | 15 | 0 | 0% | 14 | 93% | 15 | 100% |
| Axmi205 Mutant #28 @ 0.2 mg/mL (100 μg/mL FINAL) | 15 | 0 | 0% | 10 | 67% | 14 | 93% |
| Axmi205 Mutant #28 @ 0.1 mg/mL (50 μg/mL FINAL) | 15 | 0 | 0% | 6 | 40% | 13 | 87% |
| Axmi205 Mutant #28 @ 0.05 mg/mL (25 μg/mL FINAL) | 15 | 0 | 0% | 4 | 27% | 11 | 73% |
| Axmi205 Mutant #28 Buffer (Neg) | 15 | 0 | 0% | 1 | 7% | 9 | 60% |
| Axmi205 Mutant #34 @ 0.6 mg/mL (300 μg/mL FINAL) | 15 | 0 | 0% | 12 | 80% | 15 | 100% |
| Axmi205 Mutant #34 @ 0.4 mg/mL (200 μg/mL FINAL) | 15 | 0 | 0% | 10 | 67% | 15 | 100% |
| Axmi205 Mutant #34 @ 0.2 mg/mL (100 μg/mL FINAL) | 15 | 1 | 8% | 13 | 87% | 15 | 100% |
| Axmi205 Mutant #34 @ 0.1 mg/mL (50 μg/mL FINAL) | 15 | 0 | 0% | 10 | 67% | 12 | 80% |
| Axmi205 Mutant #34 @ 0.05 mg/mL (25 μg/mL FINAL) | 15 | 0 | 0% | 8 | 53% | 11 | 73% |
| Axmi205 Mutant #34 Buffer (Neg) | 15 | 0 | 0% | 0 | 0% | 2 | 17% |

Surprisingly, all 3 of the eAxmi205 mutants tested were essentially as active as native Axmi205 in controlling WCRW, while having a more desirable SGF digestion profile.

Example 12

Additional eAxmi205 Variants

Based on the information presented in Table 5 above, additional eAxmi205 mutants with an improved SGF digestion profile are readily generated by one skilled in the art. Mutants can add a new pepsin cleavage site, reduce disulfide bond formation and/or otherwise modify and "open up" the tertiary structure of the protein to increase enzyme access.

For example, eAxmi205 mutant #21 has a C482S mutation (with respect to the reference amino acid sequence of native Axmi205 of SEQ ID NO: 1). Alternatively, any other amino acid, naturally occurring or synthetic, is substituted at position 482. For example, the amino acid substitution at position 482 is a substitution of an amino acid with an aliphatic hydrophobic side chain (e.g., A, I, L or V), an amino acid with an aromatic hydrophobic side chain (e.g., F, W or Y), an amino acid with a polar neutral side chain (e.g., N, Q, M or T), an amino acid with an acidic side chain (e.g., D or E), an amino acid with a basic side chain (e.g., R, H or K), a G, or a P. In embodiments, the substitution results in a new pepsin cleavage site directly before and/or directly after the substitution at position 482 (i.e., between residues 481 and 482 and/or between residues 482 and 483). Additional mutants, eAxmi205 mutant #21F and #21D (C482F, C482D) were generated and the data for these mutations are included in Table 7.

As another non-limiting example, eAxmi205 mutant #23 has a C507S mutation (with respect to reference amino acid sequence of native Axmi205 of SEQ ID NO: 1). Alternatively, any other amino acid, naturally occurring or synthetic, is substituted at position 507. For example, the amino acid substitution at position 507 is a substitution of an amino acid with an aliphatic hydrophobic side chain (e.g., A, I, L or V), an amino acid with an aromatic hydrophobic side chain (e.g., F, W or Y), an amino acid with a polar neutral side chain (e.g., N, Q, M or T), an amino acid with an acidic side chain (e.g., D or E), an amino acid with a basic side chain (e.g., R, H or K), a G, or a P. In embodiments, the substitution results in a new pepsin cleavage site directly before and/or directly after the substitution at position 507 (i.e., between residues 506 and 507 and/or between residues 507 and 508). Additional mutants, eAxmi205 mutant #23L, #23A, #23F, #23D, and #23R (C507L, C507A, C507F, C507D, C507R) were generated and the data for these mutations are included in Table 7.

As a further illustration, eAxmi205 mutant #28 has two substitution mutations: M422S and M423L (with respect to the reference amino acid sequence of native Axmi205 of SEQ ID NO: 1). Alternatively, an eAxmi205 variant with only one of the substitutions is made, i.e., M422S or M423L. As a further alternative, any other amino acid, naturally occurring or synthetic, is substituted at position 422 and/or position 423. For example, the amino acid substitution at position 422 and/or position 423 is a substitution of an amino acid with an aliphatic hydrophobic side chain (e.g., A, I, L or V), an amino acid with an aromatic hydrophobic side chain (e.g., F, W or Y), an amino acid with a polar neutral side chain (e.g., N, C, Q, S or T), an amino acid with an acidic side chain (e.g., D or E), an amino acid with a basic side chain (e.g., R, H or K), a G, or a P. In embodiments, the substitution(s) results in a new pepsin cleavage site directly before residue 422, between residues 422 and 423 and/or directly following residue 423 (i.e., between residues 421 and 422, between residues 422 and 423 and/or between residues 423 and 424). In embodiments, the substitution is not a cysteine (C) at position 422 and/or position 423. Additional mutants, eAxmi205 mutant #28TF, #28DE, #28KR, #28SE and #28KF (M422T+M423F, M422D+M423E, M422K+M423R, M422S+M423E, M422K+M423F) were generated and the data for these mutations are included in Table 7.

eAxmi205 mutant #34 has a leucine (L) insertion between amino acids 475 and 476 (with respect to the reference amino acid sequence of native Axmi205 of SEQ ID NO: 1). Alternatively, any other amino acid, naturally occurring or synthetic, is inserted between the amino acid residues at positions 475 and 476. For example, the amino acid insertion between positions 475 and 476 is an insertion of an amino acid with an aliphatic hydrophobic side chain (e.g., A, I or V), an amino acid with an aromatic hydrophobic side chain (e.g., F, W or Y), an amino acid with a polar neutral side chain (e.g., N, C, Q, M, Q, S or T), an amino acid with an acidic side chain (e.g., D or E), an amino acid with a basic side chain (e.g., R, H or K), a G, or a P. In embodiments, the insertion results in a new pepsin cleavage site directly before and/or directly after the insertion (i.e., between residue 475 and the inserted amino acid and/or between the inserted amino acid and residue 476). In embodiments, the inserted amino acid is not a cysteine (C). Additional mutants, eAxmi205 mutant #34F, #34D and #34R (475-Phe-476, 475-Asp-476, 475-Arg-476) were generated and the data for these mutations are included in Table 7.

eAxmi205 mutant #36 has a leucine (L) insertion between amino acids 496 and 497 (with respect to the reference amino acid sequence of native Axmi205 of SEQ ID NO: 1). Alternatively, any other amino acid, naturally occurring or synthetic, is inserted between the amino acid residues at positions 496 and 497. For example, the amino acid insertion between positions 496 and 497 is an insertion of an amino acid with an aliphatic hydrophobic side chain (e.g., A, I or V), an amino acid with an aromatic hydrophobic side chain (e.g., F, W or Y), an amino acid with a polar neutral side chain (e.g., N, C, Q, M, Q, S or T), an amino acid with an acidic side chain (e.g., D or E), an amino acid with a basic side chain (e.g., R, H or K), a G, or a P. In embodiments, the insertion results in a new pepsin cleavage site directly before and/or directly after the insertion (i.e., between residue 496 and the inserted amino acid and/or between the inserted amino acid and residue 497. In embodiments, the inserted amino acid is not a cysteine (C). Additional mutants, eAxmi205 mutant #36F and #36R (496-Phe-497, 496-Arg-497) were generated and the data for these mutations are included in Table 7.

eAxmi205 mutants #5 and #6 have K402F and K402N mutations, respectively (with respect to the reference amino acid sequence of native Axmi205 of SEQ ID NO: 1). Alternatively, any other amino acid, naturally occurring or synthetic, is substituted at position 402. For example, the amino acid substitution at position 402 is a substitution of an amino acid with an aliphatic hydrophobic side chain (e.g., A, I or V), an amino acid with an aromatic hydrophobic side chain (e.g., W or Y), an amino acid with a polar neutral side chain (e.g., C, Q, M, Q, S or T), an amino acid with an acidic side chain (e.g., D or E), an amino acid with a basic side chain (e.g., R or H), a G, or a P. In embodiments, substitution results in a new pepsin cleavage site directly before or directly after the substitution at position 402 (i.e., between residues 401 and 402 or between residues 402 and 403). An additional mutant, eAxmi205 mutant #5D (K402D) was generated and the data for this mutation is included in Table 7.

eAxmi205 mutant #8 has two substitution mutations: K402L and Y404F (with respect to the reference amino acid sequence of native Axmi205 of SEQ ID NO: 1). Alternatively, any other amino acid, naturally occurring or synthetic, is substituted at position 402 and/or 404. For example, the amino acid substitution at position 402 and/or position 404 is a substitution of an amino acid with an aliphatic hydrophobic side chain (e.g., A, I, L or V), an amino acid with an aromatic hydrophobic side chain (e.g., F, W or Y), an amino acid with a polar neutral side chain (e.g., N, C, M, Q, S or T), an amino acid with an acidic side chain (e.g., D or E), an amino acid with a basic side chain (e.g., R, H or K), a G, or a P. In embodiments, the substitution(s) results in a new pepsin cleavage site directly before residue 402 and/or directly following residue 404 (i.e., between residues 401 and 402 and/or between residues 404 and 405). In embodiments, the substitution is not a cysteine (C) at position 402 and/or position 404.

As further alternatives, any combination of the mutations described in Table 5 or in this example are combined to generate additional eAxmi205 variants, for example, combination of the mutations at positions 402 and 404.

The additional eAxmi205 variants can be assessed for SGF digestion as described in Examples 3 and/or 5 and for insecticidal activity by artificial diet bioassay as described in Example 4 and/or by expression in plants (described below).

As further alternatives, additional or alternative insertions can be made in long regions of the protein without a pepsin cleavage site. Based upon the SGF results of mutants #34 and #36 and their variants, additional mutants were created in the stretch of amino acids between positions 469 and 483 of SEQ ID NO: 1 and between positions 483 and 501 of SEQ ID NO:1. Additional mutants, eAxmi205 mutant #37F and #37L (471-Phe-472, 471-Leu-472), #38F and #38L (479-

Phe-480, 479-Leu-480), and #39F and #39L (489-Phe-490, 489-Leu-490) were generated and the data for these mutations are included in Table 7.

Figure 11:
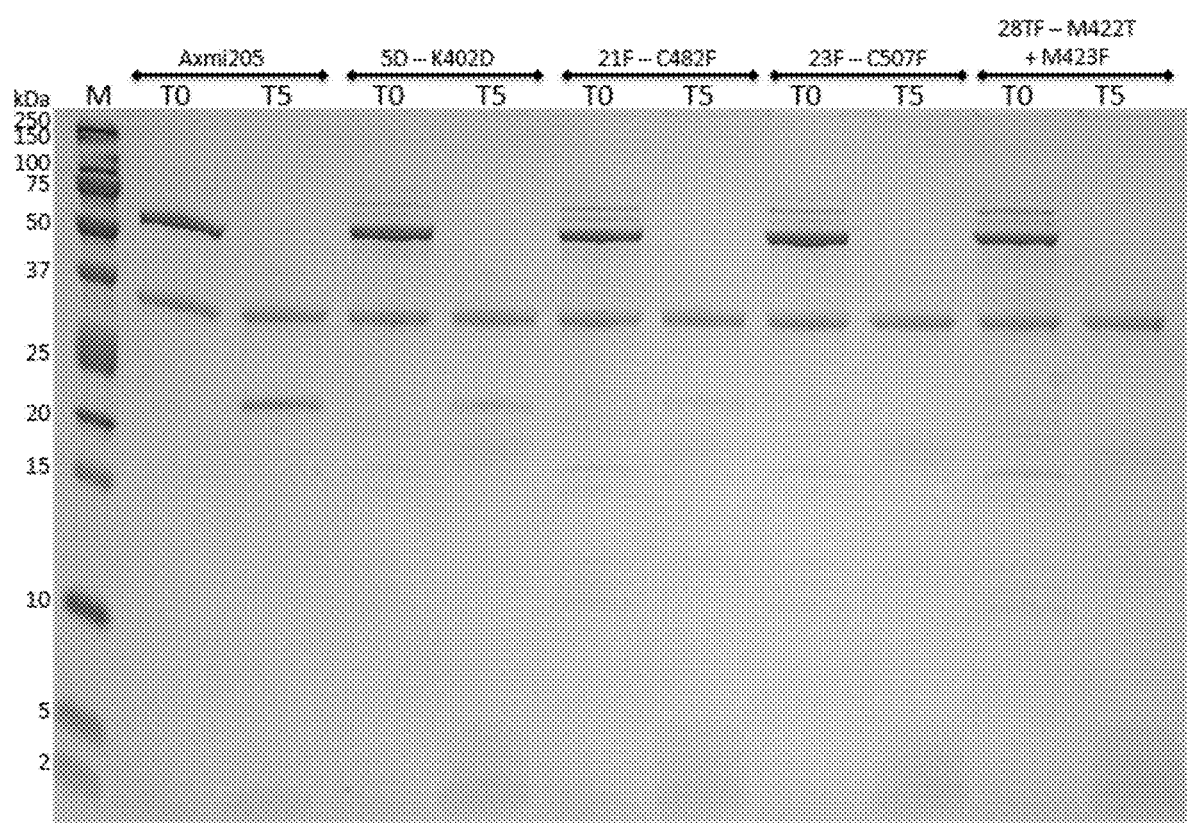
FIG. 11—Results of SGF assay at times T0 and T10 for wild-type Axmi205 and eAxmi205 mutants #5D (K402D), #21F (C482F), #23F (C507F) and #28TF (M422T & M423F).
Figure 12:
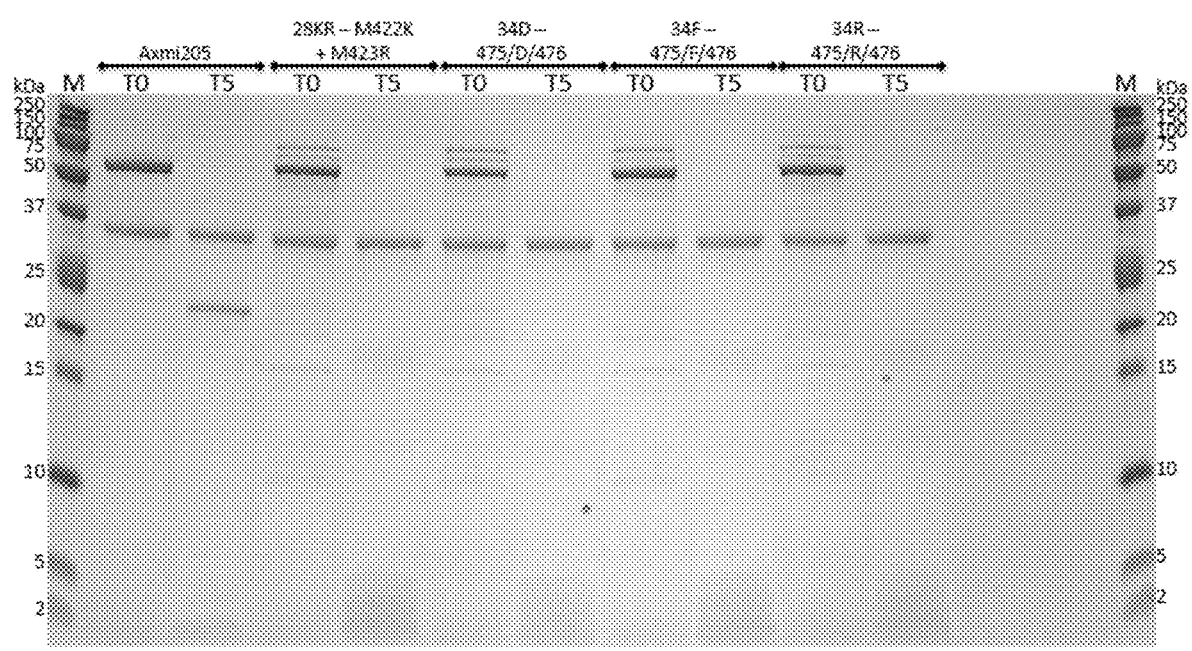
FIG. 12—Results of SGF assay at times T0 and T10 for wild-type Axmi205 and eAxmi205 mutants #28KR (M422K & M423R), #34D (475-Asp-476), #34F (475-Phe-476) and #34R (475-Arg-476).
Figure 13:
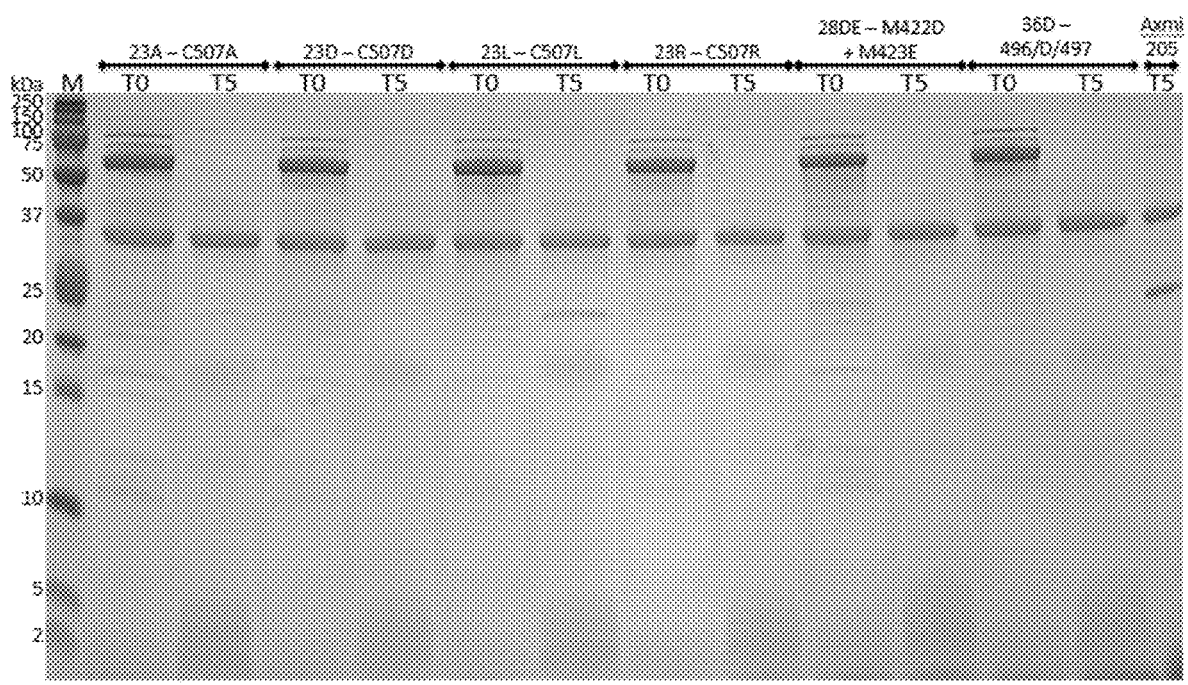
FIG. 13—Results of SGF assay at times T0 and T10 for wild-type Axmi205 and eAxmi205 mutants #23D (C507D), #23L (C507L), #23R (C507R), #28DE (M422D & M423E) and #36D (496-Asp-497).
Figure 14:
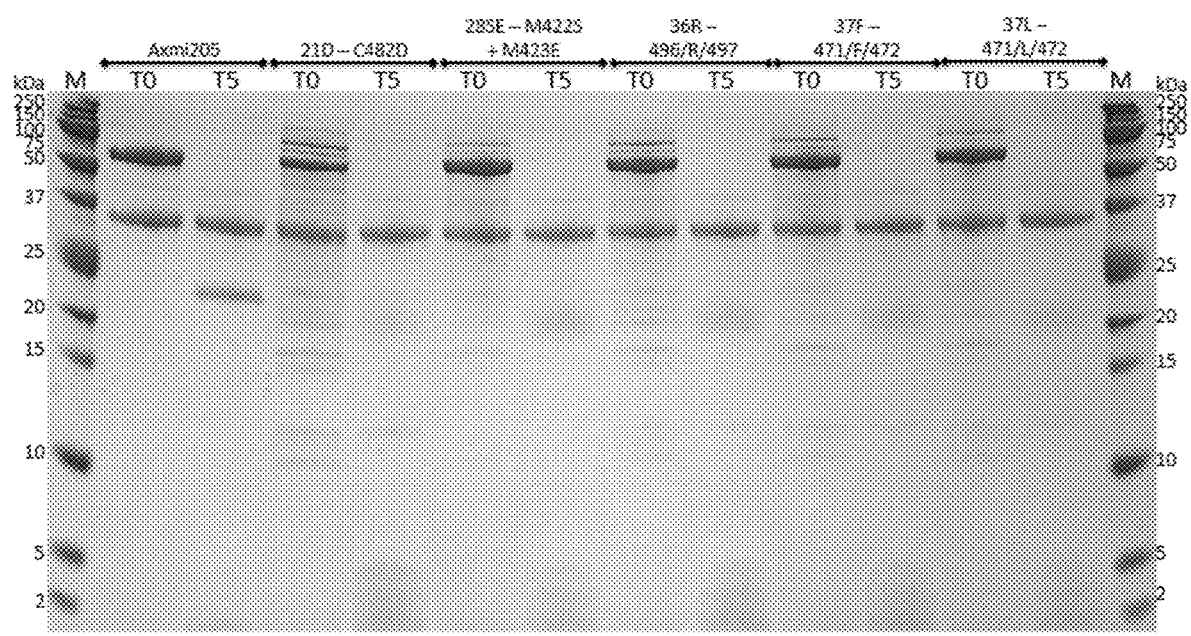
FIG. 14—Results of SGF assay at times T0 and T10 for wild-type Axmi205 and eAxmi205 mutants #21D (C482D), #28SE (M4222S & M423E), #36R (496-Arg-497), #37F (471-Phe-472) and #37L (471-Leu-472).
Figure 15:
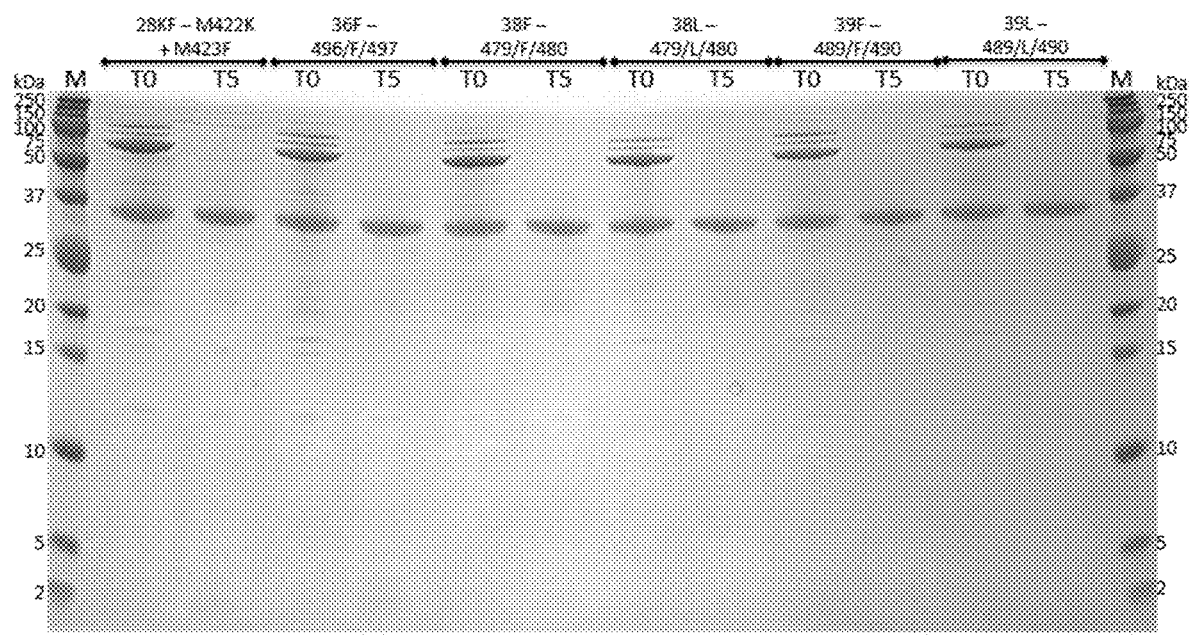
FIG. 15—Results of SGF assay at times T0 and T10 for wild-type Axmi205 and eAxmi205 mutants #28KF (M4222K & M423F), #36F (496-Phe-497), #38F (479-Phe-480), #38L (479-Leu-480), #39F (489-Phe-490), #39L (489-Leu-490).

Table 7 shows data for eAxmi205 mutants #5, #21, #23, #28, #34, #36, #37, #38, #39 and their variants as listed above during this example. These mutants were assessed for SGF digestion as described in Examples 3 and/or 5. From the data it is clear that in all cases, the additional mutants at these positions improved the digestion of the modified Axmi205 toxin. These modified Axmi205 toxins showed enhanced digestibility by a mammalian protease such that there was a lesser amount of fragments above 4 kDa remaining as compared with an Axmi205 toxin that did not comprise the modification when tested under the same conditions. The four mutants which did not pass the T10 test still should enhanced digestibility after 60 minutes. FIGS. 11-15 show SGF assay results.

TABLE 7

| # | Mutant Position | T10 Test | Improved v. WT Axmi205 at T10 |
|---|---|---|---|
| 5 | K402F | Pass | Yes |
| 5D | K402D | Fail | Yes |
| 21 | C482S | Pass | Yes |
| 21F | C482F | Fail | Yes |
| 21D | C482D | Fail | Yes |
| 23 | C507S | Pass | Yes |
| 23L | C507L | Fail | Yes |
| 23A | C507A | Pass | Yes |
| 23F | C507F | Pass | Yes |
| 23D | C507D | Pass | Yes |
| 23R | C507R | Pass | Yes |
| 28 | M422S + M423L | Pass | Yes |
| 28TF | M422T + M423F | Pass | Yes |
| 28DE | M422D + M423E | Pass | Yes |
| 28KR | M422K + M423R | Pass | Yes |
| 28SE | M422S + M423E | Pass | Yes |
| 28KF | M422K + M423F | Pass | Yes |
| 34 | 475-Leu-476 | Pass | Yes |
| 34F | 475-Phe-476 | Pass | Yes |
| 34D | 475-Asp-476 | Pass | Yes |
| 34R | 475-Arg-476 | Pass | Yes |
| 36 | 496-Leu-497 | Pass | Yes |
| 36D | 496-Asp-497 | Pass | Yes |
| 36F | 496-Phe-497 | Pass | Yes |
| 36R | 496-Arg-497 | Pass | Yes |
| 37F | 471-Phe-472 | Pass | Yes |
| 37L | 471-Leu-472 | Pass | Yes |
| 38F | 479-Phe-480 | Pass | Yes |
| 38L | 479-Leu-480 | Pass | Yes |
| 39F | 489-Phe-490 | Pass | Yes |
| 39L | 489-Leu-490 | Pass | Yes |

Any of the above mutants can be combined with one another in an effort to further improve digestibility. A key finding of these results is that certain stretches of amino acids, the stretch of amino acids between positions 469 and 483 of SEQ ID NO: 1 and between positions 483 and 501 of SEQ ID NO:1, appear to have a strong effect on pepsin cleavage. The insertion of an amino acid at different points in these two stretches led to significantly increased digestibility, indicating that they are key for pepsin cleavage.

Example 13

Expression and Activity of eAxmi205 Variants in Monocot Plants

A binary vector construct suitable for *Agrobacterium*-mediated transformation is produced. The binary vector comprises a maize optimized eAxmi205 coding sequence operably linked at the 5' end to a promoter suitable for driving expression in maize plants and operably linked at the 3' end to a terminator sequence. Examples of suitable maize codon optimized sequences include SEQ ID NO: 75 (eAxmi205 #23), SEQ ID NO: 76 (eAxmi205 #28), and SEQ ID NO: 77 (eAxmi205 #34).

The binary vector is transformed into *Agrobacterium tumefaciens* using standard molecular biology techniques known to those skilled in the art. To prepare the *Agrobacteria* for transformation, cells are cultured in liquid YPC media at 28° C. and 220 rpm overnight. *Agrobacterium* transformation of immature maize embryos is performed essentially as described in Negrotto et al., 2000, (Plant Cell Reports 19: 798-803); however, various protocols known in the art may be used.

Following transformation, selection, and regeneration, maize plants are assayed for the presence of the eAxmi204 coding sequence using TaqMan® analysis. Plants are also tested for the presence of the vector backbone. Plants negative for the vector backbone and comprising one copy of the transgene from the binary vector construct are transferred to the greenhouse and tested for resistance to WCRW damage.

Example 14

Expression and Activity of eAxmi205 Variants in Dicot Plants

Transformation of soybean to produce transgenic soybean plants is accomplished using mature seed targets of variety Williams 82 via *A. tumefaciens*-mediated transformation using explant materials and media recipes essentially as described in Hwang et al. (WO 08/112044) and Que et al. (WO 08/112267); however, various other protocols can also be used.

Following transformation, selection and regeneration, soybean plants are assayed for the presence of the eAxmi204 coding sequence using TaqMan® analysis. Plants are also tested for the presence of the vector backbone. Plants negative for the vector backbone and comprising one copy of the transgene from the binary vector construct are transferred to the greenhouse and tested for resistance to damage by Bean leaf beetle (*Cerotoma trifurcata*).

Example 15

Activity Against Resistant Corn Rootworm

The disclosed Axmi205 variants are useful to control coleopteran insect pests that have developed resistance against another coleopteran insect control agent (e.g., a protein toxin, chemical, microbial and/or RNAi control agent). The Axmi205 variants can also be combined with one or more other coleopteran insect control agents to delay or prevent the development of resistance in the coleopteran insect population.

The Axmi205 variants (e.g., #5, #6, #21, #21, #23, #28, #34 and/or #36) are tested in diet bioassay or in planta assay for activity against a corn rootworm (e.g., WCRW) colony that is resistant to a coleopteran insect control agent, such as mCry3A (e.g., maize event MIR604; Syngenta), eCry3.1Ab (e.g., maize event 5307; Syngenta), Cry3Bb1 (e.g., maize event MON88017; Monsanto), Cry34/35Ab1 (e.g., maize event DAS-59122, Dow AgroSciences), or RNAi traits, such as DvSnf7 dsRNA (e.g., maize event MON87411; Monsanto).

In one experiment, Axmi205 mutant #34 (SEQ ID NO: 69) was evaluated in an artificial diet bioassay against a WCRW colony with resistance against the toxin eCry3.1Ab, essentially as described above in Example 4. The results of 2 replicates are shown below in Table 8. Results for the additional mutants described in Example 12 are shown in Table 9.

TABLE 8

| Treatment | WCR-r Mortality | | | | | |
|---|---|---|---|---|---|---|
| | Day 4 | | | Day 6 | | |
| | Total | Dead | Mort % | Total | Dead | Mort % |
| Replicate 1 | | | | | | |
| Axmi205 Mutant #34 @ 0.4 mg/mL (200 µg/mL FINAL) | 12 | 4 | 33% | 12 | 4 | 33% |
| Axmi205 Mutant #34 @ 0.2 mg/mL (100 µg/mL FINAL) | 12 | 2 | 17% | 12 | 8 | 67% |
| Axmi205 Mutant #34 @ 0.1 mg/mL (50 µg/mL FINAL) | 12 | 0 | 0% | 12 | 3 | 25% |
| Axmi205 Mutant #34 @ 0.05 mg/mL (25 µg/mL FINAL) | 12 | 0 | 0% | 12 | 5 | 42% |
| Axmi205 Mutant #34 @ 0.025 mg/mL (12.5 µg/mL FINAL) | 12 | 1 | 8% | 12 | 3 | 25% |
| Axmi205 Mutant #34 buffer (Negative control) (1x PBS) | 12 | 1 | 8% | 12 | 1 | 8% |
| Replicate 2 | | | | | | |
| Axmi205 Mutant #34 @ 0.4 mg/mL (200 µg/mL FINAL) | 12 | 8 | 67% | 12 | 11 | 92% |
| Axmi205 Mutant #34 @ 0.2 mg/mL (100 µg/mL FINAL) | 12 | 10 | 83% | 12 | 12 | 100% |
| Axmi205 Mutant #34 @ 0.1 mg/mL (50 µg/mL FINAL) | 12 | 3 | 25% | 12 | 4 | 33% |
| Axmi205 Mutant #34 @ 0.05 mg/mL (25 µg/mL FINAL) | 12 | 4 | 33% | 12 | 7 | 58% |
| Axmi205 Mutant #34 @ 0.025 mg/mL (12.5 µg/mL FINAL) | 12 | 0 | 0% | 12 | 3 | 25% |
| Axmi205 Mutant #34 buffer (Negative control) (1x PBS) | 12 | 2 | 17% | 12 | 2 | 17% |

TABLE 9

| Treatment | WCR-s Mortality | | | | | | | |
|---|---|---|---|---|---|---|---|---|
| | Day 3 | | | | Day 6 | | | |
| | Total | Dead | Mort % | Remarks | Total | Dead | Mort % | Remarks |
| Axmi205 WT @ 0.4 mg/mL (200 ug/mL FINAL) | 12 | 10 | 83% | 1s, 1m | 12 | 12 | 100% | |
| Axmi205 21D @ 0.4 mg/mL (200 ug/mL FINAL) | 12 | 3 | 25% | mb/b | 12 | 9 | 75% | b |
| Axmi205 28SE @ 0.4 mg/mL (200 ug/mL FINAL) | 12 | 6 | 50% | mb/b | 12 | 10 | 83% | mb |
| Axmi205 28KF @ 0.4 mg/mL (200 ug/mL FINAL) | 12 | 0 | 0% | b | 12 | 0 | 0% | b |
| Axmi205 36F @ 0.4 mg/mL (200 ug/mL FINAL) | 12 | 3 | 25% | mb/b | 12 | 7 | 58% | b |
| Axmi205 36R @ 0.4 mg/mL (200 ug/mL FINAL) | 12 | 5 | 42% | mb/b | 12 | 8 | 67% | 1m, 3b |
| Axmi205 37F @ 0.4 mg/mL (200 ug/mL FINAL) | 12 | 5 | 42% | m | 12 | 10 | 83% | mb |
| Axmi205 37L @ 0.4 mg/mL (200 ug/mL FINAL) | 12 | 3 | 25% | mb/b | 12 | 6 | 50% | b |
| Axmi205 38F @ 0.4 mg/mL (200 ug/mL FINAL) | 12 | 5 | 42% | mb/b | 12 | 9 | 75% | b |
| Axmi205 38L @ 0.4 mg/mL (200 ug/mL FINAL) | 12 | 4 | 33% | mb/b | 12 | 7 | 58% | mb/b |
| Axmi205 39F @ 0.4 mg/mL (200 ug/mL FINAL) | 12 | 8 | 67% | sm | 12 | 11 | 92% | m |
| Axmi205 39L @ 0.4 mg/mL (200 ug/mL FINAL) | 12 | 2 | 17% | mb | 12 | 10 | 83% | b |
| Buffer (1xPBS) | 12 | 2 | 17% | b | 12 | 2 | 17% | b |

Example 16 eAxmi205 in Combination with an Insecticidal Interfering RNA

An eAxmi205 variant as described herein is expressed and purified as described in Example 2. dsRNA against an essential target gene in WCRW is prepared. In a non-limiting example, the dsRNA may target a gene encoding vacuolar ATP synthase, beta-tubulin, 26S proteosome subunit p28 protein, EF1α 48D, troponin I, tetraspanin, gamma-coatomer, beta-coatomer, and/or juvenile hormone epoxide hydrolase (U.S. Provisional Application Nos. 62/371,259, 62/371,261, and 62/371,262; U.S. Pat. No. 7,812,219; each herein incorporated by reference). The dsRNA and purified protein are tested for efficacy against WCRW in a diet-incorporation assay, performed essentially as described in Example 4.

Example 17

Genome Editing in Plant Cells In Situ to Generate Modified Nucleic Acid Sequences Encoding eAxmi205 Variants The following Example illustrates the use of genome editing of a plant cell genome in situ to incorporate the mutations described herein (including but not limited to the mutations described in Table 5 and Example 12) into a coding sequence for the native Axmi205 protein (SEQ ID NO: 1) or into a coding sequence for an already modified Axmi205 protein.

Targeted genome modification, also known as genome editing, is useful for introducing mutations in specific DNA sequences. These genome editing technologies, which include zinc finger nucleases (ZNFs), transcription activator-like effector nucleases (TALENS), meganucleases and clustered regularly interspaced short palindromic repeats (CRISPR) have been successfully applied to over 50 different organisms including crop plants. See, e.g., Belhaj, K., et al., Plant Methods 9, 39 (2013); Jiang, W., et al., Nucleic Acids Res, 41, e188 (2013)). The CRISPR/Cas system for genome editing is based on transient expression of Cas9 nuclease and an engineered single guide RNA (sgRNA) that specifies the targeted polynucleotide sequence.

Cas9 is a large monomeric DNA nuclease guided to a DNA target sequence with the aid of a complex of two 20-nucleotide (nt) non-coding RNAs: CRIPSR RNA (crRNA) and trans-activating crRNA (tracrRNA), which are functionally available as single synthetic RNA chimera. The Cas9 protein contains two nuclease domains homologous to RuvC and HNH nucleases. The HNH nuclease domain cleaves the complementary DNA strand, whereas the RuvC-like domain cleaves the non-complementary strand and, as a result, a blunt cut is introduced in the target DNA.

When the Cas9 and the sgRNA are transiently expressed in living maize cells, double strand breaks (DSBs) in the specific targeted DNA is created in the transgenic maize cell. Mutation at the break site is introduced through the non-homologous end joining and homology-directed DNA repair pathways.

Specific mutations, for example the eAxmi205 mutations described in Table 5 and Example 12 above, are introduced into a coding sequence for the native Axmi205 (SEQ ID NO: 1) or a modified Axmi205, through the use of recombinant plasmids expressing the Cas9 nuclease and the sgRNA target that is maize codon optimized for the axmi205 or modified axmi205 sequence in the transgenic maize. Implementation of the method is by an agroinfiltration method with *Agrobacterium tumefaciens* carrying the binary plasmid harboring the specified target sequence of interest. After the sgRNA binds to the target axmi205 or modified axmi205 coding sequence, the Cas9 nuclease makes specific cuts into the coding sequence and introduces the desired mutation(s) during DNA repair. Thus, a now mutated axmi205 coding sequence will encode an eAxmi205 variant protein, such as the variants described in Table 5, for example, where a mutation at position 507 replaces cysteine (C) with serine (S), or where a mutation at position 422 replaces methionine (M) with a serine (S) combined with a mutation at position 423 that replaces a methionine (M) with a leucine (L), or where a leucine (L) is inserted between the amino acids at positions 475 and 476 and/or between the amino acids at positions 496 and 497.

Plant cells comprising the genome edited eAxmi205 coding sequences are screened by PCR and sequencing. Calli that harbor genome edited mutations in the axmi205 or modified axmi205 coding sequences are induced to regenerate plants for phenotype evaluation for insecticidal activity of the expressed eAxmi205 protein against WCRW, Northern Corn Rootworm (*Diabrotica barberi*), Southern Corn Rootworm (*Diabrotica undecimpunctata howardi*) and/or Mexican Corn Rootworm (*Diabrotica virgifera zeaa*).

The foregoing is illustrative of the present invention and is not to be construed as limiting thereof. The invention is defined by the following claims, with equivalents of the claims to be included therein.

That which is claimed:

1. A modified Axmi205 toxin, wherein said modified Axmi205 toxin comprises an amino acid sequence having at least 99% identity to the polypeptide of SEQ ID NO: 1 and comprises an insertion of a leucine, phenylalanine, aspartic acid or arginine between the positions corresponding to amino acids A475 and G476 in the polypeptide of SEQ ID NO:1, and wherein the insertion results in enhanced digestion of the modified Axmi205 toxin by pepsin as compared with the Axmi205 toxin that does not comprise the insertion.

2. The modified Axmi205 toxin of claim 1, wherein said toxin is active against an insect pest selected from the group consisting of Western corn rootworm (*Diabrotica virgifera virgifera*), Northern Corn Rootworm (*Diabrotica barberi*), Southern Corn Rootworm (*Diabrotica undecimpunctata howardi*) and Mexican Corn Rootworm (*Diabrotica virgifera zeae*).

3. The modified Axmi205 toxin of claim 1, wherein the modified Axmi205 toxin comprises an insertion of a leucine between amino acids A475 and G476 in the polypeptide of SEQ ID NO:1 or the corresponding alanine and glycine residues in the amino acid sequence having at least 99% identity to SEQ ID NO:1.

4. The modified Axmi205 toxin of claim 1, wherein the modified Axmi205 toxin comprises the amino acid sequence of SEQ ID NO: 69.

5. A polynucleotide comprising a nucleotide sequence encoding the modified Axmi205 toxin according to claim 1.

6. The polynucleotide according to claim 5, wherein the polynucleotide comprises the nucleotide sequence of SEQ ID NO: 70 or 77.

7. A nucleic acid molecule comprising the polynucleotide according to claim 5 operably associated with a heterologous promoter.

8. A vector comprising the nucleic acid molecule according to claim 7.

9. A transgenic plant comprising the nucleic acid molecule of claim 7.

10. The transgenic plant according to claim 9, wherein the transgenic plant is a maize plant.

11. A transgenic seed of the transgenic plant according to claim 9, wherein the seed comprises the nucleic acid molecule.

12. A transgenic seed of the transgenic plant according to claim 10, wherein the seed comprises the nucleic acid molecule.

13. A method of producing a transgenic plant with increased resistance to a coleopteran insect pest, the method comprising introducing into a plant the polynucleotide of claim 5, wherein the modified Axmi205 toxin is expressed in the plant, thereby producing a transgenic plant with increased resistance to a coleopteran insect pest.

14. The method according to claim 13, wherein the introducing step comprises:
  i. transforming a plant cell with the polynucleotide and regenerating a transgenic plant from said plant cell;
  ii. crossing a first plant comprising the polynucleotide with a second plant; or
  iii. genome editing a polynucleotide sequence encoding an Axmi205 toxin in a transgenic plant.

15. The method according to claim 14, wherein the method further comprises obtaining a transgenic progeny plant for one or more generations from the transgenic plant, wherein the progeny plant comprises the polynucleotide and has increased resistance to a coleopteran insect pest.

16. A polynucleotide comprising a nucleotide sequence encoding the modified Axmi205 toxin according to claim 4.

17. A nucleic acid molecule comprising the polynucleotide according to claim 16 operably associated with a heterologous promoter.

18. A transgenic plant comprising the nucleic acid molecule of claim 17.

19. The transgenic plant according to claim 18, wherein the transgenic plant is a maize plant.

20. A transgenic seed of the transgenic plant according to claim 19, wherein the seed comprises the nucleic acid molecule.

* * * * *